United States Patent
Labéguère et al.

(10) Patent No.: US 10,047,083 B2
(45) Date of Patent: *Aug. 14, 2018

(54) DIHYDROPYRIMIDINOISOQUINOLINONES AND PHARMACEUTICAL COMPOSITIONS THEREOF FOR THE TREATMENT OF INFLAMMATORY DISORDERS

(71) Applicant: GALAPAGOS NV, Mechelen (BE)

(72) Inventors: Frédéric Gilbert Labéguère, Gagny (FR); Gregory John Robert Newsome, Paris (FR); Luke Jonathan Alvey, Versailles (FR); Laurent Raymond Maurice Sanière, Montesson (FR); Stephen Robert Fletcher, Hatfield Heath (GB)

(73) Assignee: GALAPAGOS NV, Mechelen (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/966,879

(22) Filed: Dec. 11, 2015

(65) Prior Publication Data

US 2016/0244442 A1    Aug. 25, 2016

Related U.S. Application Data

(63) Continuation of application No. 14/148,057, filed on Jan. 6, 2014, now Pat. No. 9,255,095, which is a continuation of application No. 13/721,788, filed on Dec. 20, 2012, now Pat. No. 8,927,543.

(60) Provisional application No. 61/578,979, filed on Dec. 22, 2011.

(51) Int. Cl.
    *C07D 471/04* (2006.01)
    *A61K 31/519* (2006.01)
    *A61K 31/5377* (2006.01)
    *A61K 45/06* (2006.01)

(52) U.S. Cl.
    CPC .......... *C07D 471/04* (2013.01); *A61K 31/519* (2013.01); *A61K 31/5377* (2013.01); *A61K 45/06* (2013.01)

(58) Field of Classification Search
    CPC .. A61K 31/519; A61K 45/06; A61K 31/5377; C07D 471/04
    See application file for complete search history.

(56) References Cited

U.S. PATENT DOCUMENTS

| | | | |
|---|---|---|---|
| 8,927,543 B2 | 1/2015 | Labeguere et al. | |
| 9,255,095 B2 | 2/2016 | Labeguere et al. | |
| 2013/0165437 A1 | 6/2013 | Labeguere et al. | |
| 2014/0121204 A1 | 5/2014 | Labeguere et al. | |

FOREIGN PATENT DOCUMENTS

| | | |
|---|---|---|
| DE | 2801289 A1 | 5/1979 |
| JP | 2011088847 A | 5/2011 |
| WO | 2005007092 A2 | 1/2005 |
| WO | 2007027661 A2 | 3/2007 |
| WO | 2007076092 A2 | 7/2007 |
| WO | 2010014939 A1 | 2/2010 |
| WO | 2013092791 A1 | 6/2013 |
| WO | 2013093849 A1 | 6/2013 |
| WO | 2013111150 A1 | 8/2013 |

(Continued)

OTHER PUBLICATIONS

Lattin et al (Immunome Research 2008, 4:5).*
Lingor et al (Cell Tissue Res (2012) 349:289-311).*
Vanhouette et al (Human safety, pharmacokinetics and pharmacodynamics of the GPR84 antagonist GLPG1205, a potential new approach to treat IBD , published 2014).*
Brown, A.J., et al., The Orphan G Protein-coupled Receptors GPR41 and GPR43 Are Activated by Propionate and Other Short Chain Carboxylic Acids, The Journal of Biological Chemistry, vol. 278, No. 13, pp. 11312-11319 (2003).
Le Poul, E., et al., Functional Characterization of Human Receptors for Short Chain Fatty Acids and Their Role in Polymorphonuclear Cell Activation, The Jounal of Biological Chemistry, vol. 278, No. 28, pp. 25481-25489 (2003).

(Continued)

*Primary Examiner* — Angela C Brown-Pettigrew
(74) *Attorney, Agent, or Firm* — Heslin Rothenberg Farley & Mesiti P.C.

(57) ABSTRACT

A compound according to Formula Ia:

Ia

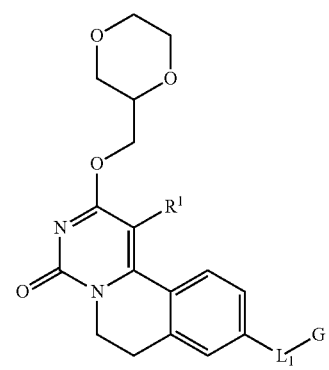

wherein $L_1$, G, and $R^1$ are as described herein.

The present invention relates to novel compounds according to Formula I that antagonize GPR84, a G-protein-coupled receptor that is involved in inflammatory conditions, and methods for the production of these novel compounds, pharmaceutical compositions comprising these compounds, and methods for the prevention and/or treatment of inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions by administering a compound of the invention.

16 Claims, No Drawings

(56) References Cited

FOREIGN PATENT DOCUMENTS

WO 2013128465 A1 9/2013
WO 2014095798 A1 6/2014

OTHER PUBLICATIONS

Stoddart, L.A., et al., International Union of Pharmacology. LXXI. Free Fatty Acid Receptors FFA1, -2, and -3: Pharmacology and Pathophysiological Functions, Pharmacological Reviews, vol. 60, No. 4, pp. 405-417 (2008).
Khachigian, L.M., Collagen antibody-induced arthritis, Protocol, vol. 1, No. 5, 2512-2516 (2006).
Lin, H-S, et al., Anti-rheumatic activities of histone deacetylase (HDAS) inhibitors in vivo in collagen-inducedarthritis in rodents, British Journal of Pharmacology vol. 150, pp. 862-872 (2007).
Salvemini, D., et al., Amelioration of Joint Disease in a Rat Model of Collagen-Induced Arthritis by M40403, a Superoxide Dismutase Mimetic, Arthritis & Rheumatism, vol. 44, No. 12, pp. 2909-2921 (2001).
Bouchard, C., et al., G protein-coupled receptor 84, a microglia-associated protein expressed in neuroinflammatory conditions, Glia, vol. 55, pp. 790-800 (2007).
Brand, D.D., et al., Collagen-induced arthritis, Nature Protocols, vol. 2, No. 5, pp. 1269-1275 (2007).
Young Kim, H., et al., Synthesis of dioxane-based antiviral agents and evaluation of their biological activities as inhibitors of sindbis virus replication, Bioorganic & Medicinal Chemistry, vol. 15, pp. 2667-2679 (2007).
Venkataraman, C., et al., The G-protein coupled receptor, GPR84 regulates IL-4 production by T lymphocytes in response to CD3 crosslinking, Immunology Letters, vol. 101, pp. 144-153 (2005).
Wittenberger, T., et al., An Expressed Sequence Tag (EST) Data Mining Strategy Succeeding in the Discovery of New G-protein Coupled Receptors, J. Molecular Biology, vol. 307, pp. 799-813 (2001).
Yousefi, S. et al., Cloning and expression analysis of a novel G-protein-coupled receptor selectively expressed on granulocytes, Journal of Leukocyte Biology, vol. 69, pp. 1045-1052 (2001).
Du Bois, R.M., Strategies for treating idiopathic pulmonary fibrosis, Du Bois, Nature Reviews Drug Discovery, vol. 9, pp. 129-140 (2010).
Sina, C., et al., G Protein Coupled Receptor 43 is Essential for Neutrophil Recruitment during Intestinal Inflammation, J Immunol, vol. 183, pp. 7514-7522 (2009).
Wang, J., et al., Medium-chain Fatty Acids as Ligands for Orphan G Protein-coupled Receptor GPR84, The Journal of Biological Chemistry, vol. 281, No. 45, pp. 34457-34464 (2006).
Berry, M.P.R., et al., An interferon-inducible neutrophil-driven blood transcriptional signature in human tuberculosis, Nature, vol. 466, pp. 973-979 (2010).
Wirtz, S., et al., Chemically induced mouse models of intestinal inflammation, Nature Protocols, vol. 2, pp. 541-546 (2007).
Nagasaki, H., et al., Inflammatory changes in adipose tissue enhance expression of GPR84, a medium-chain fatty acid receptor TNFα enhances GPR84 expression in adipocytes, FEBS Letters, vol. 586, pp. 368-372 (2012).
Bolchi, C., et al., Univocal syntheses of 2- and 3-hydroxymethyl-2,3-dihydro[1,4]dioxino[2,3-b]pyridine enantiomers, Tetrahedron: Asymmetry, vol. 16, 3380-3384 (2005).
Suzuki, M., et al., Medium-chain Fatty Acid-sensing Receptor, GPR84, Is a Proinflammatory Receptor, Journal of Biological Chemistry, vol. 288, No. 15, pp. 10684-10691 (2013).
Written Opinion of the International Searching Authority for PCT/EP2012/076275 (dated Jun. 22, 2014).
International Search Report for PCT/EP2012/076275 (dated Jun. 6, 2013).
Written Opinion of the International Searching Authority for PCT/EP2013/076818 (dated Jan. 29, 2014).
International Search Report for PCT/EP2013/076818 (dated Jan. 29, 2014).

* cited by examiner

DIHYDROPYRIMIDINOISOQUINOLINONES AND PHARMACEUTICAL COMPOSITIONS THEREOF FOR THE TREATMENT OF INFLAMMATORY DISORDERS

CROSS REFERENCE TO RELATED APPLICATIONS

This application is a continuation of U.S. patent application Ser. No. 14/148,057, filed on Jan. 6, 2014, which is a continuation of U.S. patent application Ser. No. 13/721,788, filed on Dec. 20, 2012, which claimed priority to U.S. Provisional Application No. 61/578,979, filed on Dec. 22, 2011, the entire contents of said applications being hereby incorporated herein by reference.

FIELD OF THE INVENTION

The present invention relates to novel compounds that antagonize GPR84, a G-protein-coupled receptor that is involved in inflammatory conditions.

The present invention also provides methods for the production of these novel compounds, pharmaceutical compositions comprising these compounds, and methods for the prevention and/or treatment of inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions by administering a compound of the invention.

BACKGROUND OF THE INVENTION

GPR84 was recently isolated and characterized from human B cells (Wittenberger et al., 2001, J Mol Biol, 307, 799-813) as the result of an expressed sequence tag data mining strategy, and also using a degenerate primer reverse transcriptase-polymerase chain reaction (RT-PCR) approach aimed to identify novel chemokine receptors expressed in neutrophils (Yousefi S et al. 2001 J Leukoc Biol; 69, 1045-52).

GPR84 (also known as EX33) remained an orphan GPCR until the identification of medium-chain FFAs with carbon chain lengths of 9-14 as ligands for this receptor (Wang et al. (2006) J. Biol. Chem. 281:3457-64). GPR84 was described to be activated by capric acid (C10:0), undecanoic acid (C11:0) and lauric acid (C12:0) with potencies of 5 μM, 9 μM and 11 μM, respectively. Two small molecules were also described to have some GPR84 agonist activity: 3,3' di-indolylmethane (DIM) (Wang et al. (2006) J. Biol. Chem. 281:3457-64) and embelin (WO 2007/027661A2).

GPR84 expression has been shown to be expressed in immune cells at least but not limited to polymorphonuclear leukocytes (PMN), neutrophils, monocytes, T cells, B cells. (Wang et al., 2006, The Journal of Biological Chemistry, 281, 45, 3457-3464, Yousefi et al., 2001, Journal of Leukocyte Biology, 69, 1045-1052, Venkataraman and Kuo, 2005, Immunology Letters, 101, 144-153, WO2007/027661 A2). Higher levels of GPR84 were measured in neutrophils and eosinophils than in T-cells and B-cells. GPR84 expression was demonstrated in tissues that may play a role in the propagation of the inflammatory response such as lung, spleen, bone marrow.

For example, in a recent review, Du Bois reported the current status of therapies for lung interstitial diseases, such as idiopathic pulmonary fibrosis (IPF). There are almost 300 distinct injurious or inflammatory causes of interstitial lung disease that can result in diffuse lung scarring, and the initial stages of the IPF pathology are very likely to involve inflammation (Du Bois, 2010, Nat Rev, Drug Discovery, 9, 129), and combination therapies involving anti-inflammatory treatment could be advantageously used.

The expression of GPR84 was highly up-regulated in monocytes/macrophages upon LPS stimulation (Wang et al., 2006, The Journal of Biological Chemistry, 281, 45, 3457-3464).

GPR84 knock-out (KO) mice are viable and indistinguishable from wild-type littermate controls (Venkataraman and Kuo, 2005, Immunology Letters, 101, 144-153). The proliferation of T and B cells in response to various mitogens is reported to be normal in GPR84-deficient mice (Venkataraman and Kuo, 2005, Immunology Letters, 101, 144-153). T helper 2 (Th2) differentiated T cells from GPR84 KO secreted higher levels of IL4, IL5, IL13, the 3 major Th2 cytokines, compared to wild-type littermate controls. In contrast, the production of the Th1 cytokine, INFγ, was similar in Th1 differentiated T cells from GPR84 KO and wild-type littermate (Venkataraman and Kuo, 2005, Immunology Letters, 101, 144-153).

In addition, capric acid, undecanoic acid and lauric acid dose dependently increased the secretion of interleukin-12 p40 subunit (IL-12 p40) from RAW264.7 murine macrophage-like cells stimulated with LPS. The pro-inflammatory cytokine IL-12 plays a pivotal role in promoting cell-mediated immunity to eradicate pathogens by inducing and maintaining T helper 1 ($T_h1$) responses and inhibiting T helper 2 ($T_h2$) responses. Medium-chain FFAs, through their direct actions on GPR84, may affect $T_h1/T_h2$ balance.

Berry et al. identified a whole-blood 393-gene transcriptional signature for active tuberculosis (TB) (Berry et al., 2010, Nature, 466, 973-979). GPR84 was part of this whole-blood 393-gene transcriptional signature for active TB indicating a potential role for GPR84 in infectious diseases.

GPR84 expression was also described in microglia, the primary immune effector cells of the central nervous system (CNS) from myeloid-monocytic origin (Bouchard et al., 2007, Glia, 55:790-800). As observed in peripheral immune cells, GPR84 expression in microglia was highly inducible under inflammatory conditions such as TNFa and IL1 treatment but also notably endotoxemia and experimental autoimmune encephalomyelitis (EAE), suggesting a role in neuro-inflammatory processes. Those results suggest that GPR84 would be up-regulated in CNS not only during endotoxemia and multiple sclerosis, but also in all neurological conditions in which TNFα or IL1b pro-inflammatory cytokines are produced, including brain injury, infection, Alzheimer's disease (AD), Parkinson's disease (PD).

GPR84 expression was also observed in adipocytes and shown to be enhanced by inflammatory stimuli (Nagasaki et al., 2012). The results suggest that GPR84 emerges in adipocytes in response to TNFα from infiltrating macrophages and exacerbates the vicious cycle between adiposity and diabesity, and therefore the inhibition of GPR84 activity might be beneficial for the treatment of endocrine and/or metabolic diseases.

Therefore, the present invention provides novel compounds, processes for their preparation and their use in the preparation of a medicament for the treatment of inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions.

SUMMARY OF THE INVENTION

The present invention relates to novel dihydropyrimidinoisoquinolinone compounds that antagonize GPR84, and that are potentially useful for the treatment of inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions.

The present invention also provides methods for the production of these compounds, pharmaceutical compositions comprising these compounds and methods for treating inflammatory conditions (for example inflammatory bowel diseases (IBD), rheumatoid arthritis, vasculitis, lung diseases (e.g. chronic obstructive pulmonary disease (COPD) and lung interstitial fibrosis (IPF))), neuroinflammatory conditions, infectious diseases, autoimmune diseases, endocrine and/or metabolic diseases, and/or diseases involving impairment of immune cell functions.

Accordingly, in a first aspect of the invention, a compound of the invention is disclosed having a Formula Ia:

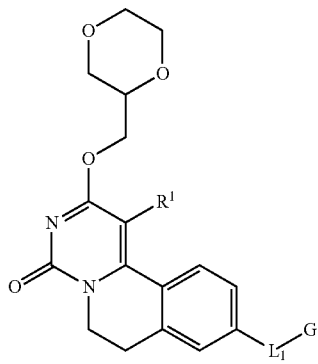

Ia wherein
$R^1$ is H, Me, or halo;
$L_1$ is absent or is —O—, —S—, or —NR$^{4a}$—;
G is
  $R^2$,
  —W-$L_2$-$R^2$, or
  —W-$L_3$-$R^3$
W is $C_{1-4}$ alkylene, $C_{2-4}$ alkenylene having one double bond, or $C_{2-4}$ alkynylene having one triple bond;
$L_2$ is absent or is —O—;
$R^2$ is
  H,
  $C_{1-8}$ alkyl, optionally substituted with one to three groups independently selected from
    OH,
    halo,
    CN,
    $C_{1-6}$ alkoxy,
    $C_{3-7}$ cycloalkyl,
    4-6 membered heterocycloalkyl comprising one to three heteroatoms independently selected from S, and O,
    5-6 membered heteroaryl comprising one to three heteroatoms independently selected from N, S, and O, and
    phenyl,
  $C_{4-7}$ cycloalkenyl comprising one double bond,
  5-7 membered heterocycloalkenyl comprising one double bond, and one to three heteroatoms independently selected from N, O, and S,
  $C_{3-7}$ cycloalkyl optionally substituted with one or more independently selected $R^5$ groups,
  4-10 membered heterocycloalkyl comprising one to two heteroatoms independently selected from S, and O, optionally substituted with one to three independently selected $R^5$ groups,
  5-10 membered heteroaryl comprising one to three heteroatoms independently selected from N, S, and O, optionally substituted with one to three independently selected $R^6$ groups, or
  $C_{6-10}$ aryl optionally substituted with one or more independently selected $R^6$ groups;
$L_3$ is —NR$^{4b}$—;
$R^3$ is
  $C_{1-4}$alkyl substituted with
    $C_{6-10}$ aryl optionally substituted with one or more independently selected $R^7$ groups, or
    5-10 membered heteroaryl comprising one to three heteroatoms independently selected from N, S, and O, optionally substituted with one or more independently selected $R^7$ groups,
  5-10 membered heteroaryl comprising one to three heteroatoms independently selected from N, S, and O, optionally substituted with one or more independently selected $R^7$ groups, or
  $C_{6-10}$ aryl optionally substituted with one or more independently selected $R^7$ groups;
Each $R^{4a}$ and $R^{4b}$ is independently selected from H, $C_{1-4}$alkyl, and $C_{3-7}$ cycloalkyl;
$R^5$ is oxo or $R^6$;
$R^6$ is
  OH,
  halo,
  —NO$_2$,
  $C_{1-6}$ alkyl optionally substituted with one to three groups independently selected from halo, and OH,
  $C_{1-6}$alkoxy optionally substituted with one to three groups independently selected from halo, and OH,
  $C_{3-7}$ cycloalkyl,
  —C(=O)OR$^8$,
  —C(=O)NR$^9$R$^{10}$,
  —NHC(=O)—$C_{1-4}$ alkyl,
  —CN,
  phenyl,
  —O-phenyl,
  4-7 membered heterocycloalkyl comprising one to three heteroatoms independently selected from N, O, and S, or
  5-6 membered heteroaryl comprising one to three heteroatoms independently selected from N, O, and S; optionally substituted with one or more independently selected $C_{1-4}$alkyl, $C_{1-4}$ alkoxy, CN, halo, and —C(=O)OR$^{11}$;

$R^7$ is $C_{1-4}$ alkyl, or halo, and each of $R^8$, $R^9$, $R^{10}$ and $R^{11}$ is independently selected from H and $C_{1-4}$ alkyl.

In a further aspect, the present invention provides pharmaceutical compositions comprising a compound of the invention, and a pharmaceutical carrier, excipient or diluent. Moreover, a compound of the present invention useful in the pharmaceutical compositions and treatment methods disclosed herein, is pharmaceutically acceptable as prepared and used. In this aspect of the invention, the pharmaceutical composition may additionally comprise further active ingredients suitable for use in combination with a compound of the invention.

In another aspect of the invention, this invention provides novel compounds of the invention for use in therapy.

In a further aspect of the invention, this invention provides a method of treating a mammal susceptible to or afflicted with a condition from among those listed herein, and particularly, such condition as may be associated with aberrant activity of GPR84 and/or aberrant GPR84 expression and/or aberrant GPR84 distribution, for example inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions, which method comprises administering a therapeutically effective amount of a compound of the invention, or one or more of the pharmaceutical compositions herein described.

In a further aspect, the present invention provides a compound of the invention for use in the treatment or prevention of a condition selected from those listed herein, particularly such conditions as may be associated with aberrant activity of GPR84 and/or aberrant GPR84 expression and/or aberrant GPR84 distribution expression such as inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions.

In additional aspects, this invention provides methods for synthesizing a compound of the invention, with representative synthetic protocols and pathways disclosed herein.

Accordingly, it is a principal object of this invention to provide a compound of the invention, which can modify the activity of GPR84 and thus prevent or treat any conditions that may be causally related thereto.

It is further an object of this invention to provide a compound of the invention that can treat or alleviate conditions or diseases or symptoms of same, such as inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions, that may be causally related to the activity and/or expression and/or distribution of GPR84.

A still further object of this invention is to provide pharmaceutical compositions that may be used in the treatment or prevention of a variety of disease states, including the diseases associated with aberrant activity of GPR84 and/or aberrant GPR84 expression and/or aberrant GPR84 distribution such as inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions.

Other objects and advantages will become apparent to those skilled in the art from a consideration of the ensuing detailed description.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms 'groups' and 'radicals' can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Alkyl' means straight or branched aliphatic hydrocarbon having the specified number of carbon atoms. Particular alkyl groups have 1 to 6 carbon atoms or 1 to 4 carbon atoms. Branched means that one or more alkyl groups such as methyl, ethyl or propyl is attached to a linear alkyl chain.

Particular alkyl groups are methyl, ethyl, n-propyl, isopropyl, n-butyl, tert-butyl, sec-butyl, n-pentyl, n-hexyl, and 1,2-dimethylbutyl. Particular alkyl groups have between 1 and 4 carbon atoms.

'Alkylene' refers to divalent alkane radical groups having the number of carbon atoms specified, in particular 1 to 6 carbon atoms and more particularly 1 to 4 carbon atoms which can be straight-chained or branched. This term is exemplified by groups such as methylene (—$CH_2$—), ethylene (—$CH_2$—$CH_2$—), the propylene isomers (e.g., —$CH_2$—$CH_2$—$CH_2$— and —$CH(CH_3)$—$CH_2$—) and the like.

'Alkenylene' refers to divalent alkene radical groups having the number of carbon atoms and the number of double bonds specified, in particular 2 to 6 carbon atoms and more particularly 2 to 4 carbon atoms which can be straight-chained or branched. This term is exemplified by groups such as —CH=CH—, —$CH_2$—CH=CH—, —C($CH_3$)=CH—, —C($CH_3$)=CH—$CH_2$—, —C($CH_3$)=C($CH_3$)—, and —$CH_2$—C($CH_3$)=CH—.

'Alkynylene' refers to divalent alkyne radical groups having the number of carbon atoms and the number of triple bonds specified, in particular 2 to 6 carbon atoms and more particularly 2 to 4 carbon atoms which can be straight-chained or branched. This term is exemplified by groups such as —C≡C—, —CH₂—C≡C—, and —C(CH₃)H—C≡CH—.

'Alkoxy' refers to the group O-alkyl, where the alkyl group has the number of carbon atoms specified. In particular the term refers to the group —O—$C_1$-$C_6$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Amino' refers to the radical —NH₂.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or poly-cyclic that includes the number of ring members specified. Particular aryl groups have from 6 to 10 ring members. Where the aryl group is a monocyclic ring system it preferentially contains 6 carbon atoms. Particularly aryl groups include phenyl, naphthyl, indenyl, and tetrahydronaphthyl.

'Carboxy' refers to the radical —C(O)OH.

'Cycloalkyl' refers to cyclic non-aromatic hydrocarbyl groups having the number of carbon atoms specified. Particular cycloalkyl groups have from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 5, and particularly from 1 to 3 heteroatoms.

'Heteroaryl' means an aromatic ring structure, mono-cyclic or polycyclic, that includes one or more heteroatoms and the number of ring members specified. Particular heteraryl groups have 5 to 10 ring members, or 5 to 6 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

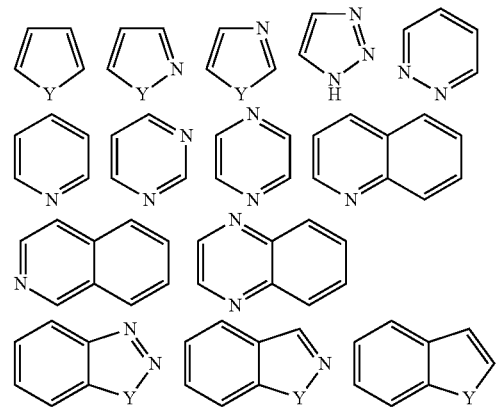

wherein each Y is selected from >C=O, NH, O and S.

As used herein, the term 'heterocycloalkyl' refers to a stable heterocyclic non-aromatic ring and/or rings containing one or more heteroatoms independently selected from N, O and S, fused thereto wherein the group contains the number of ring members specified. Particular heterocycloalkyl groups have 4-10 ring members or 5 to 7 ring members, or 5 to 6 ring members. The heterocycloalkyl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heterocycloalkyl ring will contain up to 4 heteroatoms, more typically up to 3 heteroatoms, more usually up to 2, for example a single heteroatom. In one embodiment, the heterocycloalkyl ring contains at least one ring nitrogen atom. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

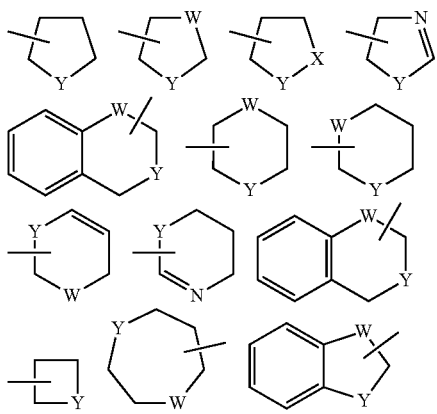

wherein each W is selected from $CH_2$, NH, O and S; and each Y is selected from NH, O, CO, $SO_2$, and S.

'Hydroxy' refers to the radical —OH.

'Nitro' refers to the radical —$NO_2$.

'Substituted' refers to a group in which one or more hydrogen atoms are each independently replaced with the same or different substituent(s).

'Thiol' refers to the group —SH.

'Thioalkoxy' refers to the group —$SR^{10}$ where $R^{10}$ is an alkyl group with the number of carbon atoms specified. In particular thioalkoxy groups where $R^{10}$ is a $C_1$-$C_6$ alkyl. Particular thioalkoxy groups are thiomethoxy, thioethoxy, n-thiopropoxy, thioisopropoxy, n-thiobutoxy, tert-thiobutoxy, sec-thiobutoxy, n-thiopentoxy, n-thiohexoxy, and 1,2-dimethylthiobutoxy. Particular thioalkoxy groups are lower thioalkoxy, i.e. with between 1 and 6 carbon atoms. Further particular thioalkoxy groups have between 1 and 4 carbon atoms.

As used herein, the term 'substituted with one or more' refers to one to four substituents. In one embodiment it refers to one to three substituents. In further embodiments it refers to one or two substituents. In a yet further embodiment it refers to one substituent.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counterion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein the term 'inflammatory condition(s)' refers to the group of conditions including, rheumatoid arthritis, osteoarthritis, juvenile idiopathic arthritis, vasculitis, psoriasis, gout, allergic airway disease (e.g. asthma, rhinitis), inflammatory bowel diseases (e.g. Crohn's disease, ulcerative colitis), and endotoxin-driven disease states (e.g. complications after bypass surgery or chronic endotoxin states contributing to e.g. chronic cardiac failure). Particularly the term refers to rheumatoid arthritis, allergic airway disease (e.g. asthma) and inflammatory bowel diseases.

As used herein, the term 'infectious diseases' refers to bacterial infectious diseases and includes but is not limited to conditions such as sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, or enterobacteria species.

As used herein the term 'autoimmune disease(s)' refers to the group of diseases including obstructive airways disease (including conditions such as COPD (Chronic obstructive pulmonary disease)), psoriasis, asthma (e.g intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, vasculitis, inflammatory bowel disease (e.g. Crohn's disease and ulcerative colitis), atherosclerosis and amyotrophic lateral sclerosis. Particularly the term refers to COPD, asthma, psoriasis, systemic lupus erythematosis, type I diabetes mellitus, vasculitis and inflammatory bowel disease.

As used herein the term 'endocrine and/or metabolic disease(s)' refers to the group of conditions involving the body's over- or under-production of certain hormones, while metabolic disorders affect the body's ability to process certain nutrients and vitamins. Endocrine disorders include hypothyroidism, congenital adrenal hyperplasia, diseases of the parathyroid gland, diabetes mellitus, diseases of the adrenal glands (including Cushing's syndrome and Addison's disease), and ovarian dysfunction (including polycystic ovary syndrome), among others. Some examples of metabolic disorders include cystic fibrosis, phenylketonuria (PKU), diabetes, hyperlipidemia, gout, and rickets.

As used herein, the term 'diseases involving impairment of immune cell functions' includes conditions with symptoms such as recurrent and drawn out viral and bacterial infections, and slow recovery. Other invisible symptoms may be the inability to kill off parasites, yeasts and bacterial pathogens in the intestines or throughout the body.

As used herein the term 'neuroinflammatory conditions' refers to diseases or disorders characterized by abrupt neurologic deficits associated with inflammation, demyelination, and axonal damage, and includes but is not limited to conditions such as Guillain-Barré syndrome (GBS), multiple sclerosis, axonal degeneration, autoimmune encephalomyelitis.

'Compound(s) of the invention', and equivalent expressions, are meant to embrace compounds of the Formula(e) as herein described, which expression includes the pharmaceutically acceptable salts, and the solvates, e.g., hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-6}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_1$ to $C_8$ alkyl, and substituted or unsubstituted $C_{6-10}$ aryl, esters of the compounds of the invention.

As used herein, the term 'isotopic variant' refers to a compound that contains unnatural proportions of isotopes at one or more of the atoms that constitute such compound For example, an 'isotopic variant' of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

The Compounds

The present invention relates to novel compounds that antagonize GPR84 and that may be useful for the treatment of inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions.

The present invention also provides methods for the production of the compounds of the invention, pharmaceutical compositions comprising the compounds of the invention and methods for treating diseases involving inflammatory conditions (for example inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions, by administering a compound of the invention. A compound of the invention is an inhibitor of GPR84.

Accordingly, in a first aspect of the invention, a compound of the invention is disclosed having a Formula Ia:

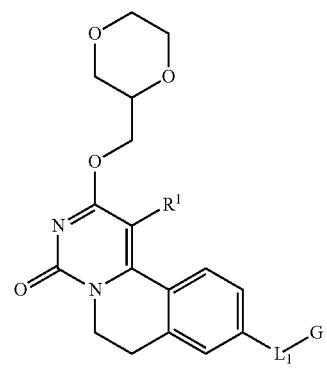

Ia wherein
R$^1$ is H, Me, or halo;
L$_1$ is absent or is —O—, —S—, or —NR$^{4a}$—;
G is
   R$^2$
   —W-L$_2$-R$^2$, or
   —W-L$_3$-R$^3$
W is C$_{1-4}$ alkylene, C$_{2-4}$ alkenylene having one double bond, or C$_{2-4}$ alkynylene having one triple bond;
L$_2$ is absent or is —O—;
R$^2$ is
   H,
   C$_{1-8}$ alkyl, optionally substituted with one to three groups independently selected from
      OH,
      halo,
      CN,
      C$_{1-6}$ alkoxy,
      C$_{3-7}$ cycloalkyl,
      4-6 membered heterocycloalkyl comprising one to three heteroatoms independently selected from S, and O, 5-6 membered heteroaryl comprising one to three heteroatoms independently selected from N, S, and O, and phenyl, C$_{4-7}$ cycloalkenyl comprising one double bond, 5-7 membered heterocycloalkenyl comprising one double bond, and one to three heteroatoms independently selected from N, O, and S, C$_{3-7}$ cycloalkyl optionally substituted with one or more independently selected R$^5$ groups, 4-10 membered heterocycloalkyl comprising one to two heteroatoms independently selected from S, and O, optionally substituted with one to three independently selected R$^5$ groups, 5-10 membered heteroaryl comprising one to three heteroatoms independently selected from N, S, and O, optionally substituted with one to three independently selected R$^6$ groups, or C$_{6-10}$ aryl optionally substituted with one or more independently selected R$^6$ groups;

L$_3$ is —NR$^{4b}$—;

R$^3$ is

C$_{1-4}$alkyl substituted with

C$_{6-10}$ aryl optionally substituted with one or more independently selected R$^7$ groups, or 5-10 membered heteroaryl comprising one to three heteroatoms independently selected from N, S, and O, optionally substituted with one or more R independently selected R$^7$ groups, 5-10 membered heteroaryl comprising one to three heteroatoms independently selected from N, S, and O, optionally substituted with one or more independently selected R$^7$ groups, or C$_{6-10}$ aryl optionally substituted with one or more independently selected R$^7$ groups;

Each R$^{4a}$ and R$^{4b}$ is independently selected from H, C$_{1-4}$alkyl, and C$_{3-7}$ cycloalkyl;

R$^5$ is oxo or R$^6$;

R$^6$ is

OH, halo,

—NO$_2$,

C$_{1-6}$ alkyl optionally substituted with one to three groups independently selected from halo, and OH, C$_{1-6}$alkoxy optionally substituted with one to three groups independently selected from halo, and OH, C$_{3-7}$ cycloalkyl,

—C(=O)OR$^8$,

—C(=O)NR$^9$R$^{10}$,

—NHC(=O)—C$_{1-4}$ alkyl,

—CN, phenyl,

—O-phenyl, 4-7 membered heterocycloalkyl comprising one to three heteroatoms independently selected from N, O, and S, or 5-6 membered heteroaryl comprising one to three heteroatoms independently selected from N, O, and S; optionally substituted with one or more independently selected C$_{1-4}$ alkyl, C$_{1-4}$ alkoxy, CN, halo, and —C(=O)OR$^{11}$;

R$^7$ is C$_{1-4}$ alkyl, or halo; and each of R$^8$, R$^9$, R$^{10}$ and R$^{11}$ is independently selected from H and C$_{1-4}$ alkyl.

In a further embodiment, a compound of the invention is disclosed having a Formula Ib:

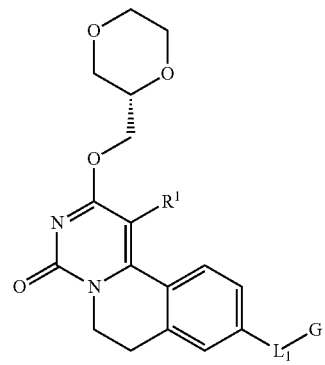

Ib wherein R$^1$, L$_1$ and G are as previously described.

In yet a further embodiment, a compound of the invention is disclosed having a Formula Ic:

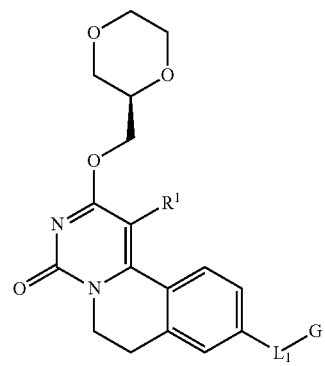

Ic wherein R$^1$, L$_1$ and G are as previously described.

In one embodiment, the compound of the invention is according to Formula Ia, Ib or Ic, wherein R$^1$ is Me, F, or Cl.

In one embodiment, the compound of the invention is according to Formula Ia, Ib or Ic, wherein R$^1$ is H.

In one embodiment, the compound of the invention is according to Formula IIa, IIb, or IIc:

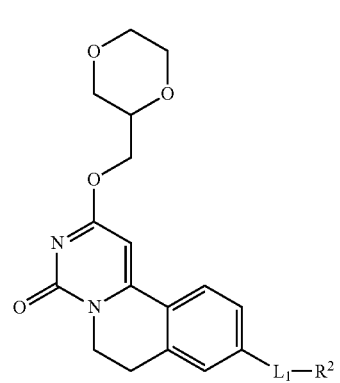

IIa

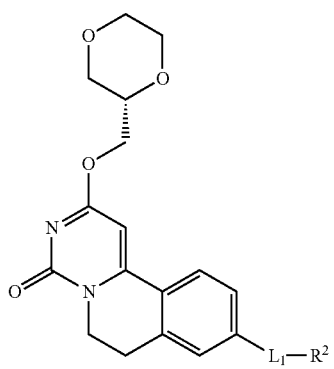
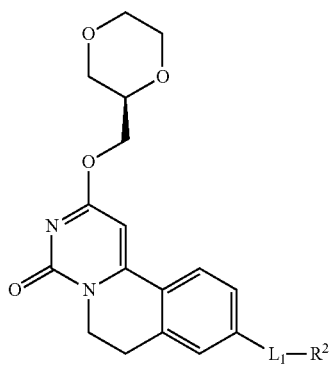
wherein L₁, and R² are as described previously.
In one embodiment, the compound of the invention is according to Formula IIIa, IIIb, or IIIc:
IIIa
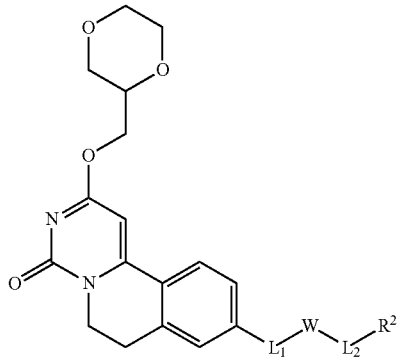
IIIb
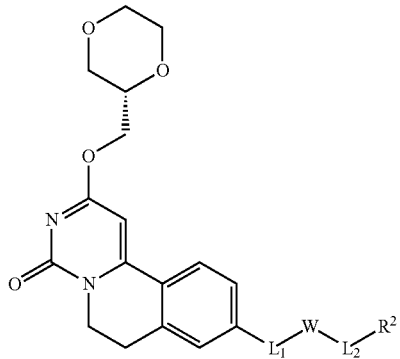
IIc
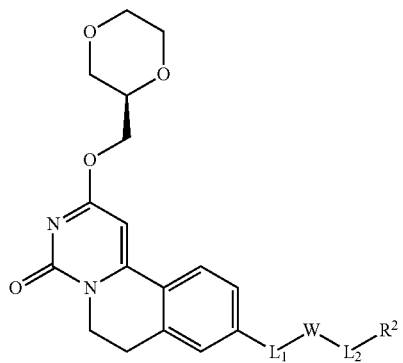
wherein $L_1$, W, $L_2$, and $R^2$ are as described previously.
In one embodiment, the compound of the invention is according to Formula IVa, IVb, or IVc:
IVa
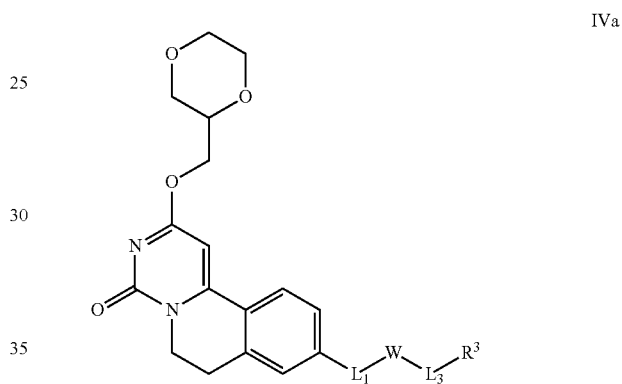
IVb
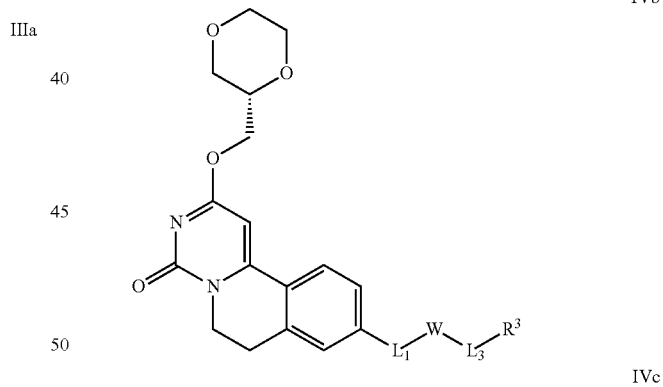
IVc
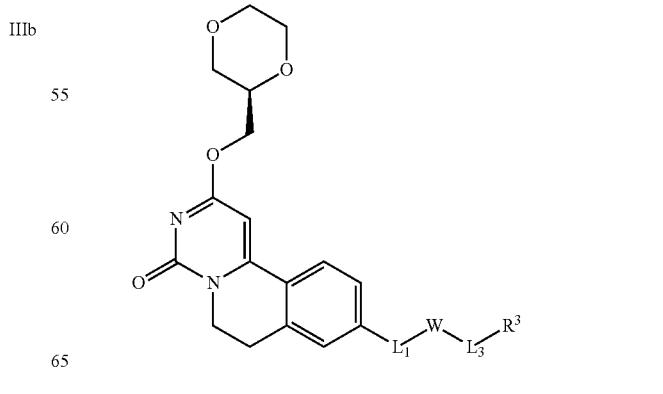
wherein $L_1$, W, $L_3$, and $R^3$ are as described previously.

In one embodiment, the compound of the invention is according to any one of Formulae Ia-IVc, wherein $L_1$ is absent, or is —O—. In a preferred embodiment, $L_1$ is absent.

In another embodiment, the compound of the invention is according to any one of Formulae Ia-IVc, wherein $L_1$ is —NR$^{4a}$—, wherein R$^{4a}$ is as described previously. In a preferred embodiment, R$^{4a}$ is H, Me, Et, or cyclopropyl. In a more preferred embodiment, R$^{4a}$ is H.

In one embodiment, the compound of the invention is according to any one of Formulae Ia-Ic, or IIIa-IVc, wherein W is $C_{1-4}$alkylene. In a preferred embodiment, W is —CH$_2$—, —CH$_2$—CH$_2$—, —CH$_2$—CH$_2$—CH(CH$_3$)—, —CH$_2$—CH(—CH$_2$—CH$_3$)—, —CH$_2$—C(CH$_3$)$_2$—, or —CH$_2$—CH$_2$—CH$_2$—. In a more preferred embodiment, W is —CH$_2$—. In another more preferred embodiment, W is —CH$_2$—CH$_2$—.

In one embodiment, the compound of the invention is according to any one of Formulae Ia-Ic, or IIIa-IVc, wherein W is $C_{2-4}$ alkenylene having one double bond. In a preferred embodiment, W is —CH=CH—, —CH$_2$—CH=CH—, or —CH=CH—CH$_2$—. In a more preferred embodiment, W is —CH=CH—. In another more preferred embodiment, W is —CH$_2$—CH=CH—.

In one embodiment, the compound of the invention is according to any one of Formulae Ia-Ic, or IIIa-IVc, wherein W is $C_{2-4}$ alkynylene having one triple bond. In a preferred embodiment, W is —C≡C—, —CH$_2$—C≡C—, or —C≡C—CH$_2$—. In a more preferred embodiment, W is —C≡C—. In another more preferred embodiment, W is —CH$_2$—C≡C—.

In one embodiment, the compound of the invention is according to any one of Formulae Ia-Ic, or IIIa-IIIc, wherein $L_2$ is absent. In another embodiment, $L_2$ is —O—.

In one embodiment, the compound of the invention is according to any one of Formulae Ia-Ic, or IIIa-IIIc, wherein $L_1$ is absent or is —O—, W is $C_{1-4}$alkylene; and $L_2$ and R$^2$ are as described previously. In a preferred embodiment, W is —CH$_2$—, —CH$_2$—CH$_2$—, or —CH$_2$—CH$_2$—CH$_2$—. In a more preferred embodiment, W is —CH$_2$—. In another preferred embodiment, W is —CH$_2$—CH$_2$—.

In another embodiment, the compound of the invention is according to any one of Formulae Ia-Ic, or IIIa-IIIc, wherein $L_1$ is absent or is —O—, W is $C_{2-4}$ alkenylene having one double bond; and $L_2$ and R$^2$ are as described previously. In a preferred embodiment, W is —CH=CH—, —CH$_2$—CH=CH—, or —CH=CH—CH$_2$—. In a more preferred embodiment, W is —CH=CH—. In another more preferred embodiment, W is —CH$_2$—CH=CH—.

In yet another embodiment, the compound of the invention is according to any one of Formulae Ia-Ic, or IIIa-IIIc, wherein $L_1$ is absent, W is $C_{2-4}$ alkynylene having one triple bond; and $L_2$ and R$^2$ are as described previously. In a preferred embodiment, W is —C≡C—, —CH$_2$—C≡C—, or —C≡C—CH$_2$—. In a more preferred embodiment, W is —C≡C—. In another more preferred embodiment, W is —CH$_2$—C≡C—.

In one embodiment, the compound of the invention is according to any one of Formulae Ia-Ic, or IIIa-IIIc, wherein $L_1$ and $L_2$ are absent, W is $C_{1-4}$ alkylene; and R$^2$ is as described previously. In a preferred embodiment, W is —CH$_2$—, —CH$_2$—CH$_2$—, or —CH$_2$—CH$_2$—CH$_2$—. In a more preferred embodiment, W is —CH$_2$—. In another more preferred embodiment, W is —CH$_2$—CH$_2$—.

In another embodiment, the compound of the invention is according to any one of Formulae Ia-Ic, or IIIa-IIIc, wherein $L_1$ and $L_2$ are absent, W is $C_{2-4}$ alkenylene having one double bond; and R$^2$ is as described previously. In a preferred embodiment, W is —CH=CH—, —CH$_2$—CH=CH—, or —CH=CH—CH$_2$—. In a more preferred embodiment, W is —CH=CH—. In another more preferred embodiment, W is —CH$_2$—CH=CH—.

In yet another embodiment, the compound of the invention is according to any one of Formulae Ia-Ic, or IIIa-IIIc, wherein $L_1$ and $L_2$ are absent, W is $C_{2-4}$ alkynylene having one triple bond; and R$^2$ is as described previously. In a preferred embodiment, W is —C≡C—, —CH$_2$—C≡C—, or —C≡C—CH$_2$—. In a more preferred embodiment, W is —C≡C—. In another more preferred embodiment, W is —CH$_2$—C≡C—.

In one embodiment, the compound of the invention is according to any one of Formulae Ia-IIIc, wherein R$^2$ is H.

In another embodiment, the compound of the invention is according to any one of Formulae any one of Formulae Ia-IIIc, wherein R$^2$ is $C_{1-8}$ alkyl. In a preferred embodiment, R$^2$ is Me, Et, n-Pr, i-Pr, i-Bu, or t-Bu. In a more preferred embodiment, R$^2$ is Me, Et, i-Pr or t-Bu. In a more preferred embodiment, R$^2$ is t-Bu.

In one embodiment, the compound of the invention is according to any one of Formulae Ia-IIIc, wherein R$^2$ is $C_{1-8}$ alkyl substituted with one to three groups selected from OH, halo, CN, $C_{1-6}$ alkoxy, $C_{3-7}$ cycloalkyl, 4-6 membered heterocycloalkyl (comprising one to three heteroatoms independently selected from S, and O), 5-6 membered heteroaryl (comprising one to three heteroatoms independently selected from N, S, and O), and phenyl. In a preferred embodiment, R$^2$ is Me, Et, n-Pr, i-Pr, i-Bu, or t-Bu substituted with one to three groups selected from OH, halo, CN, $C_{1-6}$ alkoxy, $C_{3-7}$ cycloalkyl, 4-6 membered heterocycloalkyl (comprising one to three heteroatoms independently selected from S, and O), 5-6 membered heteroaryl (comprising one to three heteroatoms independently selected from N, S, and O), and phenyl. In another preferred embodiment, is $C_{1-8}$ alkyl substituted with one to three groups selected from OH, F, Cl, CN, —OMe, —OEt, Oi-Pr, cyclopropyl, cyclobutyl, oxetanyl, tetrahydrofuranyl, tetrahydropyranyl, pyrralolyl, imidazolyl, triazolyl, oxazolyl, thiazolyl, pyridinyl, pyrimidinyl, pyrazinyl, and phenyl. In a more preferred embodiment, R$^2$ is Me, Et, n-Pr, i-Pr, i-Bu, or t-Bu substituted with one to three groups selected from OH, F, Cl, CN, —OMe, —OEt, —Oi-Pr, cyclopropyl, cyclobutyl, oxetanyl, tetrahydrofuranyl, tetrahydropyranyl, pyrralolyl, imidazolyl, triazolyl, oxazolyl, thiazolyl, pyridinyl, pyrimidinyl, pyrazinyl and phenyl.

In another embodiment, the compound of the invention is according to any one of Formulae Ia-IIIc, wherein R$^2$ is $C_{1-8}$ alkyl substituted with one group selected from OH, halo, CN, $C_{1-6}$alkoxy, $C_{3-7}$ cycloalkyl, 4-6 membered heterocycloalkyl (comprising one to three heteroatoms independently selected from S, and O), 5-6 membered heteroaryl (comprising one to three heteroatoms independently selected from N, S, and O), and phenyl. In a preferred embodiment, R$^2$ is Me, Et, n-Pr, i-Pr, i-Bu, or t-Bu substituted with one group selected from OH, halo, CN, $C_{1-6}$ alkoxy, $C_{3-7}$ cycloalkyl, 4-6 membered heterocycloalkyl (comprising one to three heteroatoms independently selected from S, and O), 5-6 membered heteroaryl (comprising one to three heteroatoms independently selected from N, S, and O), and phenyl. In another preferred embodiment, is $C_{1-8}$ alkyl substituted with one group selected from OH, F, Cl, CN, —OMe, —OEt, —Oi-Pr, cyclopropyl, cyclobutyl, oxetanyl, tetrahydrofuranyl, tetrahydropyranyl, pyrralolyl, imidazolyl, triazolyl, oxazolyl, thiazolyl, pyridinyl, pyrimidinyl, pyrazinyl, and phenyl. In a more preferred embodiment, R$^2$ is Me, Et, n-Pr, i-Pr, i-Bu, or t-Bu substituted with one group selected from OH, F, Cl, CN, —OMe, —OEt, —Oi-Pr, cyclopropyl, cyclobutyl, cyclopentyl, cyclohexyl, oxetanyl, tetrahydrofuranyl, tetrahydropyranyl, pyrralolyl, imidazolyl, triazolyl, oxazolyl, thiazolyl, pyridinyl, pyrimidinyl, pyrazinyl, and phenyl. In a most preferred embodiment, $R^2$ is —CH$_2$—OH, —C(CH$_3$)$_2$—OH, —CH(OH)CH$_3$, —CH(OH)—C$_2$H$_5$, —CH(OH)—C$_3$H$_7$, —C(OH)(C$_2$H$_5$)$_2$, —C(OH)H—CH(CH$_3$)$_2$, —C(OH)H—CH$_2$—CH(CH$_3$)$_2$, —C(OH)H—C(CH$_3$)$_3$, —CH$_2$—CN, —CH$_2$—OCH$_3$, —CH$_2$—CH$_2$—OCH$_3$, —CH(OCH$_3$)—CH$_3$, —C(OCH$_3$)H—CH(CH$_3$)$_2$, —CH$_2$—F, —CH$_2$—CH$_2$—F, —CH$_2$-cyclopropyl, —CH$_2$-cyclopentyl, —CH$_2$-oxetanyl, —CH$_2$-tetrahydrofuranyl, or —CH$_2$-tetrahydropyranyl.

In one embodiment, the compound of the invention is according to any one of Formulae Ia-IIIc, wherein $R^2$ is $C_{4-7}$ cycloalkenyl comprising one double bond. In a preferred embodiment, $R^2$ is cyclohexenyl.

In one embodiment, the compound of the invention is according to any one of Formulae Ia-IIIc, wherein $R^2$ is 5-7 membered heterocycloalkenyl comprising one double bond, and one to three heteroatoms independently selected from N, O, and S. In a preferred embodiment, $R^2$ is dihydropyranyl.

In one embodiment, the compound of the invention is according to any one of Formulae Ia-IIIc, wherein $R^2$ is $C_{3-7}$ cycloalkyl. In a preferred embodiment, $R^2$ is cyclopropyl, cyclobutyl, cyclopentyl, or cyclohexyl. In a more preferred embodiment, $R^2$ is cyclopropyl.

In another embodiment, the compound of the invention is according to any one of Formulae Ia-IIIc, wherein $R^2$ is $C_{3-7}$ cycloalkyl substituted with one to three independently selected $R^5$ groups. In a preferred embodiment, $R^2$ is $C_{3-7}$ cycloalkyl substituted with one $R^5$ group. In a more preferred embodiment, $R^2$ is cyclopropyl, cyclobutyl, cyclopentyl or cyclohexyl, each of which is substituted with one $R^5$ group. In another more preferred embodiment, $R^2$ is $C_{3-7}$ cycloalkyl substituted with one $R^5$ group, wherein $R^5$ is oxo, or $R^6$ wherein $R^6$ is selected from OH, or $C_{1-6}$ alkyl. In a most preferred embodiment, $R^2$ is cyclopropyl, cyclobutyl, cyclopentyl or cyclohexyl, each of which is substituted with one $R^5$ group, wherein $R^5$ is oxo, or $R^6$ wherein $R^6$ is selected from OH, or $C_{1-6}$ alkyl. In a further most preferred embodiment, $R^2$ is cyclopropyl, cyclobutyl, cyclopentyl or cyclohexyl, each of which is substituted with one $R^5$ group, wherein $R^5$ is $R^6$, and $R^6$ is selected from OH.

In one embodiment, the compound of the invention is according to any one of Formulae Ia-IIIc, wherein $R^2$ is 4-10 membered heterocycloalkyl comprising one to two heteroatoms independently selected from S, and O. In a preferred embodiment, $R^2$ is oxetanyl, tetrahydrofuranyl, tetrahydropyranyl, or dioxanyl.

In another embodiment, the compound of the invention is according to any one of Formulae Ia-IIIc, $R^2$ is 4-10 membered heterocycloalkyl comprising one to two heteroatoms independently selected from S, and O substituted with one to three independently selected $R^5$ groups. In a preferred embodiment, $R^2$ is 4-10 membered heterocycloalkyl comprising one to two heteroatoms independently selected from S, and O substituted with one $R^5$ group. In a more preferred embodiment, $R^2$ is 4-10 membered heterocycloalkyl comprising one to two heteroatoms independently selected from S, and O substituted with one $R^5$ group, wherein $R^5$ is selected from oxo, or $R^6$ wherein $R^6$ is selected from OH, and $C_{1-6}$ alkyl. In another more preferred embodiment, $R^2$ is oxetanyl, tetrahydrofuranyl, tetrahydropyranyl, or dioxanyl, each of which is substituted with one $R^5$ group. In a most preferred embodiment, $R^2$ is oxetanyl, tetrahydrofuranyl, tetrahydropyranyl, or dioxanyl, each of which is substituted with one $R^5$ group, wherein $R^5$ is selected from oxo, or $R^6$ wherein $R^6$ is selected from OH, and $C_{1-6}$ alkyl, In one embodiment, the compound of the invention is according to any one of Formulae Ia-IIIc, $R^2$ is 5-10 membered heteroaryl comprising one to three heteroatoms independently selected from N, S, and O. In a preferred embodiment, $R^2$ is furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl.

In another embodiment, the compound of the invention is according to any one of Formulae Ia-IIIc, $R^2$ is 5-10 membered heteroaryl comprising one to three heteroatoms independently selected from N, S, and O, substituted with one to three independently selected $R^6$ groups. In a preferred embodiment, $R^2$ is 5-10 membered heteroaryl comprising one to three heteroatoms independently selected from N, S, and O, substituted with one or two independently selected $R^6$ groups. In a more preferred embodiment, $R^2$ is furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl, substituted with one or two independently selected $R^6$ groups. In another more preferred embodiment, $R^2$ is 5-10 membered heteroaryl comprising one to three heteroatoms independently selected from N, S, and O, substituted with one or two independently selected $R^6$ groups, wherein each $R^6$ is independently selected from OH, halo, $C_{1-6}$ alkyl, $C_{1-6}$ alkyl substituted with one or more halo, $C_{1-6}$ alkoxy, —CN, $C_{3-7}$ cycloalkyl, 4-7 membered heterocycloalkyl comprising one to three heteroatoms independently selected from N, O, and S, and phenyl. In most preferred embodiment, $R^2$ is furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl, each of which is substituted with one or two independently selected $R^6$ groups, wherein each $R^6$ is independently selected from OH, halo, $C_{1-6}$ alkyl, $C_{1-6}$ alkyl substituted with one or more halo, $C_{1-6}$ alkoxy, —CN, $C_{3-7}$ cycloalkyl, 4-7 membered heterocycloalkyl comprising one to three heteroatoms independently selected from N, O, and S, and phenyl. In another most preferred embodiment, $R^2$ is 5-10 membered heteroaryl comprising one to three heteroatoms independently selected from N, S, and O, substituted with one or two independently selected $R^6$ groups, wherein each $R^6$ is independently selected from OH, F, Cl, Me, Et, Pr, i-Pr, t-Bu, —CF$_3$, —OMe, —OEt, Oi-Pr, —CN, cyclopropyl, pyrrolidinyl, morpholinyl, piperidinyl, or phenyl. In further most preferred embodiment, $R^2$ is furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl, each of which is substituted with one or two independently selected $R^6$ groups, wherein each $R^6$ is independently selected from OH, F, Cl, Me, Et, Pr, i-Pr, t-Bu, —CF$_3$, —OMe, —OEt, —Oi-Pr, —CN, cyclopropyl, pyrrolidinyl, morpholinyl, piperidinyl, and phenyl.

In another embodiment, the compound of the invention is according to any one of Formulae Ia-IIIc, $R^2$ is $C_{6-10}$ aryl. In a preferred embodiment, $R^2$ is phenyl.

In another embodiment, the compound of the invention is according to any one of Formulae Ia-IIIc, $R^2$ is $C_{6-10}$ aryl substituted with one or more independently selected $R^6$ groups. In a preferred embodiment, $R^2$ is $C_{6-10}$ aryl substituted with one or two independently selected $R^6$ groups. In a more preferred embodiment, $R^2$ is $C_{6-10}$ aryl substituted with one or two independently selected $R^6$ groups, wherein each $R^6$ group is selected from halo, CN, $C_{1-6}$ alkyl, $C_{1-6}$alkoxy, or —NHC(=O)—$C_{1-4}$ alkyl. In another more preferred embodiment, $R^2$ is $C_{6-10}$ aryl substituted with one or two independently selected $R^6$ groups, wherein each $R^6$ group is selected from —C(═O)$NR^9R^{10}$, and each $R^9$ and $R^{10}$ is independently selected from H and $C_{1-4}$ alkyl. In yet another more preferred embodiment, $R^2$ is phenyl substituted with one or two independently selected $R^6$ groups. In a most preferred embodiment, $R^2$ is phenyl substituted with one or two independently selected $R^6$ groups, wherein each $R^6$ group is selected from halo, CN, $C_{1-6}$ alkyl, $C_{1-6}$alkoxy, and —NHC(═O)—$C_{1-4}$ alkyl. In another most preferred embodiment, $R^2$ is phenyl substituted with one or two independently selected $R^6$ groups, wherein each $R^6$ group is selected from —C(═O)$NR^9R^{10}$, and each $R^9$ and $R^{10}$ is independently selected from H and $C_{1-4}$ alkyl. In a further most preferred embodiment $R^2$ is phenyl substituted with one or two independently selected $R^6$ groups, wherein each $R^6$ group is selected from F, Cl, CN, Me, —OMe, —OEt, and —NHC(═O)Me. In another further most preferred embodiment $R^2$ is phenyl substituted with one or two independently selected $R^6$ groups, wherein each $R^6$ group is selected from —C(═O)$NH_2$, and —C(═O)NHMe.

In another embodiment, the compound of the invention is according to any one of Formulae Ia-Ic, IVa, IVb or IVc, wherein $L_3$ is —$NR^{4b}$—, and $R^{4b}$ is as described previously. In a preferred embodiment, $R^{4b}$ is H, Me, Et, or cyclopropyl. In a more preferred embodiment, $R^{4a}$ is H.

In another embodiment, the compound of the invention is according to any one of Formulae Ia-Ic, IVa, IVb or IVc, wherein $R^3$ is $C_{1-4}$ alkyl substituted with $C_{6-10}$ aryl optionally substituted with one or more independently selected $R^1$ groups, or 5-10 membered heteroaryl comprising one to three heteroatoms independently selected from N, S, and O, optionally substituted with one or more R independently selected $R^1$ groups. In a preferred embodiment, $R^3$ is Me or Et, each of which is substituted with $C_{6-10}$ aryl optionally substituted with one or more independently selected $R^7$ groups), or 5-10 membered heteroaryl comprising one to three heteroatoms independently selected from N, S, and O, optionally substituted with one or more R independently selected $R^7$ groups. In another preferred embodiment, $R^3$ is $C_{1-4}$ alkyl substituted with phenyl, or pyridyl, each of which is optionally substituted with one or more independently selected $R^7$ groups. In a more preferred embodiment, $R^3$ is $C_{1-4}$ alkyl substituted with phenyl, or pyridyl. In a more preferred embodiment, $R^3$ is $C_{1-4}$ alkyl substituted with phenyl, or pyridyl, each of which is substituted with Me, Et, F, or Cl. In a most preferred embodiment, $R^3$ is Me or Et, each of which is substituted with phenyl, or pyridyl. In a more preferred embodiment, $R^3$ is Me or Et, each of which is substituted with phenyl, or pyridyl, each of which is substituted with Me, Et, F, or Cl.

In one embodiment, the compound of the invention is according to any one of Formulae Ia-Ic, IVa, IVb or IVc, wherein $R^3$ is 5-10 membered heteroaryl comprising one to three heteroatoms independently selected from N, S, and O. In a preferred embodiment, $R^3$ is pyridyl.

In one embodiment, the compound of the invention is according to any one of Formulae Ia-Ic, IVa, IVb, or IVc, wherein $R^3$ is 5-10 membered heteroaryl comprising one to three heteroatoms independently selected from N, S, and O, substituted with one or more independently selected $R^7$ groups, wherein each $R^7$ group is as described previously. In a preferred embodiment, $R^3$ is pyridyl, substituted with one or more independently selected $R^7$ groups, wherein each $R^7$ group is as described previously. In another preferred embodiment, $R^3$ is 5-10 membered heteroaryl comprising one to three heteroatoms independently selected from N, S, and O, substituted with one or more independently selected $R^7$ groups, wherein each $R^7$ group is selected from Me, Et, F, and Cl. In a more preferred embodiment, $R^3$ is pyridyl substituted with one or more independently selected $R^7$ groups, wherein each $R^7$ group is selected from Me, Et, F, and Cl. In a most preferred embodiment, $R^3$ is pyridyl substituted with one $R^7$ group selected from Me, Et, F, and Cl.

In one embodiment, the compound of the invention is according to any one of Formulae Ia-Ic, IVa, IVb, or IVc, wherein $R^3$ is $C_{6-10}$ aryl. In a preferred embodiment, $R^3$ is phenyl.

In one embodiment, the compound of the invention is according to any one of Formulae Ia-Ic, IVa, IVb, or IVc, wherein $R^3$ is $C_{6-10}$ aryl substituted with one or more independently selected $R^7$ groups, wherein each $R^7$ group is as described previously. In a preferred embodiment, $R^3$ is phenyl, substituted with one or more independently selected $R^7$ groups, wherein each $R^7$ group is as described previously. In another preferred embodiment, $R^3$ is $C_{6-10}$ aryl substituted with one or more independently selected $R^7$ groups, wherein each $R^7$ group is selected from Me, Et, F, and Cl. In a more preferred embodiment, $R^3$ is phenyl substituted with one or more independently selected $R^7$ groups, wherein each $R^7$ group is selected from Me, Et, F, and Cl. In a most preferred embodiment, $R^3$ is phenyl substituted with one $R^7$ group selected from Me, Et, F, and Cl.

In one embodiment, the compound of the invention is according to Formula Va, Vb, Vc or Vd:

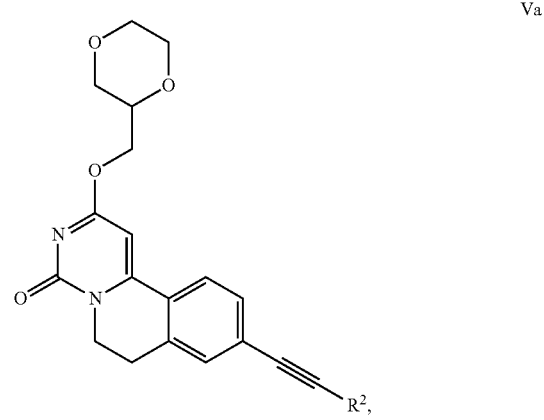

Va

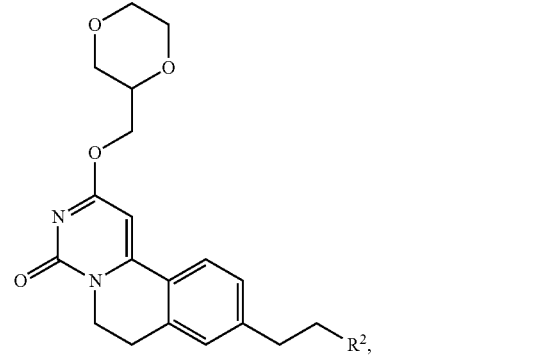

Vb

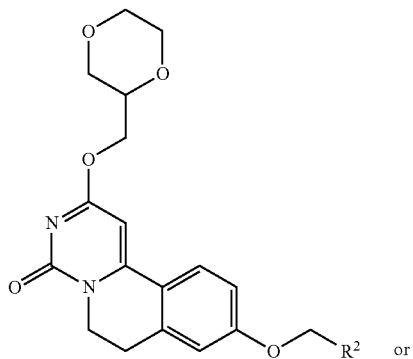

Vc

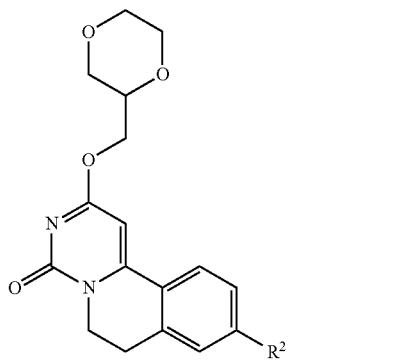

Vd wherein R² is as described previously.

In a further embodiment, the compound of the invention is not according to Formula Va, Vb, Vc or Vd.

In another embodiment, the compound of the invention is according to Formula VIa, VIb, VIc or VId:

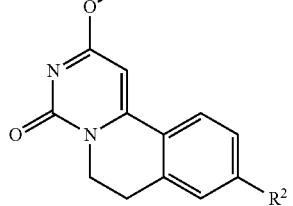

VIa

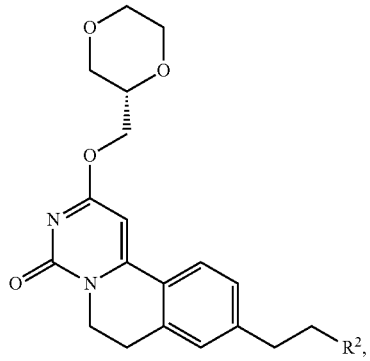

VIb

VIc

VId

wherein R² is as described previously.

In a further embodiment, the compound of the invention is not according to Formula VIa, VIb, VIc or VId.

In another embodiment, the compound of the invention is according to Formula VIIa, VIIb, VIIc or VIId:

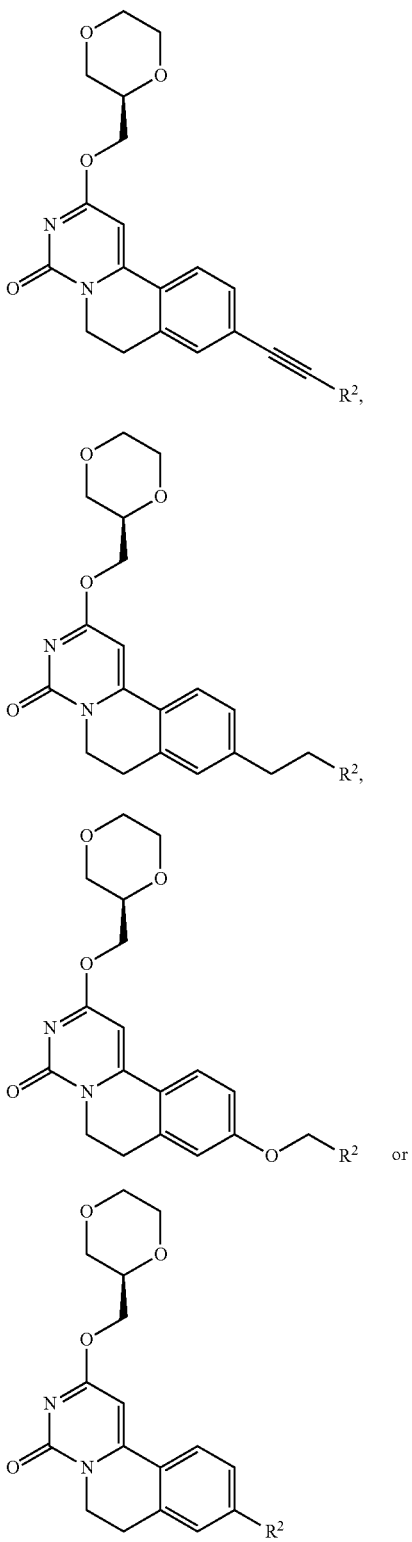

wherein R² is as described previously.

In one embodiment, the compound of the invention is according to Formula Va, Vb, VIa, VIb, VIIa, or VIIb, wherein R² is $C_{3-7}$ cycloalkyl. In a preferred embodiment, R² is cyclopropyl, cyclobutyl, cyclopentyl, or cyclohexyl. In a more preferred embodiment, R² is cyclopropyl.

In one embodiment, the compound of the invention is according to Formula Va, Vb, VIa, VIb, VIIa, or VIIb, wherein R² is not $C_{3-7}$ cycloalkyl. In a preferred embodiment, R² is not cyclopropyl, cyclobutyl, cyclopentyl, or cyclohexyl. In a more preferred embodiment, R² is not cyclopropyl.

In another embodiment, the compound of the invention is according to Formula Va, Vb, VIa, VIb, VIIa, or VIIb, wherein R² is $C_{3-7}$ cycloalkyl substituted with one to three independently selected R⁵ groups. In a preferred embodiment, R² is $C_{3-7}$ cycloalkyl substituted with one R⁵ group. In a more preferred embodiment, R² is cyclopropyl, cyclobutyl, cyclopentyl or cyclohexyl, each of which is substituted with one R⁵ group. In another more preferred embodiment, R² is $C_{3-7}$ cycloalkyl substituted with one R⁵ group, wherein R⁵ is oxo, or R⁶ wherein R⁶ is selected from OH, or $C_{1-6}$ alkyl. In a most preferred embodiment, R² is cyclopropyl, cyclobutyl, cyclopentyl or cyclohexyl, each of which is substituted with one R⁵ group, wherein R⁵ is oxo, or R⁶ wherein R⁶ is selected from OH, and $C_{1-6}$ alkyl. In a further most preferred embodiment, R² is cyclopropyl, cyclobutyl, cyclopentyl or cyclohexyl, each of which is substituted with one R⁵ group, wherein R⁵ is OH.

In another embodiment, the compound of the invention is according to Formula Va, Vb, VIa, VIb, VIIa, or VIIb, wherein R² is not $C_{3-7}$ cycloalkyl substituted with one to three independently selected R⁵ groups. In a preferred embodiment, R² is not $C_{3-7}$ cycloalkyl substituted with one R⁵ group. In a more preferred embodiment, R² is not cyclopropyl, cyclobutyl, cyclopentyl or cyclohexyl, each of which is substituted with one R⁵ group. In another more preferred embodiment, R² is not $C_{3-7}$ cycloalkyl substituted with one R⁵ group, wherein R⁵ is oxo, or R⁶ wherein R⁶ is selected from OH, and $C_{1-6}$ alkyl. In a most preferred embodiment, R² is not cyclopropyl, cyclobutyl, cyclopentyl or cyclohexyl, each of which is substituted with one R⁵ group, wherein R⁵ is oxo, or R⁶ wherein R⁶ is selected from OH, and $C_{1-6}$ alkyl. In a further most preferred embodiment, R² is not cyclopropyl, cyclobutyl, cyclopentyl or cyclohexyl, each of which is substituted with one R⁵ group, wherein R⁵ is OH.

In one embodiment, the compound of the invention is according to Formula Vc, Vd, VIc, VId, VIIc or VIId, wherein R² is 5-10 membered heteroaryl comprising one to three heteroatoms independently selected from N, S, and O. In a preferred embodiment, R² is furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl.

In one embodiment, the compound of the invention is according to Formula Vc, Vd, VIc, VId, VIIc or VIId, wherein R² is not 5-10 membered heteroaryl comprising one to three heteroatoms independently selected from N, S, and O. In a preferred embodiment, R² is not furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl.

In another embodiment, the compound of the invention is according to Formula Vc, Vd, VIc, VId, VIIc or VIId, wherein R² is 5-10 membered heteroaryl comprising one to three heteroatoms independently selected from N, S, and O, substituted with one to three independently selected R⁶ groups. In a preferred embodiment, R² is 5-10 membered heteroaryl comprising one to three heteroatoms independently selected from N, S, and O, substituted with one or two independently selected R⁶ groups. In a more preferred embodiment, R² is furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl, substituted with one or two independently selected $R^6$ groups. In another more preferred embodiment, $R^2$ is 5-10 membered heteroaryl comprising one to three heteroatoms independently selected from N, S, and O, substituted with one or two independently selected $R^6$ groups, wherein each $R^6$ is independently selected from OH, halo, $C_{1-6}$ alkyl, $C_{1-6}$ alkyl substituted with one or more halo, $C_{1-6}$ alkoxy, —CN, $C_{3-7}$ cycloalkyl, 4-7 membered heterocycloalkyl comprising one to three heteroatoms independently selected from N, O, and S, and phenyl. In a most preferred embodiment, $R^2$ is furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl, each of which is substituted with one or two independently selected $R^6$ groups, wherein each $R^6$ is independently selected from OH, halo, $C_{1-6}$ alkyl, $C_{1-6}$ alkyl substituted with one or more halo, $C_{1-6}$ alkoxy, —CN, $C_{3-7}$ cycloalkyl, 4-7 membered heterocycloalkyl comprising one to three heteroatoms independently selected from N, O, and S, and phenyl. In another most preferred embodiment, $R^2$ is 5-10 membered heteroaryl comprising one to three heteroatoms independently selected from N, S, and O, substituted with one or two independently selected $R^6$ groups, wherein each $R^6$ is independently selected from OH, F, Cl, Me, Et, Pr, i-Pr, t-Bu, —$CF_3$, —OMe, —OEt, Oi-Pr, —CN, cyclopropyl, pyrrolidinyl, morpholinyl, piperidinyl, and phenyl. In a further most preferred embodiment, $R^2$ is furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl, each of which is substituted with one or two independently selected $R^6$ groups, wherein each $R^6$ is independently selected from OH, F, Cl, Me, Et, Pr, i-Pr, t-Bu, —$CF_3$, —OMe, —OEt, —Oi-Pr, —CN, cyclopropyl, pyrrolidinyl, morpholinyl, piperidinyl, and phenyl.

In another embodiment, the compound of the invention is according to Formula Vc, Vd, VIc, VId, VIIc or VIId, wherein $R^2$ is not 5-10 membered heteroaryl comprising one to three heteroatoms independently selected from N, S, and O, substituted with one to three independently selected $R^6$ groups. In a preferred embodiment, $R^2$ is not 5-10 membered heteroaryl comprising one to three heteroatoms independently selected from N, S, and O, substituted with one or two independently selected $R^6$ groups. In a more preferred embodiment, $R^2$ is not furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl, substituted with one or two independently selected $R^6$ groups. In another more preferred embodiment, $R^2$ is not 5-10 membered heteroaryl comprising one to three heteroatoms independently selected from N, S, and O, substituted with one or two independently selected $R^6$ groups, wherein each $R^6$ is independently selected from OH, halo, $C_{1-6}$ alkyl, $C_{1-6}$ alkyl substituted with one or more halo, $C_{1-6}$ alkoxy, —CN, $C_{3-7}$ cycloalkyl, 4-7 membered heterocycloalkyl comprising one to three heteroatoms independently selected from N, O, and S, and phenyl. In a most preferred embodiment, $R^2$ is not furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl, each of which is substituted with one or two independently selected $R^6$ groups, wherein each $R^6$ is independently selected from OH, halo, $C_{1-6}$ alkyl, $C_{1-6}$ alkyl substituted with one or more halo, $C_{1-6}$ alkoxy, —CN, $C_{3-7}$ cycloalkyl, 4-7 membered heterocycloalkyl comprising one to three heteroatoms independently selected from N, O, and S, and phenyl. In another most preferred embodiment, $R^2$ is not 5-10 membered heteroaryl comprising one to three heteroatoms independently selected from N, S, and O, substituted with one or two independently selected $R^6$ groups, wherein each $R^6$ is independently selected from OH, F, Cl, Me, Et, Pr, i-Pr, t-Bu, —$CF_3$, —OMe, —OEt, Oi-Pr, —CN, cyclopropyl, pyrrolidinyl, morpholinyl, piperidinyl, and phenyl. In a further most preferred embodiment, $R^2$ is not furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl, each of which is substituted with one or two independently selected $R^6$ groups, wherein each $R^6$ is independently selected from OH, F, Cl, Me, Et, Pr, i-Pr, t-Bu, —$CF_3$, —OMe, —OEt, —Oi-Pr, —CN, cyclopropyl, pyrrolidinyl, morpholinyl, piperidinyl, and phenyl.

In another embodiment, the compound of the invention is according to Formula Vc, Vd, VIc, VId, VIIc or VIId, wherein $R^2$ is $C_{6-10}$ aryl. In a preferred embodiment, $R^2$ is phenyl.

In another embodiment, the compound of the invention is according to Formula Vc, Vd, VIc or VId, wherein $R^2$ is not $C_{6-10}$ aryl. In a preferred embodiment, $R^2$ is not phenyl.

In another embodiment, the compound of the invention is according to Formula Vc, Vd, VIc, VId, VIIc or VIId, wherein $R^2$ is $C_{6-10}$ aryl substituted with one or more independently selected $R^6$ groups. In a preferred embodiment, $R^2$ is $C_{6-10}$ aryl substituted with one or two independently selected $R^6$ groups. In a more preferred embodiment, $R^2$ is $C_{6-10}$ aryl substituted with one or two independently selected $R^6$ groups, wherein each $R^6$ group is selected from halo, CN, $C_{1-6}$ alkyl, $C_{1-6}$alkoxy, and —NHC(=O)—$C_{1-4}$ alkyl. In another more preferred embodiment, $R^2$ is $C_{6-10}$ aryl substituted with one or two independently selected $R^6$ groups, wherein each $R^6$ group is selected from —C(=O)NR$^9$R$^{10}$, and each $R^9$ and $R^{10}$ is independently selected from H and $C_{1-4}$alkyl. In another more preferred embodiment, $R^2$ is phenyl substituted with one or two independently selected $R^6$ groups. In a most preferred embodiment, $R^2$ is phenyl substituted with one or two independently selected $R^6$ groups, wherein each $R^6$ group is selected from halo, CN, $C_{1-6}$ alkyl, $C_{1-6}$ alkoxy, and —NHC(=O)—$C_{1-4}$ alkyl. In another most preferred embodiment, $R^2$ is phenyl substituted with one or two independently selected $R^6$ groups, wherein each $R^6$ group is selected from —C(=O)NR$^9$R$^{10}$, and each $R^9$ and $R^{10}$ is independently selected from H and $C_{1-4}$ alkyl. In a further most preferred embodiment $R^2$ is phenyl substituted with one or two independently selected $R^6$ groups, wherein each $R^6$ group is selected from F, Cl, CN, Me, —OMe, —OEt, and —NHC(=O)Me. In a further most preferred embodiment $R^2$ is phenyl substituted with one or two independently selected $R^6$ groups, wherein each $R^6$ group is selected from C(=O)NH$_2$, and —C(=O)NHMe.

In another embodiment, the compound of the invention is according to Formula Vc, Vd, VIc, VId, VIIc or VIId, wherein $R^2$ is not $C_{6-10}$ aryl substituted with one or more independently selected $R^6$ groups. In a preferred embodiment, $R^2$ is not $C_{6-10}$ aryl substituted with one or two independently selected $R^6$ groups. In a more preferred embodiment, $R^2$ is not $C_{6-10}$ aryl substituted with one or two independently selected $R^6$ groups, wherein each $R^6$ group is selected from halo, CN, $C_{1-6}$ alkyl, $C_{1-6}$ alkoxy, and —NHC(=O)—$C_{1-4}$ alkyl. In another more preferred embodiment, $R^2$ is not $C_{6-10}$ aryl substituted with one or two independently selected $R^6$ groups, wherein each $R^6$ group is selected from —C(=O)NR$^9$R$^{10}$, and each $R^9$ and $R^{10}$ is independently selected from H and $C_{1-4}$ alkyl. In another more preferred embodiment, $R^2$ is not phenyl substituted with one or two independently selected $R^6$ groups. In a most preferred embodiment, $R^2$ is not phenyl substituted with one or two independently selected $R^6$ groups, wherein each $R^6$ group is selected from halo, CN, $C_{1-6}$ alkyl, $C_{1-6}$ alkoxy, and —NHC(=O)—$C_{1-4}$ alkyl. In another most preferred embodiment, $R^2$ is not phenyl substituted with one or two independently selected $R^6$ groups, wherein each $R^6$ group is selected from —C(=O)N$R^9R^{10}$, and each $R^9$ and $R^{10}$ is independently selected from H and $C_{1-4}$ alkyl. In a further most preferred embodiment $R^2$ is not phenyl substituted with one or two independently selected $R^6$ groups, wherein each $R^6$ group is selected from F, Cl, CN, Me, —OMe, —OEt, and —NHC(=O)Me. In a further most preferred embodiment $R^2$ is not phenyl substituted with one or two independently selected $R^6$ groups, wherein each $R^6$ group is selected from C(=O)NH$_2$, and —C(=O)NHMe.

In one embodiment, the compound of the invention is selected from:

9-Allyloxy-2-([1,4]dioxan-2-ylmethoxy)-6,7-dihydro-pyrimido[6,1-a]isoquinolin-4-one,
2-([1,4]Dioxan-2-ylmethoxy)-9-pyridin-3-yl-6,7-dihydro-pyrimido[6,1-a]isoquinolin-4-one,
2-([1,4]Dioxan-2-ylmethoxy)-9-pyridin-4-yl-6,7-dihydro-pyrimido[6,1-a]isoquinolin-4-one,
2-[2-([1,4]Dioxan-2-ylmethoxy)-4-oxo-6,7-dihydro-4H-pyrimido[6,1-a]isoquinolin-9-yl]-benzonitrile,
3-[2-([1,4]Dioxan-2-ylmethoxy)-4-oxo-6,7-dihydro-4H-pyrimido[6,1-a]isoquinolin-9-yl]-benzonitrile,
4-[2-([1,4]Dioxan-2-ylmethoxy)-4-oxo-6,7-dihydro-4H-pyrimido[6,1-a]isoquinolin-9-yl]-benzonitrile,
[2-([1,4]Dioxan-2-ylmethoxy)-4-oxo-6,7-dihydro-4H-pyrimido[6,1-a]isoquinolin-9-yloxy]-acetonitrile,
2-([1,4]Dioxan-2-ylmethoxy)-9-(oxazol-2-ylmethoxy)-6,7-dihydro-pyrimido[6,1-a]isoquinolin-4-one,
2-([1,4]Dioxan-2-ylmethoxy)-9-(pyridin-2-ylmethoxy)-6,7-dihydro-pyrimido[6,1-a]isoquinolin-4-one,
9-(3,5-Dichloro-phenyl)-2-([1,4]dioxan-2-ylmethoxy)-6,7-dihydro-pyrimido[6,1-a]isoquinolin-4-one,
9-Benzofuran-2-yl-2-([1,4]dioxan-2-ylmethoxy)-6,7-dihydro-pyrimido[6,1-a]isoquinolin-4-one,
2-[2-([1,4]Dioxan-2-ylmethoxy)-4-oxo-6,7-dihydro-4H-pyrimido[6,1-a]isoquinolin-9-yl]-indole-1-carboxylic acid tert-butyl ester,
2-([1,4]Dioxan-2-ylmethoxy)-9-(1H-indol-2-yl)-6,7-dihydro-pyrimido[6,1-a]isoquinolin-4-one,
2-([1,4]Dioxan-2-ylmethoxy)-9-(6-methoxy-pyridin-3-yl)-6,7-dihydro-pyrimido[6,1-a]isoquinolin-4-one,
2-([1,4]Dioxan-2-ylmethoxy)-9-(6-trifluoromethyl-pyridin-3-yl)-6,7-dihydro-pyrimido[6,1-a]isoquinolin-4-one,
2-([1,4]Dioxan-2-ylmethoxy)-9-(3-methyl-3H-imidazol-4-ylethynyl)-6,7-dihydro-pyrimido[6,1-a]isoquinolin-4-one,
9-(5-tert-Butyl-[1,2,4]oxadiazol-3-ylmethoxy)-2-([1,4]dioxan-2-ylmethoxy)-6,7-dihydro-pyrimido[6,1-a]isoquinolin-4-one,
5-[2-([1,4]Dioxan-2-ylmethoxy)-4-oxo-6,7-dihydro-4H-pyrimido[6,1-a]isoquinolin-9-yl]-pyridine-2-carboxylic acid methylamide,
2-([1,4]Dioxan-2-ylmethoxy)-9-pent-1-ynyl-6,7-dihydro-pyrimido[6,1-a]isoquinolin-4-one,
2-([1,4]Dioxan-2-ylmethoxy)-9-(2-pyridin-2-yl-ethyl)-6,7-dihydro-pyrimido[6,1-a]isoquinolin-4-one,
2-([1,4]Dioxan-2-ylmethoxy)-9-(2-pyrazin-2-yl-ethyl)-6,7-dihydro-pyrimido[6,1-a]isoquinolin-4-one,
2-([1,4]Dioxan-2-ylmethoxy)-9-(1H-indol-5-yl)-6,7-dihydro-pyrimido[6,1-a]isoquinolin-4-one,
2-([1,4]Dioxan-2-ylmethoxy)-9-(2-methoxy-phenyl)-6,7-dihydro-pyrimido[6,1-a]isoquinolin-4-one,
2-([1,4]Dioxan-2-ylmethoxy)-9-(5-methoxy-pyridin-3-yl)-6,7-dihydro-pyrimido[6,1-a]isoquinolin-4-one,
2-([1,4]Dioxan-2-ylmethoxy)-9-(1H-indazol-5-yl)-6,7-dihydro-pyrimido[6,1-a]isoquinolin-4-one,
2-([1,4]Dioxan-2-ylmethoxy)-9-(4-methoxy-phenyl)-6,7-dihydro-pyrimido[6,1-a]isoquinolin-4-one,
3-[2-([1,4]Dioxan-2-ylmethoxy)-4-oxo-6,7-dihydro-4H-pyrimido[6,1-a]isoquinolin-9-yl]-benzamide,
5-[2-([1,4]Dioxan-2-ylmethoxy)-4-oxo-6,7-dihydro-4H-pyrimido[6,1-a]isoquinolin-9-yl]-2-fluoro-benzamide,
N-{3-[2-([1,4]Dioxan-2-ylmethoxy)-4-oxo-6,7-dihydro-4H-pyrimido[6,1-a]isoquinolin-9-yl]-phenyl}-acetamide,
9-Cyclopropylethynyl-2-([1,4]dioxan-2-ylmethoxy)-6,7-dihydro-pyrimido[6,1-a]isoquinolin-4-one,
2-([1,4]Dioxan-2-ylmethoxy)-9-(1-hydroxy-cyclopentyl-ethynyl)-6,7-dihydro-pyrimido[6,1-a]isoquinolin-4-one,
2-([1,4]Dioxan-2-ylmethoxy)-9-pyrimidin-5-yl-6,7-dihydro-pyrimido[6,1-a]isoquinolin-4-one,
9-Cyclohex-1-enyl-2-([1,4]dioxan-2-ylmethoxy)-6,7-dihydro-pyrimido[6,1-a]isoquinolin-4-one,
2-([1,4]Dioxan-2-ylmethoxy)-9-(1-methyl-1H-indol-5-yl)-6,7-dihydro-pyrimido[6,1-a]isoquinolin-4-one,
2-([1,4]Dioxan-2-ylmethoxy)-9-(6-methyl-pyridin-3-yl)-6,7-dihydro-pyrimido[6,1-a]isoquinolin-4-one,
2-([1,4]Dioxan-2-ylmethoxy)-9-pyridin-2-ylethynyl-6,7-dihydro-pyrimido[6,1-a]isoquinolin-4-one,
2-([1,4]Dioxan-2-ylmethoxy)-9-(3-methoxy-prop-1-ynyl)-6,7-dihydro-pyrimido[6,1-a]isoquinolin-4-one,
5-[2-([1,4]Dioxan-2-ylmethoxy)-4-oxo-6,7-dihydro-4H-pyrimido[6,1-a]isoquinolin-9-yl]-pent-4-ynenitrile,
2-([1,4]Dioxan-2-ylmethoxy)-9-(3-hydroxy-prop-1-ynyl)-6,7-dihydro-pyrimido[6,1-a]isoquinolin-4-one,
2-([1,4]Dioxan-2-ylmethoxy)-9-(4-methoxy-phenylethynyl)-6,7-dihydro-pyrimido[6,1-a]isoquinolin-4-one,
2-([1,4]Dioxan-2-ylmethoxy)-9-pyridin-3-ylethynyl-6,7-dihydro-pyrimido[6,1-a]isoquinolin-4-one,
4-[2-([1,4]Dioxan-2-ylmethoxy)-4-oxo-6,7-dihydro-4H-pyrimido[6,1-a]isoquinolin-9-yl]-N-methyl-benzamide,
2-([1,4]Dioxan-2-ylmethoxy)-9-(3-methoxy-phenyl)-6,7-dihydro-pyrimido[6,1-a]isoquinolin-4-one,
9-(2-Chloro-phenyl)-2-([1,4]dioxan-2-ylmethoxy)-6,7-dihydro-pyrimido[6,1-a]isoquinolin-4-one,
2-([1,4]Dioxan-2-ylmethoxy)-9-(4-hydroxy-but-1-ynyl)-6,7-dihydro-pyrimido[6,1-a]isoquinolin-4-one,
9-(1,5-Dimethyl-1H-pyrazol-3-ylmethoxy)-2-([1,4]dioxan-2-ylmethoxy)-6,7-dihydro-pyrimido[6,1-a]isoquinolin-4-one,
2-([1,4]Dioxan-2-ylmethoxy)-9-(1-methyl-1H-pyrazol-3-ylmethoxy)-6,7-dihydro-pyrimido[6,1-a]isoquinolin-4-one,
2-([1,4]Dioxan-2-ylmethoxy)-9-(3-methyl-[1,2,4]oxadiazol-5-ylmethoxy)-6,7-dihydro-pyrimido[6,1-a]isoquinolin-4-one,
2-([1,4]Dioxan-2-ylmethoxy)-9-(4-morpholin-4-yl-phenyl)-6,7-dihydro-pyrimido[6,1-a]isoquinolin-4-one,
3-[2-([1,4]Dioxan-2-ylmethoxy)-4-oxo-6,7-dihydro-4H-pyrimido[6,1-a]isoquinolin-9-yl]-4-fluoro-benzamide,
3-[2-([1,4]Dioxan-2-ylmethoxy)-4-oxo-6,7-dihydro-4H-pyrimido[6,1-a]isoquinolin-9-yl]-5-fluoro-benzamide,
9-(3,3-Dimethyl-but-1-ynyl)-2-([1,4]dioxan-2-ylmethoxy)-6,7-dihydro-pyrimido[6,1-a]isoquinolin-4-one,
2-([1,4]Dioxan-2-ylmethoxy)-9-pyridin-4-ylethynyl-6,7-dihydro-pyrimido[6,1-a]isoquinolin-4-one,
2-([1,4]Dioxan-2-ylmethoxy)-9-(3-methyl-isoxazol-5-ylmethoxy)-6,7-dihydro-pyrimido[6,1-a]isoquinolin-4-one,
2-([1,4]Dioxan-2-ylmethoxy)-9-(3-hydroxy-3-methyl-but-1-ynyl)-6,7-dihydro-pyrimido[6,1-a]isoquinolin-4-one,
2-([1,4]Dioxan-2-ylmethoxy)-9-(2-methoxy-pyridin-3-yl)-6,7-dihydro-pyrimido[6,1-a]isoquinolin-4-one, 2-([1,4]Dioxan-2-ylmethoxy)-6,7-dihydro-pyrimido[6,1-a]isoquinolin-4-one,
9-(3,6-Dihydro-2H-pyran-4-yl)-2-([1,4]dioxan-2-ylmethoxy)-6,7-dihydro-pyrimido[6,1-a]isoquinolin-4-one,
5-[2-([1,4]Dioxan-2-ylmethoxy)-4-oxo-6,7-dihydro-4H-pyrimido[6,1-a]isoquinolin-9-yl]-pyridine-2-carbonitrile,
2-([1,4]Dioxan-2-ylmethoxy)-9-(6-isopropoxy-pyridin-3-yl)-6,7-dihydro-pyrimido[6,1-a]isoquinolin-4-one,
2-([1,4]Dioxan-2-ylmethoxy)-9-(6-ethoxy-pyridin-3-yl)-6,7-dihydro-pyrimido[6,1-a]isoquinolin-4-one,
2-([1,4]Dioxan-2-ylmethoxy)-9-(6-morpholin-4-yl-pyridin-3-yl)-6,7-dihydro-pyrimido[6,1-a]isoquinolin-4-one,
9-(2,3-Dimethoxy-phenyl)-2-([1,4]dioxan-2-ylmethoxy)-6,7-dihydro-pyrimido[6,1-a]isoquinolin-4-one,
9-(3-Chloro-2-methoxy-pyridin-4-yl)-2-([1,4]dioxan-2-ylmethoxy)-6,7-dihydro-pyrimido[6,1-a]isoquinolin-4-one,
2-([1,4]Dioxan-2-ylmethoxy)-9-(2-methyl-pyridin-4-yl)-6,7-dihydro-pyrimido[6,1-a]isoquinolin-4-one,
3-[2-([1,4]Dioxan-2-ylmethoxy)-4-oxo-6,7-dihydro-4H-pyrimido[6,1-a]isoquinolin-9-yl]-isonicotinonitrile,
9-(2,5-Dimethoxy-phenyl)-2-([1,4]dioxan-2-ylmethoxy)-6,7-dihydro-pyrimido[6,1-a]isoquinolin-4-one,
2-([1,4]Dioxan-2-ylmethoxy)-9-(3,4,5,6-tetrahydro-2H-[1,2']bipyridinyl-5'-yl)-6,7-dihydro-pyrimido[6,1-a]isoquinolin-4-one,
2-([1,4]Dioxan-2-ylmethoxy)-9-(2-ethoxy-pyridin-3-yl)-6,7-dihydro-pyrimido[6,1-a]isoquinolin-4-one,
9-(2,6-Dimethoxy-pyridin-3-yl)-2-([1,4]dioxan-2-ylmethoxy)-6,7-dihydro-pyrimido[6,1-a]isoquinolin-4-one,
4-[2-([1,4]Dioxan-2-ylmethoxy)-4-oxo-6,7-dihydro-4H-pyrimido[6,1-a]isoquinolin-9-yl]-nicotinonitrile,
9-tert-Butoxymethyl-2-([1,4]dioxan-2-ylmethoxy)-6,7-dihydro-pyrimido[6,1-a]isoquinolin-4-one,
2-([1,4]Dioxan-2-ylmethoxy)-9-(2-pyrrolidin-1-yl-pyridin-3-yl)-6,7-dihydro-pyrimido[6,1-a]isoquinolin-4-one,
2-([1,4]Dioxan-2-ylmethoxy)-9-(6-pyrrolidin-1-yl-pyridin-3-yl)-6,7-dihydro-pyrimido[6,1-a]isoquinolin-4-one,
2-([1,4]Dioxan-2-ylmethoxy)-9-(5-phenyl-oxazol-2-ylmethoxy)-6,7-dihydro-pyrimido[6,1-a]isoquinolin-4-one,
9-(5-tert-Butyl-oxazol-2-ylmethoxy)-2-([1,4]dioxan-2-ylmethoxy)-6,7-dihydro-pyrimido[6,1-a]isoquinolin-4-one,
9-(5-Cyclopropyl-[2,4]oxadiazol-3-ylmethoxy)-2-([1,4]dioxan-2-ylmethoxy)-6,7-dihydro-pyrimido[6,1-a]isoquinolin-4-one,
2-([1,4]Dioxan-2-ylmethoxy)-9-(5-ethyl-[1,2,4]oxadiazol-3-ylmethoxy)-6,7-dihydro-pyrimido[6,1-a]isoquinolin-4-one,
2-([1,4]Dioxan-2-ylmethoxy)-9-(5-methyl-[1,2,4]oxadiazol-3-ylmethoxy)-6,7-dihydro-pyrimido[6,1-a]isoquinolin-4-one,
2-([1,4]Dioxan-2-ylmethoxy)-9-(5-isopropyl-[1,2,4]oxadiazol-3-ylmethoxy)-6,7-dihydro-pyrimido[6,1-a]isoquinolin-4-one,
9-Cyclopentylethynyl-2-([1,4]dioxan-2-ylmethoxy)-6,7-dihydro-pyrimido[6,1-a]isoquinolin-4-one,
9-Cyclohexylethynyl-2-([1,4]dioxan-2-ylmethoxy)-6,7-dihydro-pyrimido[6,1-a]isoquinolin-4-one,
2-([1,4]Dioxan-2-ylmethoxy)-9-(3-methyl-but-1-ynyl)-6,7-dihydro-pyrimido[6,1-a]isoquinolin-4-one,
2-([1,4]Dioxan-2-ylmethoxy)-9-hex-1-ynyl-6,7-dihydro-pyrimido[6,1-a]isoquinolin-4-one,
9-[3-(Benzyl-methyl-amino)-prop-1-ynyl]-2-([1,4]dioxan-2-ylmethoxy)-6,7-dihydro-pyrimido[6,1-a]isoquinolin-4-one,
2-([1,4]Dioxan-2-ylmethoxy)-9-(3-hydroxy-5-methyl-hex-1-ynyl)-6,7-dihydro-pyrimido[6,1-a]isoquinolin-4-one,
2-([1,4]Dioxan-2-ylmethoxy)-9-(3-hydroxy-but-1-ynyl)-6,7-dihydro-pyrimido[6,1-a]isoquinolin-4-one,
9-Cyclopropyl-2-([1,4]dioxan-2-ylmethoxy)-6,7-dihydro-pyrimido[6,1-a]isoquinolin-4-one,
2-([1,4]Dioxan-2-ylmethoxy)-9-(3-hydroxy-pent-1-ynyl)-6,7-dihydro-pyrimido[6,1-a]isoquinolin-4-one,
2-([1,4]Dioxan-2-ylmethoxy)-9-(3-hydroxy-4-methyl-pent-1-ynyl)-6,7-dihydro-pyrimido[6,1-a]isoquinolin-4-one,
2-([1,4]Dioxan-2-ylmethoxy)-9-(3-ethyl-3-hydroxy-pent-1-ynyl)-6,7-dihydro-pyrimido[6,1-a]isoquinolin-4-one,
2-([1,4]Dioxan-2-ylmethoxy)-9-(3-hydroxy-3-phenyl-but-1-ynyl)-6,7-dihydro-pyrimido[6,1-a]isoquinolin-4-one,
9-(3-Benzylamino-prop-1-ynyl)-2-([1,4]dioxan-2-ylmethoxy)-6,7-dihydro-pyrimido[6,1-a]isoquinolin-4-one,
2-([1,4]Dioxan-2-ylmethoxy)-9-[(furan-2-ylmethyl)-amino]-6,7-dihydro-pyrimido[6,1-a]isoquinolin-4-one,
2-([1,4]Dioxan-2-ylmethoxy)-9-(1-ethyl-1H-pyrazol-4-yl)-6,7-dihydro-pyrimido[6,1-a]isoquinolin-4-one,
2-([1,4]Dioxan-2-ylmethoxy)-9-[1-(3-methyl-butyl)-1H-pyrazol-4-yl]-6,7-dihydro-pyrimido[6,1-a]isoquinolin-4-one,
2-([1,4]Dioxan-2-ylmethoxy)-9-(5-methyl-furan-2-yl)-6,7-dihydro-pyrimido[6,1-a]isoquinolin-4-one,
2-([1,4]Dioxan-2-ylmethoxy)-9-(3-hydroxy-hex-1-ynyl)-6,7-dihydro-pyrimido[6,1-a]isoquinolin-4-one,
9-(3,5-Dimethyl-1H-pyrazol-4-yl)-2-([1,4]dioxan-2-ylmethoxy)-6,7-dihydro-pyrimido[6,1-a]isoquinolin-4-one,
2-([1,4]Dioxan-2-ylmethoxy)-9-(1H-pyrazol-4-yl)-6,7-dihydro-pyrimido[6,1-a]isoquinolin-4-one,
2-([1,4]Dioxan-2-ylmethoxy)-9-(1-propyl-1H-pyrazol-4-yl)-6,7-dihydro-pyrimido[6,1-a]isoquinolin-4-one,
2-[2-((R)-1-[1,4]Dioxan-2-ylmethoxy)-4-oxo-6,7-dihydro-4H-pyrimido[6,1-a]isoquinolin-9-yl]-benzonitrile,
2-[2-((S)-1-[1,4]Dioxan-2-ylmethoxy)-4-oxo-6,7-dihydro-4H-pyrimido[6,1-a]isoquinolin-9-yl]-benzonitrile,
9-(5-Cyclopropyl-[1,2,4]oxadiazol-3-ylmethoxy)-2-((R)-1-[1,4]dioxan-2-ylmethoxy)-6,7-dihydro-pyrimido[6,1-a]isoquinolin-4-one,
2-([1,4]Dioxan-2-ylmethoxy)-9-ethynyl-6,7-dihydro-pyrimido[6,1-a]isoquinolin-4-one,
2-([1,4]Dioxan-2-ylmethoxy)-9-pyrimidin-2-ylethynyl-6,7-dihydro-pyrimido[6,1-a]isoquinolin-4-one,
2-([1,4]Dioxan-2-ylmethoxy)-9-(3-phenylamino-prop-1-ynyl)-6,7-dihydro-pyrimido[6,1-a]isoquinolin-4-one,
2-([1,4]Dioxan-2-ylmethoxy)-9-(3-hydroxy-3-pyridin-3-yl-prop-1-ynyl)-6,7-dihydro-pyrimido[6,1-a]isoquinolin-4-one,
9-Cyclopentyloxymethyl-2-([1,4]dioxan-2-ylmethoxy)-6,7-dihydro-pyrimido[6,1-a]isoquinolin-4-one,
2-([1,4]Dioxan-2-ylmethoxy)-9-(3-methoxy-4-methyl-pent-1-ynyl)-6,7-dihydro-pyrimido[6,1-a]isoquinolin-4-one,
9-Cyclopropylethynyl-2-((R)-1-[1,4]dioxan-2-ylmethoxy)-6,7-dihydro-pyrimido[6,1-a]isoquinolin-4-one,
2-((S)-1-[1,4]Dioxan-2-ylmethoxy)-9-(3-methyl-but-1-ynyl)-6,7-dihydro-pyrimido[6,1-a]isoquinolin-4-one,
2-([1,4]Dioxan-2-ylmethoxy)-9-(3-imidazol-1-yl-prop-1-ynyl)-6,7-dihydro-pyrimido[6,1-a]isoquinolin-4-one,
9-(2-Cyclopropyl-ethyl)-2-((R)-1-[1,4]dioxan-2-ylmethoxy)-6,7-dihydro-pyrimido[6,1-a]isoquinolin-4-one,
9-Cyclopentyloxymethyl-2-((R)-1-[1,4]dioxan-2-ylmethoxy)-6,7-dihydro-pyrimido[6,1-a]isoquinolin-4-one,
2-([1,4]Dioxan-2-ylmethoxy)-9-(3-hydroxy-3-pyridin-3-yl-propyl)-6,7-dihydro-pyrimido[6,1-a]isoquinolin-4-one,
9-Allyloxy-2-((R)-1-[1,4]dioxan-2-ylmethoxy)-6,7-dihydro-pyrimido[6,1-a]isoquinolin-4-one,
9-Allyloxy-2-((S)-1-[1,4]dioxan-2-ylmethoxy)-6,7-dihydro-pyrimido[6,1-a]isoquinolin-4-one, 2-((R)-1-[1,4]Dioxan-2-ylmethoxy)-9-(tetrahydro-pyran-4-yloxymethyl)-6,7-dihydro-pyrimido[6,1-a]isoquinolin-4-one, 2-([1,4]Dioxan-2-ylmethoxy)-9-{3-[(pyridin-3-ylmethyl)-amino]-prop-1-ynyl}-6,7-dihydro-pyrimido[6,1-a]isoquinolin-4-one, 2-((R)-1-[1,4]Dioxan-2-ylmethoxy)-9-pentyl-6,7-dihydro-pyrimido[6,1-a]isoquinolin-4-one, 9-Cyclopropylethynyl-2-((S)-1-[1,4]dioxan-2-ylmethoxy)-6,7-dihydro-pyrimido[6,1-a]isoquinolin-4-one, 9-(2-Cyclopropyl-ethyl)-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(oxetan-3-yloxymethyl)-6,7-dihydro-pyrimido[6,1-a]isoquinolin-4-one, 2-((S)-1-[1,4]Dioxan-2-ylmethoxy)-9-(3-methyl-oxetan-3-ylmethoxymethyl)-6,7-dihydro-pyrimido[6,1-a]isoquinolin-4-one, 9-(2,2-Dimethyl-butylamino)-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(3-hydroxy-4-methyl-pentyl)-6,7-dihydro-pyrimido[6,1-a]isoquinolin-4-one, 2-((S)-1-[1,4]Dioxan-2-ylmethoxy)-9-(2-ethyl-hexylamino)-6,7-dihydro-pyrimido[6,1-a]isoquinolin-4-one, 2-((S)-1-[1,4]Dioxan-2-ylmethoxy)-9-(2-methoxy-ethoxy)-6,7-dihydro-pyrimido[6,1-a]isoquinolin-4-one, 2-((S)-1-[1,4]Dioxan-2-ylmethoxy)-9-(2-ethoxy-ethoxy)-6,7-dihydro-pyrimido[6,1-a]isoquinolin-4-one, 9-Cyclopropylmethoxy-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(2-fluoro-ethoxy)-6,7-dihydro-pyrimido[6,1-a]isoquinolin-4-one, 2-((S)-1-[1,4]Dioxan-2-ylmethoxy)-9-[3-(2-methoxy-ethoxy)-prop-1-ynyl]-6,7-dihydro-pyrimido[6,1-a]isoquinolin-4-one, 2-((S)-1-[1,4]Dioxan-2-ylmethoxy)-9-[3-(2-ethoxy-ethoxy)-prop-1-ynyl]-6,7-dihydro-pyrimido[6,1-a]isoquinolin-4-one, 2-((S)-1-[1,4]Dioxan-2-ylmethoxy)-9-[3-(2-fluoro-ethoxy)-prop-1-ynyl]-6,7-dihydro-pyrimido[6,1-a]isoquinolin-4-one, 9-(2,2-Dimethyl-propoxymethyl)-2-((S)-1-[1,4]dioxan-2-ylmethoxy)-6,7-dihydro-pyrimido[6,1-a]isoquinolin-4-one, 9-Cyclohexyloxymethyl-2-((S)-1-[1,4]dioxan-2-ylmethoxy)-6,7-dihydro-pyrimido[6,1-a]isoquinolin-4-one, 9-Cyclopropylmethoxymethyl-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(tetrahydro-pyran-2-ylmethoxy)-6,7-dihydro-pyrimido[6,1-a]isoquinolin-4-one, 2-((S)-1-[1,4]Dioxan-2-ylmethoxy)-9-(3-hydroxy-butyl)-6,7-dihydro-pyrimido[6,1-a]isoquinolin-4-one, 9-(4,4-Dimethyl-pentyloxy)-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(3-methoxy-4-methyl-pentyl)-6,7-dihydro-pyrimido[6,1-a]isoquinolin-4-one, 9-(3-Cyclopropyl-propoxy)-2-((S)-1-[1,4]dioxan-2-ylmethoxy)-6,7-dihydro-pyrimido[6,1-a]isoquinolin-4-one, 9-Cyclohexylamino-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(3-hydroxy-4,4-dimethyl-pentyl)-6,7-dihydro-pyrimido[6,1-a]isoquinolin-4-one, 9-Cyclopentylmethoxymethyl-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(3-methoxy-butyl)-6,7-dihydro-pyrimido[6,1-a]isoquinolin-4-one, 2-((S)-1-[1,4]Dioxan-2-ylmethoxy)-9-(3-phenylamino-propyl)-6,7-dihydro-pyrimido[6,1-a]isoquinolin-4-one, 2-((S)-1-[1,4]Dioxan-2-ylmethoxy)-9-(4-hydroxy-pentyl)-6,7-dihydro-pyrimido[6,1-a]isoquinolin-4-one, 2-((S)-1-[1,4]Dioxan-2-ylmethoxy)-9-(4-hydroxy-butyl)-6,7-dihydro-pyrimido[6,1-a]isoquinolin-4-one, 9-(Cyclohexyl-methyl-amino)-2-((S)-1-[1,4]dioxan-2-ylmethoxy)-6,7-dihydro-pyrimido[6,1-a]isoquinolin-4-one, 9-(Cyclohexylmethyl-amino)-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-[(tetrahydro-pyran-4-ylmethyl)-amino]-6,7-dihydro-pyrimido[6,1-a]isoquinolin-4-one, 2-((S)-1-[1,4]Dioxan-2-ylmethoxy)-9-(3-ethyl-3-hydroxy-pentyl)-6,7-dihydro-pyrimido[6,1-a]isoquinolin-4-one, 2-((S)-1-[1,4]Dioxan-2-ylmethoxy)-9-(3-hydroxy-3-methyl-butyl)-6,7-dihydro-pyrimido[6,1-a]isoquinolin-4-one, 2-((S)-1-[1,4]Dioxan-2-ylmethoxy)-9-(3-hydroxy-pentyl)-6,7-dihydro-pyrimido[6,1-a]isoquinolin-4-one, 9-(2,2-Dimethyl-propoxy)-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(tetrahydro-pyran-4-ylmethoxy)-6,7-dihydro-pyrimido[6,1-a]isoquinolin-4-one, 2-((S)-1-[1,4]Dioxan-2-ylmethoxy)-9-(4-hydroxy-4-methyl-pentyl)-6,7-dihydro-pyrimido[6,1-a]isoquinolin-4-one, 2-((S)-1-[1,4]Dioxan-2-ylmethoxy)-9-(tetrahydro-pyran-4-ylmethoxymethyl)-6,7-dihydro-pyrimido[6,1-a]isoquinolin-4-one, 2-([1,4]Dioxan-2-ylmethoxy)-9-methoxy-6,7-dihydro-pyrimido[6,1-a]isoquinolin-4-one, 2-((S)-1-[1,4]Dioxan-2-ylmethoxy)-9-(oxetan-3-ylmethoxy)-6,7-dihydro-pyrimido[6,1-a]isoquinolin-4-one, 9-(3-Cyclopropyl-propoxy)-2-((R)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(3-methoxy-propyl)-6,7-dihydro-pyrimido[6,1-a]isoquinolin-4-one, 2-((S)-1-[1,4]Dioxan-2-ylmethoxy)-9-[2-(1-hydroxy-cyclopentyl)-ethyl]-6,7-dihydro-pyrimido[6,1-a]isoquinolin-4-one, 2-((R)-1-[1,4]Dioxan-2-ylmethoxy)-9-(4-hydroxy-tetrahydro-pyran-4-ylethynyl)-6,7-dihydro-pyrimido[6,1-a]isoquinolin-4-one, In one embodiment, the compound of the invention is selected from:

2-((R)-1-[1,4]Dioxan-2-ylmethoxy)-9-(3-methoxy-propyl)-6,7-dihydro-pyrimido[6,1-a]isoquinolin-4-one, 2-((R)-1-[1,4]Dioxan-2-ylmethoxy)-9-[2-(1-hydroxy-cyclopentyl)-ethyl]-6,7-dihydro-pyrimido[6,1-a]isoquinolin-4-one, 2-((S)-1-[1,4]Dioxan-2-ylmethoxy)-9-(2-propoxy-ethoxy)-6,7-dihydro-pyrimido[6,1-a]isoquinolin-4-one, 2-((S)-1-[1,4]Dioxan-2-ylmethoxy)-9-(2-isopropoxy-ethoxy)-6,7-dihydro-pyrimido[6,1-a]isoquinolin-4-one, 2-((R)-1-[1,4]Dioxan-2-ylmethoxy)-9-(2-propoxy-ethoxy)-6,7-dihydro-pyrimido[6,1-a]isoquinolin-4-one, 2-((R)-1-[1,4]Dioxan-2-ylmethoxy)-9-(2-isopropoxy-ethoxy)-6,7-dihydro-pyrimido[6,1-a]isoquinolin-4-one, and 2-((S)-1-[1,4]Dioxan-2-ylmethoxy)-9-(4-methoxy-butyl)-6,7-dihydro-pyrimido[6,1-a]isoquinolin-4-one.

In one embodiment, the compound of the invention is 9-cyclopropylethynyl-2-((S)-1-[1,4]dioxan-2-ylmethoxy)-6,7-dihydro-pyrimido[6,1-a]isoquinolin-4-one.

In another embodiment, the compound of the invention is not 9-cyclopropylethynyl-2-((S)-1-[1,4]dioxan-2-yl-methoxy)-6,7-dihydro-pyrimido[6,1-a]isoquinolin-4-one.

In one embodiment a compound of the invention is not an isotopic variant.

In one aspect a compound of the invention is present as the free base.

In one aspect a compound of the invention is a pharmaceutically acceptable salt.

In one aspect a compound of the invention is present as the free base or a pharmaceutically acceptable salt.

In one aspect a compound of the invention is a solvate.

In one aspect a compound of the invention is a solvate of a pharmaceutically acceptable salt of the compound.

In certain aspects, the present invention provides prodrugs and derivatives of a compound of the invention according to the formula above. Prodrugs are derivatives of a compound of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H. Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

Clauses

1. A compound according to Formula Ia:

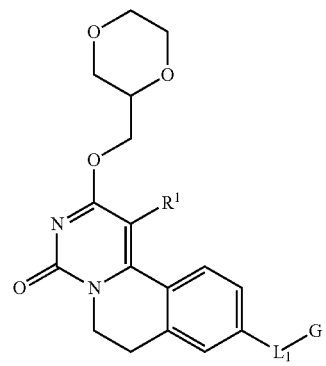

Ia wherein
$R^1$ is H, Me, or halo;
$L_1$ is absent or is —O—, —S—, or —NR$^{4a}$—;
G is
  $R^2$
  —W-L$_2$-R$^2$, or
  —W-L$_3$-R$^3$;
W is $C_{1-4}$ alkylene, $C_{2-4}$ alkenylene having one double bond, or $C_{2-4}$ alkynylene having one triple bond;
$L_2$ is absent or is —O—;
$R^2$ is
  H,
  $C_{1-8}$ alkyl, optionally substituted with one to three groups independently selected from
    OH,
    halo,
    CN,
    a $C_{1-6}$ alkoxy,
    $C_{3-7}$ cycloalkyl,
    4-6 membered heterocycloalkyl comprising one to three heteroatoms independently selected from S, and O,
    5-6 membered heteroaryl comprising one to three heteroatoms independently selected from N, S, and O, and
    phenyl,
  $C_{4-7}$ cycloalkenyl comprising one double bond,
  5-7 membered heterocycloalkenyl comprising one double bond, and one to three heteroatoms independently selected from N, O, and S,
  $C_{3-7}$ cycloalkyl optionally substituted with one or more independently selected $R^5$ groups,
  4-10 membered heterocycloalkyl comprising one to two heteroatoms independently selected from S, and O, optionally substituted with one to three independently selected $R^5$ groups,
  5-10 membered heteroaryl comprising one to three heteroatoms independently selected from N, S, and O optionally substituted with one to three independently selected $R^6$ groups, or
  $C_{6-10}$ aryl optionally substituted with one or more independently selected $R^6$ groups;
$L_3$ is —NR$^{4b}$—;
$R^3$ is
  $C_{1-4}$alkyl substituted with
    $C_{6-10}$ aryl optionally substituted with one or more independently selected $R^7$ groups, or 5-10 membered heteroaryl comprising one to three heteroatoms independently selected from N, S, and O, optionally substituted with one or more R independently selected $R^7$ groups, 5-10 membered heteroaryl comprising one to three heteroatoms independently selected from N, S, and O, optionally substituted with one or more independently selected $R^7$ group, or $C_{6-10}$ aryl optionally substituted with one or more independently selected $R^7$ groups;

Each $R^{4a}$ and $R^{4b}$ is independently selected from H, $C_{1-4}$ alkyl, and $C_{3-7}$ cycloalkyl;

$R^5$ is oxo or $R^6$;

$R^6$ is
  OH,
  halo,
  —$NO_2$,
  $C_{1-6}$ alkyl optionally substituted with one to three groups independently selected from halo, and OH,
  $C_{1-6}$alkoxy optionally substituted with one to three groups independently selected from halo, and OH,
  $C_{3-7}$ cycloalkyl,
  —C(=O)$OR^8$,
  —C(=O)$NR^9R^{10}$,
  —NHC(=O)—$C_{1-4}$ alkyl,
  —CN,
  phenyl,
  —O-phenyl,
  4-7 membered heterocycloalkyl comprising one to three heteroatoms independently selected from N, O, and S, or
  5-6 membered heteroaryl comprising one to three heteroatoms independently selected from N, O, and S, optionally substituted with one or more independently selected $C_{1-4}$alkyl, $C_{1-4}$ alkoxy, CN, halo), and —C(=O)$OR^{11}$;

$R^7$ is $C_{1-4}$ alkyl, or halo; and each of $R^8$, $R^9$, $R^{10}$ and $R^{11}$ is independently selected from H and $C_{1-4}$ alkyl, or a pharmaceutically acceptable salt, or a solvate, or a solvate of the pharmaceutically acceptable salt.

2. A compound or pharmaceutically acceptable salt thereof, according to clause 1, wherein the compound is according to Formula Ib:

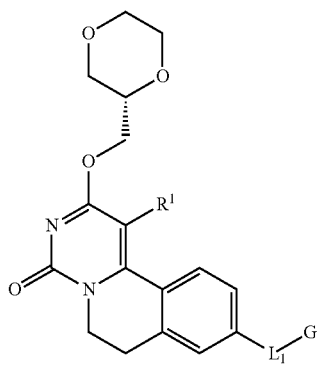

wherein $R^1$, $L_1$ and G are as previously described.

3. A compound or pharmaceutically acceptable salt thereof, according to clause 1, wherein the compound is according to Formula Ic:

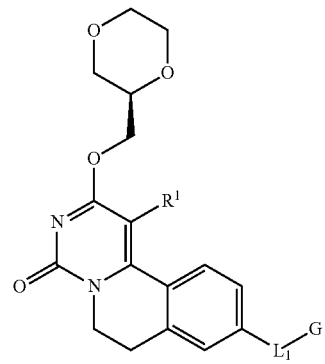

wherein $R^1$, $L_1$ and G are as previously described.

4. A compound or pharmaceutically acceptable salt thereof, according to any one of clauses 1-3, wherein $R^1$ is Me, F, or Cl.

5. A compound or pharmaceutically acceptable salt thereof, according to any one of clauses 1-3, wherein $R^1$ is H.

6. A compound or pharmaceutically acceptable salt thereof, according to clause 1 or 2, wherein the compound is according to Formula IIa, IIb or IIc:

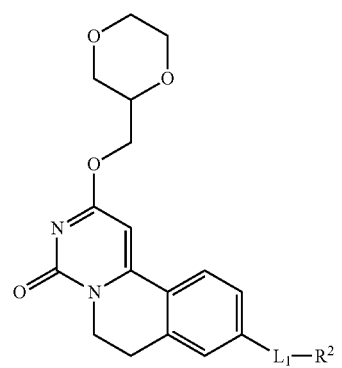

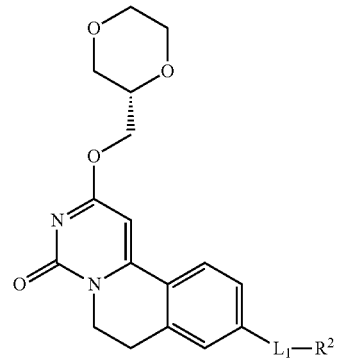

IIc

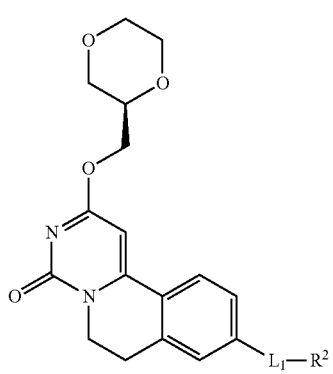

wherein $L_1$, and $R^2$ are as described in claim 1.

7. A compound or pharmaceutically acceptable salt thereof, according to clause 1 or 2, wherein the compound is according to Formula IIIa, IIIb, or IIIc:

IIIa

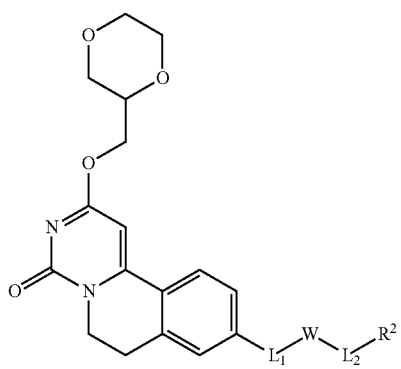

IIIb

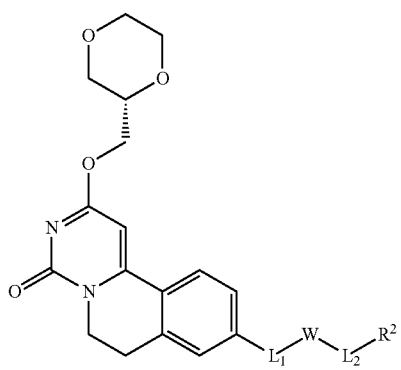

IIIc

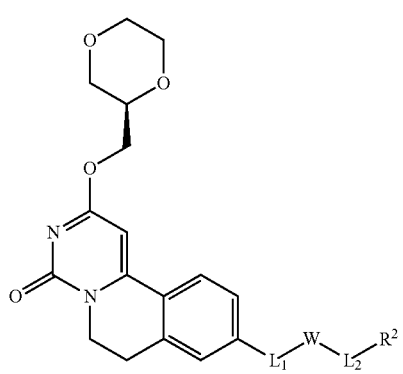

wherein $L_1$, W, $L_2$, and $R^2$ are as described previously.

8. A compound or pharmaceutically acceptable salt thereof, according to clause 1 or 2, wherein the compound is according to Formula IVa, IVb, or Vc:

IVa

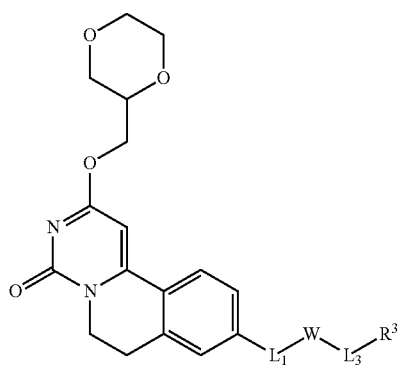

IVb

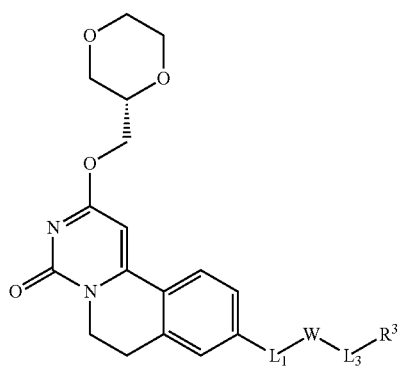

-continued

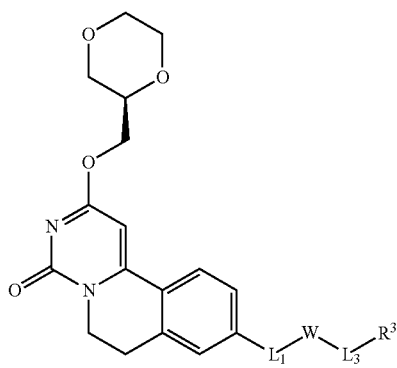

IVc wherein $L_1$, W, $L_3$, and $R^3$ are as described in claim 1.

9. A compound or pharmaceutically acceptable salt thereof, according to any one of clauses 1-8, wherein $L_1$ is absent.
10. A compound or pharmaceutically acceptable salt thereof, according to any one of clauses 1-8, wherein $L_1$ is —O—.
11. A compound or pharmaceutically acceptable salt thereof, according to any one of clauses 1-8, wherein $L_1$ is —$NR^{4a}$—, and $R^{4a}$ is H, Me, Et, or cyclopropyl.
12. A compound or pharmaceutically acceptable salt thereof, according to any one of clauses 1-8, wherein $L_1$ is —$NR^{4a}$—, and $R^{4a}$ is H.
13. A compound or pharmaceutically acceptable salt thereof, according to any one of clauses 1-5, or 7-11, wherein W is $C_{1-4}$ alkylene.
14. A compound or pharmaceutically acceptable salt thereof, according to clause 13, wherein W is —$CH_2$—, —$CH_2$—$CH_2$—, —$CH_2$—$CH_2$—$CH(CH_3)$—, —$CH_2$—$CH(CH_2$—$CH_3)$—, —$CH_2$—$C(CH_3)_2$—, or —$CH_2$—$CH_2$—$CH_2$—.
15. A compound or pharmaceutically acceptable salt thereof, according to clause 14, wherein W is —$CH_2$—$CH_2$—.
16. A compound or pharmaceutically acceptable salt thereof, according to any one of clauses 1-5, or 7-11, wherein W is $C_{2-4}$ alkenylene having one double bond.
17. A compound or pharmaceutically acceptable salt thereof, according to clause 16, wherein W is —CH═CH—, —$CH_2$—CH═CH—, or —CH═CH—$CH_2$.
18. A compound or pharmaceutically acceptable salt thereof, according to clause 17, wherein W is —CH═CH—.
19. A compound or pharmaceutically acceptable salt thereof, according to any one of clauses 1-5, or 7-11, wherein W is $C_{2-4}$ alkynylene having one triple bond.
20. A compound or pharmaceutically acceptable salt thereof, according to clause 19, wherein W is —C≡C—, —$CH_2$—C≡C—, or —C≡C—$CH_2$—.
21. A compound or pharmaceutically acceptable salt thereof, according to clause 20, wherein W is —C≡C—.
22. A compound or pharmaceutically acceptable salt thereof, according to any one of clauses 1-5, 7, or 9-21, wherein $L_2$ is —O—.
23. A compound or pharmaceutically acceptable salt thereof, according to any one of clauses 1-5, 7, or 9-21, wherein $L_2$ is absent.
24. A compound or pharmaceutically acceptable salt thereof, according to any one of clauses 1-5, 7, or 9-21, wherein $L_1$ and $L_2$ are absent, and W is —$CH_2$—, —$CH_2$—$CH_2$—, or —$CH_2$—$CH_2$—$CH_2$—.
25. A compound or pharmaceutically acceptable salt thereof, according to clause 1-5, 7, or 9-21, wherein $L_1$ and $L_2$ are absent, and W is —CH═CH—, —$CH_2$—CH═CH—, or —CH═CH—$CH_2$—.
26. A compound or pharmaceutically acceptable salt thereof, according to clause 1-5, 7, or 9-21, wherein $L_1$ and $L_2$ are absent, and W is —C≡C—, —$CH_2$—C≡C—, or —C≡C—$CH_2$—.
27. A compound or pharmaceutically acceptable salt thereof, according to any one of clauses 1-7, or 9-25, wherein $R^2$ is H.
28. A compound or pharmaceutically acceptable salt thereof, according to any one of clauses 1-7, or 9-25, wherein $R^2$ is $C_{1-8}$ alkyl.
29. A compound or pharmaceutically acceptable salt thereof, according to clause 28, wherein $R^2$ is Me, Et, n-Pr, i-Pr, i-Bu, or t-Bu.
30. A compound or pharmaceutically acceptable salt thereof, according to any one of clauses 1-7, or 9-25, wherein $R^2$ is $C_{1-8}$ alkyl substituted with one group selected from OH, halo, CN, $C_{1-6}$alkoxy, $C_{3-7}$ cycloalkyl, 4-6 membered heterocycloalkyl (comprising one to three heteroatoms independently selected from S, and O), 5-6 membered heteroaryl (comprising one to three heteroatoms independently selected from N, S, and O), and phenyl.
31. A compound or pharmaceutically acceptable salt thereof, according to any one of clauses 1-7, or 9-25, wherein $R^2$ is Me, Et, n-Pr, i-Pr, i-Bu, or t-Bu, each of which is substituted with one group selected from OH, halo, CN, $C_{1-6}$ alkoxy, $C_{3-7}$ cycloalkyl, 4-6 membered heterocycloalkyl (comprising one to three heteroatoms independently selected from S, and O), 5-6 membered heteroaryl (comprising one to three heteroatoms independently selected from N, S, and O), and phenyl.
32. A compound or pharmaceutically acceptable salt thereof, according to any one of clause 30, wherein $R^2$ is $C_{1-8}$ alkyl substituted with one group selected from OH, F, Cl, CN, —OMe, —OEt, —Oi-Pr, cyclopropyl, cyclobutyl, oxetanyl, tetrahydrofuranyl, tetrahydropyranyl, pyrralolyl, imidazolyl, triazolyl, oxazolyl, thiazolyl, pyridinyl, pyrimidinyl, pyrazinyl, and phenyl.
33. A compound or pharmaceutically acceptable salt thereof, according to any one of clauses 1-7, or 9-25, wherein $R^2$ is $C_{4-7}$ cycloalkenyl comprising one double bond.
34. A compound or pharmaceutically acceptable salt thereof, according to clause 33, wherein $R^2$ is cyclohexenyl.
35. A compound or pharmaceutically acceptable salt thereof, according to any one of clauses 1-7, or 9-25, wherein $R^2$ is 5-7 membered heterocycloalkenyl comprising one double bond, and one to three heteroatoms independently selected from N, O, and S.
36. A compound or pharmaceutically acceptable salt thereof, according to clause 35, wherein $R^2$ is dihydropyranyl.
37. A compound or pharmaceutically acceptable salt thereof, according to any one of clauses 1-7, or 9-25, wherein $R^2$ is $C_{3-7}$ cycloalkyl.
38. A compound or pharmaceutically acceptable salt thereof, according to any one of clauses 1-7, or 9-25, wherein $R^2$ is $C_{3-7}$ cycloalkyl substituted with one $R^5$ group.
39. A compound or pharmaceutically acceptable salt thereof, according to clause 38, wherein $R^5$ is oxo, or $R^6$ wherein $R^6$ is selected from OH, and $C_{1-6}$ alkyl.
40. A compound or pharmaceutically acceptable salt thereof, according to clauses 37, 38 or 39, wherein $R^2$ is cyclopropyl, cyclobutyl, cyclopentyl or cyclohexyl.
41. A compound or pharmaceutically acceptable salt thereof, according to any one of clauses 1-7, or 9-25, wherein $R^2$ is 4-10 membered heterocycloalkyl comprising one to two heteroatoms independently selected from S, and O.
42. A compound or pharmaceutically acceptable salt thereof, according to any one of clauses 1-7, or 9-25, wherein $R^2$ is 4-10 membered heterocycloalkyl comprising one to two heteroatoms independently selected from S, and O, substituted with one $R^5$ group.

43. A compound or pharmaceutically acceptable salt thereof, according to clause 42, wherein $R^5$ is selected from oxo, or $R^6$ wherein $R^6$ is selected from OH, and $C_{1-6}$ alkyl.

44. A compound or pharmaceutically acceptable salt thereof, according to clause 41, 42 or 43, wherein $R^2$ is oxetanyl, tetrahydrofuranyl, tetrahydropyranyl, or dioxanyl.

45. A compound or pharmaceutically acceptable salt thereof, according to any one of clauses 1-7, or 9-25, wherein $R^2$ is 5-10 membered heteroaryl comprising one to three heteroatoms independently selected from N, S, and O.

46. A compound or pharmaceutically acceptable salt thereof, according to any one of clauses 1-7, or 9-25, wherein $R^2$ is 5-10 membered heteroaryl comprising one to three heteroatoms independently selected from N, S, and O, substituted with one or two independently selected $R^6$ groups.

47. A compound or pharmaceutically acceptable salt thereof, according to clause 46, wherein each $R^6$ is independently selected from OH, halo, $C_{1-6}$ alkyl, $C_{1-6}$ alkyl substituted with one or more halo, $C_{1-6}$ alkoxy, —CN, $C_{3-7}$ cycloalkyl, 4-7 membered heterocycloalkyl comprising one to three heteroatoms independently selected from N, O, and S, and phenyl.

48. A compound or pharmaceutically acceptable salt thereof, according to clause 45, 46 or 47, wherein $R^2$ is furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl.

49. A compound or pharmaceutically acceptable salt thereof, according to any one of clauses 1-7, or 9-25, wherein $R^2$ is $C_{6-10}$ aryl.

50. A compound or pharmaceutically acceptable salt thereof, according to any one of clauses 1-7, or 9-25, wherein $R^2$ is $C_{6-10}$ aryl, substituted with one or two independently selected $R^6$ groups.

51. A compound or pharmaceutically acceptable salt thereof, according to clause 50, wherein $R^6$ is selected from halo, CN, $C_{1-6}$ alkyl, $C_{1-6}$ alkoxy, —NHC(=O)—$C_{1-4}$alkyl, and —C(=O)NR$^9$R$^{10}$, wherein each $R^9$ and $R_{10}$ is independently selected from H and $C_{1-4}$alkyl.

52. A compound or pharmaceutically acceptable salt thereof, according to clause 49, 50 or 51, wherein $R^2$ is phenyl.

53. A compound or pharmaceutically acceptable salt thereof, according to any one of clauses 1-5, or 8-21, wherein $L_3$ is —NR$^{4b}$—, and R$^{4b}$ is H, Me, Et, or cyclopropyl.

54. A compound or pharmaceutically acceptable salt thereof, according to any one of clauses 1-5, or 8-21, wherein $R^3$ is $C_{1-4}$ alkyl substituted with phenyl, or pyridyl.

55. A compound or pharmaceutically acceptable salt thereof, according to any one of clauses 1-5, or 8-21, wherein $R^3$ is $C_{1-4}$ alkyl substituted with phenyl, or pyridyl, each of which is substituted with Me, Et, F, or Cl 56. A compound or pharmaceutically acceptable salt thereof, according to any one of clauses 1-5, or 8-21, wherein $R^3$ is 5-10 membered heteroaryl comprising one to three heteroatoms independently selected from N, S, and O.

57. A compound or pharmaceutically acceptable salt thereof, according to any one of clauses 1-5, or 8-21, wherein $R^3$ is 5-10 membered heteroaryl comprising one to three heteroatoms independently selected from N, S, and O, substituted with one or more independently selected $R^7$ groups.

58. A compound or pharmaceutically acceptable salt thereof, according to clause 57 wherein $R^7$ is selected from Me, Et, F, and Cl.

59. A compound or pharmaceutically acceptable salt thereof, according to clause 56, 57, or 58 wherein $R^3$ is pyridyl.

60. A compound or pharmaceutically acceptable salt thereof, according to any one of clauses 1-5, or 8-21, wherein $R^3$ is $C_{6-10}$ aryl.

61. A compound or pharmaceutically acceptable salt thereof, according to any one of clauses 1-5, or 8-21, wherein $R^3$ is $C_{6-10}$ aryl, substituted with one or more independently selected $R^7$ groups.

62. A compound or pharmaceutically acceptable salt thereof, according to clause 61, wherein $R^7$ is selected from Me, Et, F, and Cl.

63. A compound or pharmaceutically acceptable salt thereof, according to clause 60, 61, or 62, wherein $R^3$ is phenyl.

64. A compound or pharmaceutically acceptable salt thereof, according to clause 1, wherein the compound is according to Formula Va:

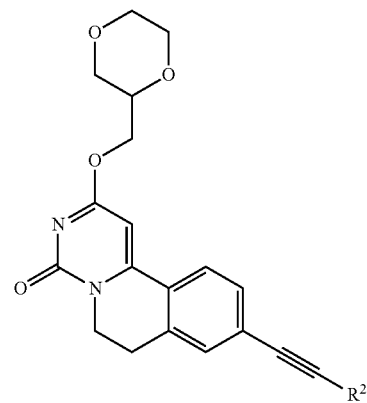

wherein $R^2$ is as described previously.

65. A compound or pharmaceutically acceptable salt thereof, according to clause 1, wherein the compound is according to Formula Vb:

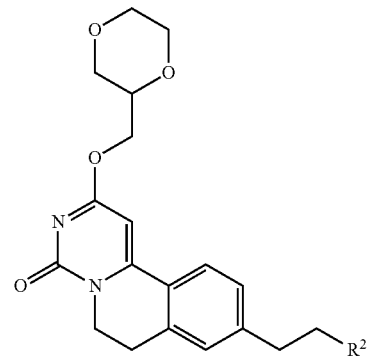

wherein $R^2$ is as described previously.

66. A compound or pharmaceutically acceptable salt thereof, according to clause 1, wherein the compound is according to Formula Vc:

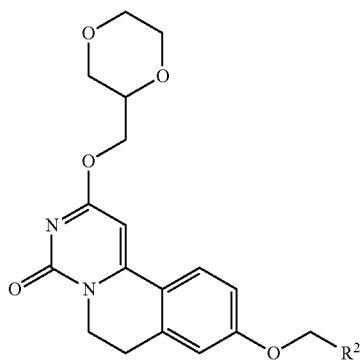

Vc wherein R² is as described previously.

67. A compound or pharmaceutically acceptable salt thereof, according to clause 1, wherein the compound is according to Formula Vd:

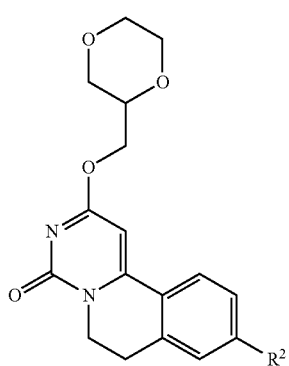

Vd wherein R² is as described previously.

68. A compound or pharmaceutically acceptable salt thereof, according to clause 1, wherein the compound is according to Formula VIa:

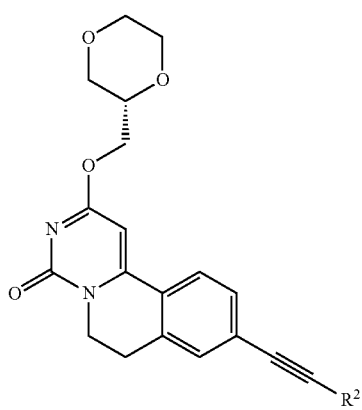

VIa wherein R² is as described previously.

69. A compound or pharmaceutically acceptable salt thereof, according to clause 1, wherein the compound is according to Formula VIb:

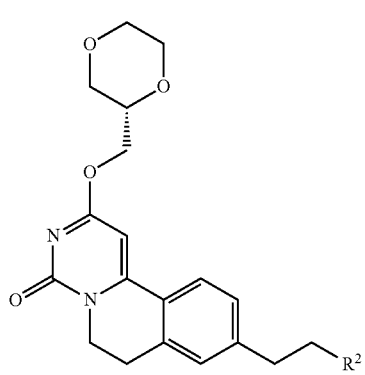

VIb wherein R² is as described previously.

70. A compound or pharmaceutically acceptable salt thereof, according to clause 1, wherein the compound is according to Formula VIc:

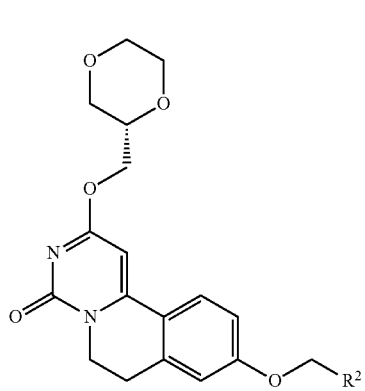

VIc wherein R² is as described previously.

71. A compound or pharmaceutically acceptable salt thereof, according to clause 1, wherein the compound is according to Formula VId:

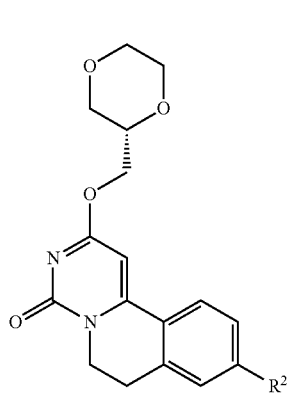

VId wherein R² is as described previously.

72. A compound or pharmaceutically acceptable salt thereof, according to clause 1, wherein the compound is according to Formula VIIa:

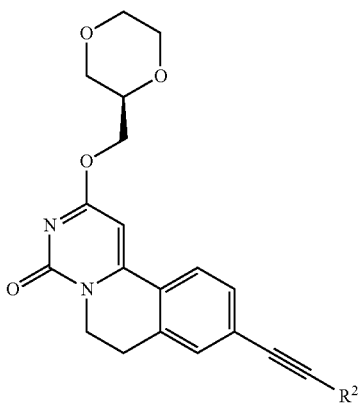

VIIa wherein R² is as described previously.

73. A compound or pharmaceutically acceptable salt thereof, according to clause 1, wherein the compound is according to Formula VIIb:

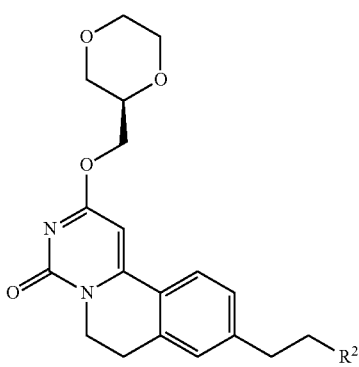

VIIb wherein R² is as described previously.

74. A compound or pharmaceutically acceptable salt thereof, according to clause 1, wherein the compound is according to Formula VIIc:

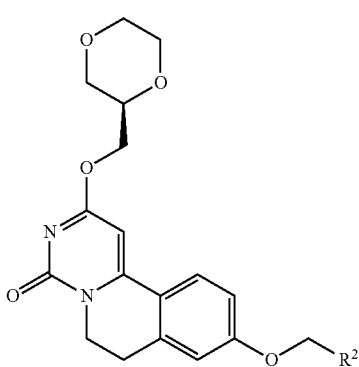

VIIc wherein R² is as described previously.

75. A compound or pharmaceutically acceptable salt thereof, according to clause 1, wherein the compound is according to Formula VIId:

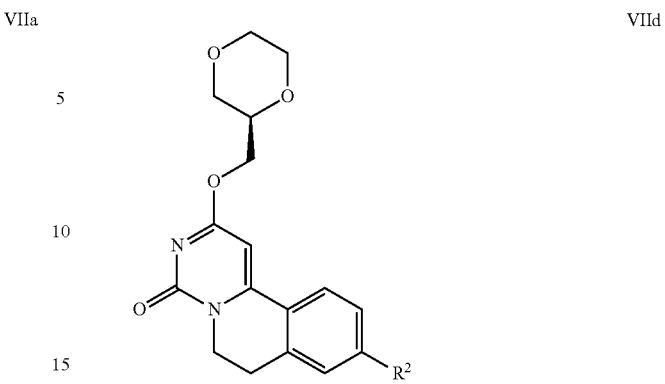

VIId wherein R² is as described previously.

76. A compound or pharmaceutically acceptable salt thereof, according to clause 64, 65, 68, 69, 72, or 73, wherein R² is $C_{3-7}$ cycloalkyl.
77. A compound or pharmaceutically acceptable salt thereof, according to clause 64, 65, 68, 69, 72, or 73, wherein R² is $C_{3-7}$ cycloalkyl substituted with one R⁵ group.
78. A compound or pharmaceutically acceptable salt thereof, according to clause 77, wherein R⁵ is oxo, or R⁶ wherein R⁶ is OH, or $C_{1-6}$ alkyl.
79. A compound or pharmaceutically acceptable salt thereof, according to clause 76, 77 or 78, wherein R² is cyclopropyl, cyclobutyl, cyclopentyl or cyclohexyl.
80. A compound or pharmaceutically acceptable salt thereof, according to clause 66, 67, 70, 71, 74, or 75, wherein R² is 5-10 membered heteroaryl comprising one to three heteroatoms independently selected from N, S, and O.
81. A compound or pharmaceutically acceptable salt thereof, according to clause 66, 67, 70, 71, 74, or 75, wherein R² is 5-10 membered heteroaryl comprising one to three heteroatoms independently selected from N, S, and O, substituted with one or two independently selected R⁶ groups.
82. A compound or pharmaceutically acceptable salt thereof, according to clause 81, wherein R⁶ is selected from OH, halo, $C_{1-6}$ alkyl, $C_{1-6}$ alkyl substituted with one or more halo, $C_{1-6}$alkoxy, —CN, $C_{3-7}$ cycloalkyl, 4-7 membered heterocycloalkyl comprising one to three heteroatoms independently selected from N, O, and S, and phenyl.
83. A compound or pharmaceutically acceptable salt thereof, according to clause 80, 81 or 82, wherein R² is furanyl, thienyl, oxazolyl, thiazolyl, oxadiazolyl, thiadiazolyl, imidazolyl, triazolyl, pyridinyl, pyrazinyl, pyrimidinyl, indanyl, or indazolyl.
84. A compound or pharmaceutically acceptable salt thereof, according to clause 66, 67, 70, 71, 74, or 75, wherein R² is $C_{6-10}$ aryl.
85. A compound or pharmaceutically acceptable salt thereof, according to clause 66, 67, 70, 71, 74, or 75, wherein R² is $C_{6-10}$ aryl substituted with one or two independently selected R⁶ groups.
86. A compound or pharmaceutically acceptable salt thereof, according to clause 85, wherein R⁶ is selected from halo, CN, $C_{1-6}$ alkyl, $C_{1-6}$ alkoxy, —NHC(=O)—$C_{1-4}$alkyl, and —C(=O)NR⁹R¹⁰, and each R⁹ and R¹⁰ is independently selected from H and $C_{1-4}$alkyl.
87. A compound or pharmaceutically acceptable salt thereof, according to clause 84, 85 or 86, wherein R² is phenyl.
88. A compound or pharmaceutically acceptable salt thereof, according to clause 1, wherein the compound is 9-cyclopropylethynyl-2-((S)-1-[1,4]dioxan-2-ylmethoxy)-6,7-dihydro-pyrimido[6,1-a]isoquinolin-4-one.
89. A compound or pharmaceutically acceptable salt thereof, according to clause 1, wherein the compound is not 9-cyclopropylethynyl-2-((S)-1-[1,4]dioxan-2-ylmethoxy)-6,7-dihydro-pyrimido[6,1-a]isoquinolin-4-one.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound. Generally, a compound of the invention is administered in a pharmaceutically effective amount. The amount of a compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of the invention can be administered by a variety of routes including oral, rectal, transdermal, subcutaneous, intra-articular, intravenous, intramuscular, intranasal and inhalation. Depending on the intended route of delivery, a compound of this invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, a compound of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate may be added as a lubricant. The mixture may be formed into 240-270 mg tablets (80-90 mg of active amide compound per tablet) in a tablet press.

Formulation 2—Capsules

A compound of the invention may be admixed as a dry powder with a starch diluent in an approximate 1:1 weight ratio. The mixture may be filled into 250 mg capsules (125 mg of active amide compound per capsule).

Formulation 3—Liquid

A compound of the invention (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Sufficient water may be then added to produce a total volume of 5 mL.

Formulation 4—Tablets

A compound of the invention may be admixed as a dry powder with a dry gelatin binder in an approximate 1:2 weight ratio. A minor amount of magnesium stearate may be added as a lubricant. The mixture is formed into 450-900 mg tablets (150-300 mg of active amide compound) in a tablet press.

Formulation 5—Injection

A compound of the invention may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

A compound of the invention may be used as a therapeutic agent for the treatment of conditions in mammals that are causally related or attributable to aberrant activity of GPR84 and/or aberrant GPR84 expression and/or aberrant GPR84 distribution.

Accordingly, a compound and pharmaceutical compositions of the invention find use as therapeutics for the prophylaxis and/or treatment of inflammatory conditions (e.g. inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions, in mammals including humans.

Accordingly, in one aspect, the present invention provides the compound of the invention, or a pharmaceutical composition comprising the compound of the invention for use as a medicament.

In another aspect, the present invention provides the compound of the invention, or a pharmaceutical composition comprising the compound of the invention for use in the manufacture of a medicament.

In yet another aspect, the present invention provides a method of treating a mammal having, or at risk of having a disease disclosed herein. In a particular aspect, the present invention provides a method of treating a mammal having, or at risk of having inflammatory conditions (e.g. inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions, in mammals including humans.

In one aspect, the present invention provides the compound of the invention, or a pharmaceutical composition comprising the compound of the invention for use as a medicine for the prophylaxis and/or treatment of inflammatory conditions. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF).

In another aspect, the present invention provides the compound of the invention, or a pharmaceutical composition comprising the compound of the invention for use in the manufacture of a medicament for the prophylaxis and/or treatment of inflammatory conditions. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF).

In additional method of treatment aspects, this invention provides methods of treatment and/or prophylaxis of a mammal susceptible to or afflicted with inflammatory conditions, which method comprises administering an effective amount of a compound of the invention, or one or more of the pharmaceutical compositions herein described. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF).

In another aspect, the present invention provides a method of treating a mammal having, or at risk of having a disease selected from inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF))), neuroinflammatory conditions, infectious diseases, autoimmune diseases, endocrine and/or metabolic diseases, and/or diseases involving impairment of immune cell functions.

In one aspect, the present invention provides the compound of the invention, or a pharmaceutical composition comprising the compound of the invention for use as a medicine for the prophylaxis and/or treatment of neuroinflammatory conditions, Guillain-Barré syndrome (GBS), multiple sclerosis, axonal degeneration, autoimmune encephalomyelitis.

In another aspect, the present invention provides the compound of the invention, or a pharmaceutical composition comprising the compound of the invention for use in the manufacture of a medicament for the prophylaxis and/or treatment of neuroinflammatory conditions, Guillain-Barré syndrome (GBS), multiple sclerosis, axonal degeneration, autoimmune encephalomyelitis.

In additional method of treatment aspects, this invention provides methods of treatment and/or prophylaxis of a mammal susceptible to or afflicted with neuroinflammatory conditions, Guillain-Barré syndrome (GBS), multiple sclerosis, axonal degeneration, autoimmune encephalomyelitis, which method comprises administering an effective amount of a compound of the invention, or one or more of the pharmaceutical compositions herein described.

In one aspect, the present invention provides the compound of the invention, or a pharmaceutical composition comprising the compound of the invention for use as a medicine for the prophylaxis and/or treatment of infectious disease. In a specific embodiment, the infectious diseases is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In another aspect, the present invention provides the compound of the invention, or a pharmaceutical composition comprising the compound of the invention for use in the manufacture of a medicament for the prophylaxis and/or treatment of infectious disease. In a specific embodiment, the infectious diseases is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In additional method of treatment aspects, this invention provides methods of treatment and/or prophylaxis of a mammal susceptible to or afflicted with infectious disease, which method comprises administering an effective amount of a compound of the invention, or one or more of the pharmaceutical compositions herein described. In a specific embodiment, the infectious diseases is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In one aspect, the present invention provides the compound of the invention, or a pharmaceutical composition comprising the compound of the invention for use as a medicine for the prophylaxis and/or treatment of autoimmune diseases, and/or diseases involving impairment of immune cell functions. In a specific embodiment, the autoimmune diseases and/or diseases involving impairment of immune cell functions is selected from COPD, asthma, psoriasis, systemic lupus erythematosis, type I diabetes mellitus, vasculitis and inflammatory bowel disease.

In another aspect, the present invention provides the compound of the invention, or a pharmaceutical composition comprising the compound of the invention for use in the manufacture of a medicament for the prophylaxis and/or treatment of autoimmune diseases and/or diseases involving impairment of immune cell functions. In a specific embodiment, the autoimmune diseases, and/or diseases involving impairment of immune cell functions is selected from COPD, asthma, psoriasis, systemic lupus erythematosis, type I diabetes mellitus, vasculitis and inflammatory bowel disease.

In additional method of treatment aspects, this invention provides methods of treatment and/or prophylaxis of a mammal susceptible to or afflicted with autoimmune diseases and/or diseases involving impairment of immune cell functions, which method comprises administering an effective amount of a compound of the invention, or one or more of the pharmaceutical compositions herein described. In a specific embodiment, the autoimmune diseases and/or diseases involving impairment of immune cell functions is selected from COPD, asthma, psoriasis, systemic lupus erythematosis, type I diabetes mellitus, vasculitis and inflammatory bowel disease.

In one aspect, the present invention provides the compound of the invention, or a pharmaceutical composition comprising the compound of the invention for use as a medicine for the prophylaxis and/or treatment of endocrine and/or metabolic diseases. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

In another aspect, the present invention provides the compound of the invention, or a pharmaceutical composition comprising the compound of the invention for use in the manufacture of a medicament for the prophylaxis and/or treatment of endocrine and/or metabolic diseases. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

In additional method of treatment aspects, this invention provides methods of treatment and/or prophylaxis of a mammal susceptible to or afflicted with endocrine and/or metabolic diseases, which method comprises administering an effective amount of a compound of the invention, or one or more of the pharmaceutical compositions herein described. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

As a further aspect of the invention there is provided a compound of the invention for use as a medicament especially in the treatment or prevention of the aforementioned conditions and diseases. Also provided herein is the use of the compound in the manufacture of a medicament for the treatment or prevention of one of the aforementioned conditions and diseases.

A particular regimen of the present method comprises the administration to a subject in suffering from an inflammatory condition, of an effective amount of a compound of the invention for a period of time sufficient to reduce the level of inflammation in the subject, and preferably terminate, the processes responsible for said inflammation. A special embodiment of the method comprises administering of an effective amount of a compound of the invention to a subject suffering from or susceptible to the development of inflammatory condition, for a period of time sufficient to reduce or prevent, respectively, inflammation of said patient, and preferably terminate, the processes responsible for said inflammation.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compounds that demonstrate the same or a similar therapeutic activity, and that are determined to be safe and efficacious for such combined administration. In a specific embodiment, co-administration of two (or more) agents allows for significantly lower doses of each to be used, thereby reducing the side effects seen.

In one embodiment, a compound of the invention is co-administered with another therapeutic agent for the treatment and/or prevention of an inflammatory condition; particular agents include, but are not limited to, immunoregulatory agents e.g. azathioprine, corticosteroids (e.g. prednisolone or dexamethasone), cyclophosphamide, cyclosporin A, tacrolimus, Mycophenolate Mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prevention of arthritis (e.g. rheumatoid arthritis); particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, and cyclosporin), and biological DMARDS (for example but without limitation Infliximab, Etanercept, Adalimumab, Rituximab, Golimumab, Certolizumab pegol, Tocilizumab, Interleukin 1 blockers and Abatacept).

In one embodiment, a compound of the invention is co-administered with another therapeutic agent for the treatment and/or prevention of autoimmune diseases; particular agents include but are not limited to: glucocorticoids, cytostatic agents (e.g. purine analogs), alkylating agents, (e.g nitrogen mustards (cyclophosphamide), nitrosoureas, platinum compounds, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g., anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab (Remicade™), etanercept (Enbrel™), or adalimumab (Humira™)), mycophenolate, Fingolimod, and Myriocin.

In one embodiment, a compound of the invention is co-administered with another therapeutic agent for the treatment and/or prevention of infectious diseases; particular agents include but are not limited to antibiotics. In a particular embodiment, a compound of the invention is co-administered with another therapeutic agent for the treatment and/or prevention of infections of any organ of the human body; particular agents include but are not limited to: aminoglycosides, ansamycins, carbacephem, carbapenems, cephalosporins, glycopeptides, lincosamides, macrolides, monobactams, nitrofurans, penicillins, polypeptides, quinolones, sulfonamides, tetracyclins, anti-mycobacterial agents, as well as chloramphenicol, fosfomycin, linezolid, metronidazole, mupirocin, rifamycin, thiamphenicol and tinidazole.

In one embodiment, a compound of the invention is co-administered with another therapeutic agent for the treatment and/or prevention of vasculitis, particular agents include but are not limited to steroids (for example prednisone, prednisolone), cyclophosphamide and eventually antibiotics in case of cutaneous infections (for example cephalexin)

In one embodiment, a compound of the invention is co-administered with another therapeutic agent for the treatment and/or prevention of IPF, particular agents include but are not limited to pirfenidone and bosentan.

In one embodiment, a compound of the invention is co-administered with another therapeutic agent for the treatment and/or prevention of asthma and/or rhinitis and/or COPD; particular agents include but are not limited to: $beta_2$-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled) Long-acting $\beta_2$-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), phosphodiesterase-4 inhibitors (e.g. Roflumilast), biological regulators of IgE response (e.g. omalizumab), antihistamines (e.g. ceterizine, cinnarizine, fexofenadine), and vasoconstrictors (e.g. oxymethazoline, xylometazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine, and intravenous magnesium sulfate.

In one embodiment, a compound of the invention is co-administered with another therapeutic agent for the treatment and/or prevention of inflammatory bowel disease (IBD); particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and ciclosporin) and biological disease modifying, immunomodulatory agents (infliximab, adalimumab, rituximab, and abatacept).

By co-administration is included any means of delivering two or more therapeutic-agents to the patient as part of the same treatment regime, as will be apparent to the skilled person. Whilst the two or more agents may be administered simultaneously in a single formulation this is not essential. The agents may be administered in different formulations and at different times.

General Synthetic Procedures

General

A compound of the invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Wiley-Blackwell; 4th Revised edition edition (2006), and references cited therein.

The following methods are presented with details as to the preparation of representative 6,7-dihydro-pyrimido[6,1-a]isoquinolin-4-one that have been listed hereinabove. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica standard (30-70 μm). Thin layer chromatography was carried out using pre-coated silica gel 60 F-254 plates (thickness 0.25 mm). $^1$H NMR spectra were recorded on a Bruker Advance 400 NMR spectrometer (400 MHz) or a Bruker Advance 300 NMR spectrometer (300 MHz). Chemical shifts (δ) for 1H NMR spectra are reported in parts per million (ppm) relative to tetramethylsilane (δ 0.00) or the appropriate residual solvent peak as internal reference. Multiplicities are given as singlet (s), doublet (d), doublet of doublet (dd), triplet (t), quartet (q), multiplet (m) and broad (br). Electrospray MS spectra were obtained either on a Waters platform LC/MS spectrometer or on an Agilent 1100 Series LC/MSD. Analytic LCMS: Columns used, Waters Acquity UPLC BEH C18 1.7 μm, 2.1 mm ID×50 mm L or Waters Acquity UPLC BEH C18 1.7 μm, 2.1 mm ID×30 mm L or Waters XBridge C18 3.5 μm, 2.1 mm ID×50 mm L. All the methods are using MeCN/H$_2$O gradients. MeCN and H$_2$O contain either 0.1% Formic Acid or NH$_3$ (10 mM). Preparative LCMS: Column used, Waters XBridge Prep C18 5 μm ODB 30 mm ID×100 mm L. All the methods are using either MeOH/H$_2$O or MeCN/H$_2$O gradients. MeOH, MeCN and H$_2$O contain either 0.1% Formic Acid or 0.1% Diethylamine. Analytic chiral LC: Column used, Chiralpak IA 5 μm 250×4.6 mm. Microwave heating was performed with a Biotage Initiator.

TABLE I

| List of abbreviations used in the experimental section: | |
|---|---|
| μL | microliter |
| AcOH | Acetic acid |
| Aq. | aqueous |
| ATP | Adenosine 5'-Triphosphate |
| BINAP | 2,2'-bis(diphenylphosphino)-1,1'-binaphthyl |
| Boc | tert-Butyloxy-carbonyl |
| Boc$_2$O | Di-tert-butyl dicarbonate |
| br s | broad singlet |
| Calcd | calculated |

TABLE I-continued

| List of abbreviations used in the experimental section: | |
|---|---|
| Cat. | Catalytic amount |
| D | doublet |
| Dd | Doublet of doublet |
| DCC | N,N'-Dicyclohexylcarbodiimide |
| DCE | 1,2-Dichloroethane |
| DCM | Dichloromethane |
| DIAD | Diisopropyl azodicarboxylate |
| DIPEA | N,N-diisopropylethylamine |
| DMAP | 4-Dimethylaminopyridine |
| DME | Dimethoxyethane |
| DMF | N,N-dimethylformamide |
| DMSO | Dimethylsulfoxide |
| DPBS | Dulbecco's Phosphate-Buffered Saline |
| DPPF | 1,1'-Bis(diphenylphosphino)ferrocene |
| EtOAc | Ethyl acetate |
| Et$_2$O | Diethyl ether |
| eq. | equivalent |
| g | gram |
| GTP☐S | guanosine 5'-O-[gamma-thio]triphosphate |
| h | hour |
| H | Heptane |
| HPLC | High-performance liquid chromatography |
| iPrOH | isopropanol |
| iPr$_2$O | Diisopropyl ether |
| KHMDS | Potassium hexamethyldisilazane |
| LCMS | Liquid Chromatography-Mass Spectrometry |
| L | Liter |
| M | multiplet |
| MeOH | Methanol |
| MeCN | Acetonitrile |
| MeI | Methyl iodide |
| MEK | Methyl ethyl ketone |
| Mg | milligram |
| Min | minute |
| mL | milliliter |
| Mmol | millimole |
| MS | mass spectrometry |
| MW | Molecular weight |
| MW (calc) | Molecular weight calculated |
| MW (obs) | Molecular weight observed |
| NADP | Nicotinamide adenine dinucleotide phosphate |
| NEAA | Non-Essential Amino Acid |
| NMP | N-Methyl-2-pyrrolidone |
| NMR | Nuclear Magnetic Resonnance |
| obsd | observed |
| Pd(OAc)$_2$ | Palladium(II) acetate |
| Pd(PPh$_3$)$_4$ | Tetrakis(triphenylphosphine)palladium(0) |
| Pd/C | Palladium on Carbon 10% |
| ppm | part-per-million |
| q | quadruplet |
| rpm | revolutions per minute |
| RT | Room temperature |
| Rt | retention time |
| RuPhos | 2-Dicyclohexylphosphino-2',6'-di-i-propoxy-1,1'-biphenyl |
| s | singlet |
| SM | Starting material |
| spA | Scintillation proximity assay |
| SPE | Solid phase extraction |
| STAB | sodiumtriacetoxyborohydride |
| t | triplet |
| TBAF | Tetra-n-butylammonium fluoride |
| TEA | Triethylamine |
| TFA | Trifluoroacetic acid |
| THF | Tetrahydrofuran |
| TLC | Thin layer chromatography |

General Synthetic Method
INTERMEDIATES
The intermediates to prepare the compounds according to the invention can be produced according to the following schemes.
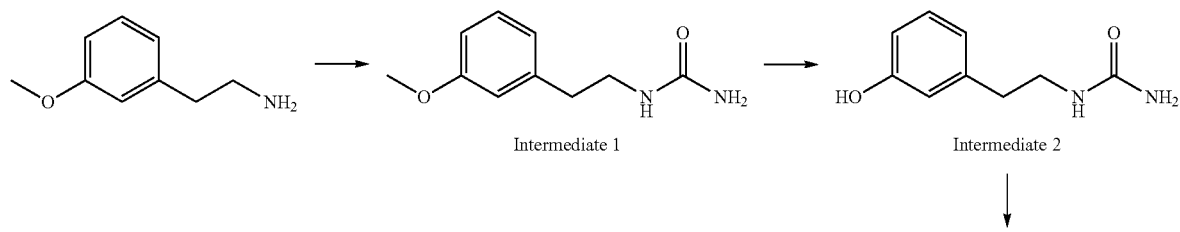
Intermediate 1    Intermediate 2
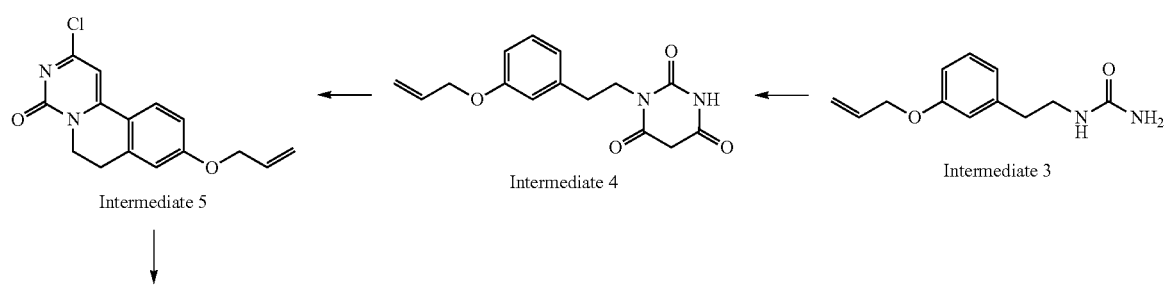
Intermediate 5    Intermediate 4    Intermediate 3

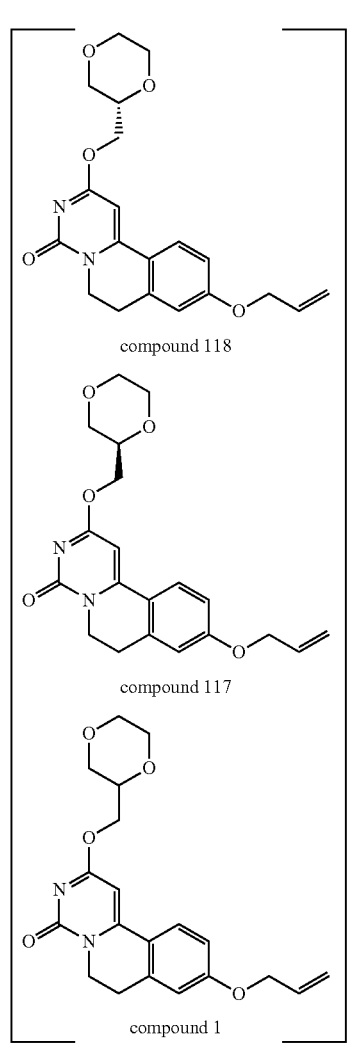

compound 118 compound 117 compound 1

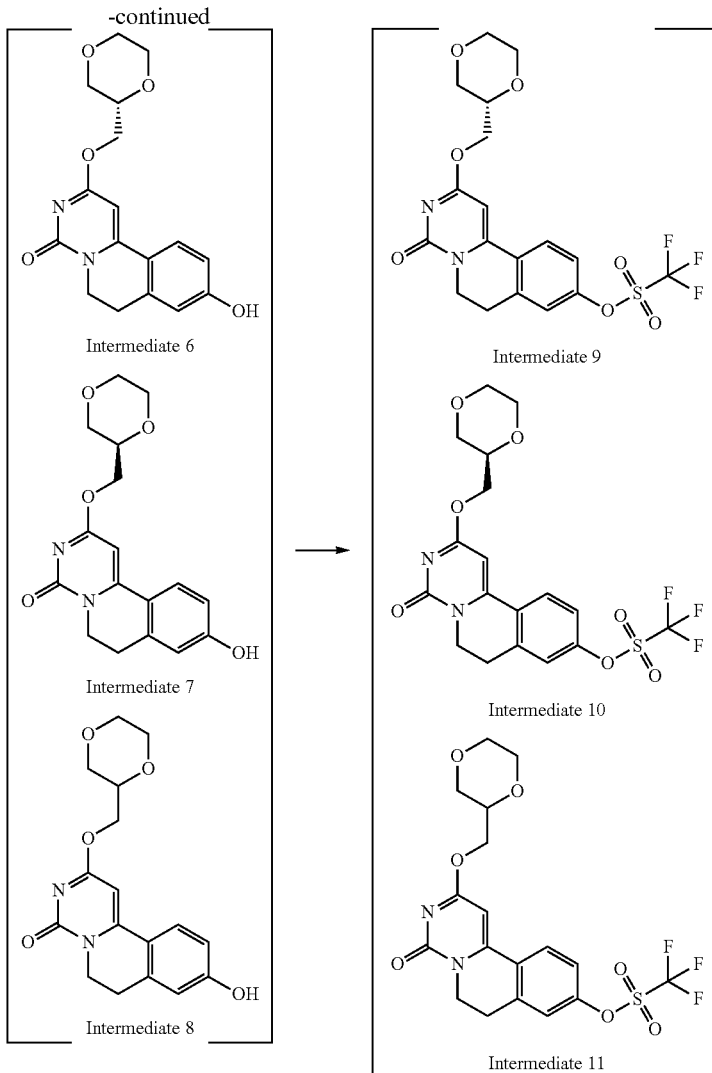

Intermediate 6

Intermediate 7

Intermediate 8

Intermediate 9

Intermediate 10

Intermediate 11

Intermediate 1: [2-(3-methoxy-phenyl)-ethyl]-urea

A solution of 3-methoxyphenethylamine (100 g, 661.3 mmol, 1 eq.), urea (157.3 g, 2619.0 mmol, 4 eq.), AcOH (36 mL) and aq. HCl (12 mL) in H$_2$O (800 mL) was heated under reflux for 5 days. The reaction mixture was cooled to RT, the solid was filtered off, washed with water and dried to afford intermediate 1.

($^1$H, CDCl$_3$) δ (ppm): 7.24 (1H, t), 6.82-6.77 (3H, m), 5.10 (1H, br s), 4.52 (2H, br), 3.81 (1H, s), 3.42 (2H, br t), 2.80 (2H, t)

Intermediate 2: [2-(3-hydroxy-phenyl)-ethyl]-urea

A solution of intermediate 1 (72 g, 370.7 mmol) in concentrated HBr (500 mL) was heated under reflux overnight. The reaction mixture was brought to basic pH by addition of NaHCO$_3$ and extracted with EtOAc. The organic layer was dried over MgSO$_4$ and concentrated under vacuum to afford intermediate 2.

($^1$H, MeOD-d4) δ (ppm): 7.15 (1H, t), 6.76-6.68 (3H, m), 3.40-3.36 (2H, t), 2.77-2.74 (2H, t)

Intermediate 3: [2-(3-allyloxy-phenyl)-ethyl]-urea

To a solution of intermediate 2 (45 g, 249.7 mmol, 1 eq.) and K$_2$CO$_3$ (103.5 g, 749.1 mmol, 3 eq.) in anhydrous DMF (300 mL) under a nitrogen atmosphere, was added allylbromide (50.5 mL, 499.4 mmol, 2 eq.). The reaction mixture was stirred for 2.5 days, then DMF was evaporated to dryness. The residue was dissolved in EtOAc, washed with saturated Na$_2$CO$_3$, brine, dried over MgSO$_4$ and concentrated under vacuum to afford intermediate 3.

($^1$H, MeOD-d4) δ (ppm): 7.24 (1H, t), 6.87-6.81 (3H, m), 6.16-6.06 (1H, m), 5.45 (1H, dd), 5.29 (1H, dd), 4.59-4.57 (2H, m), 3.38 (2H, t), 2.80 (2H, t)

Intermediate 4: 1-[2-(3-allyloxy-phenyl)-ethyl]-pyrimidine-2,4,6-trione

Sodium (20.06 g, 872 mmol, 1 eq.) was dissolved in EtOH (1.4 L). Diethyl malonate (132.4 mL, 872 mmol, 1 eq.) was added and the reaction mixture was heated under reflux for 1 h. Intermediate 3 (96 g, 436 mmol, 0.5 eq.) in EtOH (300 mL) was added and the reaction mixture was heated under reflux for 12 h. The reaction was cooled to RT, 1N aq. HCl was added and the precipitate was filtered, washed with water and dried to afford intermediate 4.

(¹H, CDCl₃) δ (ppm): 8.40 (1H, br s), 7.25 (1H, t), 6.88-6.82 (3H, m), 6.14-6.04 (1H, m), 5.45 (1H, dd), 5.32 (1H, dd), 4.58-4.56 (2H, m), 4.13 (2H, t), 3.64 (2H, s), 2.92 (2H, t)

MW (calcd): 288.3; MW (obsd): 289.3 (M+1)

Intermediate 5: 9-allyloxy-2-chloro-6,7-dihydro-pyrimido[6,1-a]isoquinolin-4-one A solution of intermediate 4 (20 g, 69.4 mmol, 1 eq.) in POCl₃ (150 mL) was stirred at 50° C. for 3 days. POCl₃ was evaporated under vacuum and the residue was dissolved in DCM and quenched with saturated NaHCO₃. The organic layer was washed with water, dried over MgSO₄ and concentrated to afford intermediate 5.

(¹H, CDCl₃) δ (ppm): 7.71 (2H, d), 6.97 (1H, dd), 6.86 (1H, d), 6.71 (1H, s), 6.13-6.04 (1H, m), 5.47 (1H, dd), 5.36 (1H, dd), 4.67-4.65 (2H, m), 4.27 (2H, t), 3.05 (2H, t)

MW (calcd): 288.7; MW (obsd): 289.3 (M+1)

General Methods

General Method A:

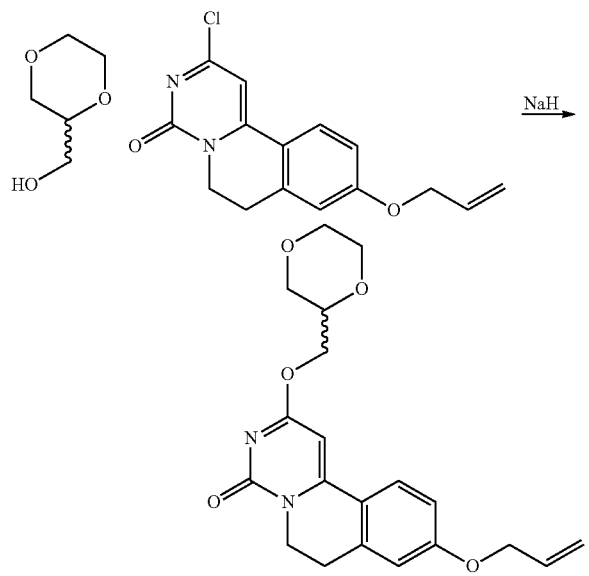

To a solution of NaH (2 eq., 60% in mineral oil) in anhydrous DCM at 0° C., is added 2-hydroxymethyl-[1,4]dioxane (2 eq.) with the appropriate chirality, after 15 min, intermediate 5 (1 eq.) is added at 0° C., and the reaction is stirred at RT until completion. Saturated NH₄Cl is added to the reaction mixture, the organic layer is washed with water, dried over MgSO₄ and concentrated. The desired product is purified by flash chromatography on silica gel.

2-Hydroxymethyl-[1,4]dioxane, (R) 2-hydroxymethyl-[1,4]dioxane and (S) 2-hydroxymethyl-[1,4]dioxane are commercially available or can easily be prepared [Young Kim et al; Bioorganic & Medicinal Chemistry 15 (2007) 2667-2679].

Illustrative Synthesis of General Method A:

Compound 118: 9-allyloxy-2-((S)-1-[1,4]dioxan-2-ylmethoxy)-6,7-dihydro-pyrimido[6,1-a]isoquinolin-4-one A solution of (R) 2-hydroxymethyl-[1,4]dioxane (56.6 g, 479 mmol, 2 eq.) and NaH (19.9 g, 479 mmol, 2 eq., 60% in mineral oil) in anhydrous DCM (300 mL) was stirred for 30 min at 0° C. Intermediate 5 (69.2 g, 240 mmol, 1 eq.) in solution in anhydrous DCM (700 mL) was added at 0° C. The reaction mixture was stirred for 2 h. Saturated NH₄Cl was added, the organic layer was washed with water, dried over MgSO₄ and evaporated to dryness. The crude product was purified by flash chromatography on silica gel (MeOH/DCM) to afford compound 118.

(¹H, CDCl₃) δ (ppm): 7.66 (1H, d), 6.94 (1H, dd), 6.83 (1H, d), 6.32 (1H, s), 6.15-6.03 (1H, m), 5.47 (1H, dd), 5.37 (1H, dd), 4.65-4.63 (2H, m), 4.51-4.39 (2H, m), 4.23 (2H, t), 4.06-3.98 (1H, m), 3.92-3.47 (6H, m), 3.01 (2H, t)

Compound 1: 9-allyloxy-2-(-1-[1,4]dioxan-2-ylmethoxy)-6,7-dihydro-pyrimido[6,1-a]isoquinolin-4-one Compound 1 was prepared using general method A starting from 2-hydroxymethyl-[1,4]dioxane.

(¹H, CDCl₃) δ (ppm): 7.66 (1H, d), 6.94 (1H, dd), 6.83 (1H, d), 6.32 (1H, s), 6.11-6.04 (1H, m), 5.47 (1H, dd), 5.35 (1H, dd), 4.65-4.63 (2H, m), 4.491-4.40 (2H, m), 4.22 (2H, t), 4.02-3.99 (1H, m), 3.90-3.46 (6H, m), 3.00 (2H, t)

MW (calcd): 370.4; MW (obsd): 371.4 (M+1)

Compound 117: 9-allyloxy-2-((R)-1-[1,4]dioxan-2-ylmethoxy)-6,7-dihydro-pyrimido[6,1-a]isoquinolin-4-one Compound 117 was prepared using general method A starting from (S) 2-hydroxymethyl-[1,4]dioxane (¹H, CDCl₃) δ (ppm): 7.66 (1H, d), 6.94 (1H, dd), 6.83 (1H, d), 6.31 (1H, s), 6.12-6.04 (1H, m), 5.49 (1H, dd), 5.36 (1H, dd), 4.65-4.63 (2H, m), 4.50-4.42 (2H, m), 4.23 (2H, t), 4.04-4.00 (1H, m), 3.91-3.50 (6H, m), 3.01 (2H, t)

MW (calcd): 370.4; MW (obsd): 371.2 (M+1)

General Method B:

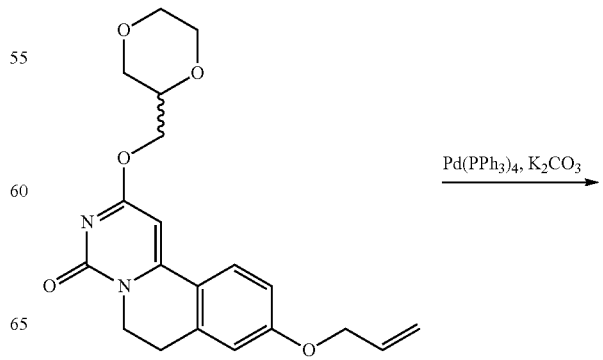

-continued

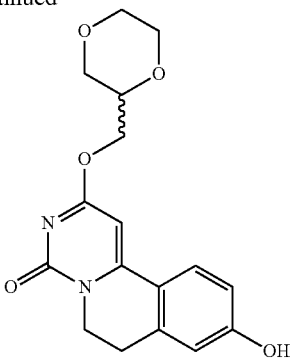

To a suspension of compound 1, 117 or 118 (1 eq.) in a mixture of DCM/MeOH (1/1) is added K₂CO₃ (2 eq.) and Pd(PPh₃)₄ (0.05 eq.). The reaction mixture is degassed before stirring at RT. After completion, water is added to the reaction mixture and the aqueous layer is separated. The pH of the aqueous solution is adjusted to pH 1 with 2M aq. HCl. The precipitate is filtered off, washed with water and dried to afford intermediate 6, 7 or 8.
Illustrative Synthesis of General Method B:

Intermediate 6: 2-((S)-1-[1,4]dioxan-2-ylmethoxy)-9-hydroxy-6,7-dihydro-pyrimido[6,1-a]isoquinolin-4-one To a suspension of compound 118 (31.15 g, 84.2 mmol, 1 eq.) in a mixture of DCM/MeOH (1/1, 800 mL) was added K₂CO₃ (23.2 g, 138.2 mmol, 2 eq.) and Pd(PPh₃)₄ (4.86 g, 4.21 mmol, 0.05 eq.). The reaction mixture was stirred at RT for 2 h. Water (800 mL) was added, and the aqueous layer was separated. The pH of the aqueous solution is adjusted to pH 1 with 2 μM aq. HCl. The precipitate was filtered off, washed with water and dried to afford intermediate 6.

($^1$H, DMSO-d6) δ (ppm): 7.84 (1H, d), 6.77 (1H, dd), 6.74 (1H, d), 6.45 (1H, s), 4.25-4.23 (2H, m), 3.99 (2H, t), 3.87-3.75 (3H, m), 3.68-3.58 (2H, m), 3.52-3.46 (1H, m), 3.40-3.30 (1H, m), 2.91 (2H, t)

MW (calcd): 330.4; MW (obsd): 331.3 (M+1)

Intermediate 7: 2-((R)-1-[1,4]dioxan-2-ylmethoxy)-9-hydroxy-6,7-dihydro-pyrimido[6,1-a]isoquinolin-4-one Intermediate 7 was prepared using general method B starting from compound 117.

($^1$H, DMSO-d6) δ (ppm): 7.83 (1H, d), 6.77 (1H, dd), 6.74 (1H, d), 6.44 (1H, s), 4.27-4.20 (2H, m), 3.98 (2H, t), 3.87-3.74 (3H, m), 3.68-3.57 (2H, m), 3.52-3.46 (1H, m), 3.40-3.34 (1H, m), 2.91 (2H, t)

Intermediate 8: 2-([1,4]dioxan-2-ylmethoxy)-9-hydroxy-6,7-dihydro-pyrimido[6,1-a]isoquinolin-4-one Intermediate 8 was prepared using general method B starting from compound 1.

($^1$H, DMSO-d6) δ (ppm): 7.84 (1H, d), 6.77 (1H, dd), 6.74 (1H, d), 6.45 (1H, s), 4.27-4.20 (2H, m); 3.99 (2H, t), 3.88-3.73 (3H, m), 3.68-3.58 (2H, m), 3.52-3.46 (1H, m), 3.40-3.34 (1H, m), 2.91 (2H, t)

MW (calcd): 330.4; MW (obsd): 331.0 (M+1)

General Method C:

A solution of intermediate 6, 7 or 8 (1 eq.), N-phenyl-bis(trifluoromethanesulfonimide) (1.2 eq.) and Et₃N (1.3 eq.) in DCM under nitrogen is stirred at RT until completion. The reaction mixture is concentrated and the crude is purified by crystallization from iPrOH to afford intermediate 9, 10 or 11.
Illustrative Synthesis of General Method C:

Intermediate 9: trifluoro-methanesulfonic acid 2-((S)-1-[1,4]dioxan-2-ylmethoxy)-4-oxo-6,7-dihydro-4H-pyrimido[6,1-a]isoquinolin-9-yl ester A solution of intermediate 6, (24 g, 72.7 mmol, 1 eq.), N-phenyl-bis(trifluoromethanesulfonimide) (31.15 g, 87.2 mmol, 1.2 eq.) and Et₃N (13.2 mL, 94.4 mmol, 1.3 eq.) in DCM (700 mL) under a nitrogen atmosphere is stirred at RT overnight. The reaction mixture is concentrated. The crude is taken in iPrOH (75 mL) heated under reflux and cool to RT. After two days at RT, the solid is filtered off and dried to afford intermediate 9.

($^1$H, CDCl₃) δ (ppm): 7.83 (1H, d), 7.35 (1H, dd), 7.29 (1H, d), 6.41 (1H, s), 4.51-4.42 (2H, m), 4.28 (2H, t), 4.06-4.01 (1H, m), 3.89-3.69 (5H, m), 3.52 (1H, m), 3.11 (2H, t)

Intermediate 10: trifluoro-methanesulfonic acid 2-((R)-1-[1,4]dioxan-2-ylmethoxy)-4-oxo-6,7-dihydro-4H-pyrimido[6,1-a]isoquinolin-9-yl ester Intermediate 10 was prepared using general method C starting from intermediate 7.

($^1$H, CDCl₃) δ (ppm): 7.83 (1H, d), 7.34 (1H, dd), 7.29 (1H, d), 6.41 (1H, s), 4.51-4.41 (2H, m), 4.28 (2H, t), 4.05-4.00 (1H, m), 3.91-3.66 (5H, m), 3.52 (1H, t), 3.11 (2H, t)

Intermediate 11: trifluoro-methanesulfonic acid 2-([1,4]dioxan-2-ylmethoxy)-4-oxo-6,7-dihydro-4H-pyrimido[6,1-a]isoquinolin-9-yl ester Intermediate 11 was prepared using general method C starting from intermediate 8.

($^1$H, DMSO-d6) δ (ppm): 8.21 (1H, d), 7.65 (1H, d), 7.54 (1H, dd), 6.75 (1H, s), 4.28-4.26 (2H, m), 4.04 (2H, t), 3.90-3.84 (1H, m), 3.81-3.75 (2H, m), 3.68-3.58 (2H, m), 3.53-3.47 (1H, m), 3.41-3.36 (1H, m), 3.10 (t, 2H)

MW (calcd): 462.4; MW (obsd): 463.3 (M+1)

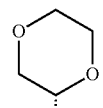

Step 1

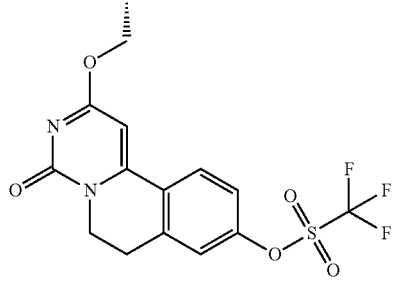

Intermediate 9

-continued

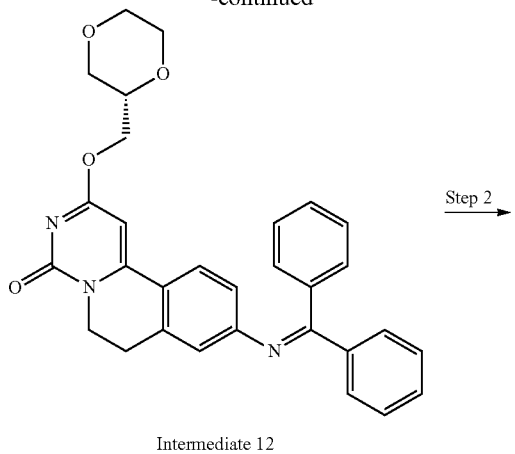

Intermediate 12

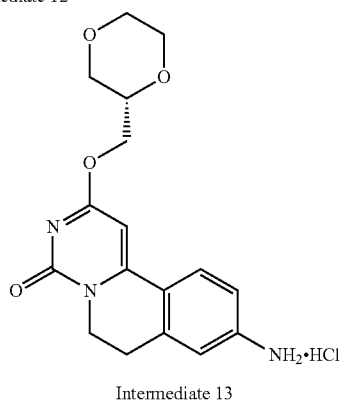

Intermediate 13

Intermediate 13: 9-amino-2-((S)-1-[1,4]dioxan-2-ylmethoxy)-6,7-dihydro-pyrimido[6,1-a]isoquinolin-4-one hydrochloride Step 1: 9-(Benzhydrylidene-amino)-2-((S)-1-[1,4]dioxan-2-ylmethoxy)-6,7-dihydro-pyrimido[6,1-a]isoquinolin-4-one (Intermediate 12)

A solution of intermediate 9 (1 g, 2.16 mmol, 1 eq.), Pd(OAc)₂ (24 mg, 0.11 mmol 0.05 eq.), Cs₂CO₃ (2.11 g, 6.48 mmol, 3 eq.) BINAP (134 mg, 0.21 mmol, 0.1 eq.) and benzophenonimine (587 mg, 3.24 mmol, 1.5 eq.) in toluene (20 mL) was heated at 150° C. in a microwave for 45 min. The solvent was evaporated to dryness and the crude mixture was taken in water and extracted with EtOAc. The organic layer was dried over MgSO₄ and concentrated under vacuum. 9-(Benzhydrylidene-amino)-2-((S)-1-[1,4]dioxan-2-ylmethoxy)-6,7-dihydro-pyrimido[6,1-a]isoquinolin-4-one intermediate 12 was obtained after purification by flash chromatography on silica gel and immediately used in next step.

Step 2: 9-amino-2-((S)-1-[1,4]dioxan-2-ylmethoxy)-6,7-dihydro-pyrimido[6,1-a]isoquinolin-4-one hydrochloride (Intermediate 13)

To a solution of intermediate 12 in a minimum of DCM/Et₂O was added HCl 2N in Et₂O (4 mL). The precipitate was filtered off and dried to afford intermediate 13.

($^1$H, DMSO-d6) δ (ppm): 7.82 (1H, d), 7.45 (3H, br), 6.68 (1H, d), 6.67 (1H, s), 6.51 (1H, s), 4.32 (2H, d), 3.99 (2H, t), 3.90-3.84 (1H, m), 3.82-3.35 (6H, m), 2.88 (2H, t)

MW (calcd): 329.4; MW (obsd): 330.2 (M+1)

General Method D:

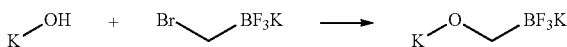

The corresponding alcohol (2 eq.) is added to a solution of NaH (2 eq., 60% in mineral oil) in THF at 0° C. The reaction is warmed to RT for 30 min then cooled again at 0° C. Bromo methyltrifluoroborate (1 eq.) is added to the reaction in one portion and the mixture is stirred at RT from few hours to 3 days (monitoring by $^{19}$F-NMR). The reaction is quenched with a solution of KHF₂ (1.5 µM, 3 eq.) and the mixture is evaporated to dryness. The residue is suspended in acetone, the inorganics are filtered off and the filtrate is evaporated to dryness. The residue is suspended in a minimum amount of acetone, Et₂O is added and the product is obtained by filtration.

Illustrative Synthesis of General Method D:

Intermediate 14: tetrahydro-2H-pyran-4-ol-methyl trifluoroborate

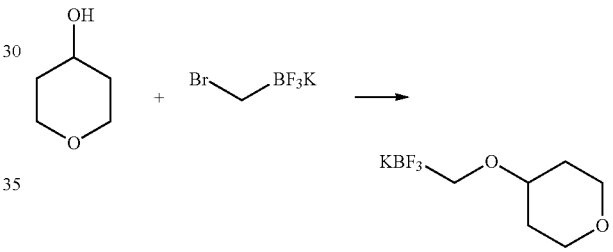

Intermediate 14

Tetrahydro-pyran-4-ol (152 mg, 1.49 mmol, 2 eq.) was added to a solution of NaH (60 mg, 1.49 mmol, 2 eq., 60% in mineral oil) in THF (4 mL) at 0° C. The reaction was warmed to RT for 30 min then cooled again at 0° C. Bromo methyltrifluoroborate (150 mg, 0.75 mmol, 1 eq.) was added to the reaction in one portion and the mixture was stirred at RT for 1 day (monitoring by $^{19}$F-NMR). The reaction was quenched with a solution of KHF₂ (1.5 mL, 1.5 µM, 3 eq.) and the mixture was evaporated to dryness. The residue was suspended in acetone, the inorganics were filtered off and the filtrate was evaporated to dryness. The residue was suspended in a minimum amount of acetone (1.5 mL), and Et₂O (6 mL) was added. Intermediate 14 was obtained by filtration.

($^1$H, DMSO-d₆) δ ppm 3.78 (2 H, d), 3.31-3.21 (2 H, m), 3.18-3.08 (1 H, m), 2.50-2.45 (2 H, m), 1.86-1.74 (2 H, m), 1.34-1.19 (2 H, m)

Intermediate 15: potassium 3-oxy-oxetanemethyltrifluoroborate

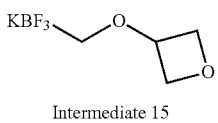

Intermediate 15

Intermediate 15 was prepared via general method D with oxetan-3-ol (the trifluoroborate reagent was recovered with the inorganics rather than the filtrate).

($^1$H, DMSO-d$_6$) δ ppm 4.56 (2 H, s), 4.32 (3 H, d), 2.40 (2 H, d)

Intermediate 16: potassium (3-methyl-3-methyloxy-oxetane-methyltrifluoroborate

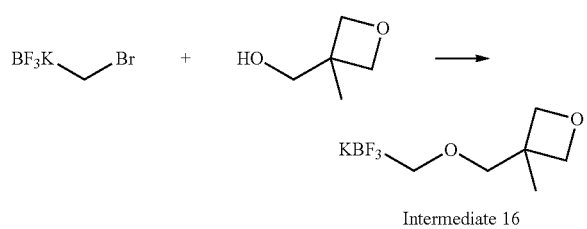

Intermediate 16

Intermediate 16 was prepared via general method D with (3-methyloxetan-3-yl) methanol (the trifluoroborate reagent was recovered with the inorganics rather than the filtrate).

($^1$H, DMSO-d$_6$) δ ppm 4.34 (2 H, d), 4.14 (2 H, d), 3.26 (2 H, s), 2.59-2.52 (2 H, m), 1.19 (3 H, s)

Intermediate 17: potassium 2,2-dimethyl-propyloxy-methyltrifluoroborate

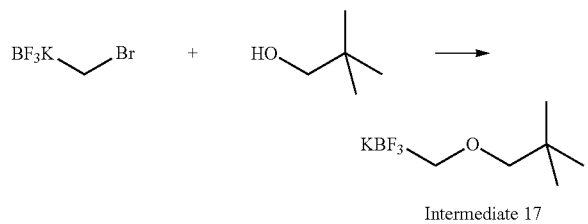

Intermediate 17

Intermediate 17 was prepared via general method D with 2,2-dimethyl-propan-1-ol.

($^1$H, DMSO-d$_6$) δ ppm 2.88 (2 H, s), 2.51-2.45 (2 H, m), 0.83 (9 H, s)

Intermediate 18: potassium cyclopropylmethoxy-methyltrifluoroborate

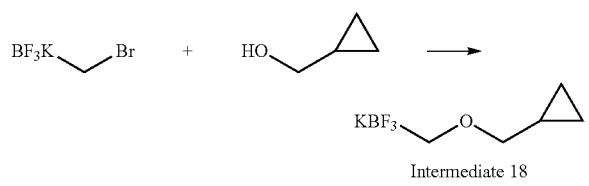

Intermediate 18

Intermediate 18 was prepared via general method D with cyclopropyl-methanol.

($^1$H, DMSO-d$_6$) δ ppm 3.00 (2 H, d), 2.46 (2 H, d), 1.00-0.82 (1 H, m), 0.46-0.31 (2 H, m), 0.13-0.00 (2 H, m)

Intermediate 19: cyclopentylmethoxy-methyltrifluoroborate

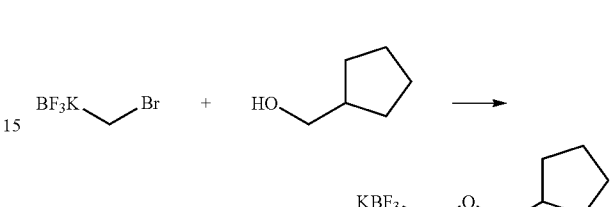

Intermediate 19

Intermediate 19 was prepared via general method D with cyclopentyl-methanol.

($^1$H, DMSO-d$_6$) δ ppm 3.04 (2 H, d), 2.46 (2 H, d), 2.08-1.94 (1 H, m), 1.47 (6 H, br. s.), 1.07-1.22 (2 H, m)

Intermediate 20: potassium 2-cyclopropyl-ethyl-trifluoroborate

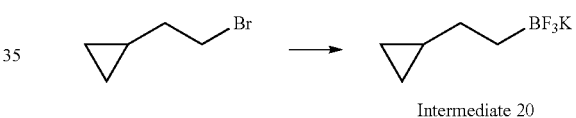

Intermediate 20

A 2-neck round bottom flask equipped with a reflux condenser and an addition funnel was charged with Mg (193 mg, 8.05 mmol, 3 eq.) and Et$_2$O (1 mL) under N$_2$. One drop of neat (2-bromo-ethyl)-cyclopropane was added followed by two drops of dibromoethane. Once the 1$^{st}$ bubbles appeared, (2-bromo-ethyl)-cyclopropane (400 mg, 2.68 mmol, 1 eq.) in Et$_2$O (5 mL) was added dropwise. Upon completion of the addition, the resulting suspension was stirred at RT for 1 h. In a separate flask, purged with N$_2$, a solution made of B(OMe)$_3$ (0.45 mL, 4.02 mmol, 1.5 eq.) in THF (6 mL) was cooled to −78° C. To this solution, the 2-cyclopropyl-ethyl magnesium bromide suspension was added dropwise via a double ended needle. The mixture was allowed to stir for 1 h at −78° C. and then was warmed to RT for 1 h. After cooling the mixture to 0° C., a saturated aqueous solution of KHF$_2$ (2.5 mL, 4.5 M, 4.1 eq.) was added dropwise and the reaction mixture was allowed to warm to RT. After 30 min, the solution was concentrated in-vacuo. The dried solids were triturated with hot acetone and filtered to remove inorganic salts. The resulting filtrate was concentrated and the solid residue was triturated with Et$_2$O. Potassium 2-cyclopropyl-ethyl-trifluoroborate was filtered and dried in-vacuo.

($^1$H, DMSO-d$_6$) δ ppm 1.07-0.92 (2 H, m), 0.66-0.53 (1 H, m), 0.27-0.21 (2 H, m), 0.067--0.07 (2 H, m), −0.117--0.17 (2 H, m)

General Method E:

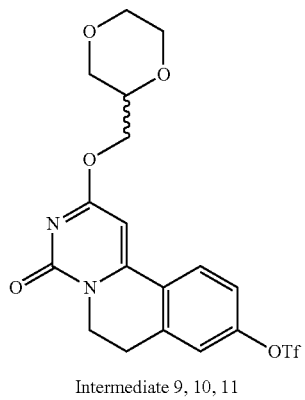

Intermediate 9, 10, 11

↓

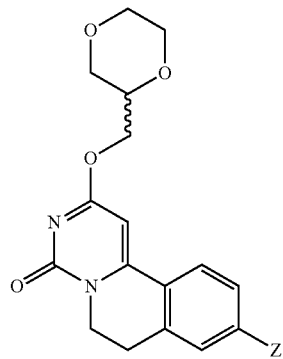

A vial is charged with intermediate 9, 10 or 11 (1 eq.), the appropriate boronic acid, boronic ester or potassium trifluoroborate (4.4 eq.), Cs₂CO₃ (2.6 eq.), (DPPF)PdCl₂.DCM (0.05 eq.), in 1,4-dioxane/H₂O (10/1, v/v), and the mixture is degassed with N₂. The vial is sealed and heated at 80° C. When the reaction is complete, the vial is cooled to RT and the reaction is either worked up or volatiles are evaporated under vacuum. The product is then obtained after purification by either flash chromatography on silica gel, preparative TLC or preparative HPLC-MS.

Illustrative Synthesis of General Method E:

Compound 2: 2-([1,4]dioxan-2-ylmethoxy)-9-pyridin-3-yl-6,7-dihydro-pyrimido[6,1-a]isoquinolin-4-one

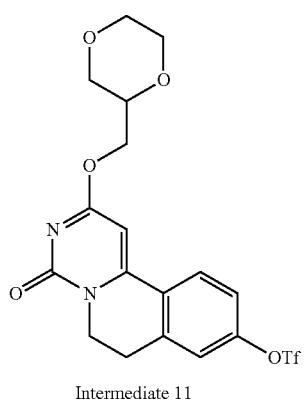

Intermediate 11

↓

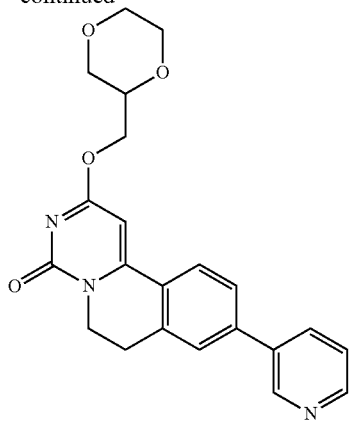

Compound 2

A vial was charged with intermediate 11 (84 mg, 0.074 mmol, 1 eq.), pyridine-3-boronic acid (40 mg, 0.327 mmol, 4.4 eq.), Cs₂CO₃ (62 mg, 0.190 mmol, 2.6 eq.), (DPPF) PdCl₂.DCM (3.3 mg, 0.004 mmol, 0.05 eq.), in 1,4-dioxane (1 mL) and H₂O (0.1 mL), and the mixture was degassed with N₂. The vial was sealed and heated at 80° C. After 1 h, the vial was cooled to RT and volatiles were evaporated under vacuum. The residue was then purified by flash chromatography on silica gel, eluting with 7.5% MeOH/ DCM to afford compound 2.

($^1$H, CDCl₃) δ ppm 8.89 (1 H, s), 8.67 (1 H, d), 7.93 (1 H, d), 7.82 (1 H, d), 7.61 (1 H, d), 7.53 (1 H, s), 7.43 (1 H, dd), 6.43 (1 H, s), 4.51-4.37 (2 H, m), 4.26 (2 H, t), 3.99 (1 H, m), 3.92-3.60 (5 H, m), 3.49 (1 H, m), 3.10 (2 H, t)

General Method F:

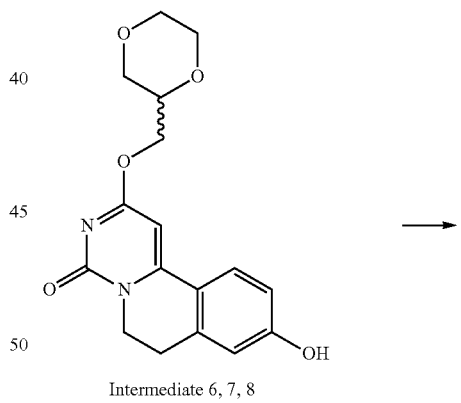

Intermediate 6, 7, 8

↓

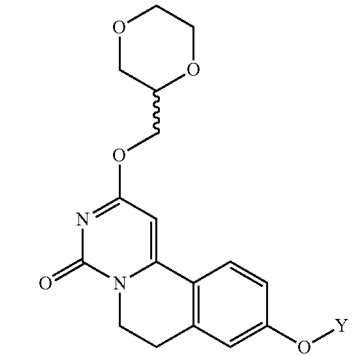

A solution of intermediate 6, 7, or 8 (1 eq.), the appropriate alkylating agent (1.5 eq.), K₂CO₃ (2 eq.), KI (1 eq.) in MEK is heated at 80° C. When the reaction is complete, the volatiles are evaporated to dryness and the residue is purified by flash chromatography on silica gel to give the desired product.

Illustrative Synthesis of General Method F:

Compound 8: 2-([1,4]dioxan-2-ylmethoxy)-9-(oxazol-2-ylmethoxy)-6,7-dihydro-pyrimido[6,1-a]isoquinolin-4-one

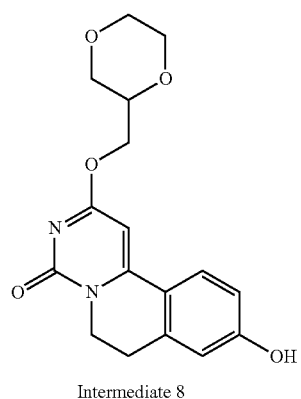

Intermediate 8

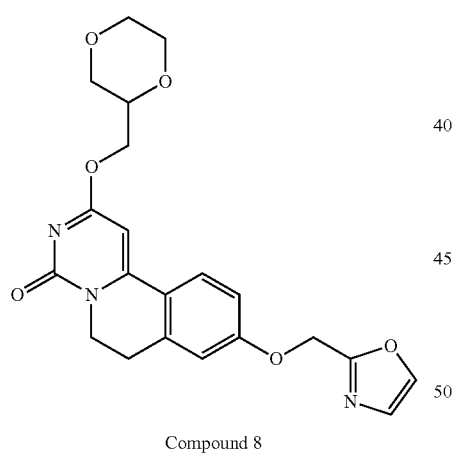

Compound 8

A solution of intermediate 8 (40 mg, 0.12 mmol, 1 eq.), 2-chloromethyloxazole (21 mg, 0.18 mmol, 1.5 eq.), K₂CO₃ (33 mg, 0.24 mmol, 2 eq.), KI (20 mg, 0.12 mmol, 1 eq.) in MEK (2 mL) was heated at 80° C. for 16 h. The reaction was evaporated to dryness and the residue was purified by flash chromatography on silica gel, eluting with 4% MeOH/DCM to give compound 8.

($^1$H, CDCl₃) δ ppm 7.72 (1 H, d), 7.68-7.60 (1 H, m), 7.18 (1 H, d), 7.02 (1 H, dd), 6.93 (1 H, d), 6.28 (1 H, s), 5.23 (2 H, s), 4.49-4.33 (2 H, m), 4.19 (2 H, t), 4.02-3.94 (1 H, m), 3.89-3.61 (5 H, m), 3.48 (1 H, dd), 2.98 (2 H, t)

MW (calcd): 411.4; MW (obsd): 412.4 (M+1)

General Method G:

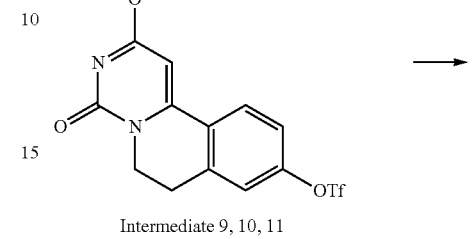

Intermediate 9, 10, 11

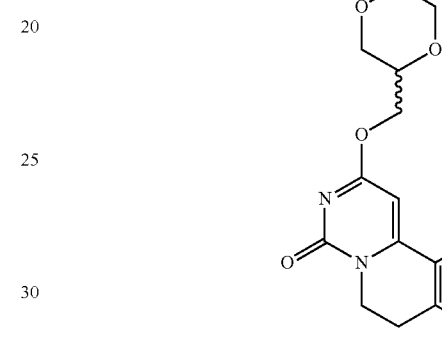

Intermediate 9, 10, 11 (1 eq.) is dissolved in DMF, the appropriate alkyne (3 eq.) is added followed by TEA (3.5 eq.), and the mixture is degassed. Pd(PPh₃)₃Cl₂ (0.05 eq.) is added with CuI (0.2 eq.) and the reaction mixture is heated at 80° C. When the reaction is gone to completion, it is cooled to RT and either worked up or volatiles are evaporated to dryness. The product is then obtained after purification by either flash chromatography on silica gel, preparative TLC or preparative HPLC-MS.

Illustrative Synthesis of General Method G:

Compound 16: 2-([1,4]dioxan-2-ylmethoxy)-9-(1-methyl-1H-imidazol-2-ylethynyl)-6,7-dihydro-pyrimido[6,1-a]isoquinolin-4-one

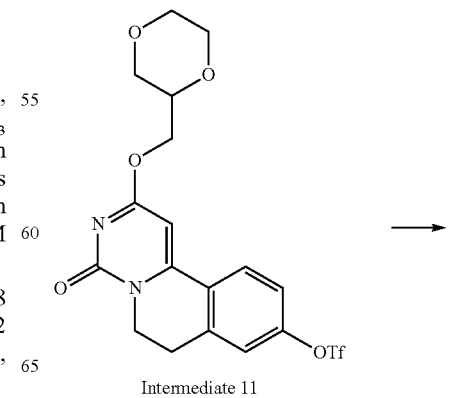

Intermediate 11

77
-continued

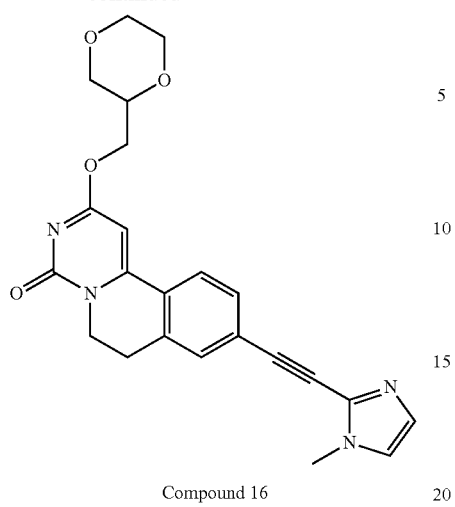

Compound 16

Intermediate 11 (1.4 g, 3.03 mmol, 1 eq.) was dissolved in DMF (20 mL), 5-ethynyl-1-methyl-1H-imidazole (0.92 mL, 9.09 mmol, 3 eq.) was added followed by TEA (1.48 mL, 10.61 mmol, 3.5 eq.). The mixture was degassed and Pd(PPh$_3$)$_3$Cl$_2$ (106 mg, 0.15 mmol, 0.05 eq.) was added with CuI (115 mg, 0.61 mmol, 0.2 eq.). The reaction mixture was heated at 80° C. for 16 h. The reaction was cooled to RT and quenched with brine, the mixture was then extracted with EtOAc. The organic layer was dried over MgSO$_4$ and the solvent was evaporated under vacuum. The crude product was then purified by flash chromatography on silica gel, eluting from 0 to 5% MeOH/DCM to give compound 16.

($^1$H, CDCl$_3$) δ ppm 7.73 (1 H, d), 7.57-7.50 (2 H, m), 7.48-7.45 (1 H, m), 7.42 (1 H, d), 6.42 (1 H, s), 4.53-4.39 (2 H, m), 4.28-4.23 (2 H, m), 4.07-3.97 (1 H, m), 3.94-3.64 (8 H, m), 3.52 (1 H, dd), 3.06 (2 H, t)

MW (calcd): 418.4; MW (obsd): 419.4 (M+1)

General Method H:

78
-continued

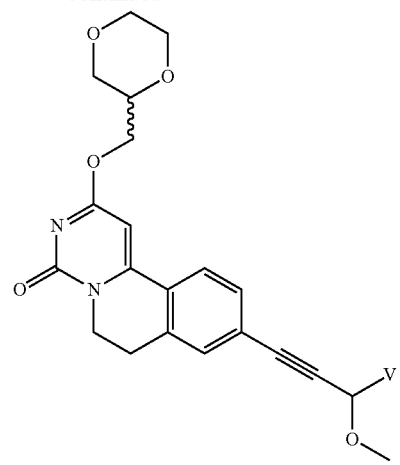

tBuOK (3 eq.) is added to a solution of the corresponding acetylenic alcohol (1 eq.) in THF, MeI (10 eq.) is then added and the reaction is stirred at RT. When the reaction has gone to completion, the reaction mixture is filtered and the filtrate is evaporated to dryness. Product is obtained after purification by preparative TLC.

Illustrative Synthesis of General Method H:

Compound 110: 2-([1,4]dioxan-2-ylmethoxy)-9-(3-methoxy-4-methyl-pent-1-ynyl)-6,7-dihydro-pyrimido[6,1-a]isoquinolin-4-one

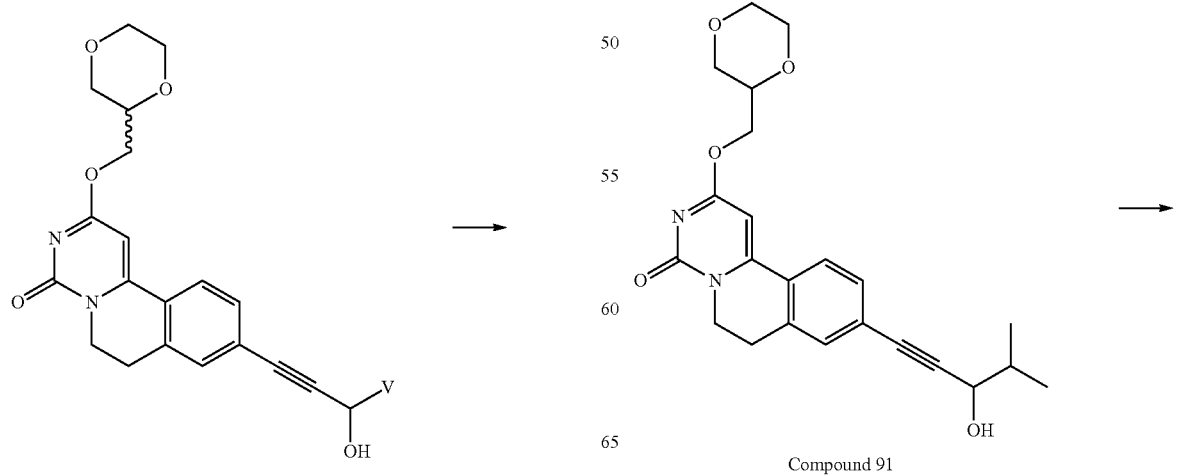

Compound 91

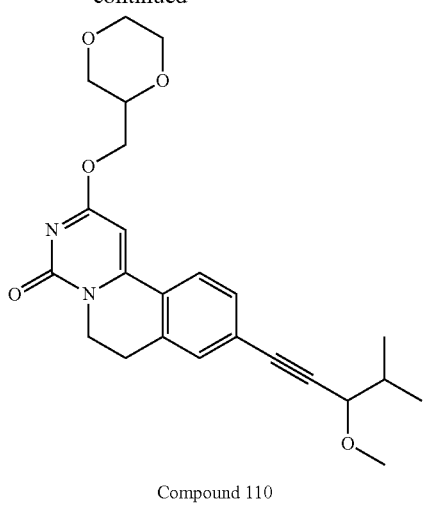

Compound 110 tBuOK (5.19 mg, 0.046 mmol, 0.95 eq.) was added to a solution of compound 90 (20 mg, 0.049 mmol, 1 eq.) in THF (2 mL), MeI (0.030 mL, 0.487 mmol, 10 eq.) was then added and the reaction was stirred at RT for 16 h. Some more tBuOK (11 mg, 0.097 mmol, 2 eq.) was added and the reaction was stirred for an extra day. The reaction mixture was filtered and the filtrate was evaporated to dryness. The crude product was purified by preparative TLC eluting with 2% MeOH/DCM to yield compound 110.

($^1$H, CDCl$_3$) δ ppm 7.70-7.60 (1 H, d), 7.50-7.42 (1 H, d), 7.39 (1 H, s), 6.37 (1 H, s), 4.50-4.35 (2 H, m), 4.25-4.15 (2 H, m), 4.05-3.95 (2 H, m), 3.92-3.60 (5 H, m), 3.56-3.45 (4 H, m), 3.05-3.95 (2 H, m), 2.15-1.95 (1 H, m), 1.15-1 (6 H, t)

MW (calcd): 424.5; MW (obsd): 425.2 (M+1)
General Method I:

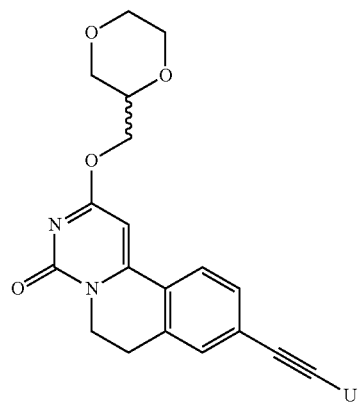

A vial is charged with Pd/C (10% w/w) and a solution of the appropriate alkyne (1 eq.) in MeOH is added. The system is purged with N$_2$ before being filled with H$_2$ then the reaction is stirred at RT until completion. The reaction is filtered through Celite and the filtrate is evaporated to dryness. Clean product is obtained after purification by either flash chromatography on silica gel, preparative TLC or preparative HPLC-MS.

Illustrative Synthesis of General Method I:

Compound 116: 2-([1,4]dioxan-2-ylmethoxy)-9-(3-hydroxy-3-pyridin-3-yl-propyl)-6,7-dihydro-pyrimido[6,1-a]isoquinolin-4-one

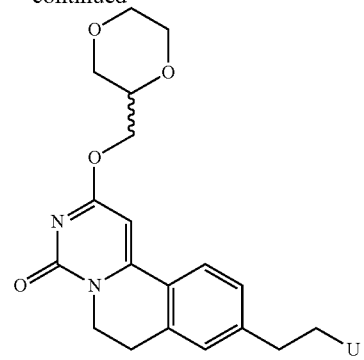

Compound 108

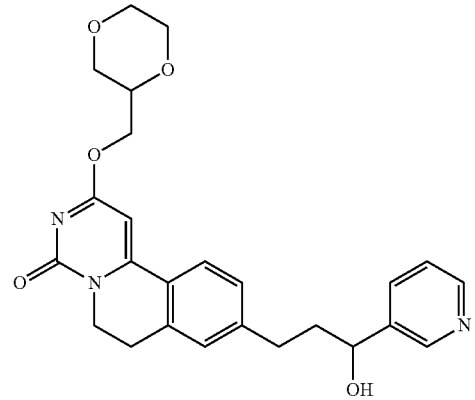

Compound 116

A vial was charged with Pd/C (9 mg, 10% w/w) and a solution of compound 108 (87 mg 0.20 mmol, 1 eq.) in MeOH (10 mL) was added. The system was purged with N₂ before being filled with H₂ then the reaction was stirred for 16 h at RT. The reaction was filtered through Celite and the filtrate was evaporated to dryness. The crude product was purified by preparative HPLC-MS to give compound 116.

($^1$H, CDCl$_3$) δ ppm 8.60-8.48 (2 H, m), 7.73 (1 H, d), 7.61 (1 H, d), 7.30 (1 H, dd), 7.20 (1 H, d), 7.12 (1 H, s), 6.35 (1 H, s), 4.77 (1 H, dd), 4.47-4.33 (2 H, m), 4.18 (2 H, t), 3.97 (1 H, m), 3.90-3.60 (5 H, m), 3.48 (1 H, t), 2.96 (2 H, t), 2.90-2.70 (2 H, m), 2.15 (1 H, m), 2.10-1.98 (1 H, m), 1.38 (1 H, t)

MW (calcd): 449.5; MW (obsd): 450.1 (M+1)

General Method J:

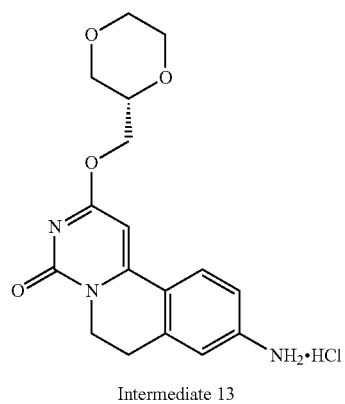

Intermediate 13

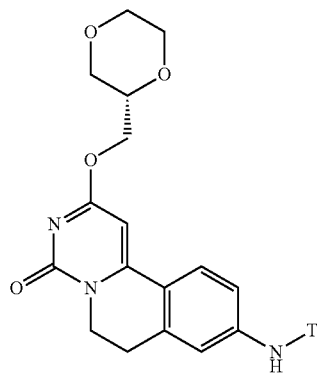

Intermediate 13 (1 eq.) is dissolved in DMF, the appropriate aldehyde (4 eq.) is added followed by KOH (1 eq.). The reaction is stirred for 15 min at RT before STAB (10 eq.) is added, the mixture is then stirred at RT until completion of the reaction. The mixture is then quenched with brine, extracted with EtOAc, the organic layer is dried over MgSO₄ and evaporated to dryness. Purification by preparative HPLC-MS affords the corresponding product.

Illustrative Synthesis of General Method J:

Compound 126: 9-(2,2-dimethyl-butylamino)-2-((S)-1-[1,4]dioxan-2-ylmethoxy)-6,7-dihydro-pyrimido[6,1-a]isoquinolin-4-one

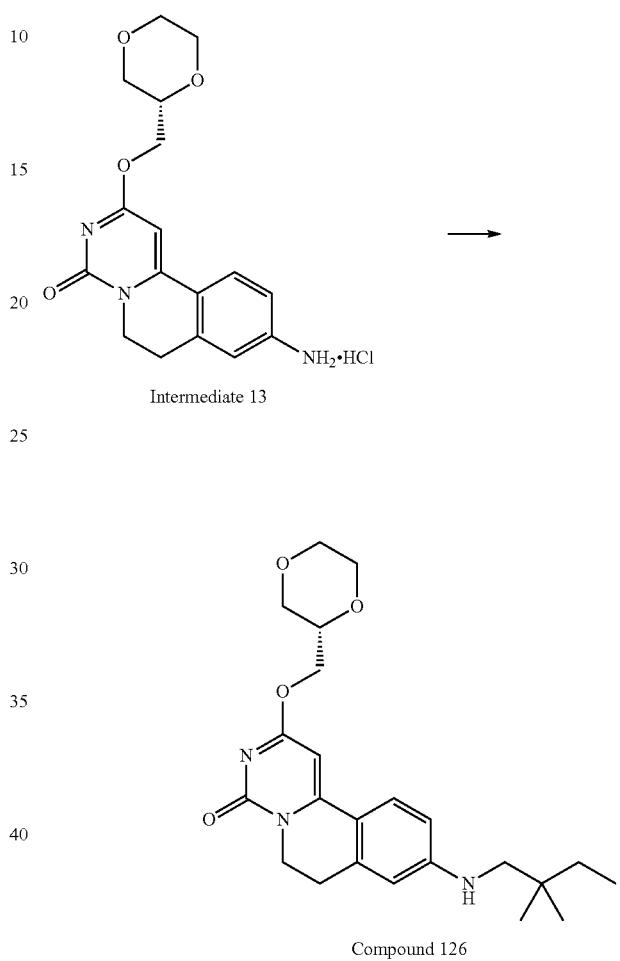

Intermediate 13 (50 mg, 0.14 mmol, 1 eq.) was dissolved in DMF (2 mL), 2,2-dimethylbutanal (56 mg, 0.56 mmol, 4 eq.) was added followed by KOH (8 mg, 0.14 mmol, 1 eq.). The reaction was stirred for 15 min at RT before STAB (297 mg, 1.40 mmol, 10 eq.) was added, the mixture was then stirred for 2 days at RT. The reaction was quenched with brine and the mixture was extracted with EtOAc. The organic layer was dried over MgSO₄ and evaporated to dryness. The crude product was purified by preparative HPLC-MS to give compound 126.

($^1$H, CDCl$_3$) δ ppm 7.50 (1 H, d), 6.63 (1 H, dd), 6.48 (1 H, s), 6.21 (1 H, s), 4.47-4.34 (2 H, m), 4.21-4.14 (2 H, m), 4.01-3.91 (1 H, m), 3.89-3.60 (5 H, m), 3.48 (1 H, dd), 2.98 (2 H, s), 2.90 (2 H, t), 1.36 (2 H, dd), 0.96 (6 H, s), 0.87 (3 H, t)

MW (calcd): 413.5; MW (obsd): 414.4 (M+1)

General Method K:

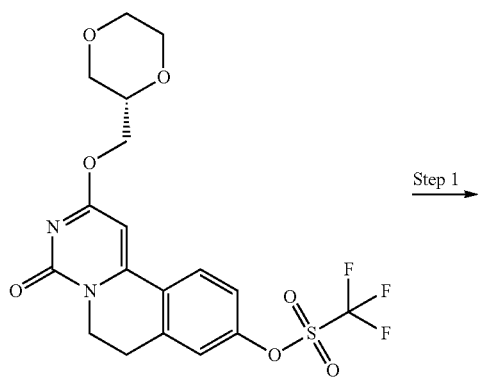

Intermediate 9

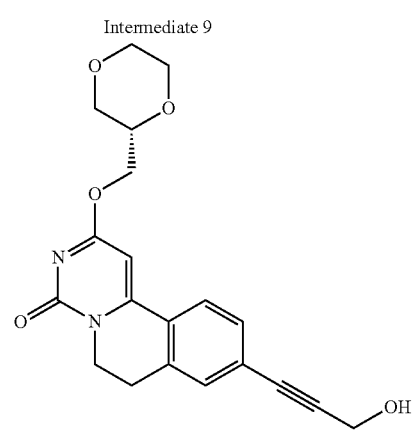

Intermediate 15

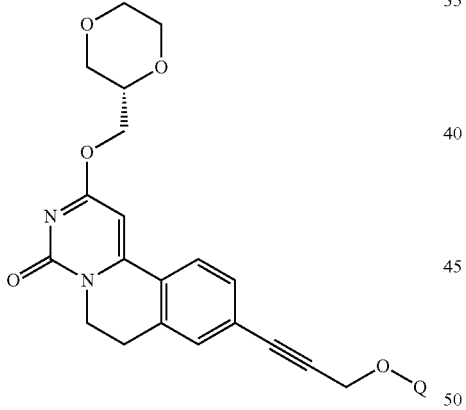

Step 1: 2-((S)-1-[1,4]dioxan-2-ylmethoxy)-9-(3-hydroxy-prop-1-ynyl)-6,7-dihydro-pyrimido[6,1-a]isoquinolin-4-one (Intermediate 15)

Intermediate 15 2-((S)-1-[1,4]dioxan-2-ylmethoxy)-9-(3-hydroxy-prop-1-ynyl)-6,7-dihydro-pyrimido[6,1-a]isoquinolin-4-one was synthesised via general method E with intermediate 9 and prop-2-yn-1-ol.

Step 2

Intermediate 15 (1 eq.) is dissolved in a mixture of THF/DMF (1/1), NaH (1.1 eq., 60% in mineral oil) is added followed by the appropriate alkylating agent (1 eq.) and the reaction is stirred at 70° C. When the reaction has gone to completion, the mixture is worked up with brine and EtOAc, the organic layer is dried over MgSO₄ and evaporated to dryness. Purification by preparative HPLC-MS provides the corresponding product.

Illustrative Synthesis of General Method K:

Compound 133: 2-((S)-1-[1,4]dioxan-2-ylmethoxy)-9-[3-(2-methoxy-ethoxy)-prop-1-ynyl]-6,7-dihydro-pyrimido[6,1-a]isoquinolin-4-one

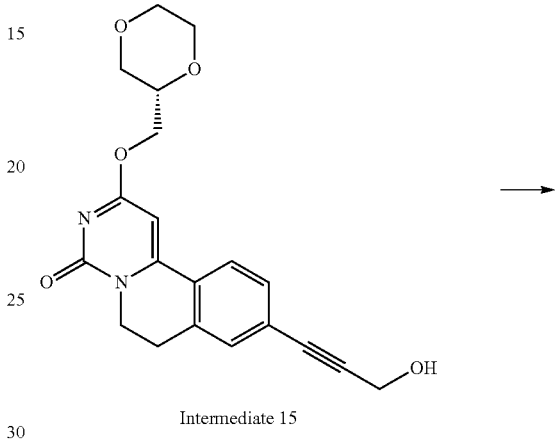

Intermediate 15

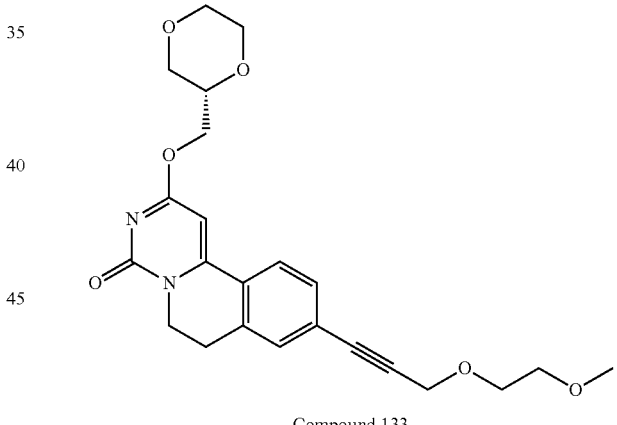

Compound 133

Intermediate 15 (92 mg, 0.25 mmol, 1 eq.) was dissolved in a mixture of THF/DMF (6 mL, 1/1), NaH (11 mg, 0.275 mmol, 1.1 eq., 60% in mineral oil) was added followed by 1-bromo-2-methoxy-ethane (35 mg, 0.25 mmol, 1 eq.) and the reaction was stirred at RT for 16 h, then at 70° C. for 1 day. The mixture was worked up with brine and EtOAc, the organic layer was dried over MgSO₄ and evaporated to dryness. The crude product was purified by preparative HPLC-MS to provide compound 133.

($^1$H, CDCl$_3$) δ ppm 7.64 (1 H, s), 7.48-7.40 (1 H, m), 7.40-7.35 (1 H, m), 6.40-6.34 (1 H, m), 4.47 (4 H, s), 4.28-4.15 (1 H, m), 3.93-3.56 (10 H, m), 3.43 (5 H, s), 3.06-2.95 (2 H, m)

MW (calcd): 426.5; MW (obsd): 427.4 (M+1)

General Method L:

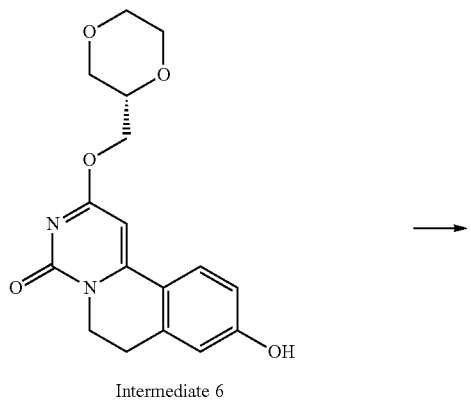

Intermediate 6

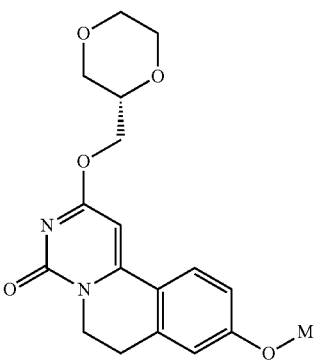

To a solution of tBuOK (2.2 eq.) in DMF is added dropwise a solution of intermediate 6 (1 eq.) in DMF at 0° C. and the mixture is stirred for 1 h. A solution of the appropriate alkylating agent (10 eq.) in DMF is added dropwise to the previous solution at 0° C., then the reaction is stirred at 80° C. When the reaction has gone to completion, the mixture is cooled to RT, quenched with water, and extracted with EtOAc. The combined organic layers are dried over Na$_2$SO$_4$ and evaporated to dryness. The product is isolated by purification by preparative TLC.

Illustrative Synthesis of General Method L:

Compound 158: 9-(2,2-dimethyl-propoxy)-2-((S)-1-[1,4]dioxan-2-ylmethoxy)-6,7-dihydro-pyrimido[6,1-a]isoquinolin-4-one

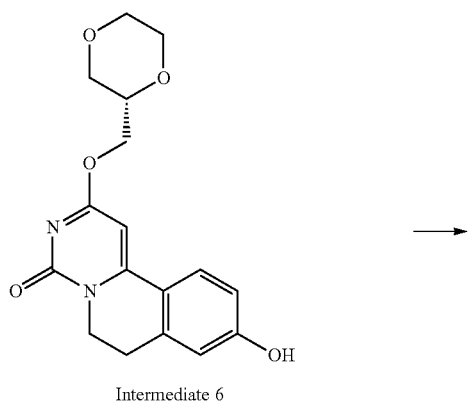

Intermediate 6

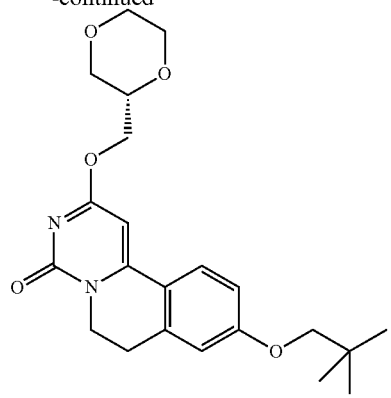

Compound 158

To a solution of tBuOK (19 mg, 0.166 mmol, 1.1 eq.) in DMF (2 mL) was added dropwise a solution of intermediate 6 (50 mg, 0.151 mmol, 1 eq.) in DMF (2 mL) at 0° C. and the mixture was stirred for 1 h. A solution of 1-iodo-2,2-dimethyl-propane (0.021 mL, 0.159 mmol, 1.05 eq.) in DMF (2 mL) was added dropwise to the previous solution at 0° C., then the reaction was stirred at 80° C. for 1 day. Extra reagents were added, 1-iodo-2,2-dimethyl-propane (0.4 mL, 10 eq.) and tBuOK (19 mg, 0.166 mmol, 1.1 eq.) and the reaction was stirred at 80° C. for one more day. The mixture was cooled to RT, quenched with water, and extracted with EtOAc. The combined organic layers were washed with brine, dried over Na$_2$SO$_4$ and evaporated to dryness. Compound 158 was obtained by purification by preparative TLC [DCM/MeOH, 98/2].

($^1$H, CDCl$_3$) δ ppm 7.70-7.56 (1 H, d), 6.95-6.85 (1 H, d), 6.80 (1 H, s), 6.28 (1 H, s), 4.50-4.35 (2 H, m), 4.25-4.10 (2 H, m), 4.05-3.92 (1 H, m), 3.10-3.57 (8 H, m), 3.55-3.40 (1 H, m), 3.05-2.90 (2 H, m), 1.05 (9H, s).

MW (calcd): 400.5; MW (obsd): 401.2 (M+1)

Compounds of the Invention

The compounds according to the invention can be produced as described below.

Compound 1: 9-Allyloxy-2-([1,4]dioxan-2-ylmethoxy)-6,7-dihydro-pyrimido[6,1-a]isoquinolin-4-one Synthesis fully described above.

Compound 2: 2-([1,4]dioxan-2-ylmethoxy)-9-pyridin-3-yl-6,7-dihydro-pyrimido[6,1-a]isoquinolin-4-one Synthesis fully described above.

Compound 3: 2-([1,4]dioxan-2-ylmethoxy)-9-pyridin-4-yl-6,7-dihydro-pyrimido[6,1-a]isoquinolin-4-one This compound is prepared via general method E using intermediate 11 and pyridine-4-boronic acid.

Compound 4: 2-[2-([1,4]dioxan-2-ylmethoxy)-4-oxo-6,7-dihydro-4H-pyrimido[6,1-a]isoquinolin-9-yl]-benzonitrile This compound is prepared via general method E using intermediate 11 and 2-cyanophenylboronic acid.

Compound 5: 3-[2-([1,4]dioxan-2-ylmethoxy)-4-oxo-6,7-dihydro-4H-pyrimido[6,1-a]isoquinolin-9-yl]-benzonitrile This compound is prepared via general method E using intermediate 11 and 3-cyanophenylboronic acid.

Compound 6: 4-[2-([1,4]dioxan-2-ylmethoxy)-4-oxo-6,7-dihydro-4H-pyrimido[6,1-a]isoquinolin-9-yl]-benzonitrile This compound is prepared via general method E using intermediate 11 and 4-cyanophenylboronic acid.

Compound 7: [2-([1,4]dioxan-2-ylmethoxy)-4-oxo-6,7-dihydro-4H-pyrimido[6,1-a]isoquinolin-9-yloxy]-acetonitrile This compound is prepared via general method F using intermediate 8 and bromo-acetonitrile, KI was not used in the experiment.

Compound 8: 2-([1,4]dioxan-2-ylmethoxy)-9-(oxazol-2-ylmethoxy)-6,7-dihydro-pyrimido[6,1-a]isoquinolin-4-one Synthesis fully described above.

Compound 9: 2-([1,4]dioxan-2-ylmethoxy)-9-(pyridin-2-ylmethoxy)-6,7-dihydro-pyrimido[6,1-a]isoquinolin-4-one This compound is prepared via general method F using intermediate 8 and pyridin-2-yl-methanol hydrochloride.

Compound 10: 9-(3,5-dichloro-phenyl)-2-([1,4]dioxan-2-ylmethoxy)-6,7-dihydro-pyrimido[6,1-a]isoquinolin-4-one This compound is prepared via general method E using intermediate 11 and 3,5-dichlorophenylboronic acid.

Compound 11: 9-benzofuran-2-yl-2-([1,4]dioxan-2-ylmethoxy)-6,7-dihydro-pyrimido[6,1-a]isoquinolin-4-one This compound is prepared via general method E using intermediate 11 and 1-benzofuran-2-ylboronic acid.

Compound 12: 2-[2-([1,4]dioxan-2-ylmethoxy)-4-oxo-6,7-dihydro-4H-pyrimido[6,1-a]isoquinolin-9-yl]-indole-1-carboxylic acid tert-butyl ester This compound is prepared via general method E using intermediate 11 and 1-(tert-butoxycarbonyl)-1H-indol-2-yl-boronic acid.

Compound 13: 2-([1,4]dioxan-2-ylmethoxy)-9-(1H-indol-2-yl)-6,7-dihydro-pyrimido[6,1-a]isoquinolin-4-one

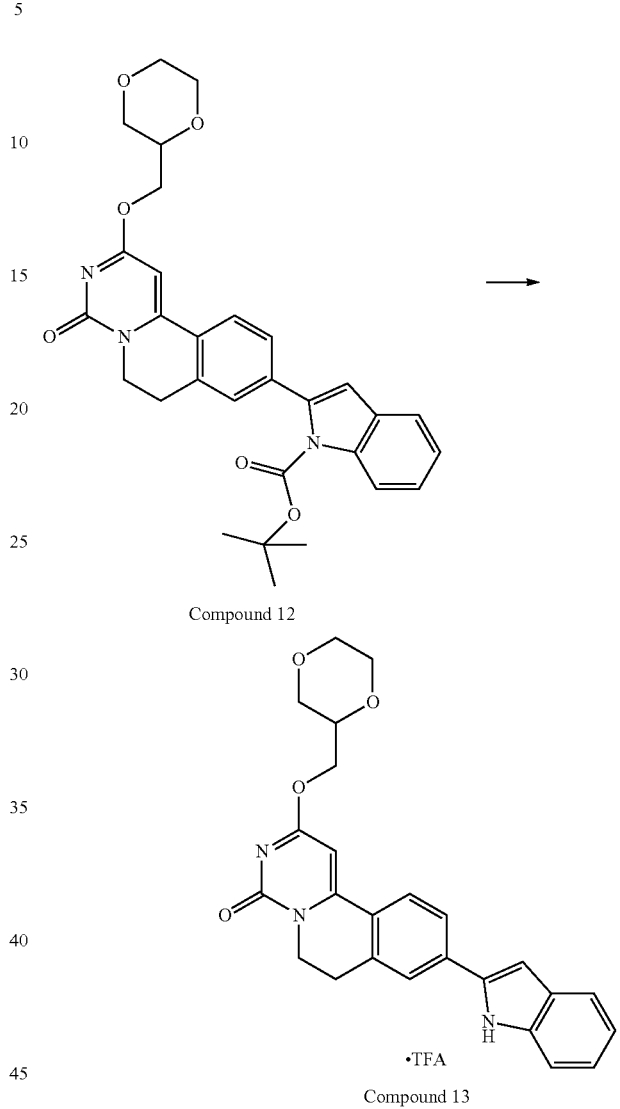

Compound 12

Compound 13

Compound 12 (57 mg, 0.11 mmol) was dissolved in a mixture of DCM/TFA (1/1, 2 mL) and the reaction was stirred at RT for 6 h. The mixture was evaporated to dryness to recover compound 13 as a TFA salt.

($^1$H DMSO-d$_6$) δ ppm 8.11 (1 H, d), 7.95-7.86 (2 H, m), 7.57 (1 H, d), 7.43 (1 H, d), 7.15 (1 H, t), 7.10 (1 H, d), 6.71 (1 H, s), 4.31-4.25 (2 H, m), 4.09 (2 H, t), 3.92-3.84 (1 H, m), 3.79 (2 H, td), 3.71-3.57 (2 H, m), 3.55-3.46 (1 H, m), 3.40 (1 H, dd), 3.08 (2 H, t)

MW (calcd): 429.5 MW (obsd): 430.5 (M+1)

Compound 14: 2-([1,4]dioxan-2-ylmethoxy)-9-(6-methoxy-pyridin-3-yl)-6,7-dihydro-pyrimido[6,1-a]isoquinolin-4-one This compound is prepared via general method E using intermediate 11 and 2-methoxy-5-pyridineboronic acid.

Compound 15: 2-([1,4]dioxan-2-ylmethoxy)-9-(6-trifluoromethyl-pyridin-3-yl)-6,7-dihydro-pyrimido[6,1-a]isoquinolin-4-one This compound is prepared via general method E using intermediate 11 and 2-(trifluoromethyl) pyridine-5-boronic acid.

Compound 16: 2-([1,4]dioxan-2-ylmethoxy)-9-(3-methyl-3H-imidazol-4-ylethynyl)-6,7-dihydro-pyrimido[6,1-a]isoquinolin-4-one Synthesis fully described above.

Compound 17: 9-(5-tert-butyl-[1,2,4]oxadiazol-3-ylmethoxy)-2-([1,4]dioxan-2-ylmethoxy)-6,7-dihydro-pyrimido[6,1-a]isoquinolin-4-one This compound is prepared via general method F using intermediate 8 and 5-(tert-butyl)-3-(chloromethyl)-1,2,4-oxadiazole.

Compound 18: 5-[2-([1,4]dioxan-2-ylmethoxy)-4-oxo-6,7-dihydro-4H-pyrimido[6,1-a]isoquinolin-9-yl]-pyridine-2-carboxylic acid methylamide This compound is prepared via general method E using intermediate 11 and 2-(N-methylaminocarbonyl) pyridine-5-boronic acid pinacol ester.

Compound 19: 2-([1,4]dioxan-2-ylmethoxy)-9-pent-1-ynyl-6,7-dihydro-pyrimido[6,1-a]isoquinolin-4-one This compound is prepared via general method G using intermediate 11 and pent-1-yne.

Compound 20: 2-([1,4]dioxan-2-ylmethoxy)-9-(2-pyridin-2-yl-ethyl)-6,7-dihydro-pyrimido[6,1-a]isoquinolin-4-one

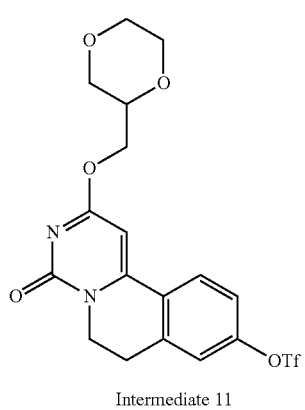

Intermediate 11

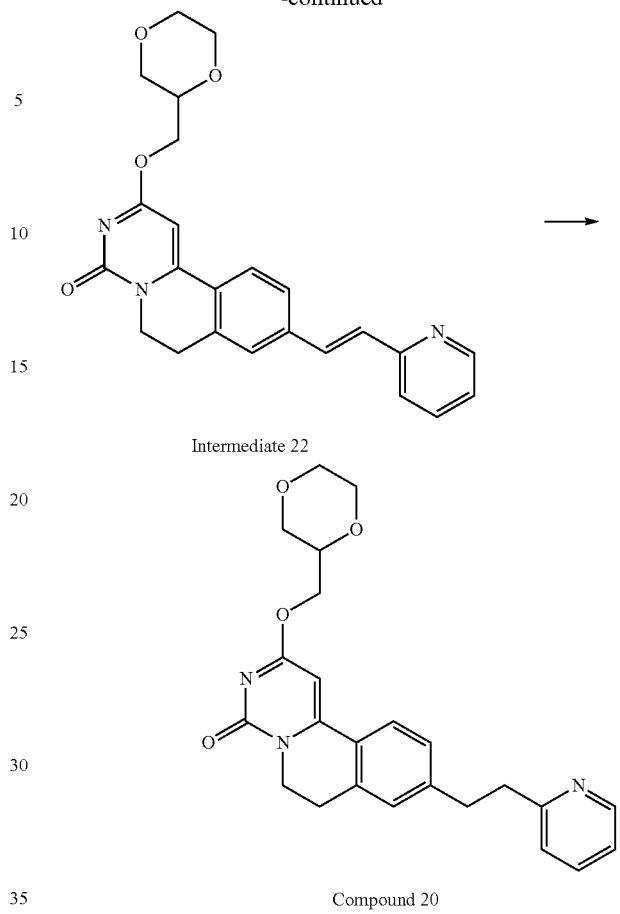

Intermediate 22

Compound 20

Step 1: 2-([1,4]dioxan-2-ylmethoxy)-9-((E)-2-pyridin-2-yl-vinyl)-6,7-dihydro-pyrimido[6,1-a]isoquinolin-4-one (intermediate 22)

A round bottom flask was charged with intermediate 11 (50 mg, 0.11 mmol, 1 eq.), 2-vinyl-pyridine (0.014 mL, 0.13 mmol, 1.2 eq.), (DPPF)PdCl$_2$.DCM (4.4 mg, 0.0054 mmol, 0.05 eq.) and TEA (0.03 mL, 0.22 mmol, 2 eq.) under N$_2$ then the flask was degassed. DMF (2 mL) was then added and the reaction was stirred at 100° C. for 16 h. The reaction was cooled to RT and evaporated to dryness, the residue was then purified by flash chromatography on silica gel, eluting from 0 to 3% MeOH/DCM affording intermediate 22 2-([1,4]dioxan-2-ylmethoxy)-9-((E)-2-pyridin-2-yl-vinyl)-6,7-dihydro-pyrimido[6,1-a]isoquinolin-4-one.

($^1$H, CDCl$_3$) δ ppm 8.66-8.59 (1 H, m), 7.74-7.53 (4 H, m), 7.46 (1 H, s), 7.39 (1 H, d), 7.30-7.15 (2 H, m), 6.37 (1 H, s), 4.48-4.34 (2 H, m), 4.21 (2 H, t), 4.02-3.93 (1 H, m), 3.89-3.59 (5 H, m), 3.53-3.42 (1 H, m), 3.03 (2 H, m)

MW (calcd): 417.5; MW (obsd): 418.4 (M+1)

Step 2: 2-([1,4]dioxan-2-ylmethoxy)-9-(2-pyridin-2-yl-ethyl)-6,7-dihydro-pyrimido[6,1-a]isoquinolin-4-one (Compound 20)

A round bottom flask was charged with intermediate 22 (45 mg, 0.11 mmol, 1 eq.), PtO$_2$ (6 mg, 0.025 mmol, 0.23 eq.) and THF (2 mL) was added. The system was purged with N$_2$ before being filled with H$_2$ then the reaction was stirred for 16 h at RT. The reaction mixture was filtered through a SPE guanidine cartridge and the solvent was evaporated to dryness. The crude product was purified by flash chromatography on silica gel, eluting from 1 to 10% MeOH/DCM to give compound 20.

($^1$H, CDCl$_3$) δ ppm 8.58 (1 H, dd), 7.66-7.56 (2 H, m), 7.22 (1 H, dd), 7.19-7.09 (3 H, m), 6.36 (1 H, s), 4.50-4.36 (2 H, m), 4.25-4.17 (2 H, m), 4.04-3.95 (1 H, m), 3.91-3.62 (5 H, m), 3.50 (1 H, dd), 3.14 (4 H, s), 2.98 (2 H, t)

MW (calcd): 419.5; MW (obsd): 420.5 (M+1)

Compound 21: 2-([1,4]dioxan-2-ylmethoxy)-9-(2-pyrazin-2-yl-ethyl)-6,7-dihydro-pyrimido[6,1-a]isoquinolin-4-one

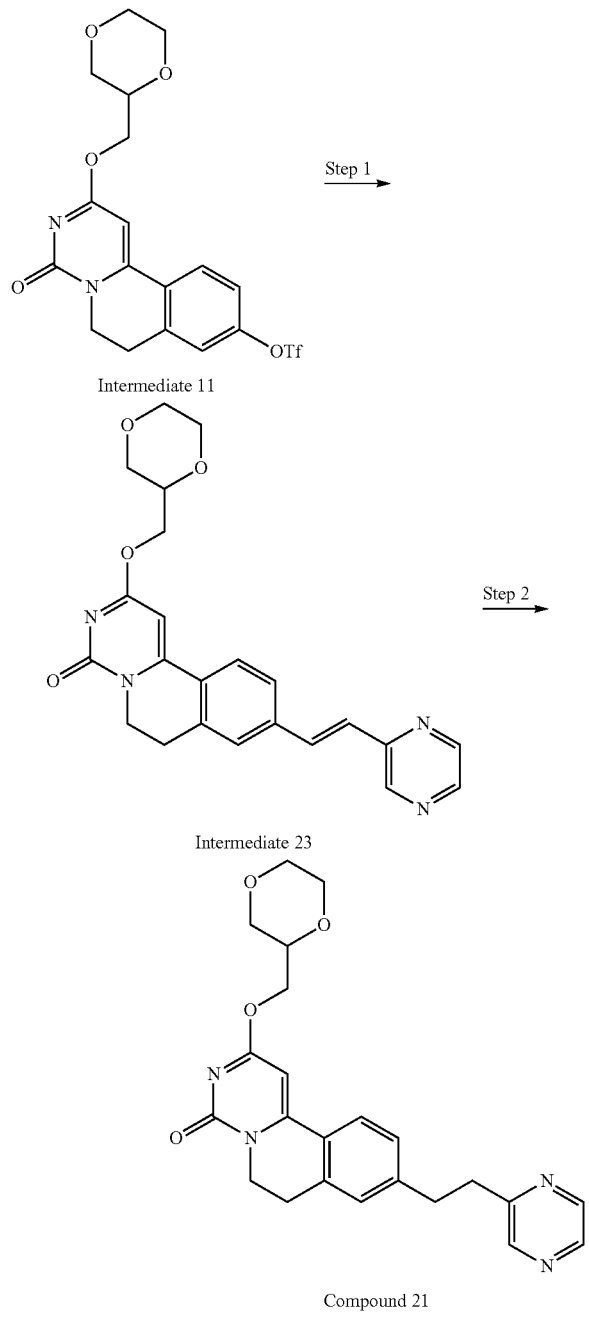

Step 1: 2-([1,4]dioxan-2-ylmethoxy)-9-((E)-2-pyrazin-2-yl-vinyl)-6,7-dihydro-pyrimido[6,1-a]isoquinolin-4-one (intermediate 23)

A round bottom flask was charged with intermediate 11 (50 mg, 0.11 mmol, 1 eq.), 2-vinyl-pyridine (0.014 mL, 0.13 mmol, 1.2 eq.), (DPPF)PdCl$_2$.DCM (4.4 mg, 0.0054 mmol, 0.05 eq.) and TEA (0.03 mL, 0.22 mmol, 2 eq.) under N$_2$ then the flask was degassed. DMF (2 mL) was then added and the reaction was stirred at 100° C. for 16 h. The reaction was cooled to RT and evaporated to dryness, the residue was then purified by flash chromatography on silica gel, eluting from 0 to 4% MeOH/DCM affording intermediate 23 2-([1,4]dioxan-2-ylmethoxy)-9-((E)-2-pyrazin-2-yl-vinyl)-6,7-dihydro-pyrimido[6,1-a]isoquinolin-4-one.

($^1$H, CDCl$_3$) δ ppm 8.69 (1 H, m), 8.63-8.58 (1 H, m), 8.49 (1 H, m), 7.84-7.71 (2 H, m), 7.63 (1 H, d), 7.53 (1 H, s), 7.31 (1 H, s), 6.42 (1 H, s), 4.52-4.39 (2 H, m), 4.30-4.22 (2 H, m), 4.02 (1 H, dd), 3.93-3.63 (5 H, m), 3.52 (1 H, dd), 3.08 (2 H, m)

MW (calcd): 418.5; MW (obsd): 419.4 (M+1)

Step 2: 2-([1,4]dioxan-2-ylmethoxy)-9-(2-pyrazin-2-yl-ethyl)-6,7-dihydro-pyrimido[6,1-a]isoquinolin-4-one (Compound 21)

A round bottom flask was charged with intermediate 23 (38 mg, 0.09 mmol, 1 eq.), PtO$_2$ (5 mg, 0.021 mmol, 0.23 eq.) and THF (2 mL) was added. The system was purged with N$_2$ before being filled with H$_2$ then the reaction was stirred for 16 h at RT. The reaction mixture was filtered through a SPE guanidine cartridge and the solvent was evaporated to dryness. The crude product was purified by flash chromatography on silica gel, eluting from 1 to 10% MeOH/DCM to give compound 21.

($^1$H, CDCl$_3$) δ ppm 8.55 (1 H, dd), 8.44 (2 H, dd), 7.63 (1 H, d), 7.22 (1 H, dd), 7.15 (1 H, s), 6.36 (1 H, s), 4.36-4.53 (2 H, m), 4.17-4.26 (2 H, m), 3.95-4.07 (1 H, m), 3.61-3.93 (5 H, m), 3.51 (1 H, dd), 3.17 (4 H, s), 2.99 (2 H, t)

MW (calcd): 420.5; MW (obsd): 421.5 (M+1)

Compound 22: 2-([1,4]dioxan-2-ylmethoxy)-9-(1H-indol-5-yl)-6,7-dihydro-pyrimido[6,1-a]isoquinolin-4-one This compound is prepared via general method E intermediate 11 and using 5-indolylboronic acid.

Compound 23: 2-([1,4]dioxan-2-ylmethoxy)-9-(2-methoxy-phenyl)-6,7-dihydro-pyrimido[6,1-a]isoquinolin-4-one This compound is prepared via general method E using intermediate 11 and 2-methoxyphenylboronic acid.

Compound 24: 2-([1,4]dioxan-2-ylmethoxy)-9-(5-methoxy-pyridin-3-yl)-6,7-dihydro-pyrimido[6,1-a]isoquinolin-4-one This compound is prepared via general method E using intermediate 11 and 3-methoxy-5-pyridineboronic acid pinacol ester.

Compound 25: 2-([1,4]dioxan-2-ylmethoxy)-9-(1H-indazol-5-yl)-6,7-dihydro-pyrimido[6,1-a]isoquinolin-4-one This compound is prepared via general method E using intermediate 11 and 1H-indazole-5-boronic acid.

Compound 26: 2-([1,4]dioxan-2-ylmethoxy)-9-(4-methoxy-phenyl)-6,7-dihydro-pyrimido[6,1-a]isoquinolin-4-one This compound is prepared via general method E using intermediate 11 and 4-methoxyphenylboronic acid.

Compound 27: 3-[2-([1,4]dioxan-2-ylmethoxy)-4-oxo-6,7-dihydro-4H-pyrimido[6,1-a]isoquinolin-9-yl]-benzamide This compound is prepared via general method E using intermediate 11 and 3-aminocarbonyphenylboronic acid.

Compound 28: 5-[2-([1,4]dioxan-2-ylmethoxy)-4-oxo-6,7-dihydro-4H-pyrimido[6,1-a]isoquinolin-9-yl]-2-fluoro-benzamide This compound is prepared via general method E using intermediate 11 and 3-(aminocarbonyl)-4-fluorobenzeneboronic acid.

Compound 29: N-{3-[2-([1,4]dioxan-2-ylmethoxy)-4-oxo-6,7-dihydro-4H-pyrimido[6,1-a]isoquinolin-9-yl]-phenyl}-acetamide This compound is prepared via general method E intermediate 11 and using 3-acetamidophenylboronic acid.

Compound 30: 9-cyclopropylethynyl-2-([1,4]dioxan-2-ylmethoxy)-6,7-dihydro-pyrimido[6,1-a]isoquinolin-4-one This compound is prepared via general method G intermediate 11 and using ethynyl-cyclopropane.

Compound 31: 2-([1,4]dioxan-2-ylmethoxy)-9-(1-hydroxy-cyclopentylethynyl)-6,7-dihydro-pyrimido[6,1-a]isoquinolin-4-one This compound is prepared via general method G intermediate 11 and using 1-ethynyl-cyclopentanol.

Compound 32: 2-([1,4]dioxan-2-ylmethoxy)-9-pyrimidin-5-yl-6,7-dihydro-pyrimido[6,1-a]isoquinolin-4-one This compound is prepared via general method E intermediate 11 and using 5-pyrimidinylboronic acid.

Compound 33: 9-cyclohex-1-enyl-2-([1,4]dioxan-2-ylmethoxy)-6,7-dihydro-pyrimido[6,1-a]isoquinolin-4-one This compound is prepared via general method E using intermediate 11 and cyclohexene-1-boronic acid pinacol ester.

Compound 34: 2-([1,4]dioxan-2-ylmethoxy)-9-(1-methyl-1H-indol-5-yl)-6,7-dihydro-pyrimido[6,1-a]isoquinolin-4-one This compound is prepared via general method E using intermediate 11 and 1-methylindole-5-boronic acid pinacol ester.

Compound 35: 2-([1,4]dioxan-2-ylmethoxy)-9-(6-methyl-pyridin-3-yl)-6,7-dihydro-pyrimido[6,1-a]isoquinolin-4-one This compound is prepared via general method E using intermediate 11 and 6-methylpyridin-3-ylboronic acid.

Compound 36: 2-([1,4]dioxan-2-ylmethoxy)-9-pyridin-2-ylethynyl-6,7-dihydro-pyrimido[6,1-a]isoquinolin-4-one This compound is prepared via general method G using intermediate 11 and 2-ethynyl-pyridine.

Compound 37: 2-([1,4]dioxan-2-ylmethoxy)-9-(3-methoxy-prop-1-ynyl)-6,7-dihydro-pyrimido[6,1-a]isoquinolin-4-one This compound is prepared via general method G using intermediate 11 and 3-methoxy-propyne.

Compound 38: 5-[2-([1,4]dioxan-2-ylmethoxy)-4-oxo-6,7-dihydro-4H-pyrimido[6,1-a]isoquinolin-9-yl]-pent-4-ynenitrile This compound is prepared via general method G using intermediate 11 and pent-4-ynenitrile.

Compound 39: 2-([1,4]dioxan-2-ylmethoxy)-9-(3-hydroxy-prop-1-ynyl)-6,7-dihydro-pyrimido[6,1-a]isoquinolin-4-one This compound is prepared via general method G using intermediate 11 and prop-2-yn-1-ol.

Compound 40: 2-([1,4]dioxan-2-ylmethoxy)-9-(4-methoxy)-9-(4-methoxy-phenylethynyl)-6,7-dihydro-pyrimido[6,1-a]isoquinolin-4-one This compound is prepared via general method G using intermediate 11 and 1-ethynyl-4-methoxy-benzene.

Compound 41: 2-([1,4]dioxan-2-ylmethoxy)-9-pyridin-3-ylethynyl-6,7-dihydro-pyrimido[6,1-a]isoquinolin-4-one This compound is prepared via general method G using intermediate 11 and 3-ethynyl-pyridine Compound 42: 4-[2-([1,4]dioxan-2-ylmethoxy)-4-oxo-6,7-dihydro-4H-pyrimido[6,1-a]isoquinolin-9-yl]-N-methyl-benzamide This compound is prepared via general method E using intermediate 11 and 4-(N-methylaminocarbonyl)phenylboronic acid.

Compound 43: 2-([1,4]dioxan-2-ylmethoxy)-9-(3-methoxy-phenyl)-6,7-dihydro-pyrimido[6,1-a]isoquinolin-4-one This compound is prepared via general method E using intermediate 11 and 3-methoxyphenylboronic acid.

Compound 44: 9-(2-chloro-phenyl)-2-([1,4]dioxan-2-ylmethoxy)-6,7-dihydro-pyrimido[6,1-a]isoquinolin-4-one This compound is prepared via general method E using intermediate 11 and 2-chlorophenylboronic acid.

Compound 45: 2-([1,4]dioxan-2-ylmethoxy)-9-(4-hydroxy-but-1-ynyl)-6,7-dihydro-pyrimido[6,1-a]isoquinolin-4-one This compound is prepared via general method G using intermediate 11 and but-3-yn-1-ol.

Compound 46: 9-(1,5-dimethyl-1H-pyrazol-3-yl-methoxy)-2-([1,4]dioxan-2-ylmethoxy)-6,7-dihydro-pyrimido[6,1-a]isoquinolin-4-one This compound is prepared via general method F using intermediate 8 and 3-chloromethyl-1,5-dimethyl-1H-pyrazole.

Compound 47: 2-([1,4]dioxan-2-ylmethoxy)-9-(1-methyl-1H-pyrazol-3-ylmethoxy)-6,7-dihydro-pyrimido[6,1-a]isoquinolin-4-one This compound is prepared via general method F using intermediate 8 and 3-chloromethyl-1-methyl-1H-pyrazole.

Compound 48: 2-([1,4]dioxan-2-ylmethoxy)-9-(3-methyl-[1,2,4]oxadiazol-5-ylmethoxy)-6,7-dihydro-pyrimido[6,1-a]isoquinolin-4-one This compound is prepared via general method F using intermediate 8 and 5-chloromethyl-3-methyl-[1,2,4]oxadiazole.

Compound 49: 2-([1,4]dioxan-2-ylmethoxy)-9-(4-morpholin-4-yl-phenyl)-6,7-dihydro-pyrimido[6,1-a]isoquinolin-4-one This compound is prepared via general method E using intermediate 11 and 4-morpholinophenylboronic acid, with CsF as base and DMF as solvent.

Compound 50: 3-[2-([1,4]dioxan-2-ylmethoxy)-4-oxo-6,7-dihydro-4H-pyrimido[6,1-a]isoquinolin-9-yl]-4-fluoro-benzamide This compound is prepared via general method E using intermediate 11 and 5-carbamoyl-2-fluorobenzeneboronic acid, with CsF as base and DMF as solvent.

Compound 51: 3-[2-([1,4]dioxan-2-ylmethoxy)-4-oxo-6,7-dihydro-4H-pyrimido[6,1-a]isoquinolin-9-yl]-5-fluoro-benzamide This compound is prepared via general method E using intermediate 11 and 3-(aminocarbonyl)-5-fluorobenzeneboronic acid, with CsF as base and DMF as solvent.

Compound 52: 9-(3,3-Dimethyl-but-1-ynyl)-2-([1,4]dioxan-2-ylmethoxy)-6,7-dihydro-pyrimido[6,1-a]isoquinolin-4-one This compound is prepared via general method G using intermediate 11 and 3,3-dimethyl-but-1-yne.

Compound 53: 2-([1,4]dioxan-2-ylmethoxy)-9-pyridin-4-ylethynyl-6,7-dihydro-pyrimido[6,1-a]isoquinolin-4-one This compound is prepared via general method G using intermediate 11 and 4-ethynyl-pyridine.

Compound 54: 2-([1,4]dioxan-2-ylmethoxy)-9-(3-methyl-isoxazol-5-ylmethoxy)-6,7-dihydro-pyrimido[6,1-a]isoquinolin-4-one This compound is prepared via general method F using intermediate 8 and 5-chloromethyl-3-methyl-isoxazole.

Compound 55: 2-([1,4]dioxan-2-ylmethoxy)-9-(3-hydroxy-3-methyl-but-1-ynyl)-6,7-dihydro-pyrimido[6,6,1-a]isoquinolin-4-one This compound is prepared via general method G using intermediate 11 and 2-methyl-but-3-yn-2-ol.

Compound 56: 2-([1,4]dioxan-2-ylmethoxy)-9-(2-methoxy-pyridin-3-yl)-6,7-dihydro-pyrimido[6,1-a]isoquinolin-4-one This compound is prepared via general method E using intermediate 11 and 2-methoxy-3-pyridinyl boronic acid.

Compound 57: 2-([1,4]dioxan-2-ylmethoxy)-6,7-dihydro-pyrimido[6,1-a]isoquinolin-4-one This compound is prepared via general method E using intermediate 11 and potassium (cyanomethyl) trifluoroborate.

Compound 58: 9-(3,6-dihydro-2H-pyran-4-yl)-2-([1,4]dioxan-2-ylmethoxy)-6,7-dihydro-pyrimido[6,1-a]isoquinolin-4-one This compound is prepared via general method E using intermediate 11 and 3,6-dihydro-2H-pyran-4-boronic acid pinacol ester.

Compound 59: 5-[2-([1,4]dioxan-2-ylmethoxy)-4-oxo-6,7-dihydro-4H-pyrimido[6,1-a]isoquinolin-9-yl]-pyridine-2-carbonitrile This compound is prepared via general method E using intermediate 11 and 2-cyanopyridine-5-boronic acid pinacol ester.

Compound 60: 2-([1,4]Dioxan-2-ylmethoxy)-9-(6-isopropoxy-pyridin-3-yl)-6,7-dihydro-pyrimido[6,1-a]isoquinolin-4-one This compound is prepared via general method E using intermediate 11 and 6-isopropoxypyridine-3-boronicacid pinacol ester.

Compound 61: 2-([1,4]dioxan-2-ylmethoxy)-9-(6-ethoxy-pyridin-3-yl)-6,7-dihydro-pyrimido[6,1-a]isoquinolin-4-one This compound is prepared via general method E using intermediate 11 and 6-ethoxypyridine-3-boronic acid.

Compound 62: 2-([1,4]dioxan-2-ylmethoxy)-9-(6-morpholin-4-yl-pyridin-3-yl)-6,7-dihydro-pyrimido[6,1-a]isoquinolin-4-one This compound is prepared via general method E using intermediate 11 and 4-[5-(4,4,5,5-tetramethyl-1,3,2-dioxaborolan-2-yl)-2-pyridinyl]morpholine.

Compound 63: 9-(2,3-dimethoxy-phenyl)-2-([1,4]dioxan-2-ylmethoxy)-6,7-dihydro-pyrimido[6,1-a]isoquinolin-4-one This compound is prepared via general method E using intermediate 11 and 2,3-dimethoxyphenylboronic acid.

Compound 64: 9-(3-chloro-2-methoxy-pyridin-4-yl)-2-([1,4]dioxan-2-ylmethoxy)-6,7-dihydro-pyrimido[6,1-a]isoquinolin-4-one This compound is prepared via general method E using intermediate 11 and 3-chloro-2-methoxypyridine-4-boronic acid.

Compound 65: 2-([1,4]dioxan-2-ylmethoxy)-9-(2-methyl-pyridin-4-yl)-6,7-dihydro-pyrimido[6,1-a]isoquinolin-4-one This compound is prepared via general method E using intermediate 11 and 2-methylpyridine-4-boronic acid pinacol ester.

Compound 66: 3-[2-([1,4]dioxan-2-ylmethoxy)-4-oxo-6,7-dihydro-4H-pyrimido[6,1-a]isoquinolin-9-yl]-isonicotinonitrile This compound is prepared via general method E using intermediate 11 and 4-cyanopyridine-3-boronic acid pinacol ester.

Compound 67: 9-(2,5-dimethoxy-phenyl)-2-([1,4]dioxan-2-ylmethoxy)-6,7-dihydro-pyrimido[6,1-a]isoquinolin-4-one This compound is prepared via general method E using intermediate 11 and 2,5-dimethoxyphenylboronic acid.

Compound 68: 2-([1,4]dioxan-2-ylmethoxy)-9-(3,4,5,6-tetrahydro-2H-[1,2']bipyridinyl-5'-yl)-6,7-dihydro-pyrimido[6,1-a]isoquinolin-4-one This compound is prepared via general method E using intermediate 11 and 1-[5-(4,4,5,5-tetramethyl-1,3,2-dioxaborolan-2-yl)-2-pyridinyl]piperidine.

Compound 69: 2-([1,4]dioxan-2-ylmethoxy)-9-(2-ethoxy-pyridin-3-yl)-6,7-dihydro-pyrimido[6,1-a]isoquinolin-4-one This compound is prepared via general method E using intermediate 11 and 2-ethoxypyridine-3-boronic acid.

Compound 70: 9-(2,6-dimethoxy-pyridin-3-yl)-2-([1,4]dioxan-2-ylmethoxy)-6,7-dihydro-pyrimido[6,1-a]isoquinolin-4-one This compound is prepared via general method E using intermediate 11 and 2,6-dimethoxy-3-pyridineboronic acid.

Compound 71: 4-[2-([1,4]dioxan-2-ylmethoxy)-4-oxo-6,7-dihydro-4H-pyrimido[6,1-a]isoquinolin-9-yl]-nicotinonitrile This compound is prepared via general method E using intermediate 11 and 3-cyanopyridine-4-boronic acid, pinacol ester.

Compound 72: 9-tert-butoxymethyl-2-([1,4]dioxan-2-ylmethoxy)-6,7-dihydro-pyrimido[6,1-a]isoquinolin-4-one This compound is prepared via general method E using intermediate 11 and potassium tert-butoxymethyltrifluoroborate.

Compound 73: 2-([1,4]dioxan-2-ylmethoxy)-9-(2-pyrrolidin-1-yl-pyridin-3-yl)-6,7-dihydro-pyrimido[6,1-a]isoquinolin-4-one This compound is prepared via general method E using intermediate 11 and 2-(pyrrolidin-1-yl)-3-(4,4,5,5-tetramethyl-1,3,2-dioxaborolan-2-yl)pyridine.

Compound 74: 2-([1,4]dioxan-2-ylmethoxy)-9-(6-pyrrolidin-1-yl-pyridin-3-yl)-6,7-dihydro-pyrimido[6,1-a]isoquinolin-4-one This compound is prepared via general method E using intermediate 11 and 2-(1-pyrrolidinyl)-5-(4,4,5,5-tetramethyl-1,3,2-dioxaborolan-2-yl)pyridine.

Compound 75: 2-([1,4]dioxan-2-ylmethoxy)-9-(5-phenyl-oxazol-2-ylmethoxy)-6,7-dihydro-pyrimido[6,1-a]isoquinolin-4-one This compound is prepared via general method F using intermediate 8 and 2-chloromethyl-5-phenyl-oxazole.

Compound 76: 9-(5-tert-butyl-oxazol-2-ylmethoxy)-2-([1,4]dioxan-2-ylmethoxy)-6,7-dihydro-pyrimido[6,1-a]isoquinolin-4-one This compound is prepared via general method F using intermediate 8 and 5-tert-butyl-2-chloromethyl-oxazole.

Compound 77: 9-(5-cyclopropyl-[1,2,4]oxadiazol-3-ylmethoxy)-2-([1,4]dioxan-2-ylmethoxy)-6,7-dihydro-pyrimido[6,1-a]isoquinolin-4-one This compound is prepared via general method F using intermediate 8 and 3-chloromethyl-5-cyclopropyl-[1,2,4]oxadiazole.

Compound 78: 2-([1,4]dioxan-2-ylmethoxy)-9-(5-ethyl-[1,2,4]oxadiazol-3-ylmethoxy)-6,7-dihydro-pyrimido[6,1-a]isoquinolin-4-one This compound is prepared via general method F using intermediate 8 and 3-chloromethyl-5-ethyl-[1,2,4]oxadiazole.

Compound 79: 2-([1,4]dioxan-2-ylmethoxy)-9-(5-methyl-[1,2,4]oxadiazol-3-ylmethoxy)-6,7-dihydro-pyrimido[6,1-a]isoquinolin-4-one This compound is prepared via general method F using intermediate 8 and 3-chloromethyl-5-methyl-[1,2,4]oxadiazole.

Compound 80: 2-([1,4]dioxan-2-ylmethoxy)-9-(5-isopropyl-[1,2,4]oxadiazol-3-ylmethoxy)-6,7-dihydro-pyrimido[6,1-a]isoquinolin-4-one This compound is prepared via general method F using intermediate 8 and 3-chloromethyl-5-isopropyl-[1,2,4]oxadiazole.

Compound 81: 9-cyclopentylethynyl-2-([1,4]dioxan-2-ylmethoxy)-6,7-dihydro-pyrimido[6,1-a]isoquinolin-4-one This compound is prepared via general method G using intermediate 11 and ethynyl-cyclopentane.

Compound 82: 9-cyclohexylethynyl-2-([1,4]dioxan-2-ylmethoxy)-6,7-dihydro-pyrimido[6,1-a]isoquinolin-4-one This compound is prepared via general method G using intermediate 11 and ethynyl-cyclohexane.

Compound 83: 2-([1,4]dioxan-2-ylmethoxy)-9-(3-methyl-but-1-ynyl)-6,7-dihydro-pyrimido[6,1-a]isoquinolin-4-one This compound is prepared via general method G using intermediate 11 and 3-methyl-but-1-yne.

Compound 84: 2-([1,4]dioxan-2-ylmethoxy)-9-hex-1-ynyl-6,7-dihydro-pyrimido[6,1-a]isoquinolin-4-one This compound is prepared via general method G using intermediate 11 and hex-1-yne.

Compound 85: 9-[3-(benzyl-methyl-amino)-prop-1-ynyl]-2-([1,4]dioxan-2-ylmethoxy)-6,7-dihydro-pyrimido[6,1-a]isoquinolin-4-one This compound is prepared via general method G using intermediate 11 and benzyl-methyl-prop-2-ynyl-amine.

Compound 86: 2-([1,4]dioxan-2-ylmethoxy)-9-(3-hydroxy-5-methyl-hex-1-ynyl)-6,7-dihydro-pyrimido[6,1-a]isoquinolin-4-one This compound is prepared via general method G using intermediate 11 and 5-methyl-hex-1-yn-3-ol, with iPr$_2$NH as base and THF as solvent.

Compound 87: 2-([1,4]dioxan-2-ylmethoxy)-9-(3-hydroxy-but-1-ynyl)-6,7-dihydro-pyrimido[6,1-a]isoquinolin-4-one This compound is prepared via general method G using intermediate 11 and but-3-yn-2-ol, with iPr$_2$NH as base and THF as solvent.

Compound 88: 9-cyclopropyl-2-([1,4]dioxan-2-ylmethoxy)-6,7-dihydro-pyrimido[6,1-a]isoquinolin-4-one This compound is prepared via general method E using intermediate 11 and potassium cyclopropyltrifluoroborate.

Compound 89: 2-([1,4]dioxan-2-ylmethoxy)-9-(3-hydroxy-pent-1-ynyl)-6,7-dihydro-pyrimido[6,1-a]isoquinolin-4-one This compound is prepared via general method G using intermediate 11 and pent-1-yn-3-ol with iPr$_2$NH as base and THF as solvent.

Compound 90: 2-([1,4]Dioxan-2-ylmethoxy)-9-(3-hydroxy-4-methyl-pent-1-ynyl)-6,7-dihydro-pyrimido[6,1-a]isoquinolin-4-one This compound is prepared via general method G using intermediate 11 and 4-methyl-pent-1-yn-3-ol with iPr$_2$NH as base and THF as solvent.

Compound 91: 2-([1,4]dioxan-2-ylmethoxy)-9-(3-ethyl-3-hydroxy-pent-1-ynyl)-6,7-dihydro-pyrimido[6,1-a]isoquinolin-4-one This compound is prepared via general method G using intermediate 11 and 3-ethyl-pent-1-yn-3-ol with iPr$_2$NH as base and THF as solvent.

Compound 92: 2-([1,4]dioxan-2-ylmethoxy)-9-(3-hydroxy-3-phenyl-but-1-ynyl)-6,7-dihydro-pyrimido[6,1-a]isoquinolin-4-one This compound is prepared via general method G using intermediate 11 and 2-phenyl-but-3-yn-2-ol with Cs$_2$CO$_3$ as base and MeCN as solvent under reflux.

Compound 93: 9-(3-benzylamino-prop-1-ynyl)-2-([1,4]dioxan-2-ylmethoxy)-6,7-dihydro-pyrimido[6,1-a]isoquinolin-4-one This compound is prepared via general method G using intermediate 11 and benzyl-prop-2-ynyl-amine with Cs$_2$CO$_3$ as base and MeCN as solvent under reflux.

Compound 94: 2-([1,4]dioxan-2-ylmethoxy)-9-[(furan-2-ylmethyl)-amino]-6,7-dihydro-pyrimido[6,1-a]isoquinolin-4-one

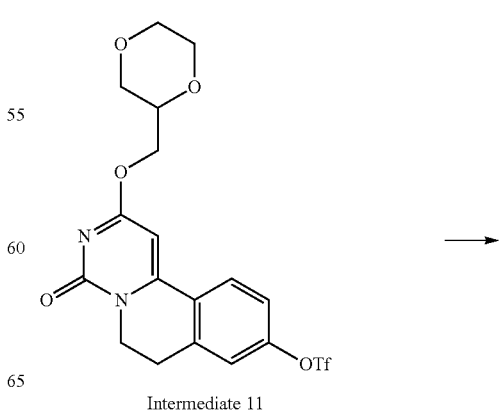

Intermediate 11

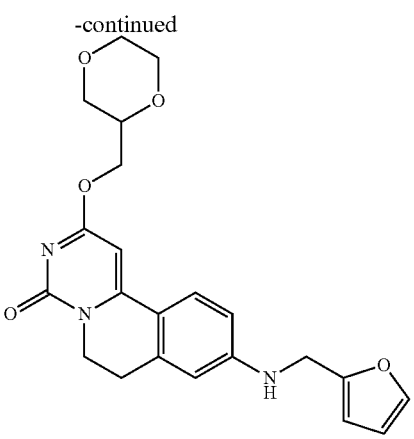

Compound 94

A suspension of intermediate 11 (200 mg, 0.433 mmol, 1 eq.), furan-2-ylmethanamine (0.038 mL, 0.433 mmol, 1 eq.) and Cs$_2$CO$_3$ (0.17 g, 0.519 mmol, 1.2 eq.) in toluene (4 mL) was degassed with Ar for 30 min before BINAP (+/−) (16 mg, 0.026 mmol, 0.06 eq.) and Pd(OAc)$_2$ (3.88 mg, 0.017 mmol, 0.04 eq.) were added. The reaction was heated to 65° C. for 16 h. The reaction was cooled to RT, BINAP (+/−) (16 mg, 0.026 mmol, 0.06 eq.) and Pd(OAc)$_2$ (3.88 mg, 0.017 mmol, 0.04 eq.) were added and the reaction was degassed. The reaction was heated to 80° C. for 1 extra day. The reaction was cooled to RT, BINAP (+/−) (16 mg, 0.026 mmol, 0.06 eq.) and Pd(OAc)$_2$ (3.88 mg, 0.017 mmol, 0.04 eq.) were added and the reaction was degassed.

The reaction was heated to 80° C. for 1 extra day. The reaction was cooled to RT and diluted with DCM and washed with 0.5N aqueous KHSO$_4$. The aqueous layer was extracted with DCM, the combined organic layers were dried over Na$_2$SO$_4$ and evaporated to dryness. The crude product was purified by preparative HPLC-MS [H$_2$O (98→2): MeCN (2→98)/0.1% HCO$_2$H] to give compound 94.

($^1$H, CDCl$_3$) δ ppm 7.57-7.48 (1 H, d), 7.38 (1 H, s), 6.68-6.55 (1 H, d), 6.49 (1 H, s), 6.35 (1 H, s), 6.28 (1 H, s), 6.20 (1 H, s), 4.60-4.50 (1 H, m), 4.38-4.30 (4 H, m), 4.22-4.15 (2 H, m), 4.03-3.93 (1 H, m), 3.95-3.60 (5 H, m), 3.55-3.40 (1 H, t), 2.98-2.85 (2 H, m)

MW (calcd): 409.4; MW (obsd): 410.2 (M+1)

Compound 95: 2-([1,4]dioxan-2-ylmethoxy)-9-(1-ethyl-1H-pyrazol-4-yl)-6,7-dihydro-pyrimido[6,1-a]isoquinolin-4-one This compound is prepared via general method E using intermediate 11 and 1-ethyl-1H-pyrazole-4-boronic acid, pinacol ester.

Compound 96: 2-([1,4]dioxan-2-ylmethoxy)-9-[1-(3-methyl-butyl)-1H-pyrazol-4-yl]-6,7-dihydro-pyrimido[6,1-a]isoquinolin-4-one This compound is prepared via general method E using intermediate 11 and 1-(3-methylbutyl)-1H-pyrazole-4-boronic acid, pinacol ester.

Compound 97: 2-([1,4]dioxan-2-ylmethoxy)-9-(5-methyl-furan-2-yl)-6,7-dihydro-pyrimido[6,1-a]isoquinolin-4-one This compound is prepared via general method E using intermediate 11 and 2-methylfurane-5-boronic acid pinacol ester.

Compound 98: 2-([1,4]dioxan-2-ylmethoxy)-9-(3-hydroxy-hex-1-ynyl)-6,7-dihydro-pyrimido[6,1-a]isoquinolin-4-one This compound is prepared via general method G using intermediate 11 and hex-1-yn-3-ol, Cs$_2$CO$_3$ as base and MeCN as solvent under reflux.

Compound 99: 9-(3,5-dimethyl-1H-pyrazol-4-yl)-2-([1,4]dioxan-2-ylmethoxy)-6,7-dihydro-pyrimido[6,1-a]isoquinolin-4-one This compound is prepared via general method E using intermediate 11 and 3,5-dimethylpyrazole-4-boronic acid pinacol ester.

Compound 100: 2-([1,4]dioxan-2-ylmethoxy)-9-(1H-pyrazol-4-yl)-6,7-dihydro-pyrimido[6,1-a]isoquinolin-4-one This compound is prepared via general method E using intermediate 11 and pyrazole-4-boronic acid pinacol ester.

Compound 101: 2-([1,4]dioxan-2-ylmethoxy)-9-(1-propyl-1H-pyrazol-4-yl)-6,7-dihydro-pyrimido[6,1-a]isoquinolin-4-one This compound is prepared via general method E using intermediate 11 and 1-propyl-1H-pyrazole-4-boronic acid, pinacol ester.

Compound 102: 2-[2-((R)-1-[1,4]dioxan-2-ylmethoxy)-4-oxo-6,7-dihydro-4H-pyrimido[6,1-a]isoquinolin-9-yl]-benzonitrile This compound is prepared via general method E using intermediate 10 and 2-cyanophenylboronic acid pinacol ester.

Compound 103: 2-[2-((S)-1-[1,4]dioxan-2-ylmethoxy)-4-oxo-6,7-dihydro-4H-pyrimido[6,1-a]isoquinolin-9-yl]-benzonitrile This compound is prepared via general method E using intermediate 9 and 2-cyanophenylboronic acid pinacol ester.

Compound 104: 9-(5-cyclopropyl-[1,2,4]oxadiazol-3-ylmethoxy)-2-((R)-1-[1,4]dioxan-2-ylmethoxy)-6,7-dihydro-pyrimido[6,1-a]isoquinolin-4-one This compound is prepared via general method F using intermediate 7 and 3-chloromethyl-5-cyclopropyl-[1,2,4]oxadiazole.

Compound 105: 2-([1,4]dioxan-2-ylmethoxy)-9-ethynyl-6,7-dihydro-pyrimido[6,1-a]isoquinolin-4-one

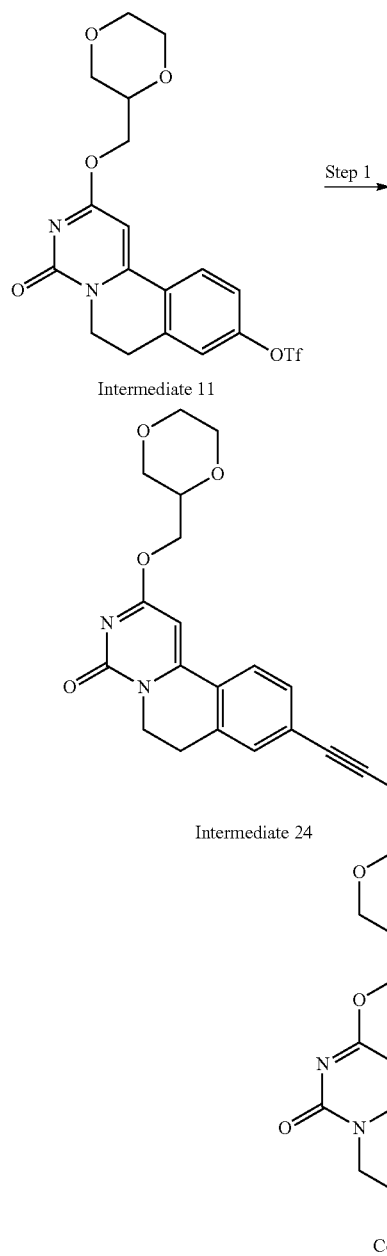

Intermediate 11

Step 1 →

Intermediate 24

Step 2 →

Compound 105

Step 1: 2-([1,4]dioxan-2-ylmethoxy)-9-prop-1-ynyl-6,7-dihydro-pyrimido[6,1-a]isoquinolin-4-one (Intermediate 24)

Intermediate 24 2-([1,4]dioxan-2-ylmethoxy)-9-prop-1-ynyl-6,7-dihydro-pyrimido[6,1-a]isoquinolin-4-one is synthesised via general method E with intermediate 11 and ethynyl-trimethyl-silane.

($^1$H, CDCl$_3$) δ ppm 7.66-7.61 (1 H, m), 7.47-7.43 (1 H, m), 7.42-7.38 (1 H, m), 6.37 (1 H, s), 4.50-4.36 (2 H, m), 4.23-4.16 (2 H, m), 4.04-3.93 (1 H, m), 3.90-3.60 (4H, m), 3.53-3.44 (1 H, m), 3.02-2.97 (1 H, m), 0.27 (7H, s)

MW (calcd): 410.5; MW (obsd): 411.4 (M+1)

Step 2: 2-([1,4]dioxan-2-ylmethoxy)-9-ethynyl-6,7-dihydro-pyrimido[6,1-a]isoquinolin-4-one (Compound 105)

TBAF (4.06 mL, 4.06 mmol, 1.2 eq.) was added dropwise to a solution of intermediate 24 (1.39 g, 3.39 mmol, 1 eq.) in THF (40 mL) at 0° C. and the reaction was stirred for 1 h at 0° C. The reaction was then evaporated to dryness, and the residue was re-dissolved in HCl 1N. The aqueous phase was extracted with DCM, the combined organic layers were dried over MgSO$_4$ and the solvent evaporated under vacuum. The crude product was purified by flash chromatography on silica gel, eluting from 0 to 5% MeOH/DCM to furnish compound 105.

($^1$H, CDCl$_3$) δ ppm 7.65 (1 H, s), 7.51-7.46 (1 H, m), 7.45-7.41 (1 H, m), 6.37 (1 H, s), 4.49-4.36 (2 H, m), 4.21 (2 H, s), 4.04-3.94 (1 H, m), 3.90-3.61 (5 H, m), 3.53-3.44 (1 H, m), 3.25 (1 H, s), 3.00 (2 H, s)

MW (calcd): 330.3; MW (obsd): 331

Compound 106: 2-([1,4]dioxan-2-ylmethoxy)-9-pyrimidin-2-ylethynyl-6,7-dihydro-pyrimido[6,1-a]isoquinolin-4-one

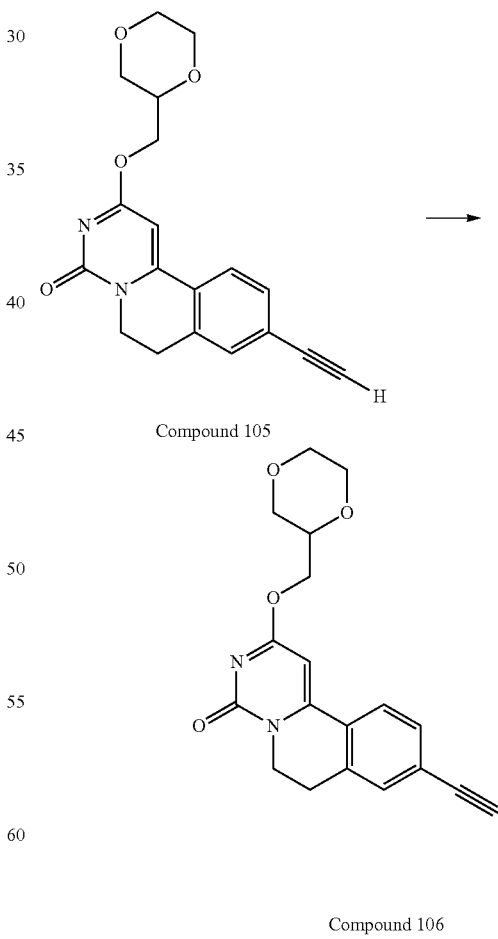

Compound 105

→

Compound 106

Compound 105 (50 mg, 0.15 mmol, 1 eq.) was dissolved in DMF (3 mL), 5-bromo-pyrimidine (47 mg, 0.30 mmol, 2 eq.) was added followed by TEA (0.062 mL, 0.44 mmol, 3 eq.), and the mixture was degassed. Pd(PPh$_3$)$_3$Cl$_2$ (5 mg, 0.0074 mmol, 0.05 eq.) was added with CuI (6 mg, 0.029 mmol, 0.2 eq.) and the reaction mixture was heated at 80° C. for 16 h. The volatiles were evaporated to dryness and the crude product was purified by flash chromatography on silica gel, eluting from 0 to 5% MeOH/DCM to give compound 106.

Compound 107: 2-([1,4]dioxan-2-ylmethoxy)-9-(3-phenylamino-prop-1-ynyl)-6,7-dihydro-pyrimido[6,1-a]isoquinolin-4-one This compound is prepared via general method G using intermediate 11 and phenyl-prop-2-ynyl-amine with iPr$_2$NH as base and THF as solvent.

Compound 108: 2-([1,4]dioxan-2-ylmethoxy)-9-(3-hydroxy-3-pyridin-3-yl-prop-1-ynyl)-6,7-dihydro-pyrimido[6,1-a]isoquinolin-4-one This compound is prepared via general method G using intermediate 11 and 1-pyridin-3-yl-prop-2-yn-1-ol.

Compound 109: 9-cyclopentyloxymethyl-2-([1,4]dioxan-2-ylmethoxy)-6,7-dihydro-pyrimido[6,1-a]isoquinolin-4-one This compound is prepared via general method E using intermediate 11 and potassium cyclopentoxymethyltrifluoroborate.

Compound 110: 2-([1,4]dioxan-2-ylmethoxy)-9-(3-methoxy-4-methyl-pent-1-ynyl)-6,7-dihydro-pyrimido[6,1-a]isoquinolin-4-one Synthesis fully described above.

Compound 111: 9-cyclopropylethynyl-2-((R)-1-[1,4]dioxan-2-ylmethoxy)-6,7-dihydro-pyrimido[6,1-a]isoquinolin-4-one This compound is prepared via general method G using intermediate 10 and ethynyl-cyclopropane.

Compound 112: 2-((S)-1-[1,4]dioxan-2-ylmethoxy)-9-(3-methyl-but-1-ynyl)-6,7-dihydro-pyrimido[6,1-a]isoquinolin-4-one This compound is prepared via general method G using intermediate 9 and 3-methyl-but-1-yne.

Compound 113: 2-([1,4]Dioxan-2-ylmethoxy)-9-(3-imidazol-1-yl-prop-1-ynyl)-6,7-dihydro-pyrimido[6,1-a]isoquinolin-4-one This compound is prepared via general method G using intermediate 11 and 1-prop-2-ynyl-1H-imidazole.

Compound 114: 9-(2-cyclopropyl-ethyl)-2-((R)-1-[1,4]dioxan-2-ylmethoxy)-6,7-dihydro-pyrimido[6,1-a]isoquinolin-4-one

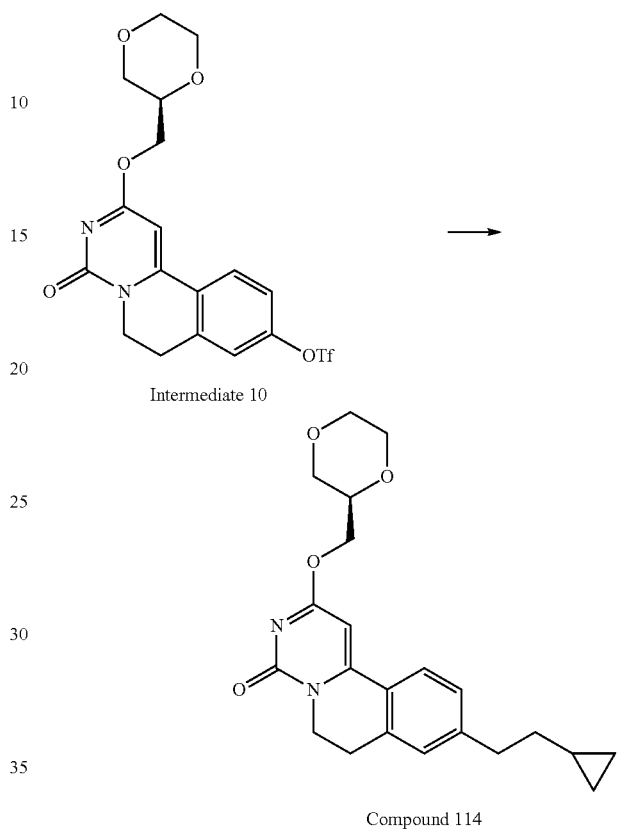

Intermediate 10

Compound 114

A round bottom flask was charged with intermediate 10 (2 g, 4.33 mmol, 1 eq.), intermediate 20 (1.1 g, 6.5 mmol, 1.5 eq.), K$_2$CO$_3$ (1.8 g, 13 mmol, 3 eq.), Pd(OAc)$_2$ (19 mg, 0.087 mmol, 0.02 eq.), RuPhos (81 mg, 0.173 mmol, 0.04 eq.), toluene (30 mL) and H$_2$O (3 mL). The mixture was degassed with N$_2$ and was heated at 80° C. for 16 h. The reaction was cooled to RT, quenched with brine and extracted with EtOAc. The organic layer was dried over MgSO$_4$ and evaporated to dryness. The crude product was purified by flash chromatography on silica gel, eluting from 70 to 90% EtOAc/H to give compound 114.

($^1$H, CDCl$_3$) δ ppm 7.64-7.58 (1 H, m), 7.24-7.19 (1 H, m), 7.13 (1 H, s), 6.35 (1 H, s), 4.49-4.36 (2 H, m), 4.25-4.17 (2 H, m), 4.03-3.95 (1 H, m), 3.90-3.61 (5 H, m), 3.54-3.45 (1 H, m), 3.02-2.95 (2 H, m), 2.81-2.72 (2 H, m), 1.59-1.49 (2 H, m), 0.77-0.64 (1 H, m), 0.49-0.42 (2 H, m), 0.10-0.02 (2 H, m)

MW (calcd): 382.5; MW (obsd): 383.4 (M+1)

Compound 115: 9-cyclopentyloxymethyl-2-((R)-1-[1,4]dioxan-2-ylmethoxy)-6,7-dihydro-pyrimido[6,1-a]isoquinolin-4-one This compound is prepared via general method E using intermediate 10 and potassium cyclopentoxymethyltrifluoroborate.

Compound 116: 2-([1,4]dioxan-2-ylmethoxy)-9-(3-hydroxy-3-pyridin-3-yl-propyl)-6,7-dihydro-pyrimido[6,1-a]isoquinolin-4-one Synthesis fully described above.

Compound 117: 9-allyloxy-2-((R)-1-[1,4]dioxan-2-ylmethoxy)-6,7-dihydro-pyrimido[6,1-a]isoquinolin-4-one Synthesis fully described above.

Compound 118: 9-allyloxy-2-((S)-1-[1,4]dioxan-2-ylmethoxy)-6,7-dihydro-pyrimido[6,1-a]isoquinolin-4-one Synthesis fully described above.

Compound 119: 2-((R)-1-[1,4]dioxan-2-ylmethoxy)-9-(tetrahydro-pyran-4-yloxymethyl)-6,7-dihydro-pyrimido[6,1-a]isoquinolin-4-one This compound is prepared via general method E using intermediate 10 and intermediate 14.

Compound 120: 2-([1,4]dioxan-2-ylmethoxy)-9-{3-[(pyridin-3-ylmethyl)-amino]-prop-1-ynyl}-6,7-dihydro-pyrimido[6,1-a]isoquinolin-4-one This compound is prepared via general method G using intermediate 11 and prop-2-yn-1-yl(pyridin-3-ylmethyl)amine.

Compound 121: 2-((R)-1-[1,4]dioxan-2-ylmethoxy)-9-pentyl-6,7-dihydro-pyrimido[6,1-a]isoquinolin-4-one This Compound is prepared via general method I using compound 111.

Compound 122: 9-cyclopropylethynyl-2-((S)-1-[1,4]dioxan-2-ylmethoxy)-6,7-dihydro-pyrimido[6,1-a]isoquinolin-4-one Intermediate 9 (13.5 g, 29.20 mmol, 1 eq.) was dissolved in degassed DMF (1000 mL) under an nitrogen atmosphere, ethynyl cyclopropane (3.5 g, 53.00 mmol, 1.8 eq.) was added followed by Pd(PPh$_3$)$_3$Cl$_2$ (1.11 g, 1.58 mmol, 0.05 eq.), CuI (1.9 g, 9.98 mmol, 0.34 eq.) and TEA (12.5 mL, 89.7 mmol, 3.1 eq.). The reaction mixture was stirred 3 h at 80° C. and 15 h at room temperature. The reaction was concentrated under vacuum. The crude product was then purified by trituration in hot iPrOH to afford compound 122.

($^1$H, CDCl$_3$) δ ppm 7.63 (1 H, d), 7.39 (1 H, dd), 7.31 (1 H, s), 6.36 (1 H, s), 4.50-4.39 (2 H, m), 4.20 (2 H, t), 4.02-3.98 (1 H, m), 3.89-3.66 (5 H, m), 3.49 (1 H, t), 2.96 (2 H, t), 1.59-1.48 (1 H, m), 0.98-0.81 (4 H, m)
MW (calcd): 378.4; MW (obsd): 379.4
ee=98.3%

Compound 123: 9-(2-cyclopropyl-ethyl)-2-((S)-1-[1,4]dioxan-2-ylmethoxy)-6,7-dihydropyrimido[6,1-a]isoquinolin-4-one

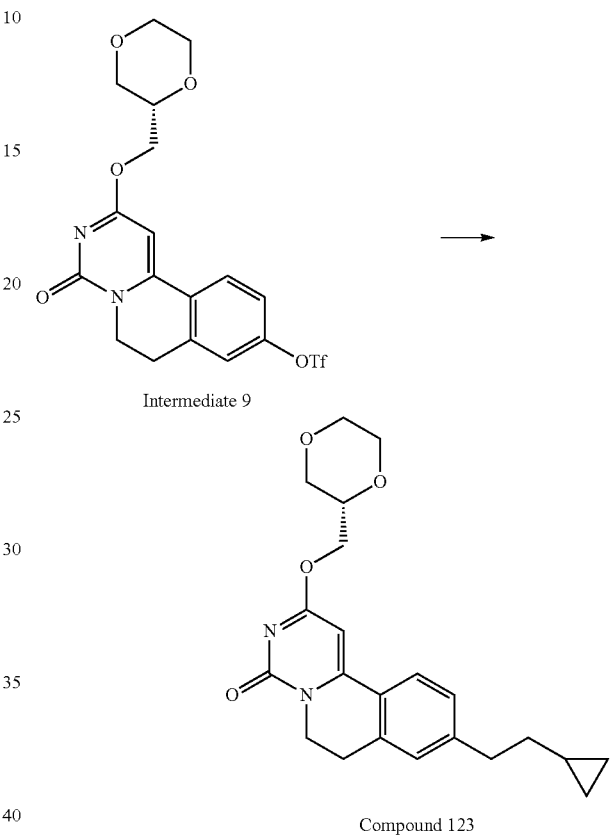

Intermediate 9

Compound 123

A round bottom flask was charged with intermediate 9 (2.08 g, 4.51 mmol, 1 eq.), intermediate 20 (1.35 g, 7.67 mmol, 1.7 eq.), K$_2$CO$_3$ (1.87 g, 13.53 mmol, 3 eq.), Pd(OAc)$_2$ (20 mg, 0.09 mmol, 0.02 eq.), RuPhos (84 mg, 0.18 mmol, 0.04 eq.), toluene (30 mL) and H$_2$O (3 mL). The mixture was degassed with N$_2$ and was heated at 80° C. for 1.5 days. The reaction was cooled to RT and some more reagents were added, potassium 2-cyclopropyl-ethyl-trifluoroborate (0.3 eq.), Pd(OAc)$_2$ (0.02 eq.), RuPhos (0.04 eq.), the reaction was degassed and the reaction was heated at 80° C. for 16 h. The reaction was cooled to RT, quenched with H$_2$O and extracted with EtOAc. The organic layer was dried over MgSO$_4$ and evaporated to dryness. The crude product was purified by flash chromatography on silica gel, eluting from 80 to 90% EtOAc/H to compound 123.

($^1$H, CDCl$_3$) δ ppm 7.64-7.58 (1 H, m), 7.24-7.19 (1 H, m), 7.13 (1 H, s), 6.35 (1 H, s), 4.49-4.36 (2 H, m), 4.24-4.17 (2 H, m), 4.03-3.95 (1 H, m), 3.91-3.62 (5 H, m), 3.49 (1 H, dd), 3.03-2.95 (2 H, m), 2.81-2.73 (2 H, m), 1.59-1.50 (2 H, m), 0.71 (1 H, s), 0.49-0.42 (2 H, m), 0.09-0.03 (2 H, m)
MW (calcd): 382.5; MW (obsd): 383.4

Compound 124: 2-((S)-1-[1,4]dioxan-2-ylmethoxy)-9-(oxetan-3-yloxymethyl)-6,7-dihydro-pyrimido[6,1-a]isoquinolin-4-one This compound is prepared via general method E using intermediate 9 and intermediate 15.

Compound 125: 2-((S)-1-[1,4]dioxan-2-ylmethoxy)-9-(3-methyl-oxetan-3-ylmethoxymethyl)-6,7-dihydro-pyrimido[6,1-a]isoquinolin-4-one This compound is prepared via general method E using intermediate 9 and intermediate 16.

Compound 126: 9-(2,2-dimethyl-butylamino)-2-((S)-1-[1,4]dioxan-2-ylmethoxy)-6,7-dihydro-pyrimido[6,1-a]isoquinolin-4-one Synthesis fully described above.

Compound 127: 2-((S)-1-[1,4]dioxan-2-ylmethoxy)-9-(3-hydroxy-4-methyl-pentyl)-6,7-dihydro-pyrimido[6,1-a]isoquinolin-4-one

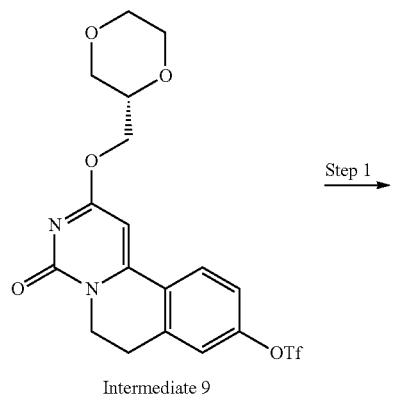

Intermediate 9

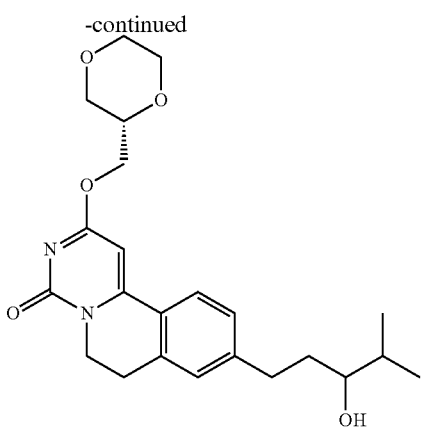

Compound 127

Step 1: 2-((S)-1-[1,4]Dioxan-2-ylmethoxy)-9-(3-hydroxy-4-methyl-pent-1-ynyl)-6,7-dihydro-pyrimido[6,1-a]isoquinolin-4-one (Intermediate 25)

Intermediate 25 is prepared via general method G using intermediate 9, 4-Methyl-pent-1-yn-3-ol, iPr$_2$NH as base and THF as solvent.

($^1$H, CDCl$_3$) ppm 7.65-7.60 (1 H, d), 7.48-7.40 (1 H, m), 7.37 (1 H, s), 6.36 (1 H, s), 4.50-4.30 (3 H, m), 4.25-4.15 (2 H, m), 4.05-3.95 (1 H, m), 3.92-3.60 (6 H, m), 3.68-3.40 (1 H, m), 3.05-2.92 (2 H, m), 2.10-1.95 (1 H, m), 1.93-1.80 (1 H, m), 1.15-1.00 (6 H, m)

MW (calcd): 410.5; MW (obsd): 411.2 (M+1)

Step 2: 2-((S)-1-[1,4]dioxan-2-ylmethoxy)-9-(3-hydroxy-4-methyl-pentyl)-6,7-dihydro-pyrimido[6,1-a]isoquinolin-4-one (Compound 127)

Compound 127 is prepared via general method I using intermediate 25.

Compound 128: 2-((S)-1-[1,4]dioxan-2-ylmethoxy)-9-(2-ethyl-hexylamino)-6,7-dihydro-pyrimido[6,1-a]isoquinolin-4-one This compound is prepared via general method J using intermediate 13 and 2-ethyl-hexanal.

Compound 129: 2-((S)-1-[1,4]dioxan-2-ylmethoxy)-9-(2-methoxy-ethoxy)-6,7-dihydro-pyrimido[6,1-a]isoquinolin-4-one This compound is prepared via general method F using intermediate 6 and 1-bromo-2-methoxy-ethane, KI was not used in this experiment.

Compound 130: 2-((S)-1-[1,4]dioxan-2-ylmethoxy)-9-(2-ethoxy-ethoxy)-6,7-dihydro-pyrimido[6,1-a]isoquinolin-4-one This compound is prepared via general method F using intermediate 6 and 1-bromo-2-ethoxy-ethane, KI was not used in this experiment.

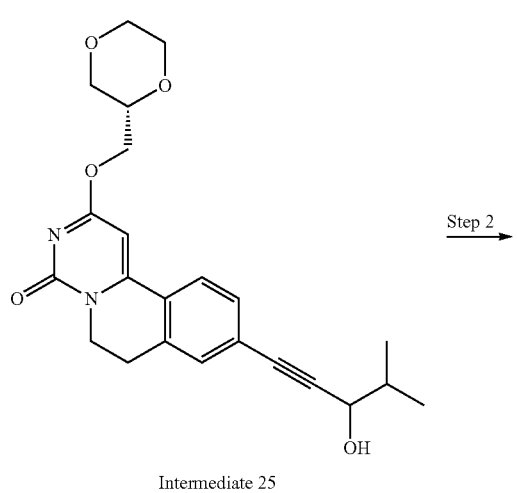

Intermediate 25

Compound 131: 9-cyclopropylmethoxy-2-((S)-1-[1,4]dioxan-2-ylmethoxy)-6,7-dihydro-pyrimido[6,1-a]isoquinolin-4-one This compound is prepared via general method F using intermediate 6 and bromomethyl-cyclopropane, KI was not used in this experiment.

Compound 132: 2-((S)-1-[1,4]dioxan-2-ylmethoxy)-9-(2-fluoro-ethoxy)-6,7-dihydro-pyrimido[6,1-a]isoquinolin-4-one This compound is prepared via general method F using intermediate 6 and 1-bromo-2-fluoro-ethane, KI was not used in this experiment.

Compound 133: 2-((S)-1-[1,4]dioxan-2-ylmethoxy)-9-[3-(2-methoxy-ethoxy)-prop-1-ynyl]-6,7-dihydro-pyrimido[6,1-a]isoquinolin-4-one Synthesis fully described above.

Compound 134: 2-((S)-1-[1,4]dioxan-2-ylmethoxy)-9-[3-(2-ethoxy-ethoxy)-prop-1-ynyl]-6,7-dihydro-pyrimido[6,1-a]isoquinolin-4-one This compound is prepared via general method K using intermediate 21 and 1-bromo-2-ethoxy-ethane.

Compound 135: 2-((S)-1-[1,4]dioxan-2-ylmethoxy)-9-[3-(2-fluoro-ethoxy)-prop-1-ynyl]-6,7-dihydro-pyrimido[6,1-a]isoquinolin-4-one This compound is prepared via general method K using intermediate 21 and 1-bromo-2-fluoro-ethane.

Compound 136: 9-(2,2-dimethyl-propoxymethyl)-2-((S)-1-[1,4]dioxan-2-ylmethoxy)-6,7-dihydro-pyrimido[6,1-a]isoquinolin-4-one This compound is prepared via general method E using intermediate 9, in a mixture of DME/H₂O (2/1), in a microwave at 120° C. for 20 min and intermediate 17.

Compound 137: 9-cyclohexyloxymethyl-2-((S)-1-[1,4]dioxan-2-ylmethoxy)-6,7-dihydro-pyrimido[6,1-a]isoquinolin-4-one This compound is prepared via general method E using intermediate 9 and potassium cyclohexyloxymethyltrifluoroborate in a mixture of DME/H₂O (2/1), in a microwave at 120° C. for 20 min.

Compound 138: 9-cyclopropylmethoxymethyl-2-((S)-1-[1,4]dioxan-2-ylmethoxy)-6,7-dihydro-pyrimido[6,1-a]isoquinolin-4-one This compound is prepared via general method E using intermediate 9, in a mixture of DME/H₂O (2/1), in a microwave at 120° C. for 20 min and intermediate 18.

Compound 139: 2-((S)-1-[1,4]dioxan-2-ylmethoxy)-9-(tetrahydro-pyran-2-ylmethoxy)-6,7-dihydro-pyrimido[6,1-a]isoquinolin-4-one This compound is prepared via general method F using intermediate 6 and 2-bromomethyl-tetrahydro-pyran, KI was not used in this experiment.

Compound 140: 2-((S)-1-[1,4]dioxan-2-ylmethoxy)-9-(3-hydroxy-butyl)-6,7-dihydro-pyrimido[6,1-a]isoquinolin-4-one

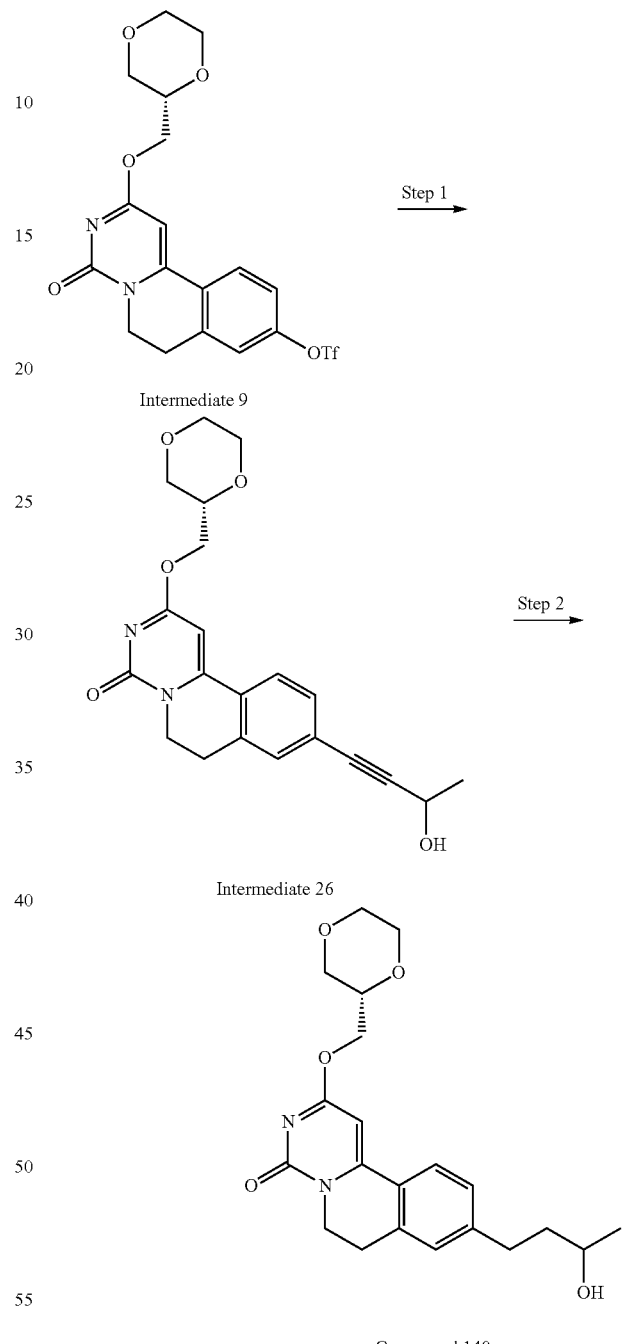

Compound 140

Step 1: 2-((S)-1-[1,4]Dioxan-2-ylmethoxy)-9-(3-hydroxy-but-1-ynyl)-6,7-dihydro-pyrimido[6,1-a]isoquinolin-4-one (Intermediate 26)

Intermediate 26 was prepared via general method G using intermediate 9 and but-3-yn-2-ol, the crude product was used in the next step without characterization.

Step 2: 2-((S)-1-[1,4]dioxan-2-ylmethoxy)-9-(3-hydroxy-butyl)-6,7-dihydro-pyrimido[6,1-a]isoquinolin-4-one (Compound 140)

Compound 140 was prepared via general method I using intermediate 26.

Compound 141: 9-(4,4-dimethyl-pentyloxy)-2-((S)-1-[1,4]dioxan-2-ylmethoxy)-6,7-dihydro-pyrimido[6,1-a]isoquinolin-4-one

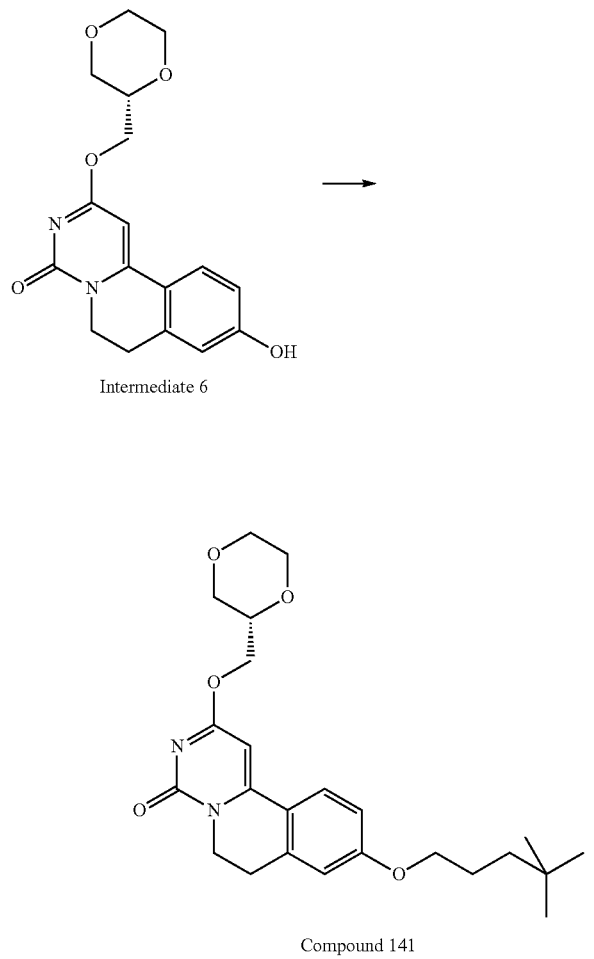

Intermediate 6 (0.1 g, 0.303 mmol, 1 eq.), 4,4-dimethyl-pentan-1-ol (35 mg, 0.303 mmol, 1 eq.) and PPh$_3$ (95 mg, 0.363 mmol, 1.2 eq.) were suspended in 1,4-dioxane (5 mL) and the mixture was degassed with N$_2$. DIAD (0.065 mL, 0.333 mmol, 1.1 eq.) was added dropwise and the reaction was stirred at RT for 2 h. The reaction mixture was evaporated to dryness and the residue was purified by preparative TLC eluting with EtOAc to give compound 141.

($^1$H, CDCl$_3$) δ ppm 7.70-7.58 (1 H, d), 6.95-6.82 (1 H, d), 6.77 (1 H, s), 6.27 (1 H, s), 4.50-4.32 (2 H, m), 4.38-4.15 (2 H, m), 4.05-3.92 (3 H, m), 3.92-3.60 (5 H, m), 3.55-3.42 (1 H, t), 3.05-2.92 (2 H, m), 1.85-1.70 (2 H, m), 1.40-1.30 (2 H, m), 0.92 (9 H, s)

MW (calcd): 428.5; MW (obsd): 429.2 (M+1)

Compound 142: 2-((S)-1-[1,4]dioxan-2-ylmethoxy)-9-(3-methoxy-4-methyl-pentyl)-6,7-dihydro-pyrimido[6,1-a]isoquinolin-4-one

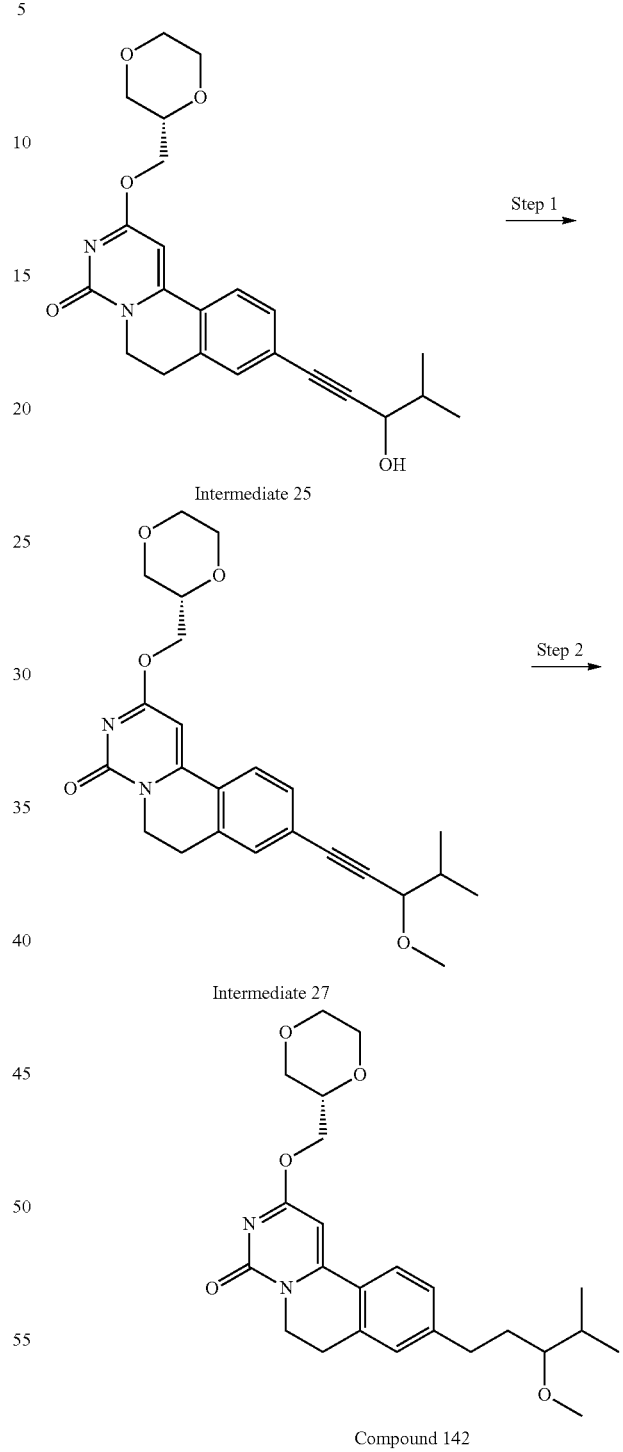

Step 1: 2-((S)-1-[1,4]Dioxan-2-ylmethoxy)-9-(3-methoxy-4-methyl-pent-1-ynyl)-6,7-dihydro-pyrimido[6,1-a]isoquinolin-4-one (Intermediate 27)

Intermediate 27 is prepared via general method H using intermediate 25.

MW (calcd): 424.5; MW (obsd): 425.2 (M+1)

Step 2: 2-((S)-1-[1,4]dioxan-2-ylmethoxy)-9-(3-methoxy-4-methyl-pentyl)-6,7-dihydro-pyrimido[6,1-a]isoquinolin-4-one (Compound 142)

Compound 142 is prepared via general method I using intermediate 27.

Compound 143: 9-(3-cyclopropyl-propoxy)-2-((S)-1-[1,4]dioxan-2-ylmethoxy)-6,7-dihydro-pyrimido[6,1-a]isoquinolin-4-one

Compound 145: 9-cyclohexylamino-2-((S)-1-[1,4]dioxan-2-ylmethoxy)-6,7-dihydro-pyrimido[6,1-a]isoquinolin-4-one This compound is prepared via general method J using intermediate 13 and cyclohexanone.

Compound 146: 2-((S)-1-[1,4]dioxan-2-ylmethoxy)-9-(3-hydroxy-4,4-dimethyl-pentyl)-6,7-dihydro-pyrimido[6,1-a]isoquinolin-4-one

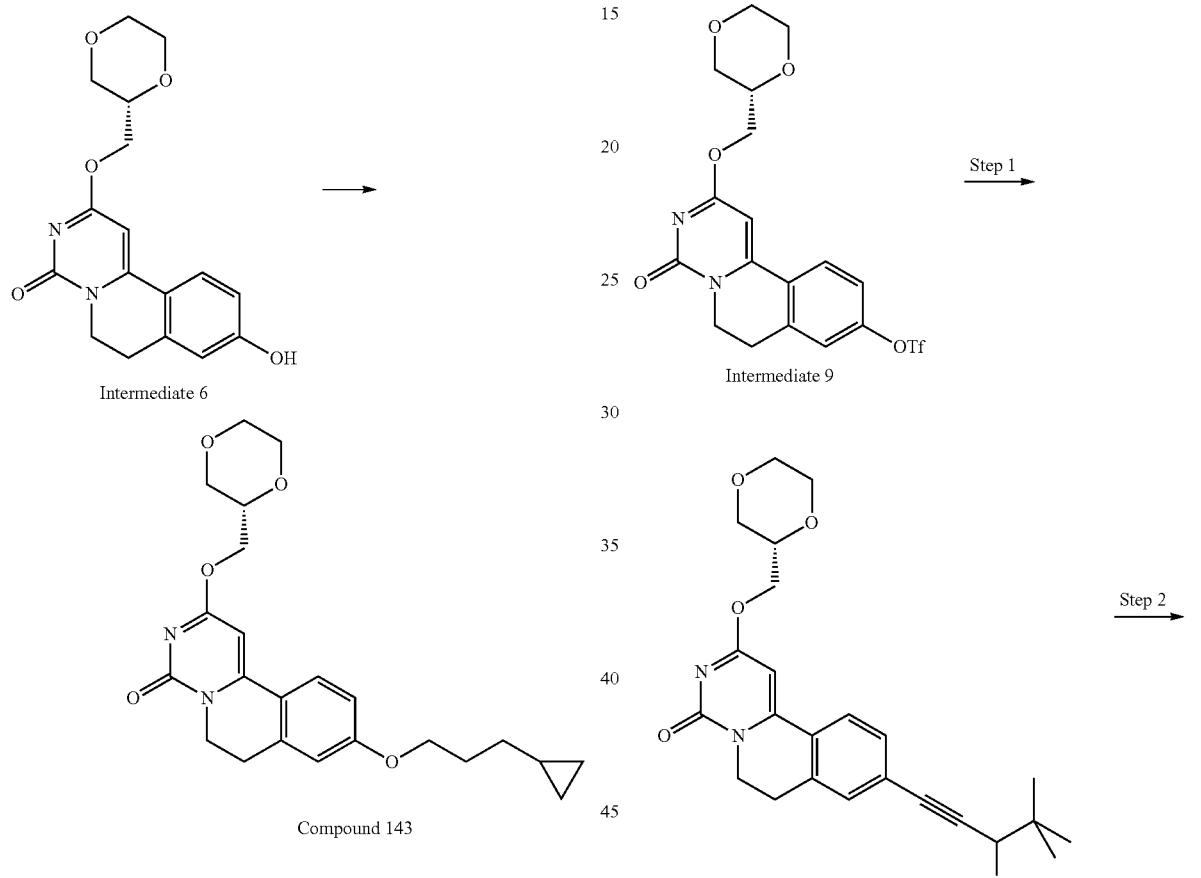

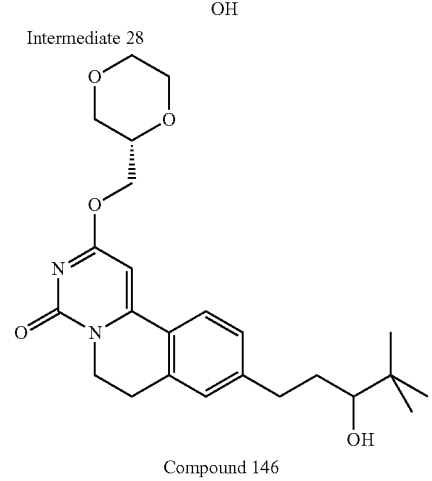

Intermediate 6 (2.12 g, 2.42 mmol, 1 eq.), 4,4-dimethyl-pentan-1-ol (0.77 g, 7.71 mmol, 1.2 eq.) and PPh$_3$ (2.02 g, 7.71 mmol, 1.2 eq.) were suspended in 1,4-dioxane (50 mL) and the mixture was degassed with N$_2$. DIAD (1.56 mL, 7.71 mmol, 1.1 eq.) was added dropwise and the reaction was stirred at RT for 2 h. The reaction mixture was quenched with brine and extracted with EtOAc, the organic phase was dried over MgSO$_4$ and evaporated to dryness. Compound 143 was obtained by purification by flash chromatography on silica gel, eluting from 60 to 100% EtOAc/H.

($^1$H, CDCl$_3$) δ ppm 7.66-7.60 (1 H, m), 6.91-6.86 (1 H, m), 6.80-6.76 (1 H, m), 6.28 (1 H, s), 4.48-4.35 (2 H, m), 4.24-4.17 (2 H, m), 4.11-4.04 (2 H, m), 4.02-3.95 (1 H, m), 3.91-3.61 (5 H, m), 3.54-3.45 (1 H, m), 3.03-2.94 (2 H, m), 1.98-1.88 (2 H, m), 1.45-1.36 (2 H, m), 0.78-0.66 (1 H, m), 0.50-0.43 (2 H, m), 0.09-0.03 (2 H, m)

MW (calcd): 412.5; MW (obsd): 413.5

Step 1: 2-((S)-1-[1,4]Dioxan-2-ylmethoxy)-9-(3-hydroxy-4, 4-dimethyl-pent-1-ynyl)-6,7-dihydro-pyrimido[6,1-a]isoquinolin-4-one (Intermediate 28)

Intermediate 28 is prepared via general method G using intermediate 9.
MW (calcd): 424.5; MW (obsd): 425.4 (M+1)

Step 2: 2-((S)-1-[1,4]dioxan-2-ylmethoxy)-9-(3-hydroxy-4, 4-dimethyl-pentyl)-6,7-dihydro-pyrimido[6,1-a]isoquinolin-4-one (Compound 146)

Compound 146 is prepared via general method I using intermediate 28.

Compound 147: 9-cyclopentylmethoxymethyl-2-((S)-1-[1,4]dioxan-2-ylmethoxy)-6,7-dihydro-pyrimido[6,1-a]isoquinolin-4-one This compound is prepared via general method E using intermediate 9, in a mixture of DME/H$_2$O (2/1), in a microwave at 120° C. for 20 min and intermediate 19.

Compound 148: 2-((S)-1-[1,4]dioxan-2-ylmethoxy)-9-(3-methoxy-butyl)-6,7-dihydro-pyrimido[6,1-a]isoquinolin-4-one

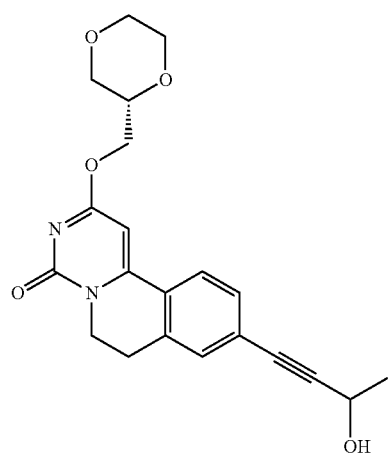

Intermediate 26

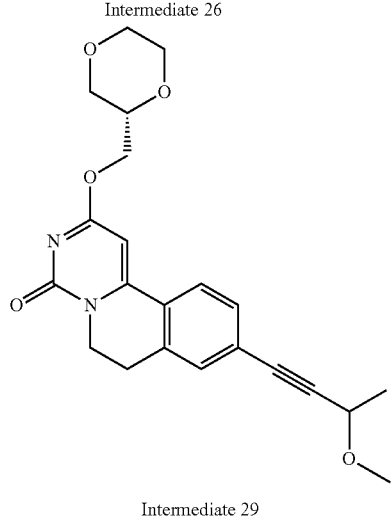

Intermediate 29

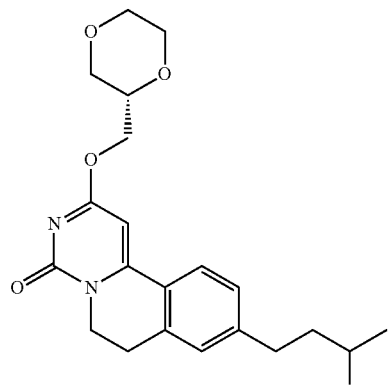

Compound 148

Step 1: 2-((S)-1-[1,4]Dioxan-2-ylmethoxy)-9-(3-methoxy-but-1-ynyl)-6,7-dihydro-pyrimido[6,1-a]isoquinolin-4-one (Intermediate 29)

Intermediate 29 is prepared via general method H using intermediate 26.
MW (calcd): 396.4; MW (obsd): 397.2 (M+1)

Step 1: 2-((S)-1-[1,4]dioxan-2-ylmethoxy)-9-(3-methoxy-butyl)-6,7-dihydro-pyrimido[6,1-a]isoquinolin-4-one (Compound 148)

Compound 148 is prepared via general method I using intermediate 29.

Compound 149: 2-((S)-1-[1,4]dioxan-2-ylmethoxy)-9-(3-phenylamino-propyl)-6,7-dihydro-pyrimido[6,1-a]isoquinolin-4-one Intermediate 9

-continued

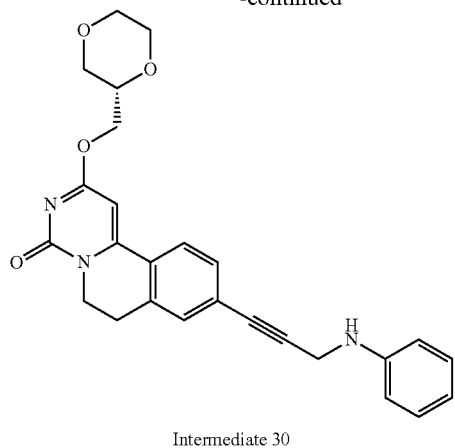

Intermediate 30

Compound 150: 2-((S)-1-[1,4]dioxan-2-ylmethoxy)-9-(4-hydroxy-pentyl)-6,7-dihydro-pyrimido[6,1-a]isoquinolin-4-one

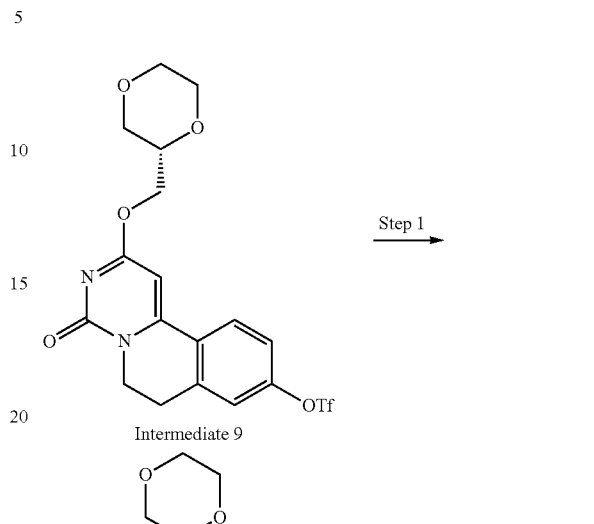

Intermediate 9

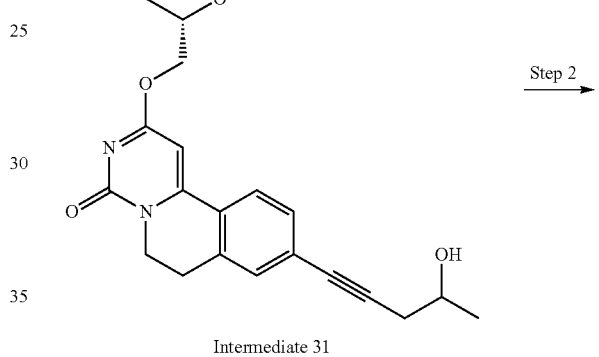

Intermediate 31

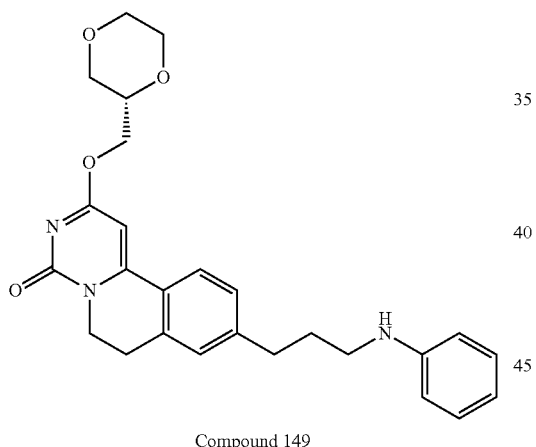

Compound 149

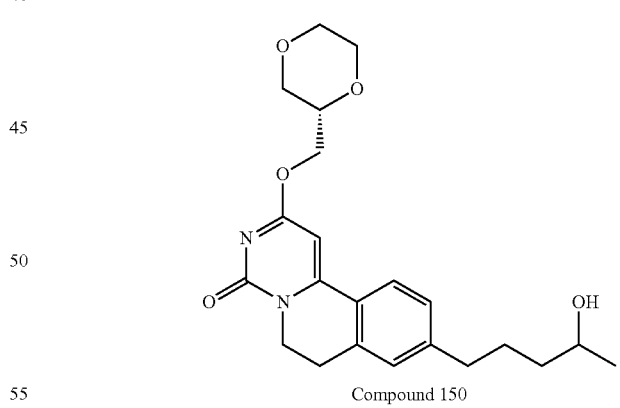

Compound 150

Step 1: 2-((S)-1-[1,4]Dioxan-2-ylmethoxy)-9-(3-phenylamino-prop-1-ynyl)-6,7-dihydro-pyrimido[6,1-a]isoquinolin-4-one (Intermediate 30)

Intermediate 30 is prepared via general method G using intermediate 9 and phenyl-prop-2-ynyl-amine.

MW (calcd): 443.5; MW (obsd): 444.2 (M+1)

Step 2: 2-((S)-1-[1,4]dioxan-2-ylmethoxy)-9-(3-phenylamino-propyl)-6,7-dihydro-pyrimido[6,1-a]isoquinolin-4-one (Compound 149)

Compound 149 is prepared via general method I using intermediate 30.

Step 1: 2-((S)-1-[1,4]Dioxan-2-ylmethoxy)-9-(4-hydroxy-pent-1-ynyl)-6,7-dihydro-pyrimido[6,1-a]isoquinolin-4-one (Intermediate 31)

Intermediate 31 was prepared via general method G using intermediate 9, pent-4-yn-2-ol, iPr$_2$NH as base and THF as solvent.

MW (calcd): 396.4; MW (obsd): 397.2 (M+1)

Step 2: 2-((S)-1-[1,4]dioxan-2-ylmethoxy)-9-(4-hydroxy-pentyl)-6,7-dihydro-pyrimido[6,1-a]isoquinolin-4-one (Compound 150)

Compound 150 was prepared via general method I using intermediate 31.

Compound 151: 2-((S)-1-[1,4]dioxan-2-ylmethoxy)-9-(4-hydroxy-butyl)-6,7-dihydro-pyrimido[6,1-a]isoquinolin-4-one

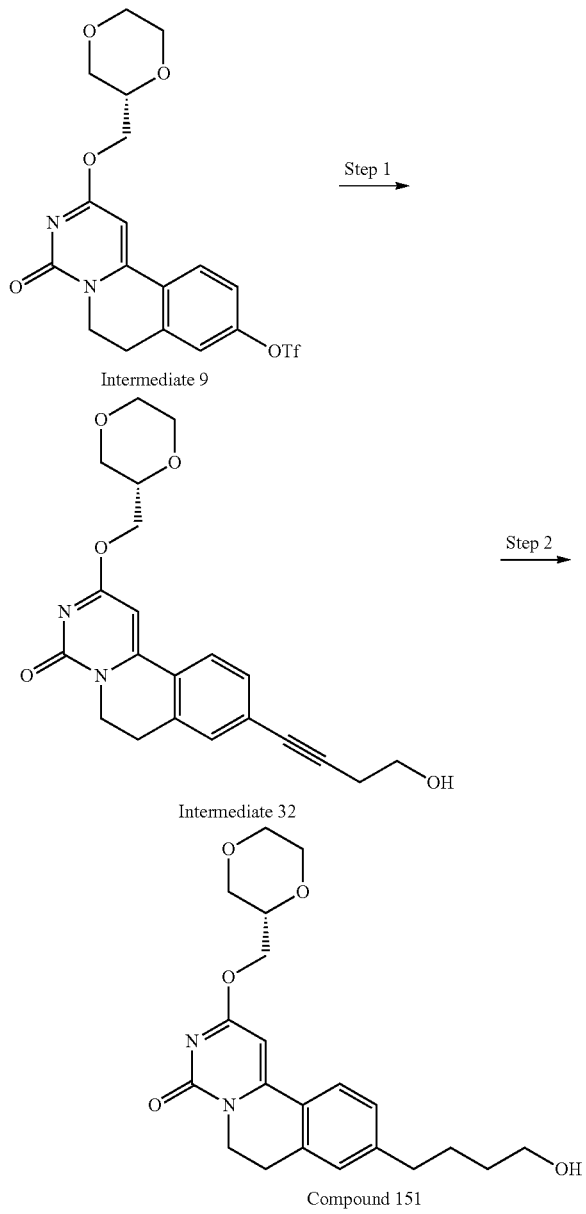

Intermediate 9

Intermediate 32

Compound 151

Step 1: 2-((S)-1-[1,4]Dioxan-2-ylmethoxy)-9-(4-hydroxy-but-1-ynyl)-6,7-dihydro-pyrimido[6,1-a]isoquinolin-4-one (Intermediate 32)

Intermediate 32 was prepared via general method G using intermediate 9, but-3-yn-1-ol, iPr$_2$NH as base and THF as solvent.

($^1$H, CDCl$_3$) δ ppm 7.70-7.65 (1 H, m), 7.45-7.35 (1 H, m), 7.34 (1 H, s), 6.35 (1 H, s), 4.50-4.32 (2 H, m), 4.28-4.10 (2 H, m), 4.05-3.90 (1 H, m), 3.95-3.60 (7 H, m), 3.55-3.40 (1 H, m), 3.05-2.90 (2 H, m), 2.80-2.65 (2 H, m), 2.00-1.80 (1 H, m)

MW (calcd): 382.4; MW (obsd): 383.2 (M+1)

Step 2: 2-((S)-1-[1,4]dioxan-2-ylmethoxy)-9-(4-hydroxy-butyl)-6,7-dihydro-pyrimido[6,1-a]isoquinolin-4-one (Compound 151)

Compound 151 was prepared via general method I using intermediate 32.

Compound 152: 9-(cyclohexyl-methyl-amino)-2-((S)-1-[1,4]dioxan-2-ylmethoxy)-6,7-dihydro-pyrimido[6,1-a]isoquinolin-4-one

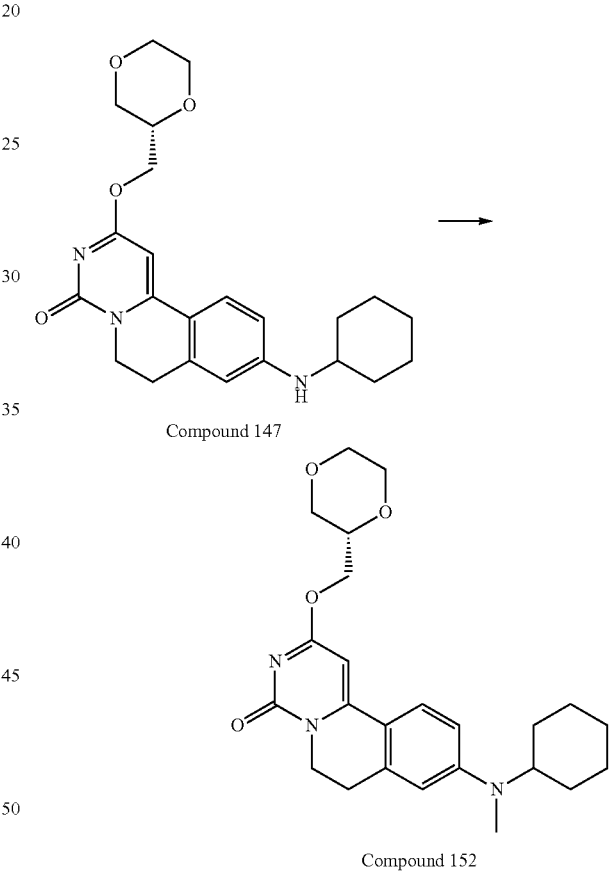

Compound 147

Compound 152

MeI (0.007 mg, 0.11 mmol, 1.2 eq.) was added to compound 147 (38 mg, 0.092 mmol, 1 eq.) and NaH (6 mg, 0.15 mmol, 1.6 eq.) in DMF (5 mL) and the reaction was stirred at RT for 16 h. Some more NaH (6 mg, 0.15 mmol, 1.6 eq.) and MeI (0.07 mg, 0.11 mmol, 1.2 eq.) were added to the reaction mixture and it was stirred for a further 2 days. The mixture was quenched with brine and extracted with EtOAc. The organic layers were dried over MgSO$_4$ and evaporated to dryness. The residue was purified by preparative HPLC-MS to provide compound 152.

($^1$H, CDCl$_3$) δ ppm 7.57-7.50 (1 H, m), 6.71 (1 H, d), 6.53 (1 H, br. s.), 6.21 (1 H, s), 4.51-4.33 (2 H, m), 4.26-4.14 (2 H, m), 4.06-3.93 (1 H, m), 3.92-3.56 (6 H, m), 3.56-3.41 (1

H, m), 3.00-2.90 (2 H, m), 2.88 (3 H, s), 2.04-1.63 (2 H, m), 1.60-1.31 (5 H, m), 1.28-1.08 (1 H, m)

MW (calcd): 425.5; MW (obsd): 426.4

Compound 153: 9-(cyclohexylmethyl-amino)-2-((S)-1-[1,4]dioxan-2-ylmethoxy)-6,7-dihydro-pyrimido[6,1-a]isoquinolin-4-one This compound is prepared via general method J using intermediate 13 and cyclohexanecarbaldehyde.

Compound 154: 2-((S)-1-[1,4]dioxan-2-ylmethoxy)-9-[(tetrahydro-pyran-4-ylmethyl)-amino]-6,7-dihydro-pyrimido[6,1-a]isoquinolin-4-one This compound is prepared via general method J using intermediate 13 and tetrahydro-pyran-4-carbaldehyde.

Compound 155: 2-((S)-1-[1,4]dioxan-2-ylmethoxy)-9-(3-ethyl-3-hydroxy-pentyl)-6,7-dihydro-pyrimido[6,1-a]isoquinolin-4-one

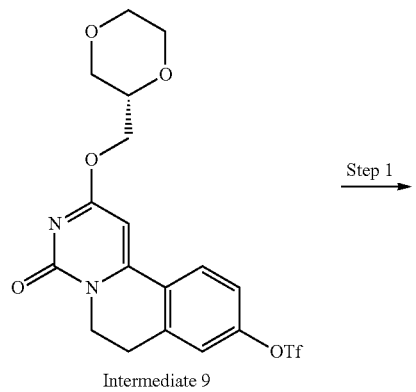

Intermediate 9

Step 1 →

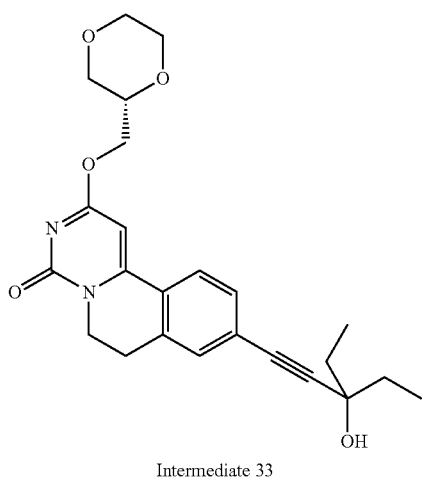

Intermediate 33

Step 2 →

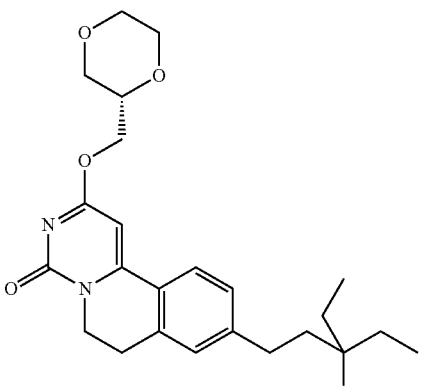

Compound 155

Step 1: 2-((S)-1-[1,4]Dioxan-2-ylmethoxy)-9-(3-ethyl-3-hydroxy-pent-1-ynyl)-6,7-dihydro-pyrimido[6,1-a]isoquinolin-4-one (Intermediate 33)

Intermediate 33 is prepared via general method G using intermediate 9 and 3-ethyl-pent-1-yn-3-ol.

($^1$H, CDCl$_3$) δ ppm 7.51-7.46 (1 H, m), 7.28-7.24 (1 H, m), 7.22-7.19 (1 H, m), 6.20 (1 H, s), 4.30-4.19 (2 H, m), 4.08-4.00 (2 H, m), 3.87-3.79 (1 H, m), 3.75-3.47 (5 H, m), 3.39-3.30 (1 H, m), 3.03 (1 H, br. S), 2.88-2.80 (2 H, m), 1.746-1.56 (4 H, m), 0.97 (6 H, s)

MW (calcd): 424.5; MW (obsd): 425.5 (M+1)

Step 2: 2-((S)-1-[1,4]dioxan-2-ylmethoxy)-9-(3-ethyl-3-hydroxy-pentyl)-6,7-dihydro-pyrimido[6,1-a]isoquinolin-4-one (Compound 155)

Compound 155 is prepared via general method I using intermediate 33.

Compound 156: 2-((S)-1-[1,4]dioxan-2-ylmethoxy)-9-(3-hydroxy-3-methyl-butyl)-6,7-dihydro-pyrimido[6,1-a]isoquinolin-4-one

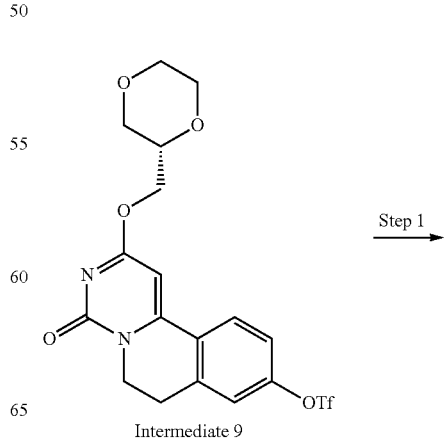

Intermediate 9

Step 1 →

125

-continued

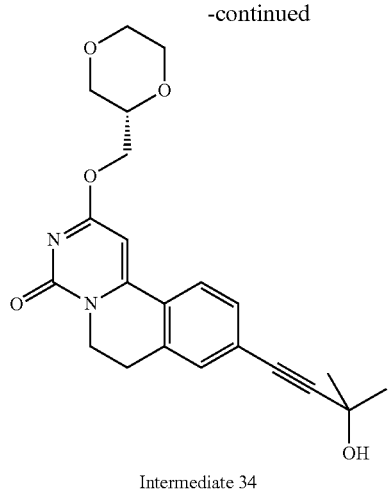

Intermediate 34

Compound 156

Step 1: 2-((S)-1-[1,4]Dioxan-2-ylmethoxy)-9-(3-hydroxy-3-methyl-but-1-ynyl)-6,7-dihydro-pyrimido[6,1-a]isoquinolin-4-one (Intermediate 34)

Intermediate 34 is prepared via general method G using intermediate 9 and 2-methyl-but-3-yn-2-ol.

($^1$H, CDCl$_3$) δ ppm 7.58 (1 H, d), 7.38-7.33 (1 H, m), 7.32-7.29 (1 H, m), 6.32 (1 H, s), 4.43-4.32 (2 H, m), 4.18-4.12 (2 H, m), 3.99-3.91 (1 H, m), 3.87-3.58 (5 H, m), 3.50-3.42 (1 H, m), 2.97-2.90 (2 H, m), 1.60 (6 H, s)

MW (calcd): 396.4; MW (obsd): 397.3 (M+1)

Step 2: 2-((S)-1-[1,4]dioxan-2-ylmethoxy)-9-(3-hydroxy-3-methyl-butyl)-6,7-dihydro-pyrimido[6,1-a]isoquinolin-4-one (Compound 156)

Compound 156 is prepared via general method I using intermediate 34.

126

Compound 157: 2-((S)-1-[1,4]dioxan-2-ylmethoxy)-9-(3-hydroxy-pentyl)-6,7-dihydro-pyrimido[6,1-a]isoquinolin-4-one

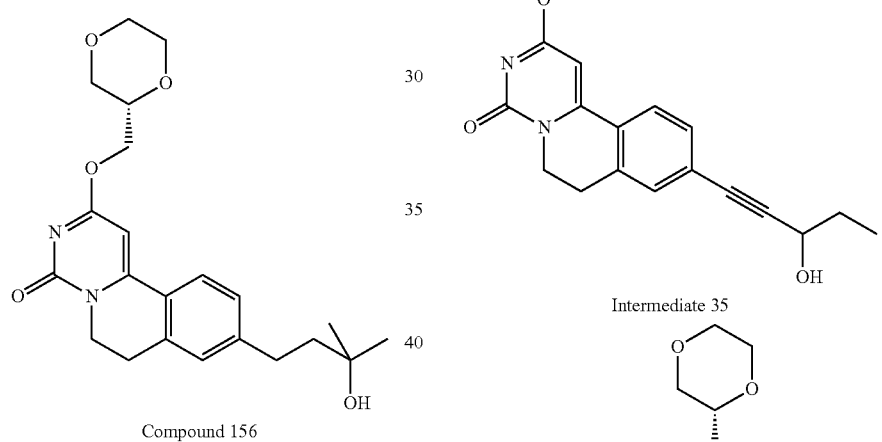

Intermediate 9

Intermediate 35

Compound 157

Step 1: 2-((S)-1-[1,4]Dioxan-2-ylmethoxy)-9-(3-hydroxy-pent-1-ynyl)-6,7-dihydro-pyrimido[6,1-a]isoquinolin-4-one (Intermediate 35)

Intermediate 35 is prepared via general method G using intermediate 9 and pent-1-yn-3-ol.

($^1$H, CDCl$_3$) δ ppm 7.62-7.57 (1 H, m), 7.41-7.35 (1 H, m), 7.33 (1 H, s), 6.34 (1 H, s), 4.60-4.53 (1 H, m), 4.45-4.33

(2 H, m), 4.20-4.14 (2 H, m), 4.00-3.92 (1 H, m), 3.88-3.59 (5 H, m), 3.51-3.42 (1 H, m), 2.99-2.90 (2 H, m), 1.90-1.74 (2 H, m), 1.07 (3 H, t)

Step 2: 2-((S)-1-[1,4]dioxan-2-ylmethoxy)-9-(3-hydroxy-pentyl)-6,7-dihydro-pyrimido[6,1-a]isoquinolin-4-one (Compound 157)

Compound 157 is prepared via general method I using intermediate 35.

Compound 158: 9-(2,2-dimethyl-propoxy)-2-((S)-1-[1,4]dioxan-2-ylmethoxy)-6,7-dihydro-pyrimido[6,1-a]isoquinolin-4-one Synthesis fully described above.

Compound 159: 2-((S)-1-[1,4]dioxan-2-ylmethoxy)-9-(tetrahydro-pyran-4-ylmethoxy)-6,7-dihydro-pyrimido[6,1-a]isoquinolin-4-one This compound is prepared via general method L with intermediate 6 and methanesulfonic acid tetrahydro-pyran-4-ylmethyl ester.

Compound 160: 2-((S)-1-[1,4]dioxan-2-ylmethoxy)-9-(4-hydroxy-4-methyl-pentyl)-6,7-dihydro-pyrimido[6,1-a]isoquinolin-4-one

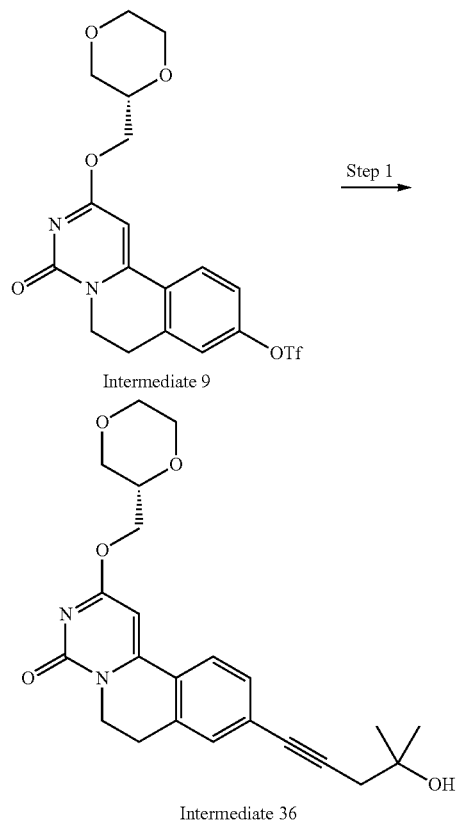

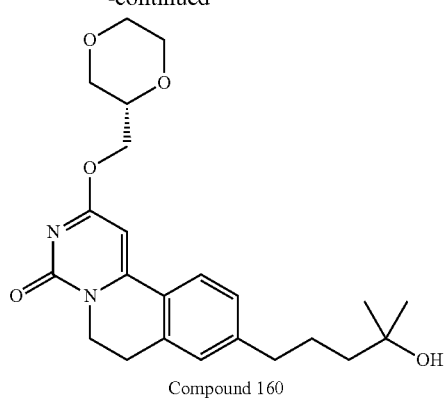

Compound 160

Step 1: 2-((S)-1-[1,4]Dioxan-2-ylmethoxy)-9-(4-hydroxy-4-methyl-pent-1-ynyl)-6,7-dihydro-pyrimido[6,1-a]isoquinolin-4-one (intermediate 36)

A vial was charged with intermediate 9 (0.15 g, 0.324 mmol, 1 eq.), 2-methyl-5-trimethylsilanyl-pent-4-yn-2-ol (66 mg, 0.389 mmol, 1.2 eq), CuI (2.5 mg, 0.013 mmol, 0.04 eq.), iPr$_2$NH (0.41 mL, 2.92 mmol, 9 eq.) and THF (2 mL). The solution was purged with Ar for 15 min., and Pd(PPh$_3$)Cl$_2$ (11 mg, 0.016 mmol, 0.05 eq.) was added with TBAF (0.39 mL, 0.39 mmol, 1.2 eq., 1M in THF). The vial was sealed and the reaction was heated to 80° C. for 16 h. The reaction mixture was evaporated to dryness and the crude product was purified by preparative TLC [DCM/MeOH, 98/2] to afford intermediate 36 2-((S)-1-[1,4]dioxan-2-ylmethoxy)-9-(4-hydroxy-4-methyl-pent-1-ynyl)-6,7-dihydro-pyrimido[6,1-a]isoquinolin-4-one.

($^1$H, CDCl$_3$) δ ppm 7.70-7.58 (1 H, m), 7.45-7.38 (1 H, m), 7.35 (1 H, s), 6.37 (1 H, s), 4.50-4.30 (2 H, m), 4.28-4.15 (2 H, m), 4.05-3.95 (1 H, m), 3.95-3.55 (5 H, m), 3.55-3.40 (1 H, m), 3.05-2.95 (2 H, m), 2.62 (2 H, s), 1.39 (6 H, s)

MW (calcd): 410.5; MW (obsd): 411.4

Step 2: 2-((S)-1-[1,4]dioxan-2-ylmethoxy)-9-(4-hydroxy-4-methyl-pentyl)-6,7-dihydro-pyrimido[6,1-a]isoquinolin-4-one (Compound 160)

Compound 160 is prepared via general method I using intermediate 36.

Compound 161: 2-((S)-1-[1,4]dioxan-2-ylmethoxy)-9-(tetrahydro-pyran-4-ylmethoxymethyl)-6,7-dihydro-pyrimido[6,1-a]isoquinolin-4-one This compound is prepared via general method E using intermediate 9 and potassium 4-(tetrahydropyranylmethoxy)methyltrifluoroborate.

Compound 162: 2-([1,4]dioxan-2-ylmethoxy)-9-methoxy-6,7-dihydro-pyrimido[6,1-a]isoquinolin-4-one ($^1$H, CDCl$_3$) δ ppm 7.73-7.66 (1 H, m), 6.98-6.90 (1 H, m), 6.85-6.80 (1 H, m), 6.69 (1 H, s), 4.00-4.20 (2 H, m), 3.91 (3 H, s), 3.04 (2 H, m)

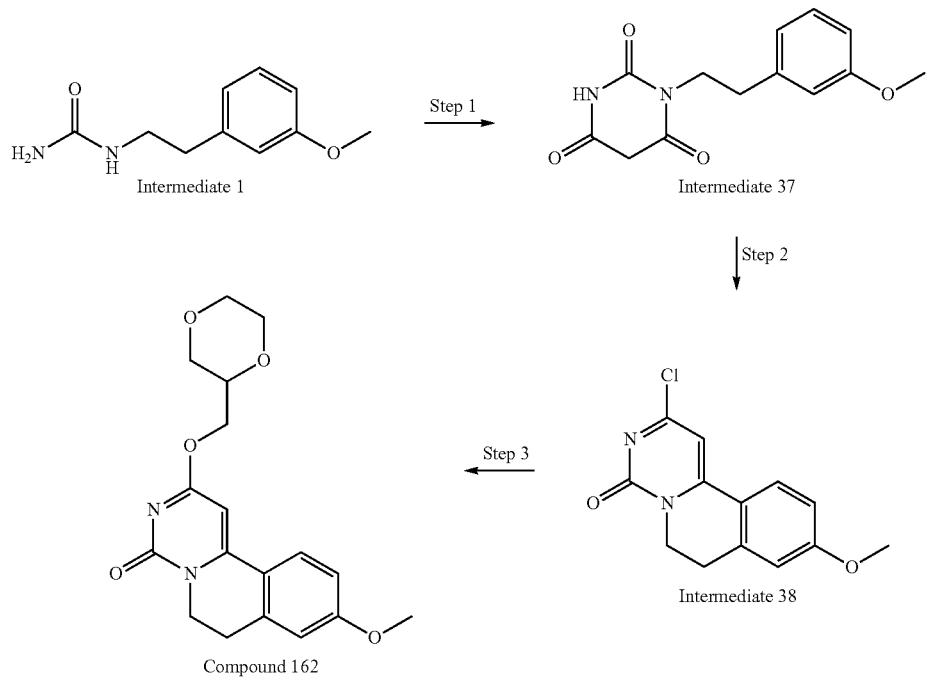

Step 1: 1-[2-(3-methoxy-phenyl)-ethyl]-pyrimidine-2,4,6-trione (intermediate 37)

Sodium (236 mg, 10.2 mmol, 2 eq.) was added to degassed EtOH (18 mL), when sodium dissolved completely, ethyl malonate (1.56 mL, 10.2 mmol, 2 eq.) was added and the reaction was refluxed for 1 h. Intermediate 1 (995 mg, 5.12 mmol, 1 eq.) in EtOH (4 mL) was then added and the reaction was refluxed for 1 day. The desired intermediate 37 1-[2-(3-methoxy-phenyl)-ethyl]-pyrimidine-2,4,6-trione precipitated upon addition of 2N aqueous HCl, it was filtered and washed with H$_2$O and finally dried.

($^1$H, DMSO-d$_6$) δ ppm 7.27-7.18 (1 H, m), 6.84-6.72 (3 H, m), 3.92-3.83 (2 H, m), 3.75 (3 H, s), 3.62 (2 H, s), 2.80-2.70 (2 H, m)

MW (calcd): 262.3; MW (obsd): 263.3 (M+1)

Step 2: 2-chloro-9-methoxy-6,7-dihydro-pyrimido[6,1-a]isoquinolin-4-one (intermediate 38)

Intermediate 37 (920 mg, 3.51 mmol, 1 eq.) was heated in POCl$_3$ (5 mL) at 50° C. for 2 days. The volatiles were evaporated under vacuum, the residue was dissolved in DCM and washed with a saturated aqueous solution of NaHCO$_3$, before drying over MgSO$_4$. Evaporation of the organic phase gave intermediate 38 2-chloro-9-methoxy-6,7-dihydro-pyrimido[6,1-a]isoquinolin-4-one, which was used in the next step without further purification.

Step 3: 2-([1,4]dioxan-2-ylmethoxy)-9-methoxy-6,7-dihydro-pyrimido[6,1-a]isoquinolin-4-one (compound 162)

[1,4]Dioxan-2-yl-methanol (42 mg, 0.36 mmol, 2 eq.) was dissolved in DCM (3 mL) with NaH (14 mg, 0.36 mmol, 2 eq., 60% in mineral oil). After 30 min, intermediate 38 (50 mg, 0.18 mmol, 1 eq.) was added to the mixture and the reaction was stirred at RT for 16 h. The reaction mixture was evaporated to dryness and the crude product was purified by preparative HPLC-MS to provide compound 162.

($^1$H, CDCl$_3$) δ ppm 7.68-7.62 (1 H, m), 6.95-6.87 (1 H, m), 6.82-6.77 (1 H, m), 6.29 (1 H, s), 4.51-4.35 (2 H, m), 4.26-4.17 (2 H, m), 4.05-3.92 (1 H, m), 3.91-3.60 (8 H, m), 3.55-3.44 (1 H, m), 3.04-2.94 (2 H, m)

MW (calcd): 344.4; MW (obsd): 345.0

Compound 163: 2-((S)-1-[1,4]dioxan-2-ylmethoxy)-9-(oxetan-3-ylmethoxy)-6,7-dihydro-pyrimido[6,1-a]isoquinolin-4-one This compound is prepared via general method L using intermediate 6 and methanesulfonic acid oxetan-3-ylmethyl ester.

Compound 164: 9-(3-cyclopropyl-propoxy)-2-((R)-1-[1,4]dioxan-2-ylmethoxy)-6,7-dihydropyrimido[6,1-a]isoquinolin-4-one A solution of intermediate 6 (1.15 g, 3.48 mmol, 1 eq.) and 3-cyclopropan-1-ol (0.349 g, 3.48 mmol, 1 eq.) in 1,4-dioxane was degassed with Argon for 10 min. PPh$_3$ (1.096 g, 4.18 mmol, 1.2 eq.) was added and the reaction mixture was degassed with Argon an additional 5 min. DIAD (0.745 mL, 3.83 mmol, 1.1 eq.) was added dropwise at 0° C. The reaction mixture was stirred at RT for 16 h. 3-Cyclopropylpropan-1-ol (0.150 mg, 1.49 mmol, 0.43 eq.) and PPh₃ (0.30 g, 1.14 mmol, 0.33 eq.) were added. The reaction mixture was cooled to 0° C. and DIAD (0.350 mL, 1.80 mmol, 5.2 eq.) was added. After 1 h at RT, the reaction mixture was concentrated under vacuum and the crude product was purified by flash chromatography on silica-gel to afford compound 164.

($^1$H, DMSO-d$_6$) δ ppm 7.93 (1H, d), 6.97-6.92 (2 H, m), 6.53 (1H, s), 4.24-4.23 (2H, m), 4.08 (2H, t), 4.00 (2H, t), 3.98-3.74 (3H, m), 3.68-3.57 (2H, m), 3.51-3.48 (1H, m), 3.37 (1H, t), 2.96 (2H, t), 1.84-1.80 (2H, m), 1.36-1.30 (2H, m), 0.81-0.63 (1H, m), 0.42-0.39 (2H, m), 0.04-0.02 (2H, m)

MW (calcd): 412.5; MW (obsd): 413.0 (M+1)

Compound 165: 2-((S)-1-[1,4]dioxan-2-ylmethoxy)-9-(3-methoxy-propyl)-6,7-dihydro-pyrimido[6,1-a]isoquinolin-4-one

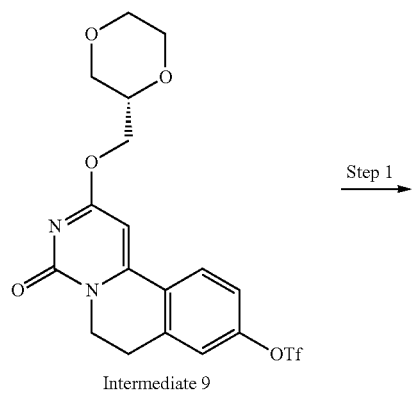

Intermediate 9

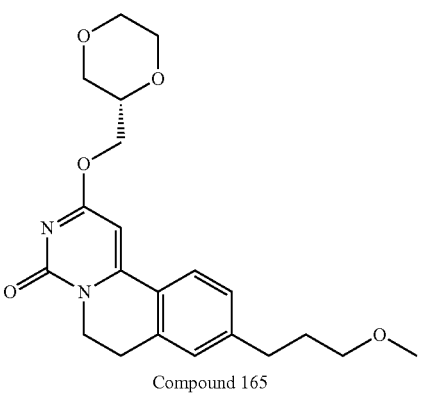

Compound 165

Step 1: 2-((S)-1-[1,4]Dioxan-2-ylmethoxy)-9-(3-methoxy-prop-1-ynyl)-6,7-dihydro-pyrimido[6,1-a]isoquinolin-4-one (Intermediate 39)

Intermediate 39 was prepared via general method G using intermediate 9 and 3-methoxy-propyne.

($^1$H, CDCl$_3$) δ ppm 7.68 (1 H, d), 7.48 (1 H, d), 7.42 (1 H, s), 6.40 (1 H, s), 4.50-4.41 (2 H, m), 4.38 (2 H, s), 4.23 (2 H, t), 4.05-3.98 (1 H, m), 3.89-3.70 (5 H, m), 3.55-3.50 (4 H, m), 3.03 (2 H, t)

MW (calcd): 382.4; MW (obsd): 383.4 (M+1)

Step 2: 2-((S)-1-[1,4]dioxan-2-ylmethoxy)-9-(3-methoxy-propyl)-6,7-dihydro-pyrimido[6,1-a]isoquinolin-4-one (Compound 165)

Compound 165 was prepared via general method I using intermediate 39.

Compound 166: 2-((S)-1-[1,4]dioxan-2-ylmethoxy)-9-[2-(1-hydroxy-cyclopentyl)-ethyl]-6,7-dihydro-pyrimido[6,1-a]isoquinolin-4-one

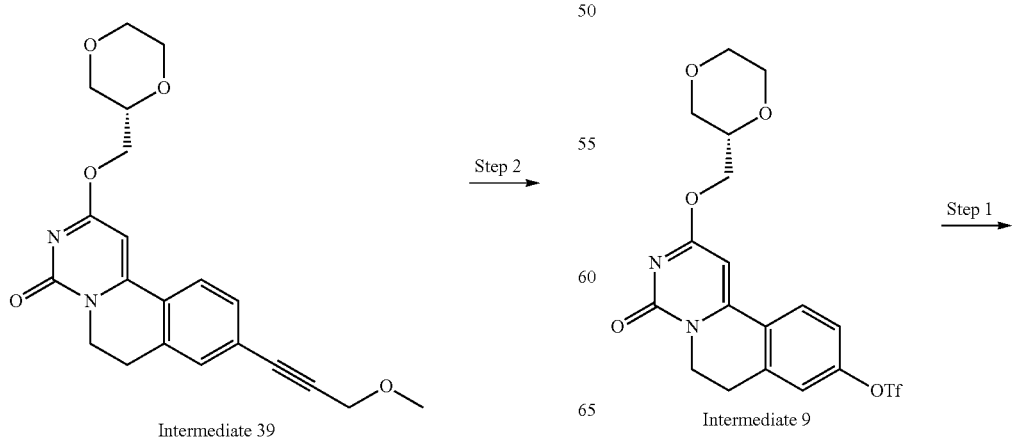

Intermediate 39

Intermediate 9

134

Compound 168: 2-((R)-1-[1,4]Dioxan-2-yl-methoxy)-9-(3-methoxy-propyl)-6,7-dihydro-pyrimido[6,1-a]isoquinolin-4-one

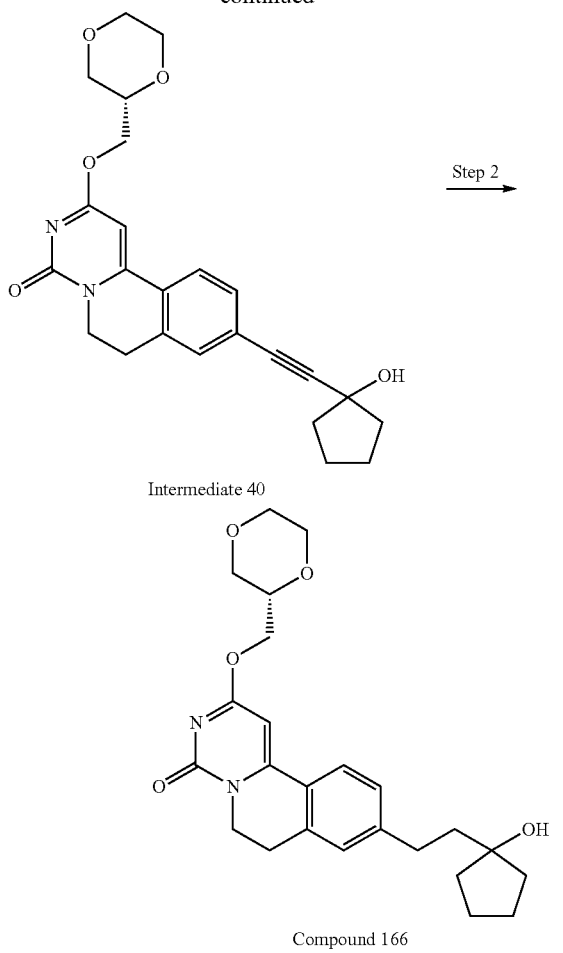

Intermediate 40

Compound 166

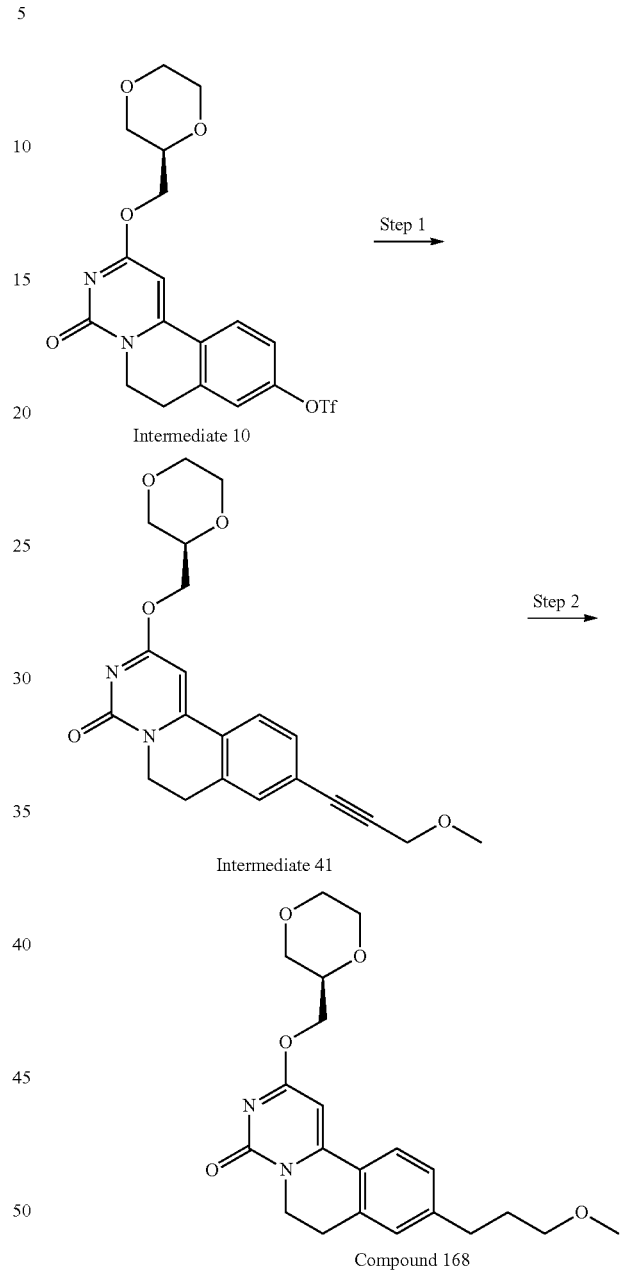

Intermediate 10

Intermediate 41

Compound 168

Step 1: 2-((S)-1-[1,4]Dioxan-2-ylmethoxy)-9-(1-hydroxy-cyclopentylethynyl)-6,7-dihydro-pyrimido[6,1-a]isoquinolin-4-one (Intermediate 40)

Intermediate 40 is prepared via general method G using intermediate 9 and 3-methoxy-propyne.

($^1$H, CDCl$_3$) δ ppm 7.54 (1 H, d), 7.31 (1 H, d), 7.26 (1 H, s), 6.28 (1 H, s), 4.39-4.30 (2 H, m), 4.12 (2 H, t), 3.95-3.91 (1 H, m), 3.82-3.58 (5 H, m), 3.50 (1H, m), 3.16 (1 H, s), 2.89 (2 H, t), 2.05-1.98 (4 H, m), 1.90-1.70 (4H, m)

Step 2: 2-((S)-1-[1,4]dioxan-2-ylmethoxy)-9-[2-(1-hydroxy-cyclopentyl)-ethyl]-6,7-dihydro-pyrimido[6,1-a]isoquinolin-4-one (Compound 166)

Compound 166 was prepared via general method I using intermediate 40.

Compound 167: 2-((R)-1-[1,4]Dioxan-2-yl-methoxy)-9-(4-hydroxy-tetrahydro-pyran-4-ylethynyl)-6,7-dihydro-pyrimido[6,1-a]isoquinolin-4-one This compound is prepared via general method G using intermediate 10 and 4-Ethynyl-tetrahydro-pyran-4-ol.

Step 1: 2-((R)-1-[1,4]Dioxan-2-ylmethoxy)-9-(3-methoxy-prop-1-ynyl)-6,7-dihydro-pyrimido[6,1-a]isoquinolin-4-one (Intermediate 40)

Intermediate 41 is prepared via general method G using intermediate 10 and 3-methoxy-propyne.

($^1$H, CDCl$_3$) lppm 7.56 (1 H, d), 7.48 (1 H, d), 7.33 (1 H, s), 6.27 (1 H, s), 4.32-4.27 (2 H, m), 4.23 (2 H, s), 4.08 (2 H, t), 3.88-3.85 (1 H, m), 3.76-3.49 (5 H, m), 3.40-3.34 (4 H, m), 2.90 (2 H, t)

Step 2: 2-((R)-1-[1,4]dioxan-2-ylmethoxy)-9-(3-methoxy-propyl)-6,7-dihydro-pyrimido[6,1-a]isoquinolin-4-one (Compound 165)

Compound 168 is prepared via general method I using intermediate 41.

Compound 169: 2-((R)-1-[1,4]Dioxan-2-yl-methoxy)-9-[2-(1-hydroxy-cyclopentyl)-ethyl]-6,7-dihydro-pyrimido[6,1-a]isoquinolin-4-one Step 1: 2-((S)-1-[1,4]Dioxan-2-ylmethoxy)-9-(1-hydroxy-cyclopentylethynyl)-6,7-dihydro-pyrimido[6,1-a]isoquinolin-4-one (Intermediate 42)

Intermediate 42 is prepared via general method G using intermediate 10 and 1-Ethynyl-cyclopentanol.
($^1$H, CDCl$_3$) δ ppm 7.47 (1 H, d), 7.25 (1 H, d), 7.20 (1 H, s), 6.22 (1 H, s), 4.32-4.24 (2 H, m), 4.05 (2 H, t), 3.88-3.85 (1H, m), 3.77-3.52 (5 H, m), 3.38 (1H, t), 2.83 (2 H, t), 2.02-1.90 (4H, m), 1.85-1.67 (4H, m)

Step 2: 2-((R)-1-[1,4]Dioxan-2-ylmethoxy)-9-(1-hydroxy-cyclopentylethynyl)-6,7-dihydro-pyrimido[6,1-a]isoquinolin-4-one (Compound 169)

Compound 169 is prepared via general method I using intermediate 42.

Compound 170: 2-((S)-1-[1,4]Dioxan-2-yl-methoxy)-9-(2-propoxy-ethoxy)-6,7-dihydro-pyrimido[6,1-a]isoquinolin-4-one

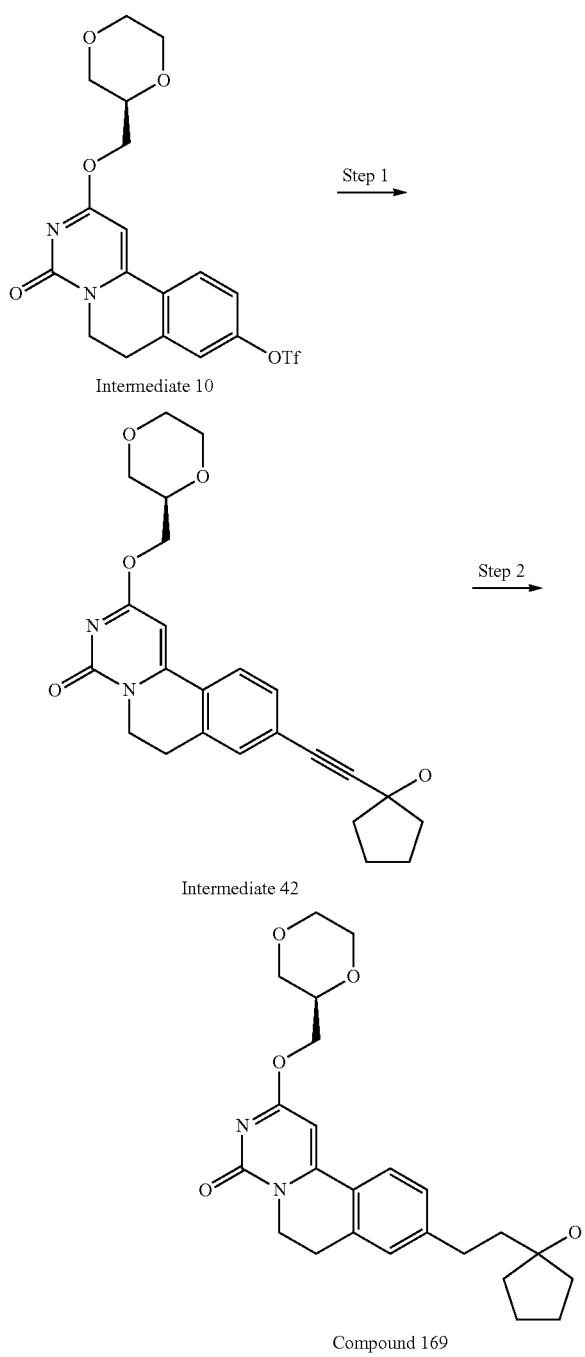

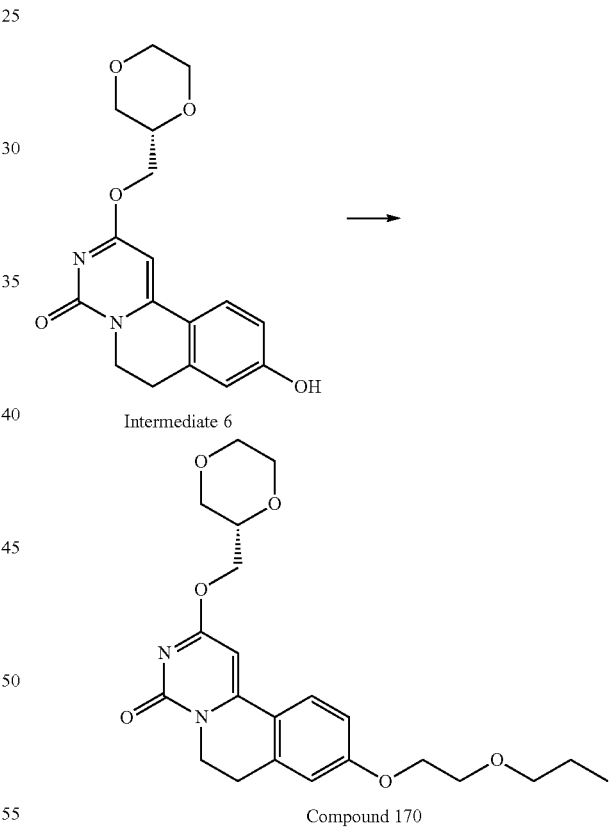

Intermediate 6 (0.15 g, 0.45 mmol, 1 eq.), 2-Propoxy-ethanol (63 μL, 0.55 mmol, 1.2 eq.) and PPh$_3$ (144 mg, 0.55 mmol, 1.2 eq.) were suspended in 1,4-dioxane (5 mL) and the mixture was degassed with N$_2$. DIAD (0.108 mL, 0.55 mmol, 1.2 eq.) was added and the reaction was stirred at RT overnight. 0.5 eq. of DIAD and PPh3 were added, and the reaction mixture was stirred at room temperature for an extra 2 h. Reaction mixture was diluted with brine, extracted with EtOAc, dried over MgSO$_4$ and concentrated. Crude product was purified on silicagel column to give compound 170.

137

Compound 171: 2-((S)-1-[1,4]Dioxan-2-yl-methoxy)-9-(2-isopropoxy-ethoxy)-6,7-dihydro-pyrimido[6,1-a]isoquinolin-4-one

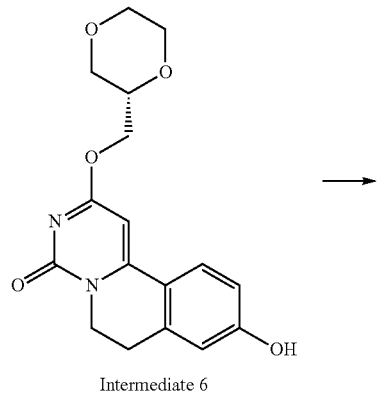

Intermediate 6

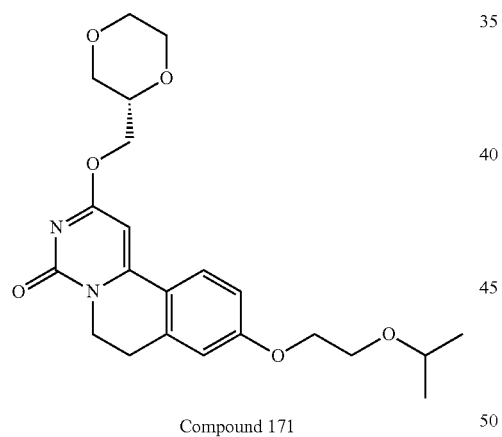

Compound 171

138

Compound 172: 2-((R)-1-[1,4]Dioxan-2-yl-methoxy)-9-(2-propoxy-ethoxy)-6,7-dihydro-pyrimido[6,1-a]isoquinolin-4-one

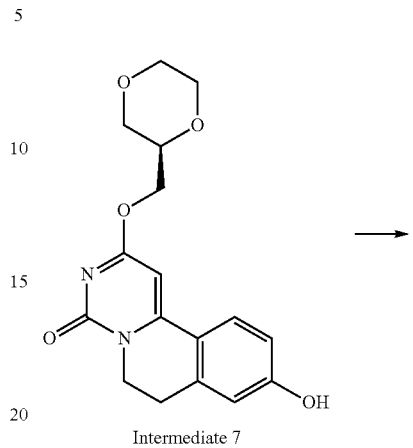

Intermediate 7

Compound 172

Intermediate 6 (0.15 g, 0.45 mmol, 1 eq.), 2-isopropoxy-ethanol (63 µL, 0.55 mmol, 1.2 eq.) and PPh$_3$ (144 mg, 0.55 mmol, 1.2 eq.) were suspended in 1,4-dioxane (5 mL) and the mixture was degassed with N$_2$. DIAD (0.108 mL, 0.55 mmol, 1.2 eq.) was added and the reaction was stirred at RT for 5 h. 0.5 eq. of DIAD and PPh$_3$ were added, and the reaction mixture was stirred at room temperature overnight. Reaction mixture was diluted with brine, extracted with EtOAc, dried over MgSO$_4$ and concentrated. The crude product was purified on silicagel column to give compound 171.

Intermediate 7 (0.25 g, 0.76 mmol, 1 eq.), 2-Propoxy-ethanol (105 µL, 0.91 mmol, 1.2 eq.) and PPh$_3$ (238 mg, 0.91 mmol, 1.2 eq.) were suspended in 1,4-dioxane (10 mL) and the mixture was degassed with N$_2$. DIAD (0.180 mL, 0.91 mmol, 1.2 eq.) was added and the reaction was stirred at RT overnight. 0.3 eq. of DIAD and PPh$_3$ were added, and the reaction mixture was stirred at room temperature for an extra 24 h. Reaction mixture was diluted with brine, extracted with EtOAc, dried over MgSO$_4$ and concentrated. Crude product was purified on silicagel column to give compound 172.

Compound 173: 2-((R)-1-[1,4]Dioxan-2-yl-methoxy)-9-(2-isopropoxy-ethoxy)-6,7-dihydro-pyrimido[6,1-a]isoquinolin-4-one

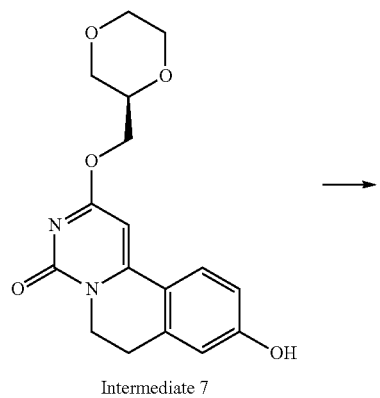

Intermediate 7

→

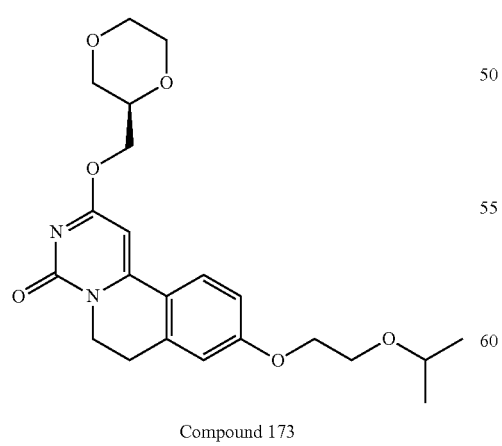

Compound 173

Intermediate 7 (0.25 g, 0.76 mmol, 1 eq.), 2-isopropoxy-ethanol (105 µL, 0.91 mmol, 1.2 eq.) and PPh$_3$ (238 mg, 0.91 mmol, 1.2 eq.) were suspended in 1,4-dioxane (10 mL) and the mixture was degassed with N$_2$. DIAD (0.180 mL, 0.91 mmol, 1.2 eq.) was added and the reaction was stirred at RT for 5 h. 0.3 eq. of DIAD and PPh$_3$ were added, and the reaction mixture was stirred at room temperature overnight. Reaction mixture was diluted with brine, extracted with EtOAc, dried over MgSO$_4$ and concentrated. Crude product was purified on silicagel column to give compound 173.

Compound 174: 2-((S)-1-[1,4]Dioxan-2-yl-methoxy)-9-(4-methoxy-butyl)-6,7-dihydro-pyrimido[6,1-a]isoquinolin-4-one Step 1: potassium 3-methoxy-propyl-trifluoroborate

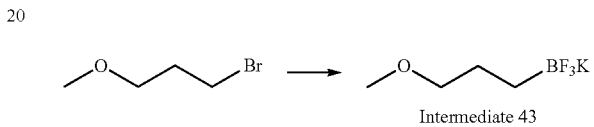

Intermediate 43

In a 2-neck round bottom flask equipped with a reflux condenser and an addition funnel was charged with Mg (471 mg, 19.20 mmol, 3 eq.) and Et$_2$O (2 mL) under N$_2$. One drop of neat (2-bromo-ethyl)-cyclopropane was added followed by two drops of dibromoethane. Once the 1$^{st}$ bubbles appeared, 1-Bromo-3-methoxy-propane (1 g, 6.54 mmol, 1 eq.) in Et$_2$O (10 mL) was added dropwise. Upon completion of the addition, the resulting suspension was stirred at RT for 1 h. In a separate flask, purged with N$_2$, a solution made of B(OMe)$_3$ (1.1 mL, 9.81 mmol, 1.5 eq.) in THF (12 mL) was cooled to −78° C. To this solution, the 3-methoxy-propyl magnesium bromide suspension was added dropwise via a double ended needle. The mixture was allowed to stir for 1 h at −78° C. and then was warmed to RT for 1 h. After cooling the mixture to 0° C., a saturated aqueous solution of KHF$_2$ (5.8 mL, 4.5 M, 4.1 eq.) was added dropwise and the reaction mixture was allowed to warm to RT. After 30 min, the solution was concentrated in-vacuo. The dried solids were triturated with hot acetone and filtered to remove inorganic salts. The resulting filtrate was concentrated and the solid residue was triturated with Et$_2$O. Potassium 3-methoxy-propyl-trifluoroborate, intermediate 43, was filtered and dried in-vacuo.

($^1$H, DMSO-d$_6$) δ ppm 3.19-3.13 (5 H, m), 1.38-1.29 (2 H, m), −0.1-0.19 (2 H, m)

Step 2: 2-((S)-1-[1,4]Dioxan-2-ylmethoxy)-9-(4-methoxy-butyl)-6,7-dihydro-pyrimido[6,1-a]isoquinolin-4-one Compound 174 is prepared via general method E using intermediates 9 and 43.

TABLE II

Mass spectral data of the Compounds of the Invention
MW: Molecular weight calc: calculated obs: observed

| Cpd # | Structures | Name | MW (calc) | MW (obsd) |
|---|---|---|---|---|
| 1 | 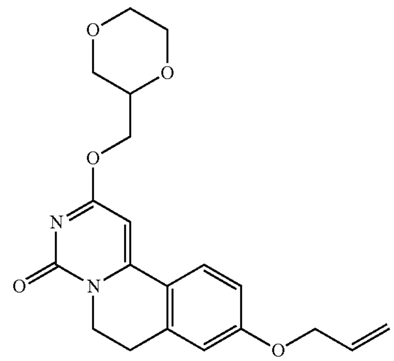 [SMILES: C=CCOc1ccc2c(c1)CCn1c-2cc(OCC2COCCO2)nc1=O] | 9-Allyloxy-2-([1,4]dioxan-2-ylmethoxy)-6,7-dihydro-pyrimido[6,1-a]isoquinolin-4-one | 370 | 371 |
| 2 | 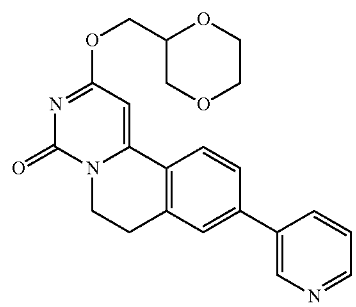 [SMILES: O=c1nc(OCC2COCCO2)cc2n1CCc1cc(-c3cccnc3)ccc1-2] | 2-([1,4]Dioxan-2-ylmethoxy)-9-pyridin-3-yl-6,7-dihydro-pyrimido[6,1-a]isoquinolin-4-one | 391 | NA |
| 3 | 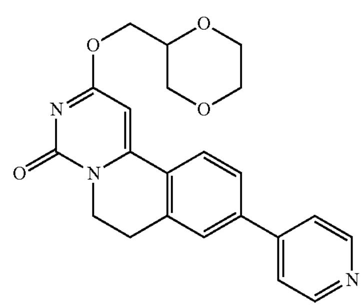 [SMILES: O=c1nc(OCC2COCCO2)cc2n1CCc1cc(-c3ccncc3)ccc1-2] | 2-([1,4]Dioxan-2-ylmethoxy)-9-pyridin-4-yl-6,7-dihydro-pyrimido[6,1-a]isoquinolin-4-one | 391 | 392 |
| 4 | 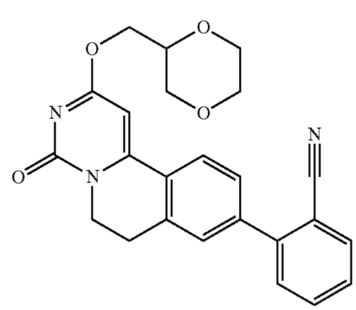 [SMILES: N#Cc1ccccc1-c1ccc2c(c1)CCn1c-2cc(OCC2COCCO2)nc1=O] | 2-[2-([1,4]Dioxan-2-ylmethoxy)-4-oxo-6,7-dihydro-4H-pyrimido[6,1-a]isoquinolin-9-yl]-benzonitrile | 415 | 416 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 5 | 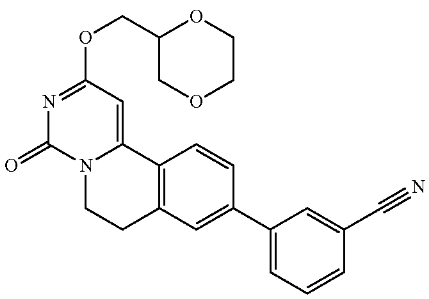 [SMILES: N#Cc1cccc(-c2ccc3c(c2)CCn2c-3cc(OCC3COCCO3)nc2=O)c1] | 3-[2-([1,4]Dioxan-2-ylmethoxy)-4-oxo-6,7-dihydro-4H-pyrimido[6,1-a]isoquinolin-9-yl]-benzonitrile | 415 | 416 |
| 6 | 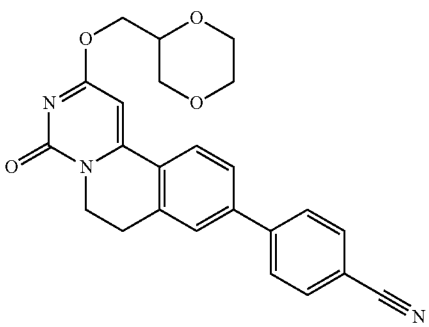 [SMILES: N#Cc1ccc(-c2ccc3c(c2)CCn2c-3cc(OCC3COCCO3)nc2=O)cc1] | 4-[2-([1,4]Dioxan-2-ylmethoxy)-4-oxo-6,7-dihydro-4H-pyrimido[6,1-a]isoquinolin-9-yl]-benzonitrile | 415 | 416 |
| 7 | 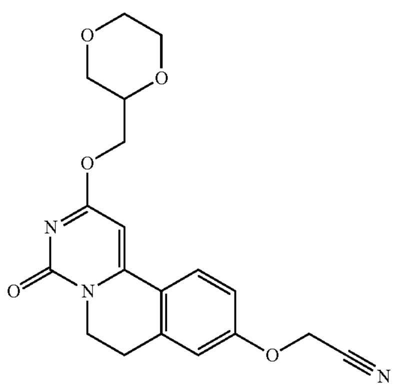 [SMILES: N#CCOc1ccc2c(c1)CCn1c-2cc(OCC2COCCO2)nc1=O] | [2-([1,4]Dioxan-2-ylmethoxy)-4-oxo-6,7-dihydro-4H-pyrimido[6,1-a]isoquinolin-9-yloxy]-acetonitrile | 369 | 370 |
| 8 | 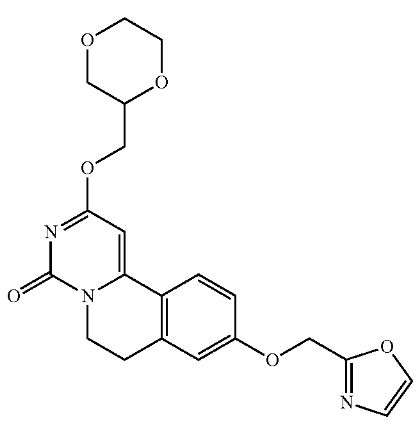 [SMILES: O=c1nc(OCC2COCCO2)cc2n1CCc1cc(OCc3ncco3)ccc1-2] | 2-([1,4]Dioxan-2-ylmethoxy)-9-(oxazol-2-ylmethoxy)-6,7-dihydro-pyrimido[6,1-a]isoquinolin-4-one | 411 | 412 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 9 | 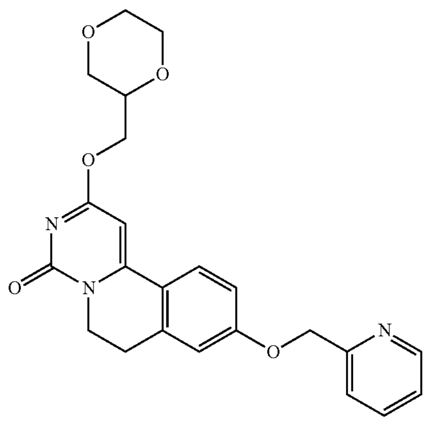 [SMILES: O=c1nc(OCC2COCCO2)cc2n1CCc1cc(OCc3ccccn3)ccc1-2] | 2-([1,4]Dioxan-2-ylmethoxy)-9-(pyridin-2-ylmethoxy)-6,7-dihydro-pyrimido[6,1-a]isoquinolin-4-one | 421 | 422 |
| 10 | 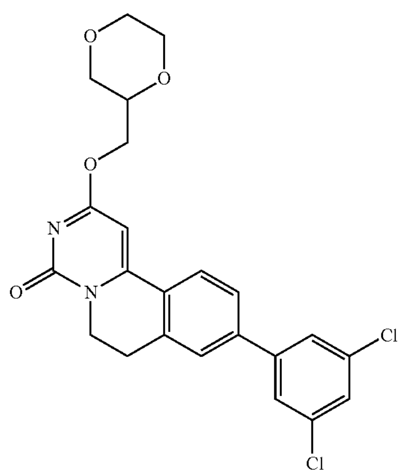 [SMILES: O=c1nc(OCC2COCCO2)cc2n1CCc1cc(-c3cc(Cl)cc(Cl)c3)ccc1-2] | 9-(3,5-Dichloro-phenyl)-2-([1,4]dioxan-2-ylmethoxy)-6,7-dihydro-pyrimido[6,1-a]isoquinolin-4-one | 458 | 459 |
| 11 | 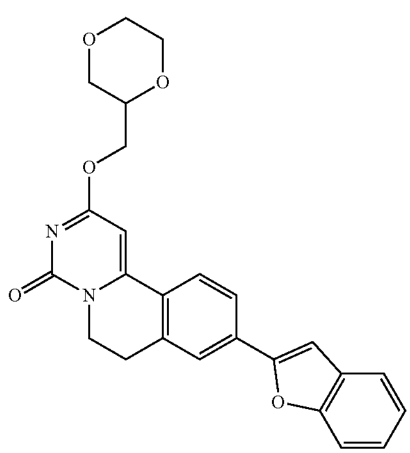 [SMILES: O=c1nc(OCC2COCCO2)cc2n1CCc1cc(-c3cc4ccccc4o3)ccc1-2] | 9-Benzofuran-2-yl-2-([1,4]dioxan-2-ylmethoxy)-6,7-dihydro-pyrimido[6,1-a]isoquinolin-4-one | 430 | NA |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 12 | 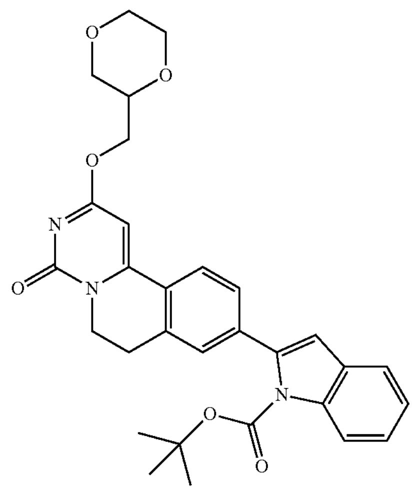 [SMILES: CC(C)(C)OC(=O)n1c(-c2ccc3c(c2)CCn2c-3cc(OCC3COCCO3)nc2=O)cc2ccccc21] | 2-[2-([1,4]Dioxan-2-ylmethoxy)-4-oxo-6,7-dihydro-4H-pyrimido[6,1-a]isoquinolin-9-yl]-indole-1-carboxylic acid tert-butyl ester | 529 | 530 |
| 13 | 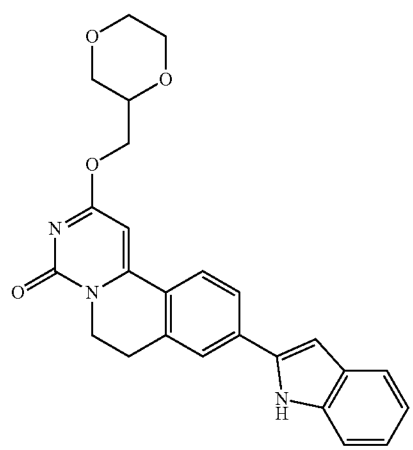 [SMILES: O=c1nc(OCC2COCCO2)cc2n1CCc1cc(-c3cc4ccccc4[nH]3)ccc1-2] | 2-([1,4]Dioxan-2-ylmethoxy)-9-(1H-indol-2-yl)-6,7-dihydro-pyrimido[6,1-a]isoquinolin-4-one | 429 | 430 |
| 14 | 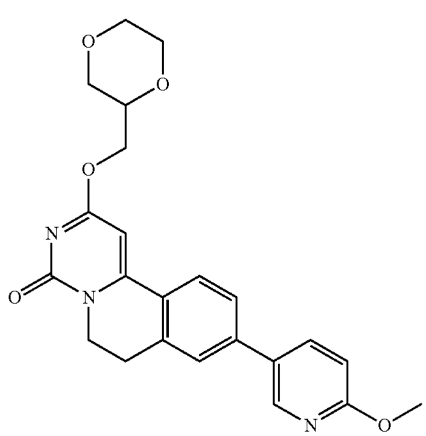 [SMILES: COc1ccc(-c2ccc3c(c2)CCn2c-3cc(OCC3COCCO3)nc2=O)cn1] | 2-([1,4]Dioxan-2-ylmethoxy)-9-(6-methoxy-pyridin-3-yl)-6,7-dihydro-pyrimido[6,1-a]isoquinolin-4-one | 421 | 422 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 15 | 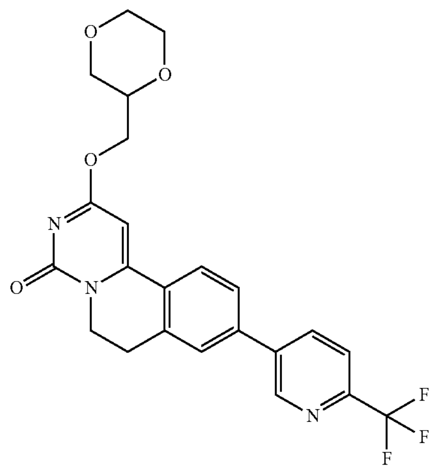 [SMILES: O=c1nc(OCC2COCCO2)cc2n1CCc1cc(-c3ccc(C(F)(F)F)nc3)ccc1-2] | 2-([1,4]Dioxan-2-ylmethoxy)-9-(6-trifluoromethyl-pyridin-3-yl)-6,7-dihydro-pyrimido[6,1-a]isoquinolin-4-one | 459 | 460 |
| 16 | 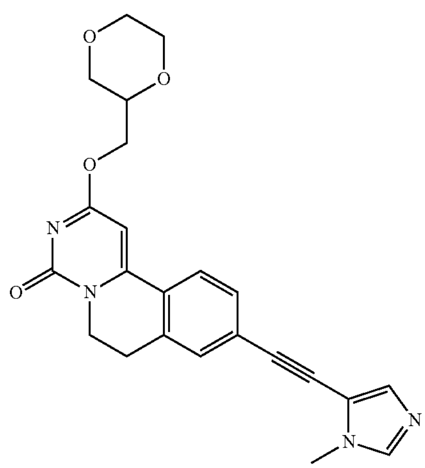 [SMILES: Cn1cncc1C#Cc1ccc2c(c1)CCn1c-2cc(OCC2COCCO2)nc1=O] | 2-([1,4]Dioxan-2-ylmethoxy)-9-(3-methyl-3H-imidazol-4-ylethynyl)-6,7-dihydro-pyrimido[6,1-a]isoquinolin-4-one | 418 | 419 |
| 17 | 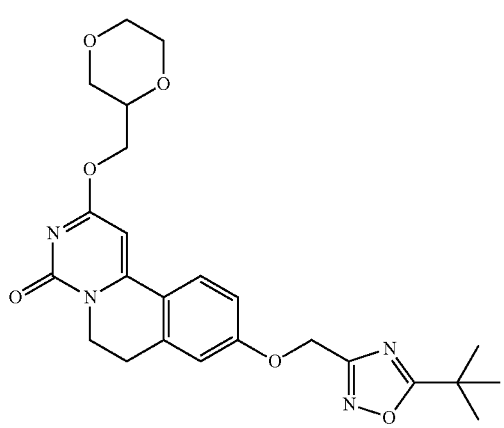 [SMILES: CC(C)(C)c1nc(COc2ccc3c(c2)CCn2c-3cc(OCC3COCCO3)nc2=O)no1] | 9-(5-tert-Butyl-[1,2,4]oxadiazol-3-ylmethoxy)-2-([1,4]dioxan-2-ylmethoxy)-6,7-dihydro-pyrimido[6,1-a]isoquinolin-4-one | 468 | 469 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 18 | 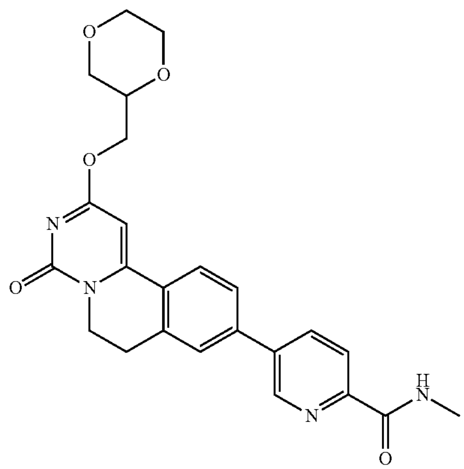 [SMILES: CNC(=O)c1ccc(-c2ccc3c(c2)CCn2c-3cc(OCC3COCCO3)nc2=O)cn1] | 5-[2-([1,4]Dioxan-2-ylmethoxy)-4-oxo-6,7-dihydro-4H-pyrimido[6,1-a]isoquinolin-9-yl]-pyridine-2-carboxylic acid methylamide | 448 | 449 |
| 19 | 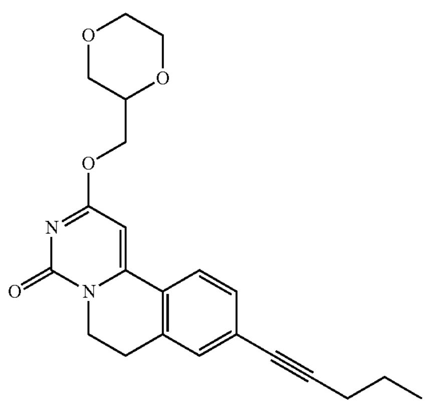 [SMILES: CCCC#Cc1ccc2c(c1)CCn1c-2cc(OCC2COCCO2)nc1=O] | 2-([1,4]Dioxan-2-ylmethoxy)-9-pent-1-ynyl-6,7-dihydro-pyrimido[6,1-a]isoquinolin-4-one | 380 | 381 |
| 20 | 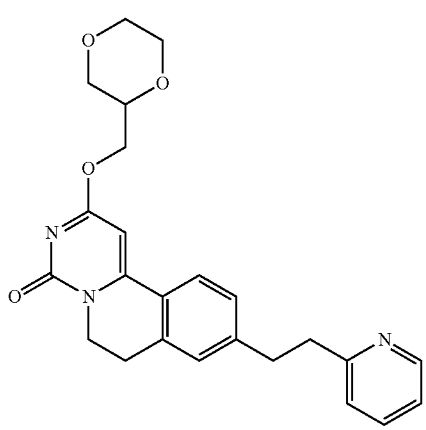 [SMILES: O=c1nc(OCC2COCCO2)cc2n1CCc1cc(CCc3ccccn3)ccc1-2] | 2-([1,4]Dioxan-2-ylmethoxy)-9-(2-pyridin-2-yl-ethyl)-6,7-dihydro-pyrimido[6,1-a]isoquinolin-4-one | 419 | 420 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 21 | 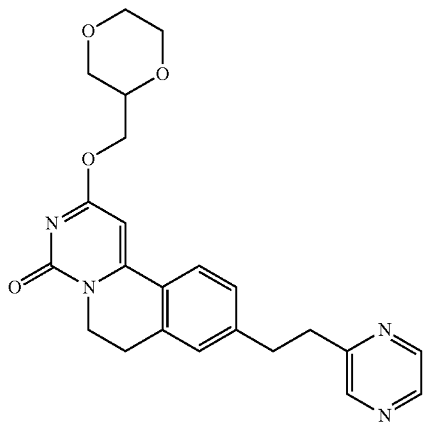 [SMILES: O=c1nc(OCC2COCCO2)cc2n1CCc1cc(CCc3cnccn3)ccc1-2] | 2-([1,4]Dioxan-2-ylmethoxy)-9-(2-pyrazin-2-yl-ethyl)-6,7-dihydro-pyrimido[6,1-a]isoquinolin-4-one | 420 | 421 |
| 22 | 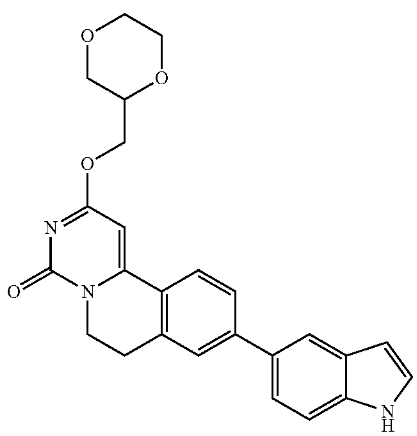 [SMILES: O=c1nc(OCC2COCCO2)cc2n1CCc1cc(-c3ccc4[nH]ccc4c3)ccc1-2] | 2-([1,4]Dioxan-2-ylmethoxy)-9-(1H-indol-5-yl)-6,7-dihydro-pyrimido[6,1-a]isoquinolin-4-one | 429 | 430 |
| 23 | 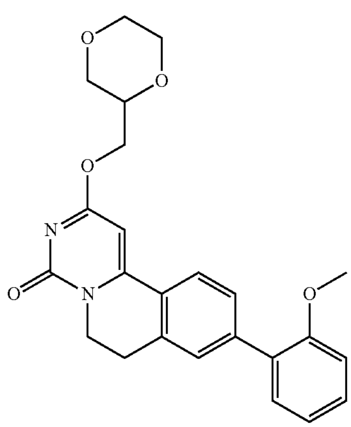 [SMILES: COc1ccccc1-c1ccc2c(c1)CCn1c-2cc(OCC2COCCO2)nc1=O] | 2-([1,4]Dioxan-2-ylmethoxy)-9-(2-methoxy-phenyl)-6,7-dihydro-pyrimido[6,1-a]isoquinolin-4-one | 420 | 421 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 24 | 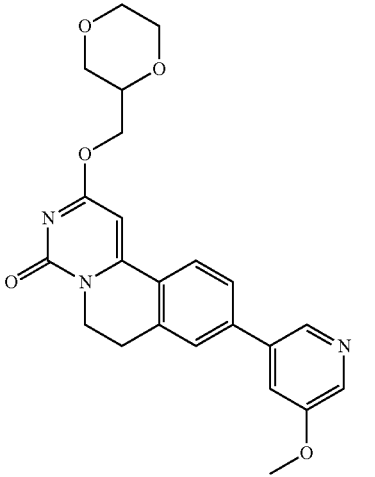 [SMILES: COc1cncc(-c2ccc3c(c2)CCn2c-3cc(OCC3COCCO3)nc2=O)c1] | 2-([1,4]Dioxan-2-ylmethoxy)-9-(5-methoxy-pyridin-3-yl)-6,7-dihydro-pyrimido[6,1-a]isoquinolin-4-one | 421 | 422 |
| 25 | 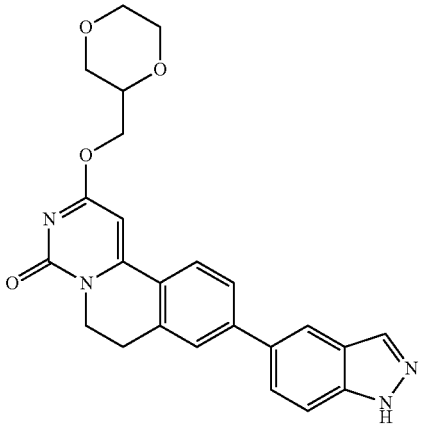 [SMILES: O=c1nc(OCC2COCCO2)cc2n1CCc1cc(-c3ccc4[nH]ncc4c3)ccc1-2] | 2-([1,4]Dioxan-2-ylmethoxy)-9-(1H-indazol-5-yl)-6,7-dihydro-pyrimido[6,1-a]isoquinolin-4-one | 430 | 431 |
| 26 | 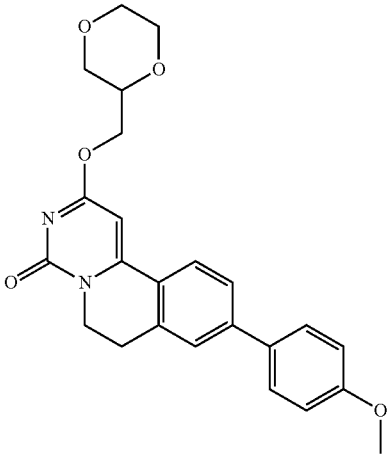 [SMILES: COc1ccc(-c2ccc3c(c2)CCn2c-3cc(OCC3COCCO3)nc2=O)cc1] | 2-([1,4]Dioxan-2-ylmethoxy)-9-(4-methoxy-phenyl)-6,7-dihydro-pyrimido[6,1-a]isoquinolin-4-one | 420 | 421 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 27 | 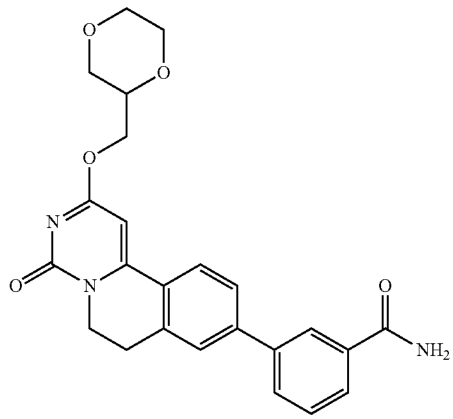 [SMILES: NC(=O)c1cccc(-c2ccc3c(c2)CCn2c-3cc(OCC3COCCO3)nc2=O)c1] | 3-[2-([1,4]Dioxan-2-ylmethoxy)-4-oxo-6,7-dihydro-4H-pyrimido[6,1-a]isoquinolin-9-yl]-benzamide | 433 | 434 |
| 28 | 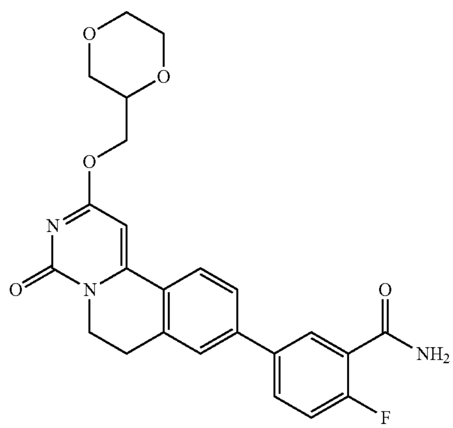 [SMILES: NC(=O)c1cc(-c2ccc3c(c2)CCn2c-3cc(OCC3COCCO3)nc2=O)ccc1F] | 5-[2-([1,4]Dioxan-2-ylmethoxy)-4-oxo-6,7-dihydro-4H-pyrimido[6,1-a]isoquinolin-9-yl]-2-fluoro-benzamide | 451 | 452 |
| 29 | 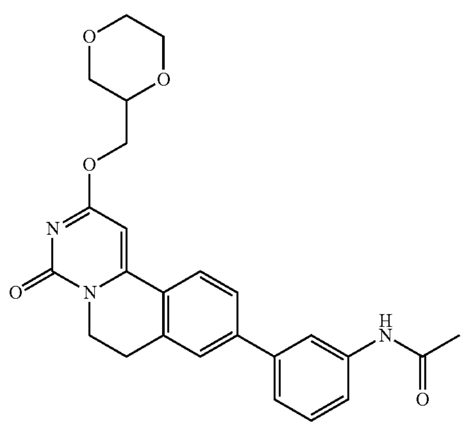 [SMILES: CC(=O)Nc1cccc(-c2ccc3c(c2)CCn2c-3cc(OCC3COCCO3)nc2=O)c1] | N-{3-[2-([1,4]Dioxan-2-ylmethoxy)-4-oxo-6,7-dihydro-4H-pyrimido[6,1-a]isoquinolin-9-yl]-phenyl}-acetamide | 447 | 448 |

TABLE II-continued

Mass spectral data of the Compounds of the Invention
MW: Molecular weight calc: calculated obs: observed

| Cpd # | Structures | Name | MW (calc) | MW (obsd) |
| --- | --- | --- | --- | --- |
| 30 | 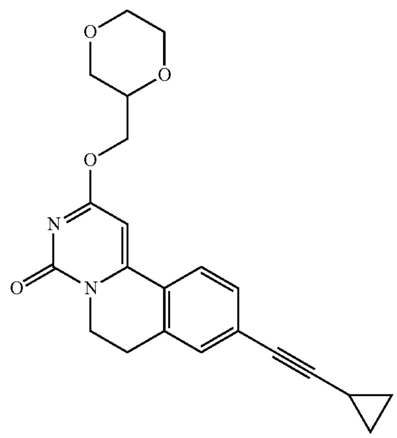 | 9-Cyclopropylethynyl-2-([1,4]dioxan-2-ylmethoxy)-6,7-dihydro-pyrimido[6,1-a]isoquinolin-4-one | 378 | 379 |
| 31 | 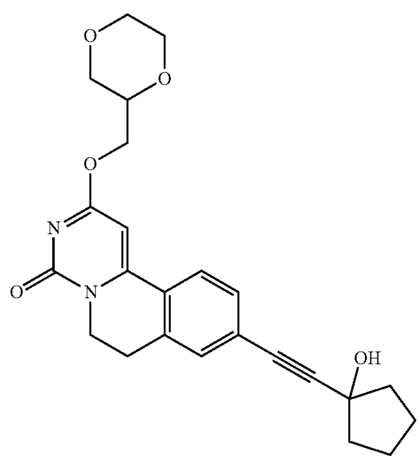 [SMILES: O=c1nc(OCC2COCCO2)cc2n1CCc1cc(C#CC3(O)CCCC3)ccc1-2] | 2-([1,4]Dioxan-2-ylmethoxy)-9-(1-hydroxy-cyclopentylethynyl)-6,7-dihydro-pyrimido[6,1-a]isoquinolin-4-one | 422 | 423 |
| 32 | 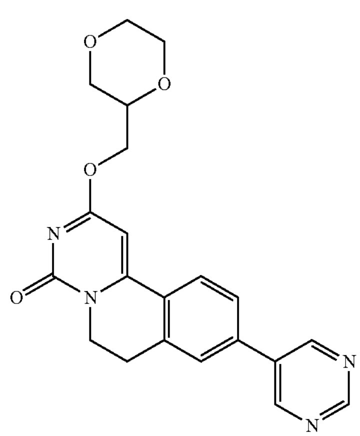 [SMILES: O=c1nc(OCC2COCCO2)cc2n1CCc1cc(-c3cncnc3)ccc1-2] | 2-([1,4]Dioxan-2-ylmethoxy)-9-pyrimidin-5-yl-6,7-dihydro-pyrimido[6,1-a]isoquinolin-4-one | 392 | 393 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 33 | 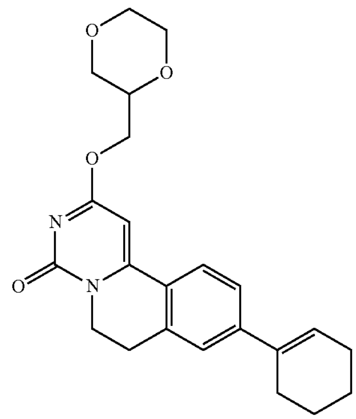 [SMILES: O=c1nc(OCC2COCCO2)cc2n1CCc1cc(C3=CCCCC3)ccc1-2] | 9-Cyclohex-1-enyl-2-([1,4]dioxan-2-ylmethoxy)-6,7-dihydro-pyrimido[6,1-a]isoquinolin-4-one | 394 | 395 |
| 34 | 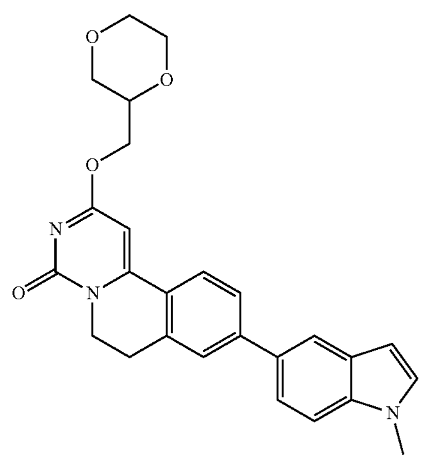 [SMILES: Cn1ccc2cc(-c3ccc4c(c3)CCn3c-4cc(OCC4COCCO4)nc3=O)ccc21] | 2-([1,4]Dioxan-2-ylmethoxy)-9-(1-methyl-1H-indol-5-yl)-6,7-dihydro-pyrimido[6,1-a]isoquinolin-4-one | 443 | 444 |
| 35 | 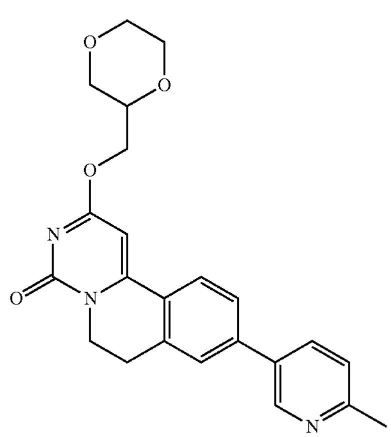 [SMILES: Cc1ccc(-c2ccc3c(c2)CCn2c-3cc(OCC3COCCO3)nc2=O)cn1] | 2-([1,4]Dioxan-2-ylmethoxy)-9-(6-methyl-pyridin-3-yl)-6,7-dihydro-pyrimido[6,1-a]isoquinolin-4-one | 405 | 406 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 36 | 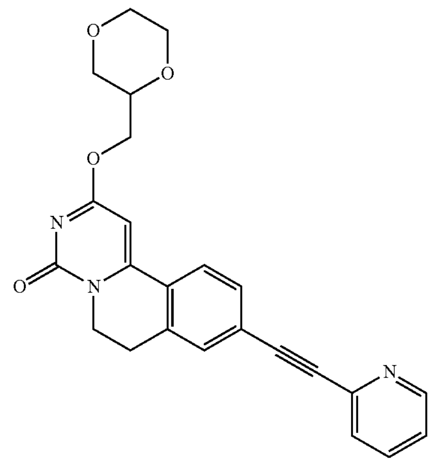 [SMILES: O=c1nc(OCC2COCCO2)cc2n1CCc1cc(C#Cc3ccccn3)ccc1-2] | 2-([1,4]Dioxan-2-ylmethoxy)-9-pyridin-2-ylethynyl-6,7-dihydro-pyrimido[6,1-a]isoquinolin-4-one | 415 | 416 |
| 37 | 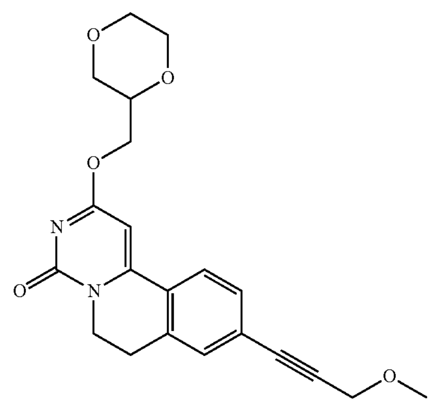 [SMILES: COCC#Cc1ccc2c(c1)CCn1c-2cc(OCC2COCCO2)nc1=O] | 2-([1,4]Dioxan-2-ylmethoxy)-9-(3-methoxy-prop-1-ynyl)-6,7-dihydro-pyrimido[6,1-a]isoquinolin-4-one | 382 | 383 |
| 38 | 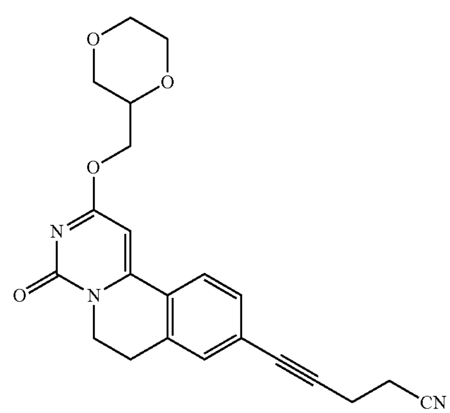 [SMILES: N#CCCC#Cc1ccc2c(c1)CCn1c-2cc(OCC2COCCO2)nc1=O] | 5-[2-([1,4]Dioxan-2-ylmethoxy)-4-oxo-6,7-dihydro-4H-pyrimido[6,1-a]isoquinolin-9-yl]-pent-4-ynenitrile | 391 | 392 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 39 | 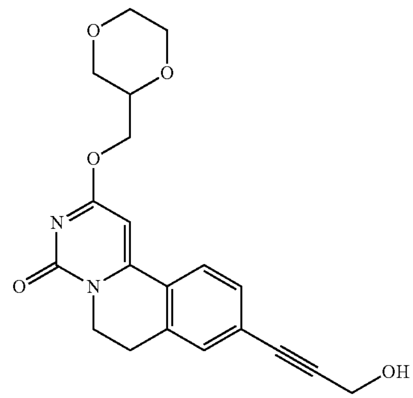 [SMILES: O=c1nc(OCC2COCCO2)cc2n1CCc1cc(C#CCO)ccc1-2] | 2-([1,4]Dioxan-2-ylmethoxy)-9-(3-hydroxy-prop-1-ynyl)-6,7-dihydro-pyrimido[6,1-a]isoquinolin-4-one | 368 | 369 |
| 40 | 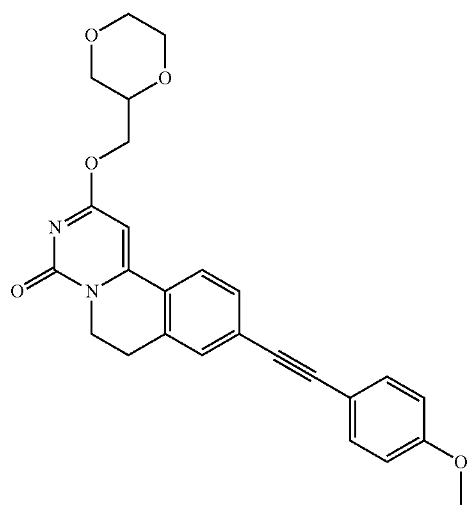 [SMILES: COc1ccc(C#Cc2ccc3c(c2)CCn2c-3cc(OCC3COCCO3)nc2=O)cc1] | 2-([1,4]Dioxan-2-ylmethoxy)-9-(4-methoxy-phenylethynyl)-6,7-dihydro-pyrimido[6,1-a]isoquinolin-4-one | 444 | 445 |
| 41 | 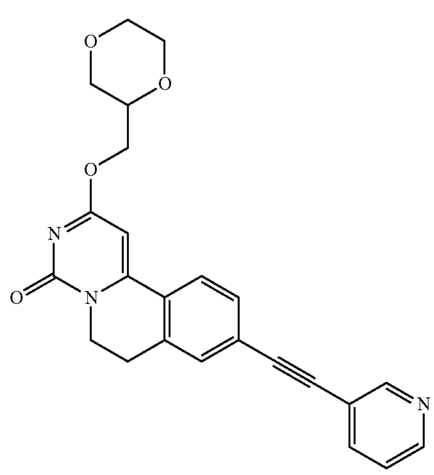 [SMILES: O=c1nc(OCC2COCCO2)cc2n1CCc1cc(C#Cc3cccnc3)ccc1-2] | 2-([1,4]Dioxan-2-ylmethoxy)-9-pyridin-3-ylethynyl-6,7-dihydro-pyrimido[6,1-a]isoquinolin-4-one | 415 | 416 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 42 | 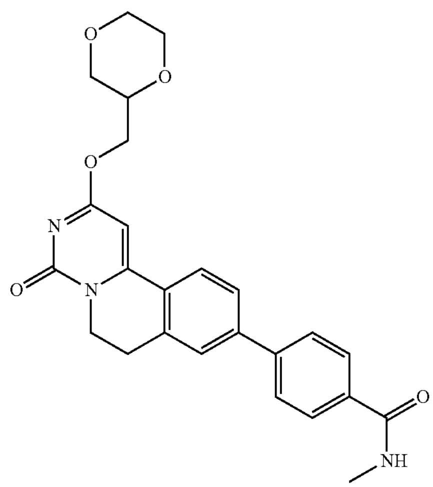 [SMILES: CNC(=O)c1ccc(-c2ccc3c(c2)CCn2c-3cc(OCC3COCCO3)nc2=O)cc1] | 4-[2-([1,4]Dioxan-2-ylmethoxy)-4-oxo-6,7-dihydro-4H-pyrimido[6,1-a]isoquinolin-9-yl]-N-methyl-benzamide | 447 | NA |
| 43 | 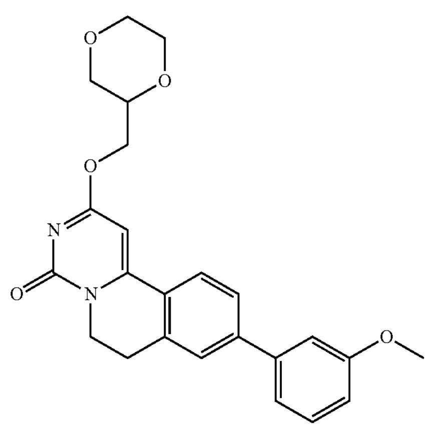 [SMILES: COc1cccc(-c2ccc3c(c2)CCn2c-3cc(OCC3COCCO3)nc2=O)c1] | 2-([1,4]Dioxan-2-ylmethoxy)-9-(3-methoxy-phenyl)-6,7-dihydro-pyrimido[6,1-a]isoquinolin-4-one | 420 | 421 |
| 44 | 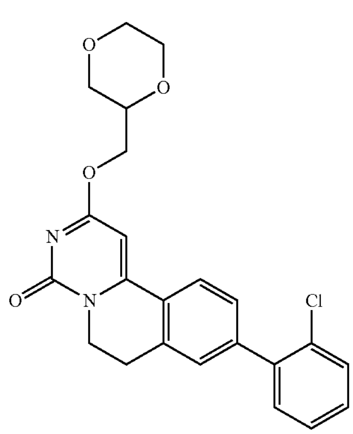 [SMILES: O=c1nc(OCC2COCCO2)cc2n1CCc1cc(-c3ccccc3Cl)ccc1-2] | 9-(2-Chloro-phenyl)-2-([1,4]dioxan-2-ylmethoxy)-6,7-dihydro-pyrimido[6,1-a]isoquinolin-4-one | 424 | 425 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 45 | 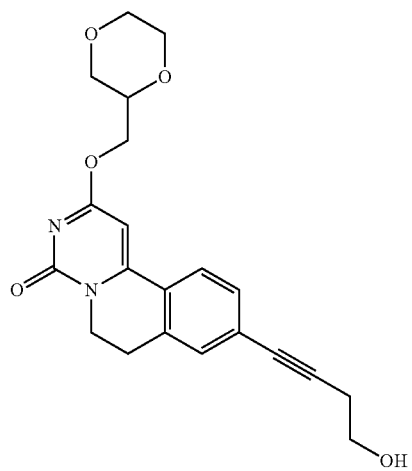 [SMILES: O=c1nc(OCC2COCCO2)cc2n1CCc1cc(C#CCCO)ccc1-2] | 2-([1,4]Dioxan-2-ylmethoxy)-9-(4-hydroxy-but-1-ynyl)-6,7-dihydro-pyrimido[6,1-a]isoquinolin-4-one | 382 | NA |
| 46 | 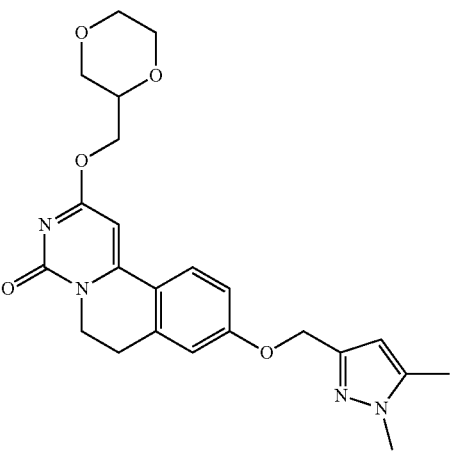 [SMILES: Cc1cc(COc2ccc3c(c2)CCn2c-3cc(OCC3COCCO3)nc2=O)nn1C] | 9-(1,5-Dimethyl-1H-pyrazol-3-ylmethoxy)-2-([1,4]dioxan-2-ylmethoxy)-6,7-dihydro-pyrimido[6,1-a]isoquinolin-4-one | 438 | 439 |
| 47 | 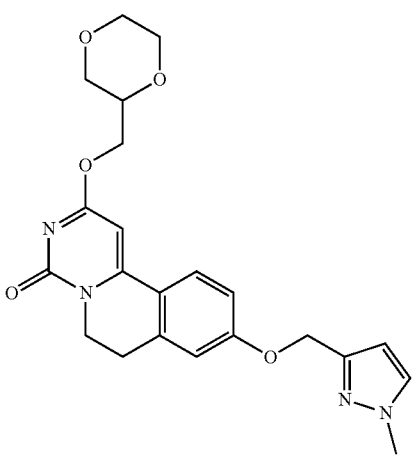 [SMILES: Cn1ccc(COc2ccc3c(c2)CCn2c-3cc(OCC3COCCO3)nc2=O)n1] | 2-([1,4]Dioxan-2-ylmethoxy)-9-(1-methyl-1H-pyrazol-3-ylmethoxy)-6,7-dihydro-pyrimido[6,1-a]isoquinolin-4-one | 424 | 425 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 48 | 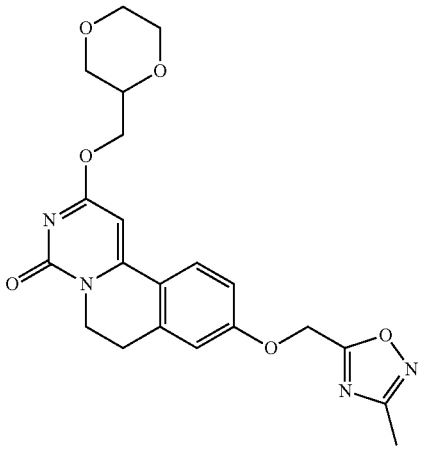 [SMILES: Cc1noc(COc2ccc3c(c2)CCn2c-3cc(OCC3COCCO3)nc2=O)n1] | 2-([1,4]Dioxan-2-ylmethoxy)-9-(3-methyl-[1,2,4]oxadiazol-5-ylmethoxy)-6,7-dihydro-pyrimido[6,1-a]isoquinolin-4-one | 426 | 427 |
| 49 | 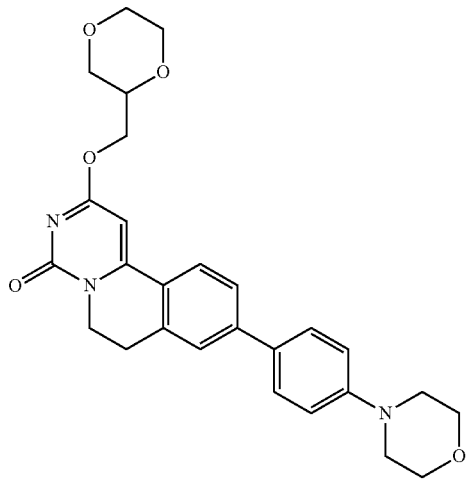 [SMILES: O=c1nc(OCC2COCCO2)cc2n1CCc1cc(-c3ccc(N4CCOCC4)cc3)ccc1-2] | 2-([1,4]Dioxan-2-ylmethoxy)-9-(4-morpholin-4-yl-phenyl)-6,7-dihydro-pyrimido[6,1-a]isoquinolin-4-one | 475 | 476 |
| 50 | 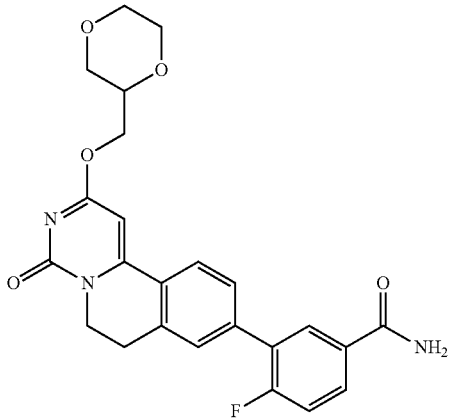 [SMILES: NC(=O)c1ccc(F)c(-c2ccc3c(c2)CCn2c-3cc(OCC3COCCO3)nc2=O)c1] | 3-[2-([1,4]Dioxan-2-ylmethoxy)-4-oxo-6,7-dihydro-4H-pyrimido[6,1-a]isoquinolin-9-yl]-4-fluoro-benzamide | 451 | 452 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 51 | 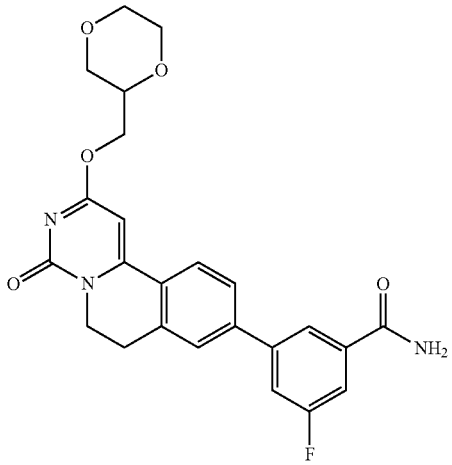 [SMILES: NC(=O)c1cc(F)cc(-c2ccc3c(c2)CCn2c-3cc(OCC3COCCO3)nc2=O)c1] | 3-[2-([1,4]Dioxan-2-ylmethoxy)-4-oxo-6,7-dihydro-4H-pyrimido[6,1-a]isoquinolin-9-yl]-5-fluoro-benzamide | 451 | 452 |
| 52 | 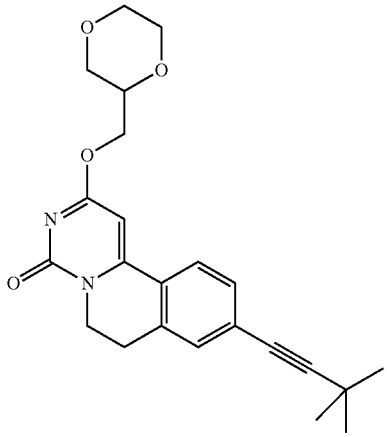 [SMILES: CC(C)(C)C#Cc1ccc2c(c1)CCn1c-2cc(OCC2COCCO2)nc1=O] | 9-(3,3-Dimethyl-but-1-ynyl)-2-([1,4]dioxan-2-ylmethoxy)-6,7-dihydro-pyrimido[6,1-a]isoquinolin-4-one | 394 | 395 |
| 53 | 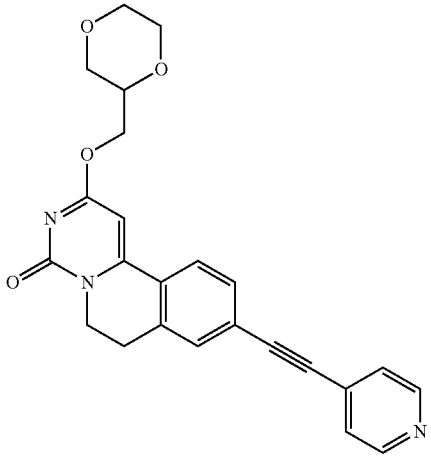 [SMILES: O=c1nc(OCC2COCCO2)cc2n1CCc1cc(C#Cc3ccncc3)ccc1-2] | 2-([1,4]Dioxan-2-ylmethoxy)-9-pyridin-4-ylethynyl-6,7-dihydro-pyrimido[6,1-a]isoquinolin-4-one | 415 | 416 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 54 | 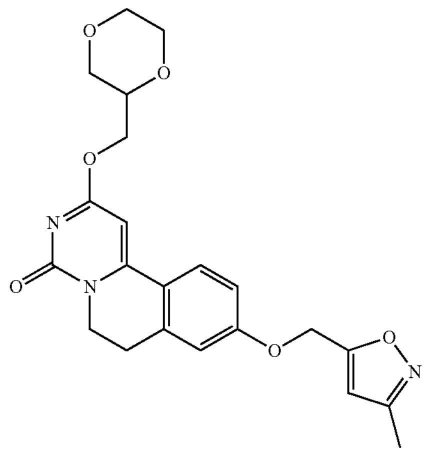 [SMILES: Cc1cc(COc2ccc3c(c2)CCn2c-3cc(OCC3COCCO3)nc2=O)on1] | 2-([1,4]Dioxan-2-ylmethoxy)-9-(3-methyl-isoxazol-5-ylmethoxy)-6,7-dihydro-pyrimido[6,1-a]isoquinolin-4-one | 425 | 426 |
| 55 | 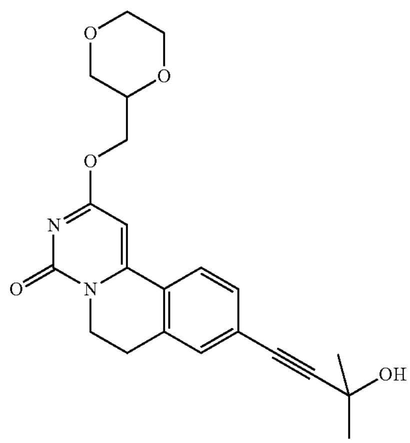 [SMILES: CC(C)(O)C#Cc1ccc2c(c1)CCn1c-2cc(OCC2COCCO2)nc1=O] | 2-([1,4]Dioxan-2-ylmethoxy)-9-(3-hydroxy-3-methyl-but-1-ynyl)-6,7-dihydro-pyrimido[6,1-a]isoquinolin-4-one | 396 | 397 |
| 56 | 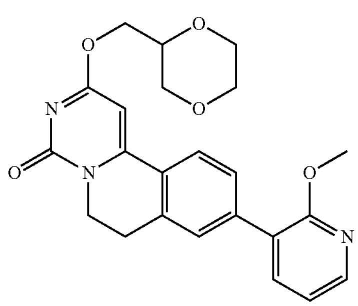 [SMILES: COc1ncccc1-c1ccc2c(c1)CCn1c-2cc(OCC2COCCO2)nc1=O] | 2-([1,4]Dioxan-2-ylmethoxy)-9-(2-methoxy-pyridin-3-yl)-6,7-dihydro-pyrimido[6,1-a]isoquinolin-4-one | 421 | 422 |
| 57 | 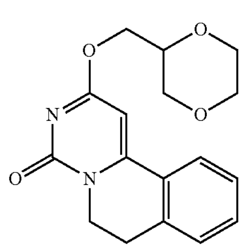 [SMILES: O=c1nc(OCC2COCCO2)cc2n1CCc1ccccc1-2] | 2-([1,4]Dioxan-2-ylmethoxy)-6,7-dihydro-pyrimido[6,1-a]isoquinolin-4-one | 314 | NA |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 58 | 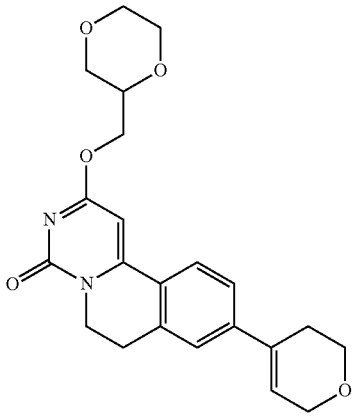 [SMILES: O=c1nc(OCC2COCCO2)cc2n1CCc1cc(C3=CCOCC3)ccc1-2] | 9-(3,6-Dihydro-2H-pyran-4-yl)-2-([1,4]dioxan-2-ylmethoxy)-6,7-dihydro-pyrimido[6,1-a]isoquinolin-4-one | 396 | 397 |
| 59 | 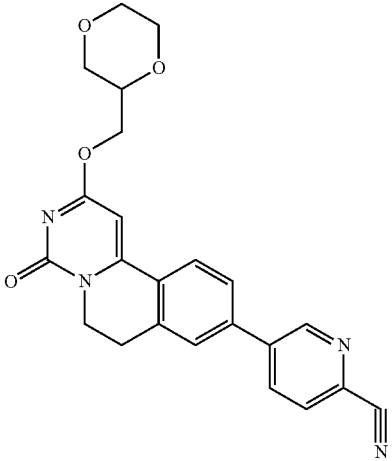 [SMILES: N#Cc1ccc(-c2ccc3c(c2)CCn2c-3cc(OCC3COCCO3)nc2=O)cn1] | 5-[2-([1,4]Dioxan-2-ylmethoxy)-4-oxo-6,7-dihydro-4H-pyrimido[6,1-a]isoquinolin-9-yl]-pyridine-2-carbonitrile | 416 | 417 |
| 60 | 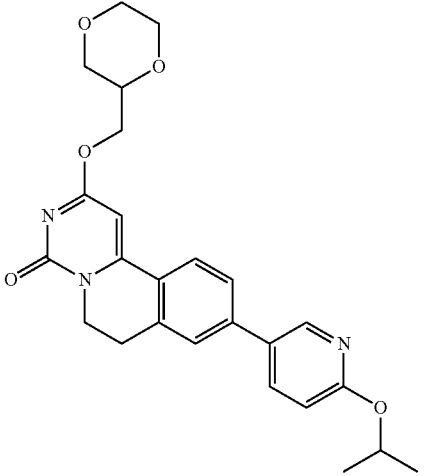 [SMILES: CC(C)Oc1ccc(-c2ccc3c(c2)CCn2c-3cc(OCC3COCCO3)nc2=O)cn1] | 2-([1,4]Dioxan-2-ylmethoxy)-9-(6-isopropoxy-pyridin-3-yl)-6,7-dihydro-pyrimido[6,1-a]isoquinolin-4-one | 449 | 450 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 61 | 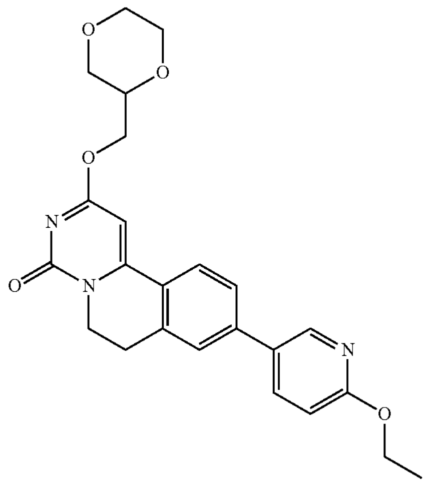 [SMILES: CCOc1ccc(-c2ccc3c(c2)CCn2c-3cc(OCC3COCCO3)nc2=O)cn1] | 2-([1,4]Dioxan-2-ylmethoxy)-9-(6-ethoxy-pyridin-3-yl)-6,7-dihydro-pyrimido[6,1-a]isoquinolin-4-one | 435 | 436 |
| 62 | 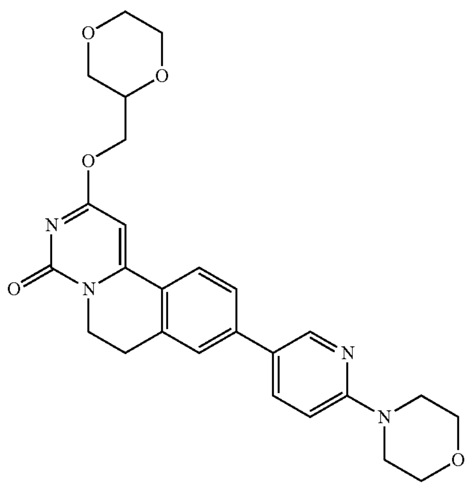 [SMILES: O=c1nc(OCC2COCCO2)cc2n1CCc1cc(-c3ccc(N4CCOCC4)nc3)ccc1-2] | 2-([1,4]Dioxan-2-ylmethoxy)-9-(6-morpholin-4-yl-pyridin-3-yl)-6,7-dihydro-pyrimido[6,1-a]isoquinolin-4-one | 476 | 477 |
| 63 | 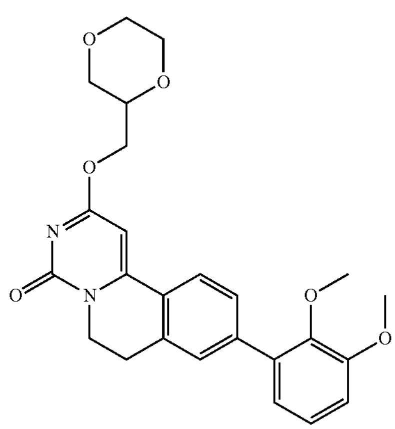 [SMILES: COc1cccc(-c2ccc3c(c2)CCn2c-3cc(OCC3COCCO3)nc2=O)c1OC] | 9-(2,3-Dimethoxy-phenyl)-2-([1,4]dioxan-2-ylmethoxy)-6,7-dihydro-pyrimido[6,1-a]isoquinolin-4-one | 450 | 451 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 64 | 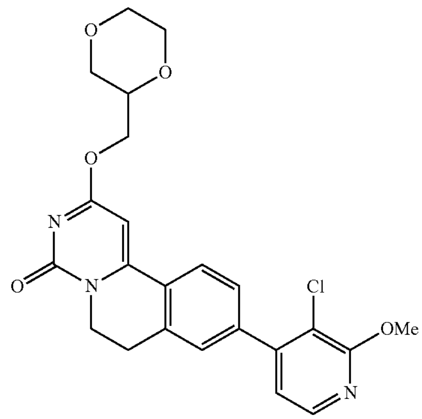 [SMILES: COc1nccc(-c2ccc3c(c2)CCn2c-3cc(OCC3COCCO3)nc2=O)c1Cl] | 9-(3-Chloro-2-methoxy-pyridin-4-yl)-2-([1,4]dioxan-2-ylmethoxy)-6,7-dihydro-pyrimido[6,1-a]isoquinolin-4-one | 455 | 456 |
| 65 | 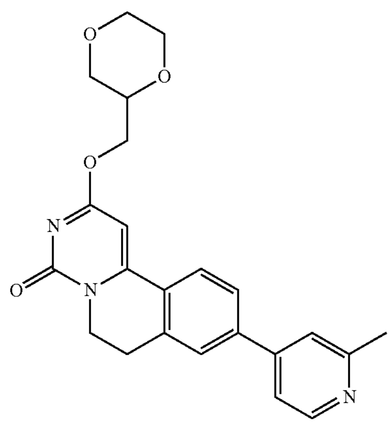 [SMILES: Cc1cc(-c2ccc3c(c2)CCn2c-3cc(OCC3COCCO3)nc2=O)ccn1] | 2-([1,4]Dioxan-2-ylmethoxy)-9-(2-methyl-pyridin-4-yl)-6,7-dihydro-pyrimido[6,1-a]isoquinolin-4-one | 405 | 406 |
| 66 | 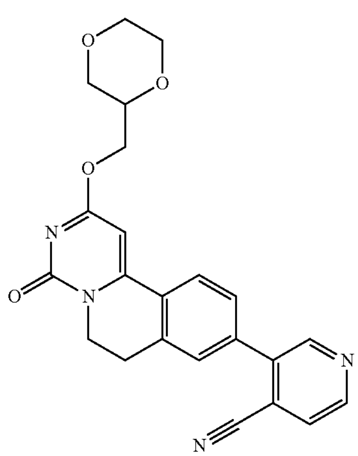 [SMILES: N#Cc1ccncc1-c1ccc2c(c1)CCn1c-2cc(OCC2COCCO2)nc1=O] | 3-[2-([1,4]Dioxan-2-dimethoxy)-4-oxo-6,7-dihydro-4H-pyrimido[6,1-a]isoquinolin-9-yl]-isonicotinonitrile | 416 | 417 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 67 | 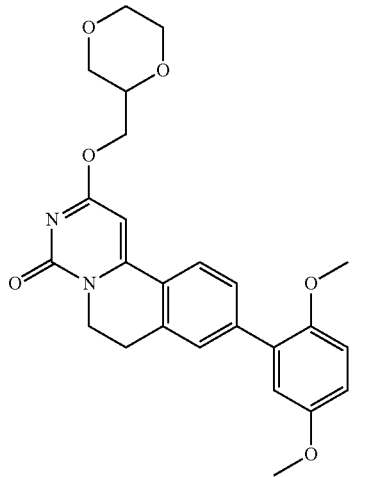 [SMILES: COc1ccc(OC)c(-c2ccc3c(c2)CCn2c-3cc(OCC3COCCO3)nc2=O)c1] | 9-(2,5-Dimethoxy-phenyl)-2-([1,4]dioxan-2-ylmethoxy)-6,7-dihydro-pyrimido[6,1-a]isoquinolin-4-one | 450 | 451 |
| 68 | 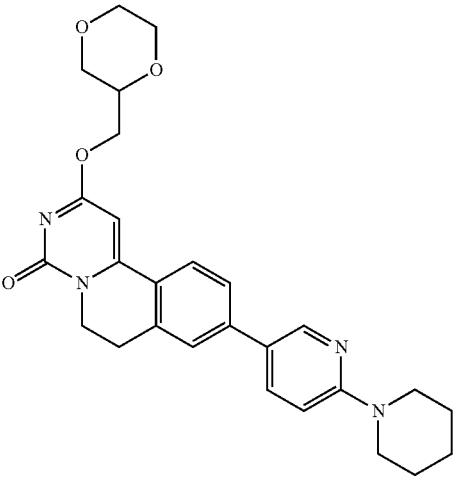 [SMILES: O=c1nc(OCC2COCCO2)cc2n1CCc1cc(-c3ccc(N4CCCCC4)nc3)ccc1-2] | 2-([1,4]Dioxan-2-ylmethoxy)-9-(3,4,5,6-tetrahydro-2H-[1,2']bipyridinyl-5'-yl)-6,7-dihydro-pyrimido[6,1-a]isoquinolin-4-one | 474 | 475 |
| 69 | 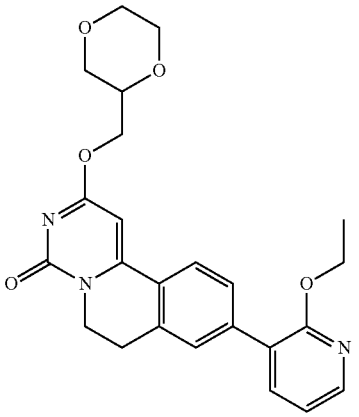 [SMILES: CCOc1ncccc1-c1ccc2c(c1)CCn1c-2cc(OCC2COCCO2)nc1=O] | 2-([1,4]Dioxan-2-ylmethoxy)-9-(2-ethoxy-pyridin-3-yl)-6,7-dihydro-pyrimido[6,1-a]isoquinolin-4-one | 435 | 436 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 70 | 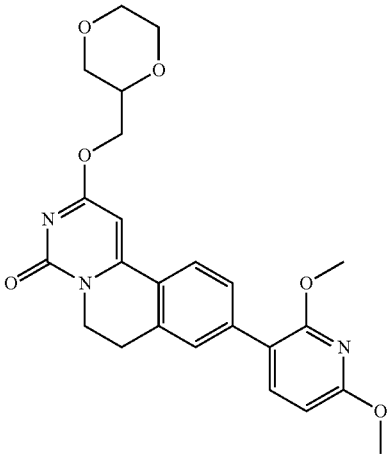 [SMILES: COc1ccc(-c2ccc3c(c2)CCn2c-3cc(OCC3COCCO3)nc2=O)c(OC)n1] | 9-(2,6-Dimethoxy-pyridin-3-yl)-2-([1,4]dioxan-2-ylmethoxy)-6,7-dihydro-pyrimido[6,1-a]isoquinolin-4-one | 451 | 452 |
| 71 | 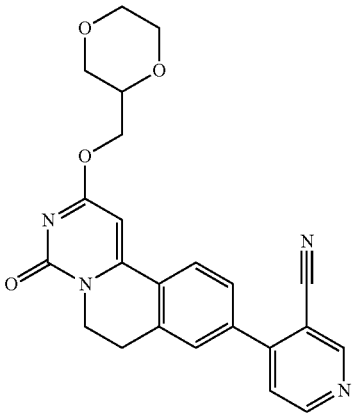 [SMILES: N#Cc1cnccc1-c1ccc2c(c1)CCn1c-2cc(OCC2COCCO2)nc1=O] | 4-[2-([1,4]Dioxan-2-ylmethoxy)-4-oxo-6,7-dihydro-4H-pyrimido[6,1-a]isoquinolin-9-yl]-nicotinonitrile | 416 | 417 |
| 72 | 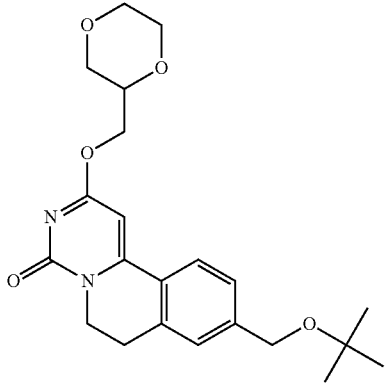 [SMILES: CC(C)(C)OCc1ccc2c(c1)CCn1c-2cc(OCC2COCCO2)nc1=O] | 9-tert-Butoxymethyl-2-([1,4]dioxan-2-ylmethoxy)-6,7-dihydro-pyrimido[6,1-a]isoquinolin-4-one | 400 | 401 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 73 | 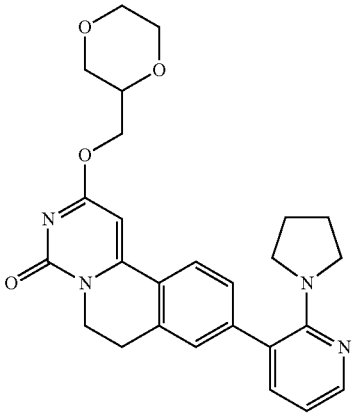 [SMILES: O=c1nc(OCC2COCCO2)cc2n1CCc1cc(-c3cccnc3N3CCCC3)ccc1-2] | 2-([1,4]Dioxan-2-ylmethoxy)-9-(2-pyrrolidin-1-yl-pyridin-3-yl)-6,7-dihydro-pyrimido[6,1-a]isoquinolin-4-one | 460 | 461 |
| 74 | 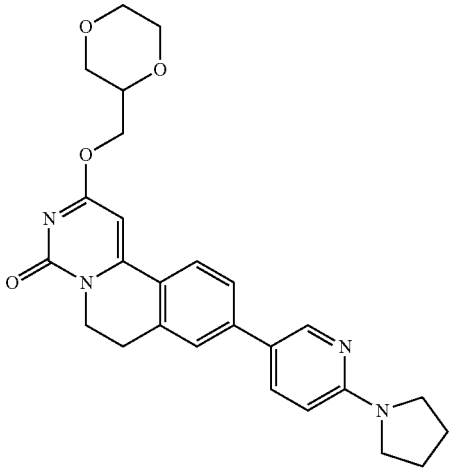 [SMILES: O=c1nc(OCC2COCCO2)cc2n1CCc1cc(-c3ccc(N4CCCC4)nc3)ccc1-2] | 2-([1,4]Dioxan-2-ylmethoxy)-9-(6-pyrrolidin-1-yl-pyridin-3-yl)-6,7-dihydro-pyrimido[6,1-a]isoquinolin-4-one | 460 | 461 |
| 75 | 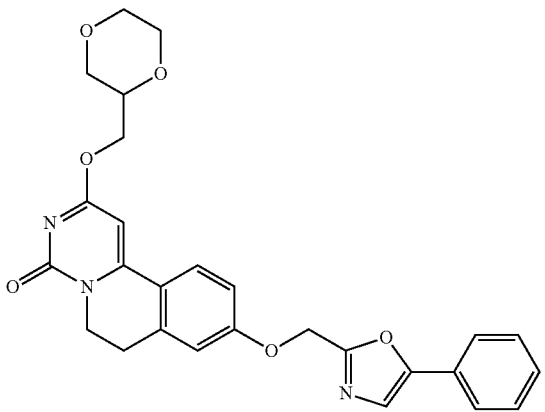 [SMILES: O=c1nc(OCC2COCCO2)cc2n1CCc1cc(OCc3ncc(-c4ccccc4)o3)ccc1-2] | 2-([1,4]Dioxan-2-ylmethoxy)-9-(5-phenyl-oxazol-2-ylmethoxy)-6,7-dihydro-pyrimido[6,1-a]isoquinolin-4-one | 487 | 488 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 76 | 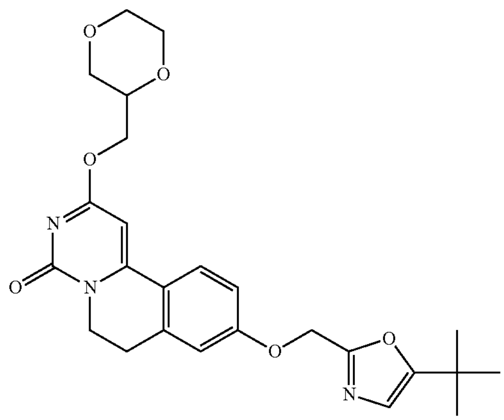 [SMILES: CC(C)(C)c1cnc(COc2ccc3c(c2)CCn2c-3cc(OCC3COCCO3)nc2=O)o1] | 9-(5-tert-Butyl-oxazol-2-ylmethoxy)-2-([1,4]dioxan-2-ylmethoxy)-6,7-dihydro-pyrimido[6,1-a]isoquinolin-4-one | 467 | NA |
| 77 | 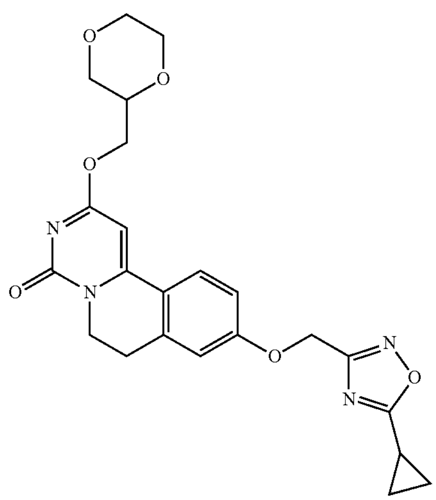 [SMILES: O=c1nc(OCC2COCCO2)cc2n1CCc1cc(OCc3noc(C4CC4)n3)ccc1-2] | 9-(5-Cyclopropyl-[1,2,4]oxadiazol-3-ylmethoxy)-2-([1,4]dioxan-2-ylmethoxy)-6,7-dihydro-pyrimido[6,1-a]isoquinolin-4-one | 452 | 453 |
| 78 | 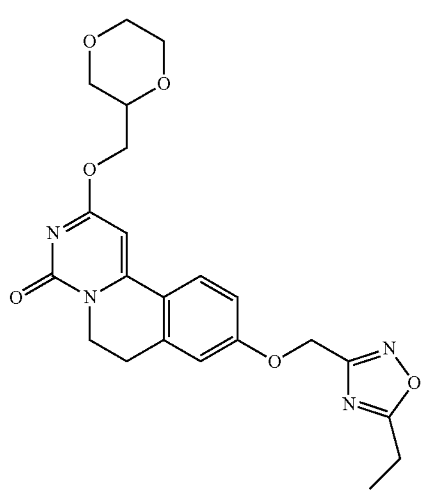 [SMILES: CCc1nc(COc2ccc3c(c2)CCn2c-3cc(OCC3COCCO3)nc2=O)no1] | 2-([1,4]Dioxan-2-ylmethoxy)-9-(5-ethyl-[1,2,4]oxadiazol-3-ylmethoxy)-6,7-dihydro-pyrimido[6,1-a]isoquinolin-4-one | 440 | 441 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 79 | 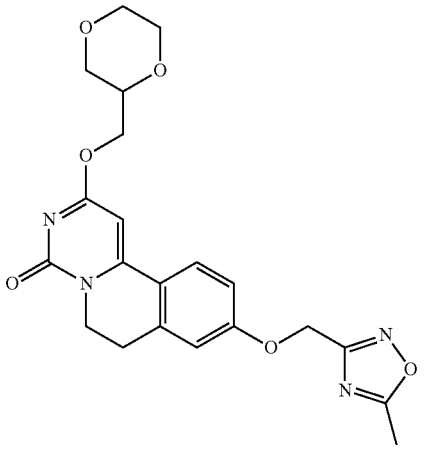 [SMILES: Cc1nc(COc2ccc3c(c2)CCn2c-3cc(OCC3COCCO3)nc2=O)no1] | 2-([1,4]Dioxan-2-ylmethoxy)-9-(5-methyl-[1,2,4]oxadiazol-3-ylmethoxy)-6,7-dihydro-pyrimido[6,1-a]isoquinolin-4-one | 426 | 427 |
| 80 | 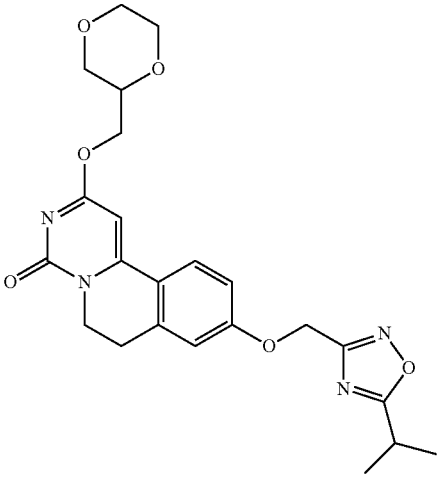 [SMILES: CC(C)c1nc(COc2ccc3c(c2)CCn2c-3cc(OCC3COCCO3)nc2=O)no1] | 2-([1,4]Dioxan-2-ylmethoxy)-9-(5-isopropyl-[1,2,4]oxadiazol-3-ylmethoxy)-6,7-dihydro-pyrimido[6,1-a]isoquinolin-4-one | 454 | 455 |
| 81 | 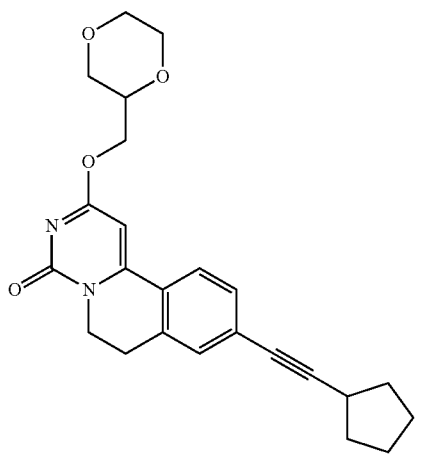 [SMILES: O=c1nc(OCC2COCCO2)cc2n1CCc1cc(C#CC3CCCC3)ccc1-2] | 9-Cyclopentylethynyl-2-([1,4]dioxan-2-ylmethoxy)-6,7-dihydro-pyrimido[6,1-a]isoquinolin-4-one | 406 | 407 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 82 | 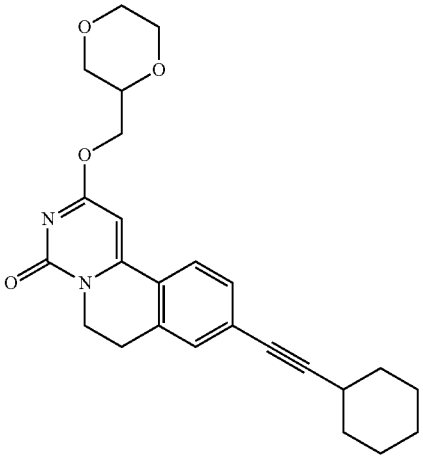 [SMILES: O=c1nc(OCC2COCCO2)cc2n1CCc1cc(C#CC3CCCCC3)ccc1-2] | 9-Cyclohexylethynyl-2-([1,4]dioxan-2-ylmethoxy)-6,7-dihydro-pyrimido[6,1-a]isoquinolin-4-one | 420 | 421 |
| 83 | 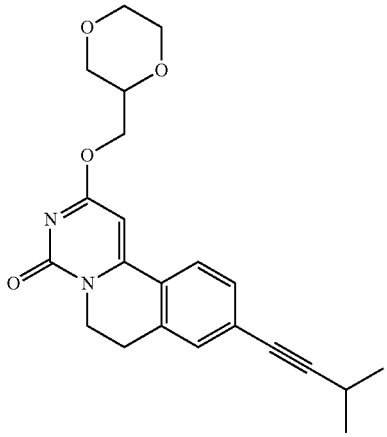 [SMILES: CC(C)C#Cc1ccc2c(c1)CCn1c-2cc(OCC2COCCO2)nc1=O] | 2-([1,4]Dioxan-2-ylmethoxy)-9-(3-methyl-but-1-ynyl)-6,7-dihydro-pyrimido[6,1-a]isoquinolin-4-one | 380 | 381 |
| 84 | 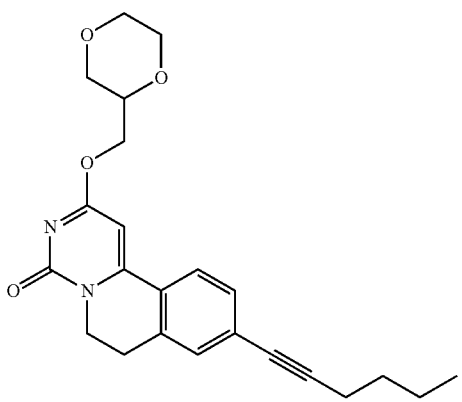 [SMILES: CCCCC#Cc1ccc2c(c1)CCn1c-2cc(OCC2COCCO2)nc1=O] | 2-([1,4]Dioxan-2-ylmethoxy)-9-hex-1-ynyl-6,7-dihydro-pyrimido[6,1-a]isoquinolin-4-one | 394 | 395 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 85 | 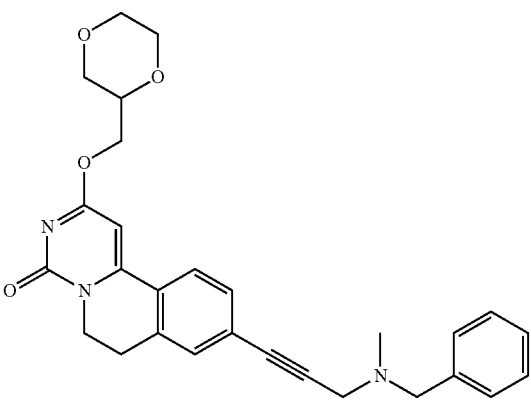 [SMILES: CN(CC#Cc1ccc2c(c1)CCn1c-2cc(OCC2COCCO2)nc1=O)Cc1ccccc1] | 9-[3-(Benzyl-methyl-amino)-prop-1-ynyl]-2-([1,4]dioxan-2-ylmethoxy)-6,7-dihydro-pyrimido[6,1-a]isoquinolin-4-one | 471 | 472 |
| 86 | 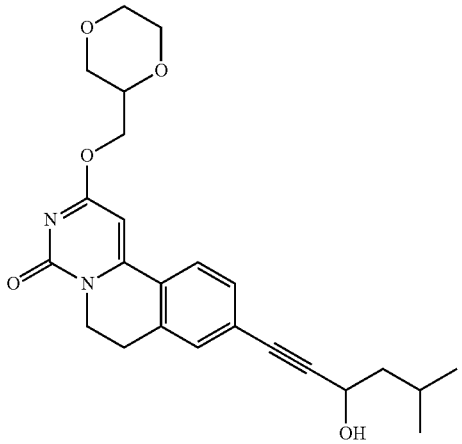 [SMILES: CC(C)CC(O)C#Cc1ccc2c(c1)CCn1c-2cc(OCC2COCCO2)nc1=O] | 2-([1,4]Dioxan-2-ylmethoxy)-9-(3-hydroxy-5-methyl-hex-1-ynyl)-6,7-dihydro-pyrimido[6,1-a]isoquinolin-4-one | 424 | 425 |
| 87 | 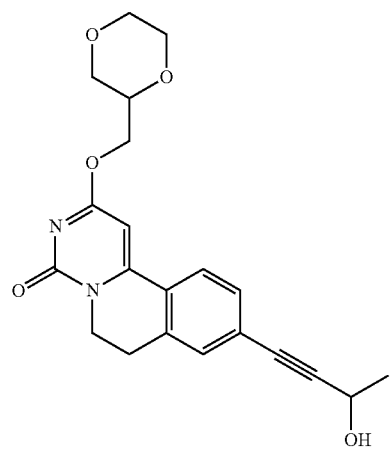 [SMILES: CC(O)C#Cc1ccc2c(c1)CCn1c-2cc(OCC2COCCO2)nc1=O] | 2-([1,4]Dioxan-2-ylmethoxy)-9-(3-hydroxy-but-1-ynyl)-6,7-dihydro-pyrimido[6,1-a]isoquinolin-4-one | 382 | 383 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 88 | 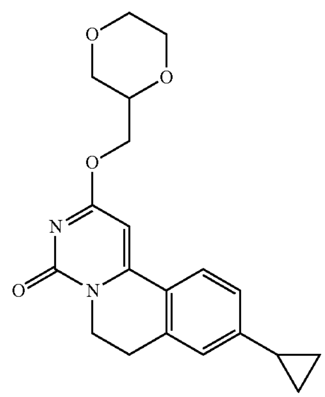 [SMILES: O=c1nc(OCC2COCCO2)cc2n1CCc1cc(C3CC3)ccc1-2] | 9-Cyclopropyl-2-([1,4]dioxan-2-ylmethoxy)-6,7-dihydro-pyrimido[6,1-a]isoquinolin-4-one | 354 | 355 |
| 89 | 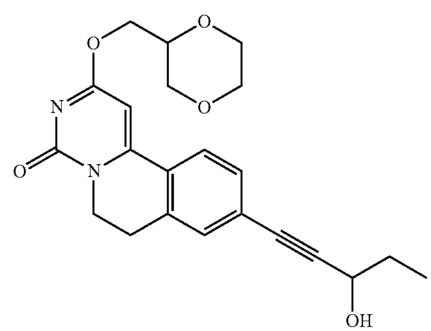 [SMILES: CCC(O)C#Cc1ccc2c(c1)CCn1c-2cc(OCC2COCCO2)nc1=O] | 2-([1,4]Dioxan-2-ylmethoxy)-9-(3-hydroxy-pent-1-ynyl)-6,7-dihydro-pyrimido[6,1-a]isoquinolin-4-one | 396 | 397 |
| 90 | 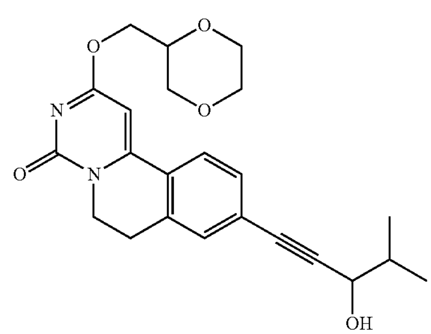 [SMILES: CC(C)C(O)C#Cc1ccc2c(c1)CCn1c-2cc(OCC2COCCO2)nc1=O] | 2-([1,4]Dioxan-2-ylmethoxy)-9-(3-hydroxy-4-methyl-pent-1-ynyl)-6,7-dihydro-pyrimido[6,1-a]isoquinolin-4-one | 410 | 411 |
| 91 | 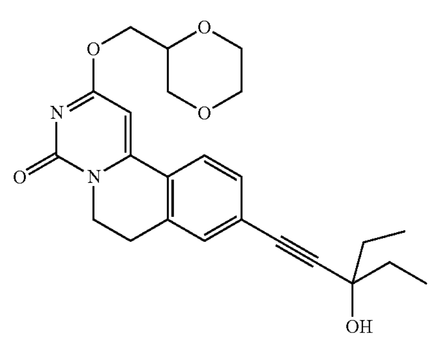 [SMILES: CCC(O)(C#Cc1ccc2c(c1)CCn1c-2cc(OCC2COCCO2)nc1=O)CC] | 2-([1,4]Dioxan-2-ylmethoxy)-9-(3-ethyl-3-hydroxy-pent-1-ynyl)-6,7-dihydro-pyrimido[6,1-a]isoquinolin-4-one | 424 | 425 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 92 | 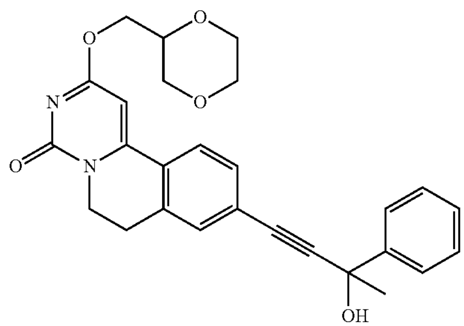 [SMILES: CC(O)(C#Cc1ccc2c(c1)CCn1c-2cc(OCC2COCCO2)nc1=O)c1ccccc1] | 2-([1,4]Dioxan-2-ylmethoxy)-9-(3-hydroxy-3-phenyl-but-1-ynyl)-6,7-dihydro-pyrimido[6,1-a]isoquinolin-4-one | 458 | 459 |
| 93 | 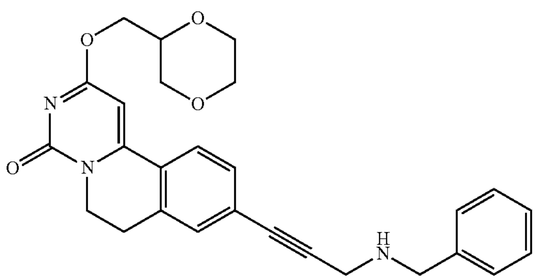 [SMILES: O=c1nc(OCC2COCCO2)cc2n1CCc1cc(C#CCNCc3ccccc3)ccc1-2] | 9-(3-Benzylamino-prop-1-ynyl)-2-([1,4]dioxan-2-ylmethoxy)-6,7-dihydro-pyrimido[6,1-a]isoquinolin-4-one | 457 | 458 |
| 94 | 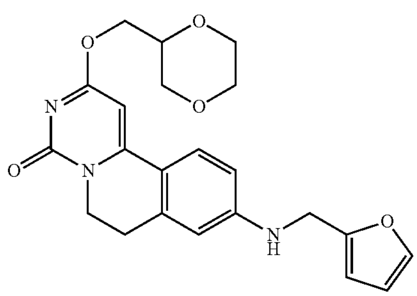 [SMILES: O=c1nc(OCC2COCCO2)cc2n1CCc1cc(NCc3ccco3)ccc1-2] | 2-([1,4]Dioxan-2-ylmethoxy)-9-[(furan-2-ylmethyl)-amino]-6,7-dihydro-pyrimido[6,1-a]isoquinolin-4-one | 409 | 410 |
| 95 | 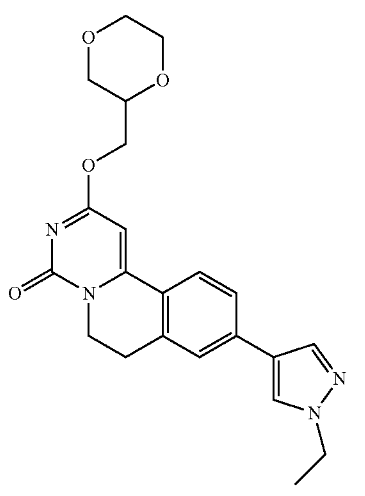 [SMILES: CCn1cc(-c2ccc3c(c2)CCn2c-3cc(OCC3COCCO3)nc2=O)cn1] | 2-([1,4]Dioxan-2-ylmethoxy)-9-(1-ethyl-1H-pyrazol-4-yl)-6,1-dihydro-pyrimido[6,1-a]isoquinolin-4-one | 408 | 409 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 96 | 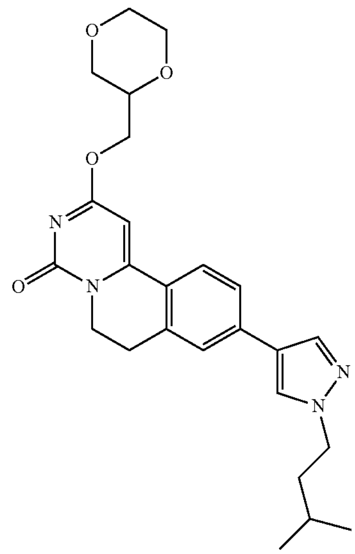 [SMILES: CC(C)CCn1cc(-c2ccc3c(c2)CCn2c-3cc(OCC3COCCO3)nc2=O)cn1] | 2-([1,4]Dioxan-2-ylmethoxy)-9-[1-(3-methyl-butyl)-1H-pyrazol-4-yl]-6,7-dihydro-pyrimido[6,1-a]isoquinolin-4-one | 450 | 451 |
| 97 | 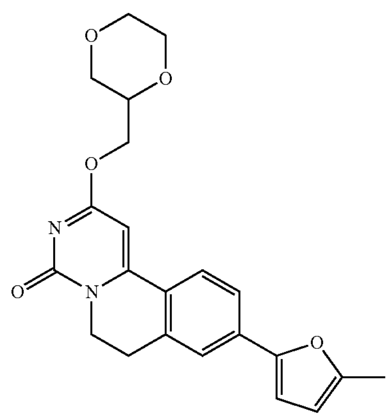 [SMILES: Cc1ccc(-c2ccc3c(c2)CCn2c-3cc(OCC3COCCO3)nc2=O)o1] | 2-([1,4]Dioxan-2-ylmethoxy)-9-(5-methyl-furan-2-yl)-6,7-dihydro-pyrimido[6,1-a]isoquinolin-4-one | 394 | 395 |
| 98 | 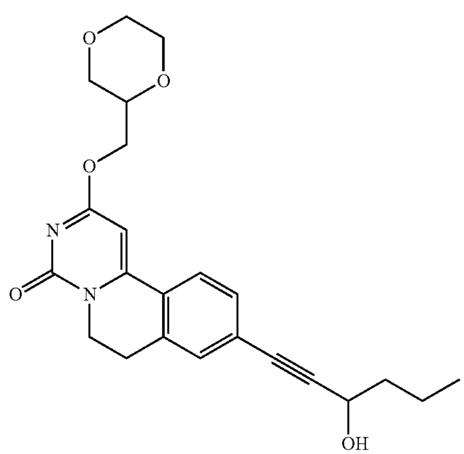 [SMILES: CCCC(O)C#Cc1ccc2c(c1)CCn1c-2cc(OCC2COCCO2)nc1=O] | 2-([1,4]Dioxan-2-ylmethoxy)-9-(3-hydroxy-hex-1-ynyl)-6,7-dihydro-pyrimido[6,1-a]isoquinolin-4-one | 410 | 411 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 99 | 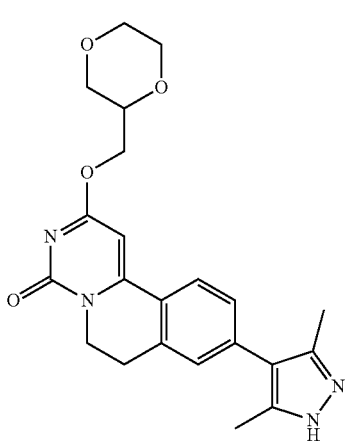 [SMILES: Cc1n[nH]c(C)c1-c1ccc2c(c1)CCn1c-2cc(OCC2COCCO2)nc1=O] | 9-(3,5-Dimethyl-1H-pyrazol-4-yl)-2-([1,4]dioxan-2-ylmethoxy)-6,7-dihydro-pyrimido[6,1-a]isoquinolin-4-one | 408 | 409 |
| 100 | 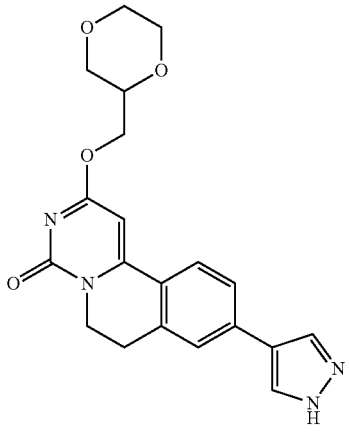 [SMILES: O=c1nc(OCC2COCCO2)cc2n1CCc1cc(-c3cn[nH]c3)ccc1-2] | 2-([1,4]Dioxan-2-ylmethoxy)-9-(1H-pyrazol-4-yl)-6,7-dihydro-pyrimido[6,1-a]isoquinolin-4-one | 380 | 381 |
| 101 | 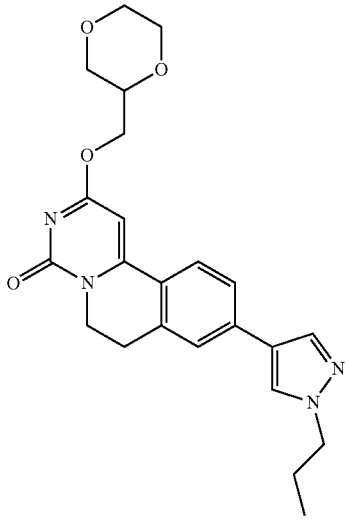 [SMILES: CCCn1cc(-c2ccc3c(c2)CCn2c-3cc(OCC3COCCO3)nc2=O)cn1] | 2-([1,4]Dioxan-2-ylmethoxy)-9-(1-propyl-1H-pyrazol-4-yl)-6,7-dihydro-pyrimido[6,1-a]isoquinolin-4-one | 422 | 423 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 102 | 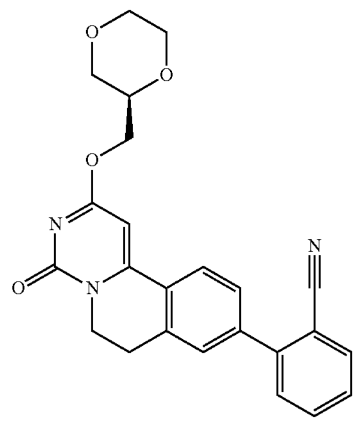 [SMILES: N#Cc1ccccc1-c1ccc2c(c1)CCn1c-2cc(OC[C@H]2COCCO2)nc1=O] | 2-[2-((R)-1-[1,4]Dioxan-2-ylmethoxy)-4-oxo-6,7-dihydro-4H-pyrimido[6,1-a]isoquinolin-9-yl]-benzonitrile | 415 | 416 |
| 103 | 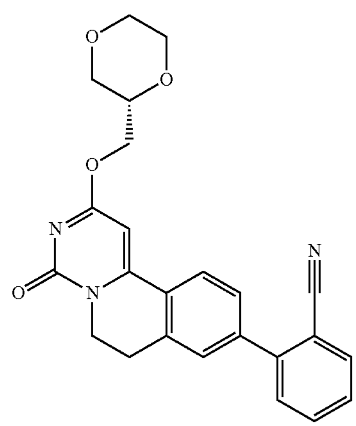 [SMILES: N#Cc1ccccc1-c1ccc2c(c1)CCn1c-2cc(OC[C@@H]2COCCO2)nc1=O] | 2-[2-((S)-1-[1,4]Dioxan-2-ylmethoxy)-4-oxo-6,7-dihydro-4H-pyrimido[6,1-a]isoquinolin-9-yl]-benzonitrile | 415 | 416 |
| 104 | 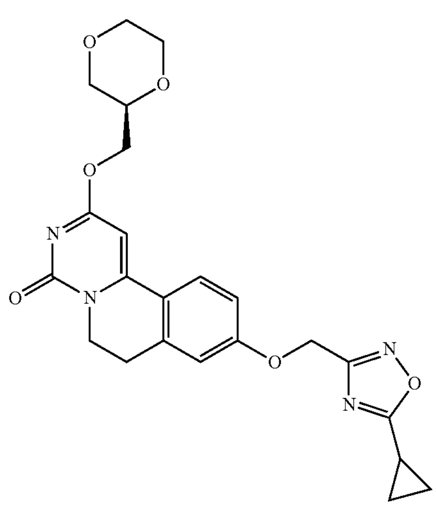 [SMILES: O=c1nc(OC[C@H]2COCCO2)cc2n1CCc1cc(OCc3noc(C4CC4)n3)ccc1-2] | 9-(5-Cyclopropyl-[1,2,4]oxadiazol-3-ylmethoxy)-2-((R)-1-[1,4]dioxan-2-ylmethoxy)-6,7-dihydro-pyrimido[6,1-a]isoquinolin-4-one | 452 | 453 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 105 | 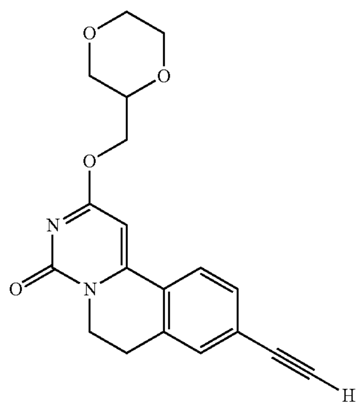 [SMILES: C#Cc1ccc2c(c1)CCn1c-2cc(OCC2COCCO2)nc1=O] | 2-([1,4]Dioxan-2-ylmethoxy)-9-ethynyl-6,7-dihydro-pyrimido[6,1-a]isoquinolin-4-one | 338 | 331 |
| 106 | 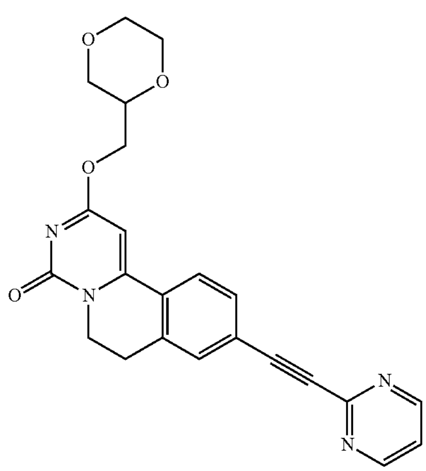 [SMILES: O=c1nc(OCC2COCCO2)cc2n1CCc1cc(C#Cc3ncccn3)ccc1-2] | 2-([1,4]Dioxan-2-ylmethoxy)-9-pyrimidin-2-ylethynyl-6,7-dihydro-pyrimido[6,1-a]isoquinolin-4-one | 416 | 417 |
| 107 | 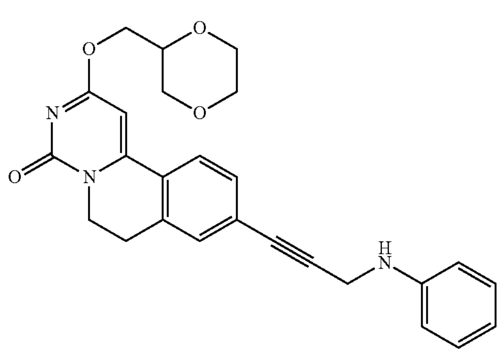 [SMILES: O=c1nc(OCC2COCCO2)cc2n1CCc1cc(C#CCNc3ccccc3)ccc1-2] | 2-([1,4]Dioxan-2-ylmethoxy)-9-(3-phenylamino-prop-1-ynyl)-6,7-dihydro-pyrimido[6,1-a]isoquinolin-4-one | 443 | 444 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 108 | 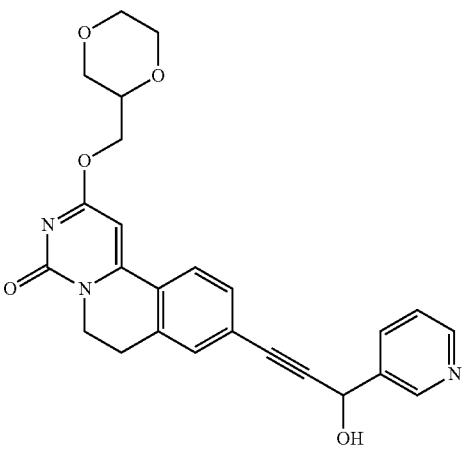 [SMILES: O=c1nc(OCC2COCCO2)cc2n1CCc1cc(C#CC(O)c3cccnc3)ccc1-2] | 2-([1,4]Dioxan-2-ylmethoxy)-9-(3-hydroxy-3-pyridin-3-yl-prop-1-ynyl)-6,7-dihydro-pyrimido[6,1-a]isoquinolin-4-one | 445 | 446 |
| 109 | 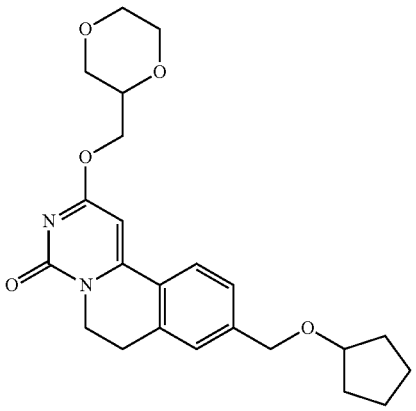 [SMILES: O=c1nc(OCC2COCCO2)cc2n1CCc1cc(COC3CCCC3)ccc1-2] | 9-Cyclopentyloxymethyl-2-([1,4]dioxan-2-ylmethoxy)-6,7-dihydro-pyrimido[6,1-a]isoquinolin-4-one | 412 | 413 |
| 110 | 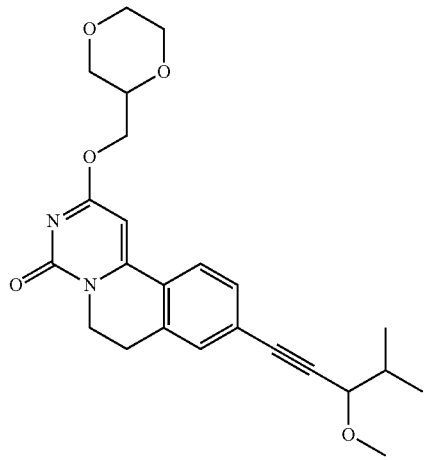 [SMILES: COC(C#Cc1ccc2c(c1)CCn1c-2cc(OCC2COCCO2)nc1=O)C(C)C] | 2-([1,4]Dioxan-2-ylmethoxy)-9-(3-methoxy-4-methyl-pent-1-ynyl)-6,7-dihydro-pyrimido[6,1-a]isoquinolin-4-one | 424 | 425 |

়
TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 111 | 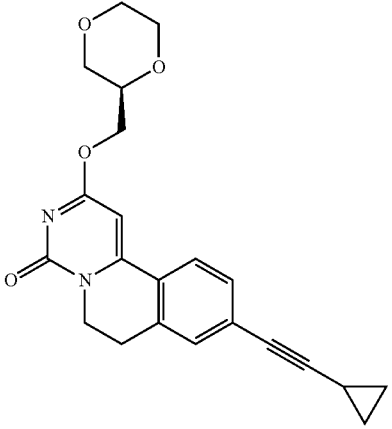 [SMILES: O=c1nc(OC[C@H]2COCCO2)cc2n1CCc1cc(C#CC3CC3)ccc1-2] | 9-Cyclopropylethynyl-2-((R)-1-[1,4]dioxan-2-ylmethoxy)-6,7-dihydro-pyrimido[6,1-a]isoquinolin-4-one | 378 | 379 |
| 112 | 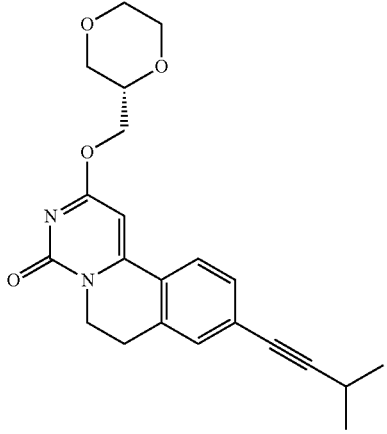 [SMILES: CC(C)C#Cc1ccc2c(c1)CCn1c-2cc(OC[C@@H]2COCCO2)nc1=O] | 2-((S)-1-[1,4]Dioxan-2-ylmethoxy)-9-(3-methyl-but-1-ynyl)-6,7-dihydro-pyrimido[6,1-a]isoquinolin-4-one | 380 | 381 |
| 113 | 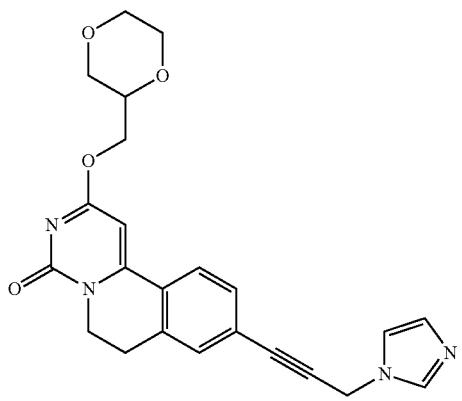 [SMILES: O=c1nc(OCC2COCCO2)cc2n1CCc1cc(C#CCn3ccnc3)ccc1-2] | 2-([1,4]Dioxan-2-ylmethoxy)-9-(3-imidazol-1-yl-prop-1-ynyl)-6,7-dihydro-pyrimido[6,1-a]isoquinolin-4-one | 418 | 419 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 114 | 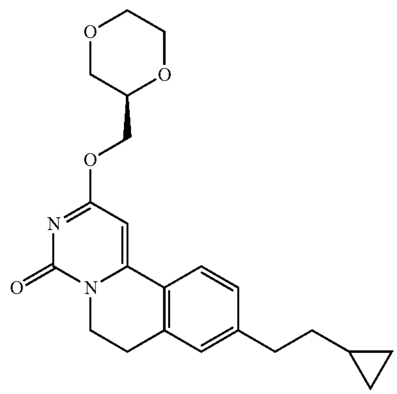 [SMILES: O=c1nc(OC[C@H]2COCCO2)cc2n1CCc1cc(CCC3CC3)ccc1-2] | 9-(2-Cyclopropyl-ethyl)-2-((R)-1-[1,4]dioxan-2-ylmethoxy)-6,7-dihydro-pyrimido[6,1-a]isoquinolin-4-one | 382 | 383 |
| 115 | 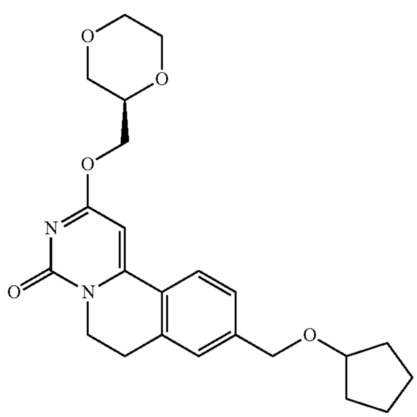 [SMILES: O=c1nc(OC[C@H]2COCCO2)cc2n1CCc1cc(COC3CCCC3)ccc1-2] | 9-Cyclopentyloxymethyl-2-((R)-1-[1,4]dioxan-2-ylmethoxy)-6,7-dihydro-pyrimido[6,1-a]isoquinolin-4-one | 412 | 413 |
| 116 | 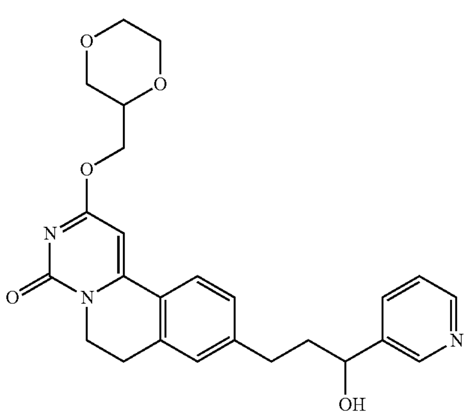 [SMILES: O=c1nc(OCC2COCCO2)cc2n1CCc1cc(CCC(O)c3cccnc3)ccc1-2] | 2-([1,4]Dioxan-2-ylmethoxy)-9-(3-hydroxy-3-pyridin-3-yl-propyl)-6,7-dihydro-pyrimido[6,1-a]isoquinolin-4-one | 449 | 450 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 117 | 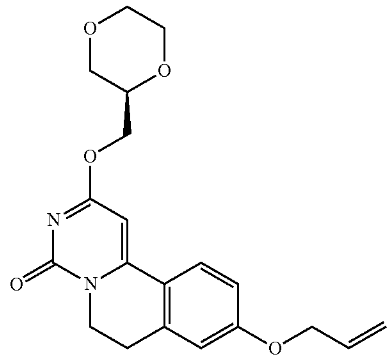 [SMILES: C=CCOc1ccc2c(c1)CCn1c-2cc(OC[C@H]2COCCO2)nc1=O] | 9-Allyloxy-2-((R)-1-[1,4]dioxan-2-ylmethoxy)-6,7-dihydro-pyrimido[6,1-a]isoquinolin-4-one | 370 | 371 |
| 118 | 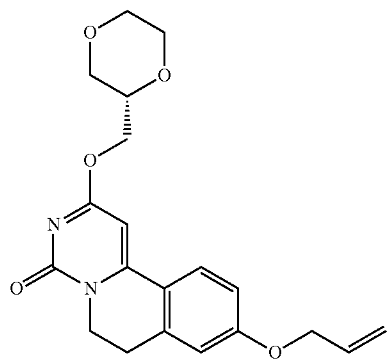 [SMILES: C=CCOc1ccc2c(c1)CCn1c-2cc(OC[C@@H]2COCCO2)nc1=O] | 9-Allyloxy-2-((S)-1-[1,4]dioxan-2-ylmethoxy)-6,7-dihydro-pyrimido[6,1-a]isoquinolin-4-one | 370 | 371 |
| 119 | 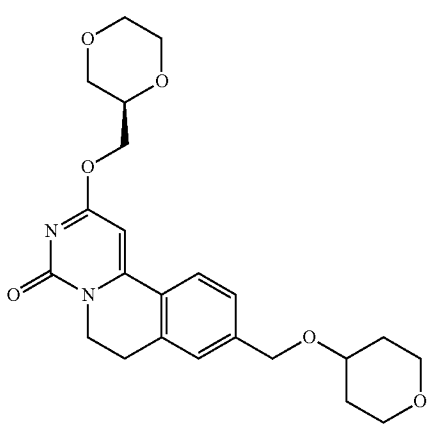 [SMILES: O=c1nc(OC[C@H]2COCCO2)cc2n1CCc1cc(COC3CCOCC3)ccc1-2] | 2-((R)-1-[1,4]Dioxan-2-ylmethoxy)-9-(tetrahydro-pyran-4-yloxymethyl)-6,7-dihydro-pyrimido[6,1-a]isoquinolin-4-one | 428 | 429 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 120 | 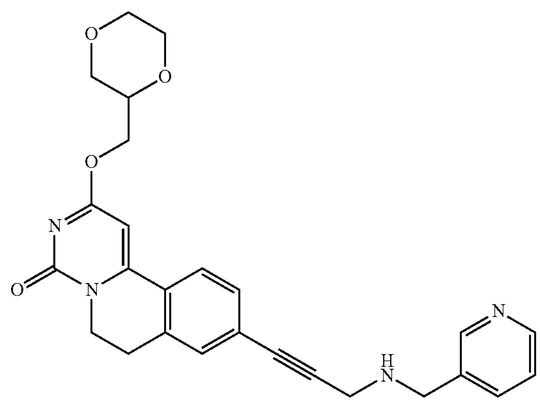 [SMILES: O=c1nc(OCC2COCCO2)cc2n1CCc1cc(C#CCNCc3cccnc3)ccc1-2] | 2-([1,4]Dioxan-2-ylmethoxy)-9-{(pyridin-3-ylmethyl)-amino]-prop-1-ynyl}-6,7-dihydro-pyrimido[6,1-a]isoquinolin-4-one | 458 | 459 |
| 121 | 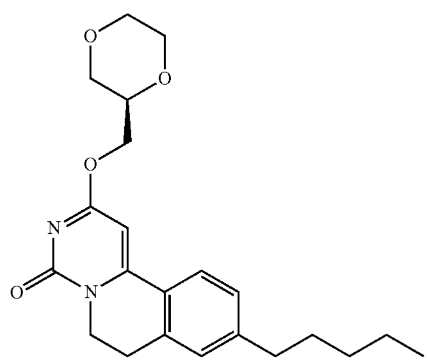 [SMILES: CCCCCc1ccc2c(c1)CCn1c-2cc(OC[C@H]2COCCO2)nc1=O] | 2-((R)-1-[1,4]Dioxan-2-ylmethoxy)-9-pentyl-6,7-dihydro-pyrimido[6,1-a]isoquinolin-4-one | 384 | 385 |
| 122 | 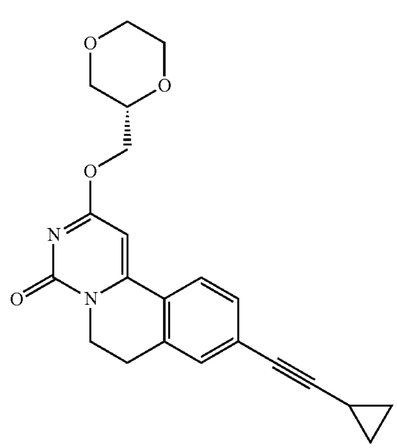 [SMILES: O=c1nc(OC[C@@H]2COCCO2)cc2n1CCc1cc(C#CC3CC3)ccc1-2] | 9-Cyclopropylethynyl-2-((S)-1-[1,4]dioxan-2-ylmethoxy)-6,7-dihydro-pyrimido[6,1-a]isoquinolin-4-one | 378 | 379 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 123 | 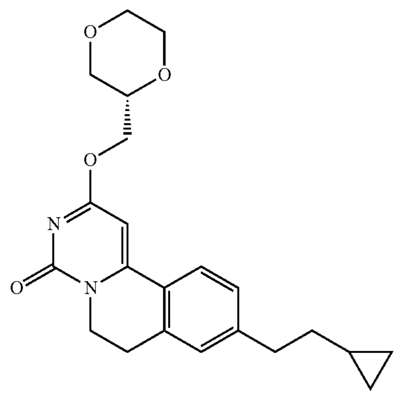 [SMILES: O=c1nc(OC[C@@H]2COCCO2)cc2n1CCc1cc(CCC3CC3)ccc1-2] | 9-(2-Cyclopropyl-ethyl)-2-((S)-1-[1,4]dioxan-2-ylmethoxy)-6,7-dihydro-pyrimido[6,1-a]isoquinolin-4-one | 382 | 383 |
| 124 | 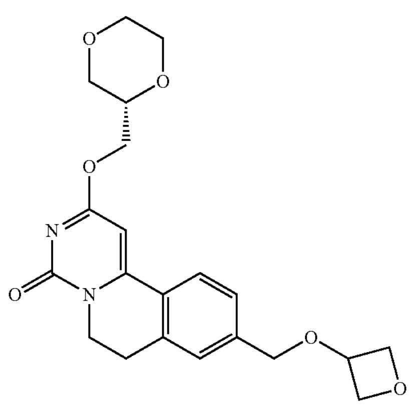 [SMILES: O=c1nc(OC[C@@H]2COCCO2)cc2n1CCc1cc(COC3COC3)ccc1-2] | 2-((S)-1-[1,4]Dioxan-2-ylmethoxy)-9-(oxetan-3-yloxymethyl)-6,7-dihydro-pyrimido[6,1-a]isoquinolin-4-one | 400 | 401 |
| 125 | 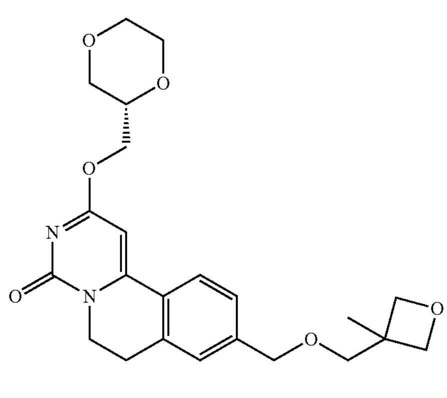 [SMILES: CC1(COCc2ccc3c(c2)CCn2c-3cc(OC[C@@H]3COCCO3)nc2=O)COC1] | 2-((S)-1-[1,4]Dioxan-2-ylmethoxy)-9-(3-methyl-oxetan-3-ylmethoxymethyl)-6,7-dihydro-pyrimido[6,1-a]isoquinolin-4-one | 428 | 429 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 126 | 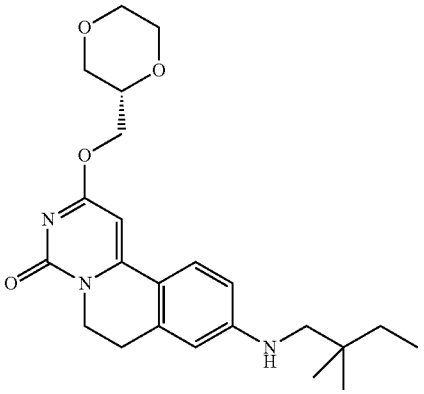 [SMILES: CCC(C)(C)CNc1ccc2c(c1)CCn1c-2cc(OC[C@@H]2COCCO2)nc1=O] | 9-(2,2-Dimethyl-butylamino)-2-((S)-1-[1,4]dioxan-2-ylmethoxy)-6,7-dihydro-pyrimido[6,1-a]isoquinolin-4-one | 413 | 414 |
| 127 | 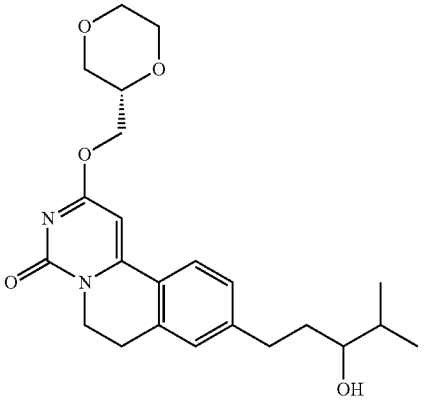 [SMILES: CC(C)C(O)CCc1ccc2c(c1)CCn1c-2cc(OC[C@@H]2COCCO2)nc1=O] | 2-((S)-1-[1,4]Dioxan-2-ylmethoxy)-9-(3-hydroxy-4-methyl-pentyl)-6,7-dihydro-pyrimido[6,1-a]isoquinolin-4-one | 414 | 415 |
| 128 | 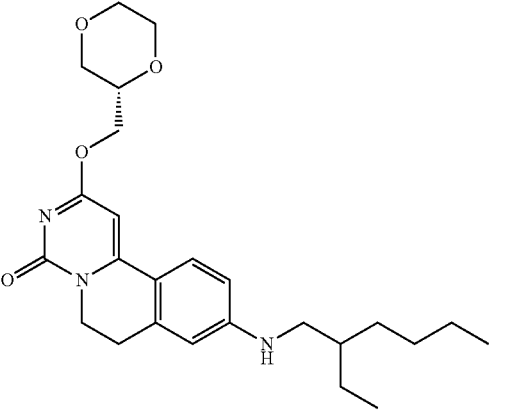 [SMILES: CCCCC(CC)CNc1ccc2c(c1)CCn1c-2cc(OC[C@@H]2COCCO2)nc1=O] | 2-((S)-1-[1,4]Dioxan-2-ylmethoxy)-9-(2-ethyl-hexylamino)-6,7-dihydro-pyrimido[6,1-a]isoquinolin-4-one | 441 | 442 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 129 | 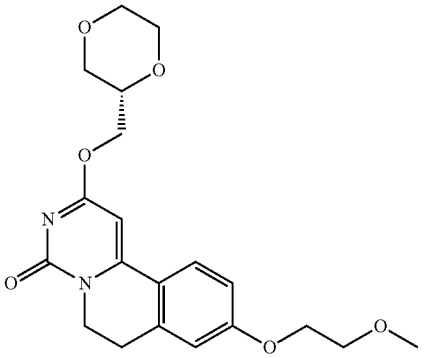 [SMILES: COCCOc1ccc2c(c1)CCn1c-2cc(OC[C@@H]2COCCO2)nc1=O] | 2-((S)-1-[1,4]Dioxan-2-ylmethoxy)-9-(2-methoxy-ethoxy)-6,7-dihydro-pyrimido[6,1-a]isoquinolin-4-one | 388 | 389 |
| 130 | 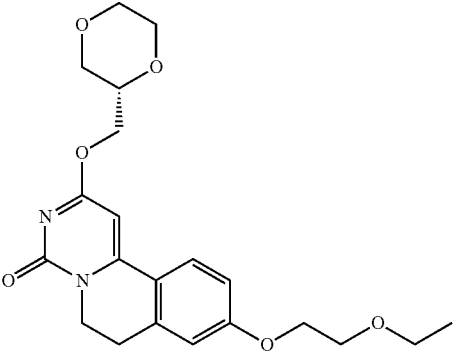 [SMILES: CCOCCOc1ccc2c(c1)CCn1c-2cc(OC[C@@H]2COCCO2)nc1=O] | 2-((S)-1-[1,4]Dioxan-2-ylmethoxy)-9-(2-ethoxy-ethoxy)-6,7-dihydro-pyrimido[6,1-a]isoquinolin-4-one | 402 | 403 |
| 131 | 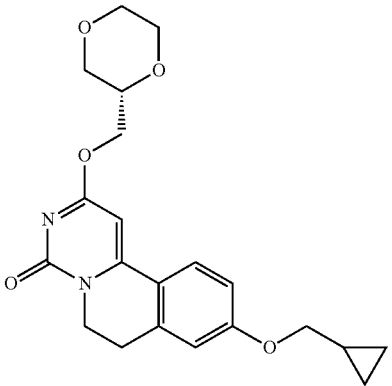 [SMILES: O=c1nc(OC[C@@H]2COCCO2)cc2n1CCc1cc(OCC3CC3)ccc1-2] | 9-Cyclopropylmethoxy-2-((S)-1-[1,4]dioxan-2-ylmethoxy)-6,7-dihydro-pyrimido[6,1-a]isoquinolin-4-one | 384 | 385 |
| 132 | 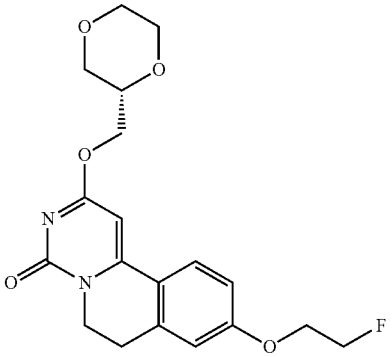 [SMILES: O=c1nc(OC[C@@H]2COCCO2)cc2n1CCc1cc(OCCF)ccc1-2] | 2-((S)-1-[1,4]Dioxan-2-ylmethoxy)-9-(2-fluoro-ethoxy)-6,7-dihydro-pyrimido[6,1-a]isoquinolin-4-one | 376 | 377 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 133 | 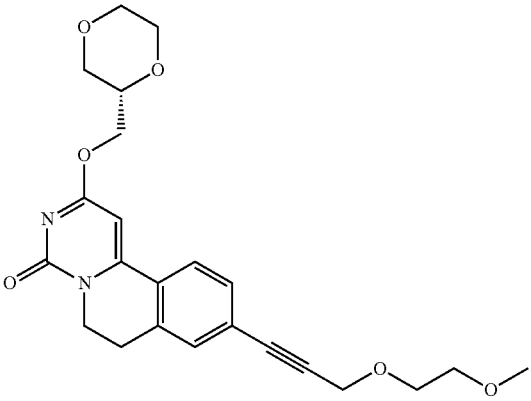 [SMILES: COCCOCC#Cc1ccc2c(c1)CCn1c-2cc(OC[C@@H]2COCCO2)nc1=O] | 2-((S)-1-[1,4]Dioxan-2-ylmethoxy)-9-[3-(2-methoxy-ethoxy)-prop-1-ynyl]-6,7-dihydro-pyrimido[6,1-a]isoquinolin-4-one | 426 | 427 |
| 134 | 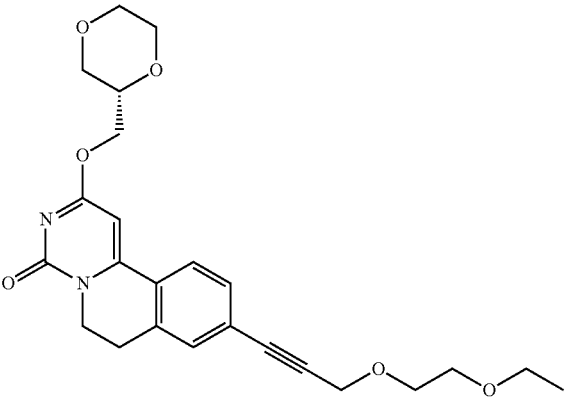 [SMILES: CCOCCOCC#Cc1ccc2c(c1)CCn1c-2cc(OC[C@@H]2COCCO2)nc1=O] | 2-((S)-1-[1,4]Dioxan-2-ylmethoxy)-9-[3-(2-ethoxy-ethoxy)-prop-1-ynyl]-6,7-dihydro-pyrimido[6,1-a]isoquinolin-4-one | 440 | 441 |
| 135 | 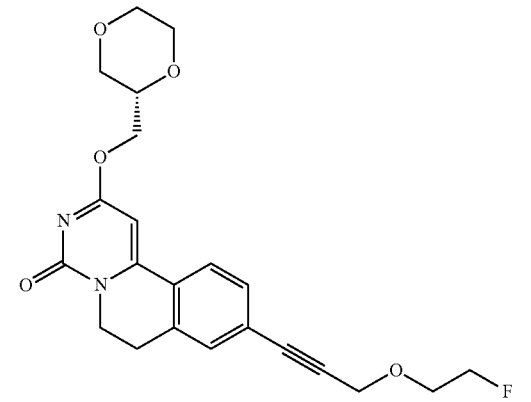 [SMILES: O=c1nc(OC[C@@H]2COCCO2)cc2n1CCc1cc(C#CCOCCF)ccc1-2] | 2-((S)-1-[1,4]Dioxan-2-ylmethoxy)-9-[3-(2-fluoro-ethoxy)-prop-1-ynyl]-6,7-dihydro-pyrimido[6,1-a]isoquinolin-4-one | 414 | 415 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 136 | 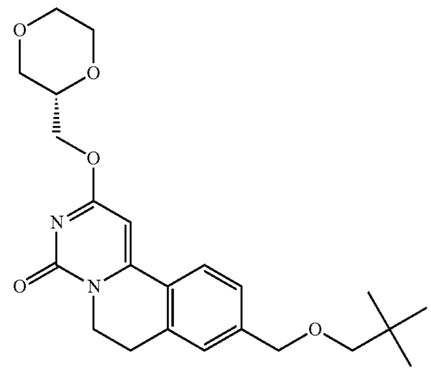 [SMILES: CC(C)(C)COCc1ccc2c(c1)CCn1c-2cc(OC[C@@H]2COCCO2)nc1=O] | 9-(2,2-Dimethyl-propoxymethyl)-2-((S)-1-[1,4]dioxan-2-ylmethoxy)-6,7-dihydro-pyrimido[6,1-a]isoquinolin-4-one | 414 | 415 |
| 137 | 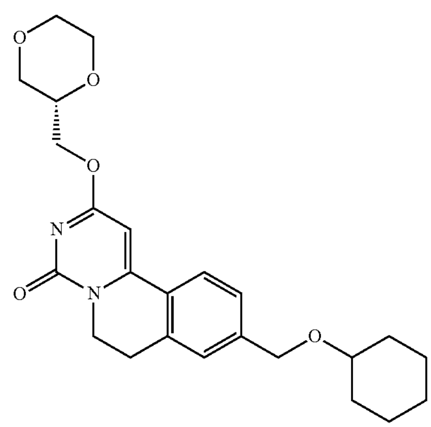 [SMILES: O=c1nc(OC[C@@H]2COCCO2)cc2n1CCc1cc(COC3CCCCC3)ccc1-2] | 9-Cyclohexyloxymethyl-2-((S)-1-[1,4]dioxan-2-ylmethoxy)-6,7-dihydro-pyrimido[6,1-a]isoquinolin-4-one | 426 | 427 |
| 138 | 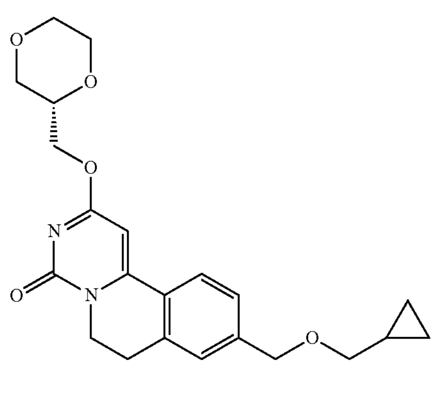 [SMILES: O=c1nc(OC[C@@H]2COCCO2)cc2n1CCc1cc(COCC3CC3)ccc1-2] | 9-Cyclopropylmethoxymethyl-2-((S)-1-[1,4]dioxan-2-ylmethoxy)-6,7-dihydro-pyrimido[6,1-a]isoquinolin-4-one | 398 | 399 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 139 | 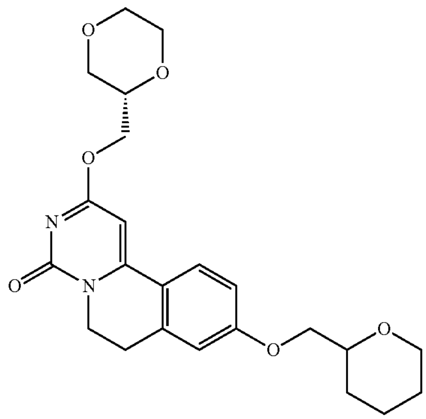 [SMILES: O=c1nc(OC[C@@H]2COCCO2)cc2n1CCc1cc(OCC3CCCCO3)ccc1-2] | 2-((S)-1-[1,4]Dioxan-2-ylmethoxy)-9-(tetrahydro-pyran-2-ylmethoxy)-6,7-dihydro-pyrimido[6,1-a]isoquinolin-4-one | 428 | 429 |
| 140 | 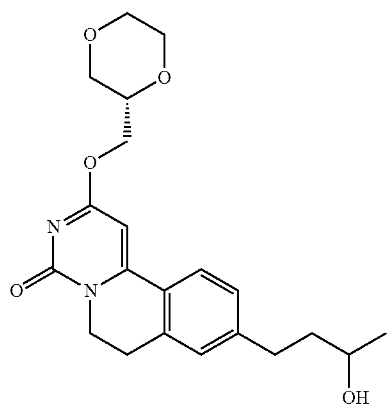 [SMILES: CC(O)CCc1ccc2c(c1)CCn1c-2cc(OC[C@@H]2COCCO2)nc1=O] | 2-((S)-1-[1,4]Dioxan-2-ylmethoxy)-9-(3-hydroxy-butyl)-6,7-dihydro-pyrimido[6,1-a]isoquinolin-4-one | 386 | 387 |
| 141 | 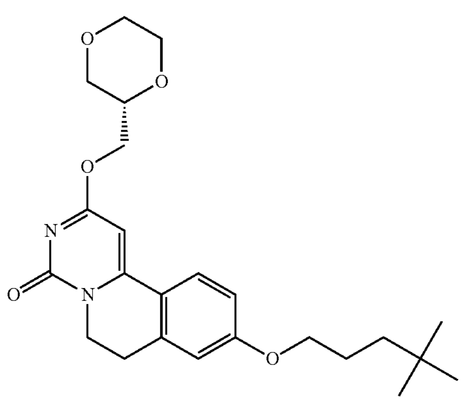 [SMILES: CC(C)(C)CCCOc1ccc2c(c1)CCn1c-2cc(OC[C@@H]2COCCO2)nc1=O] | 9-(4,4-Dimethyl-pentyoxy)-2-((S)-1-[1,4]dioxan-2-ylmethoxy)-6,7-dihydro-pyrimido[6,1-a]isoquinolin-4-one | 428 | 429 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 142 | 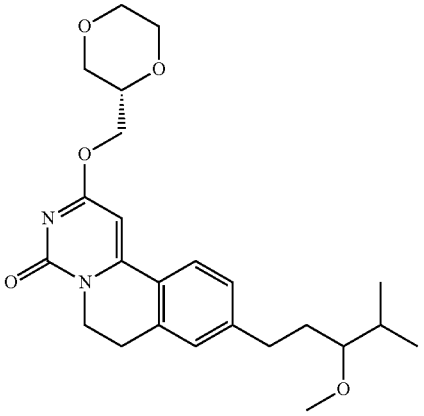 [SMILES: COC(CCc1ccc2c(c1)CCn1c-2cc(OC[C@@H]2COCCO2)nc1=O)C(C)C] | 2-((S)-1-[1,4]Dioxan-2-ylmethoxy)-9-(3-methoxy-4-methyl-pentyl)-6,7-dihydro-pyrimido[6,1-a]isoquinolin-4-one | 428 | 429 |
| 143 | 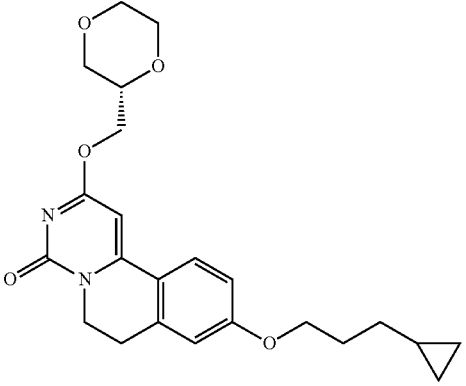 [SMILES: O=c1nc(OC[C@@H]2COCCO2)cc2n1CCc1cc(OCCCC3CC3)ccc1-2] | 9-(3-Cyclopropyl-propoxy)-2-((S)-1-[1,4]dioxan-2-ylmethoxy)-6,7-dihydro-pyrimido[6,1-a]isoquinolin-4-one | 412 | 413 |
| 145 | 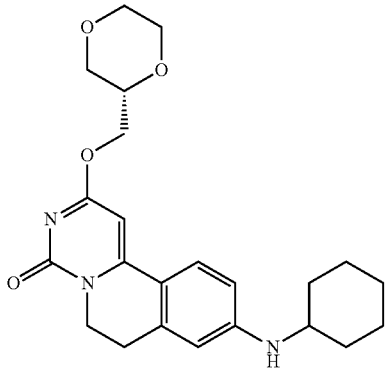 [SMILES: O=c1nc(OC[C@@H]2COCCO2)cc2n1CCc1cc(NC3CCCCC3)ccc1-2] | 9-Cyclohexylamino-2-((S)-1-[1,4]dioxan-2-ylmethoxy)-6,7-dihydro-pyrimido[6,1-a]isoquinolin-4-one | 411 | 413 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 146 | 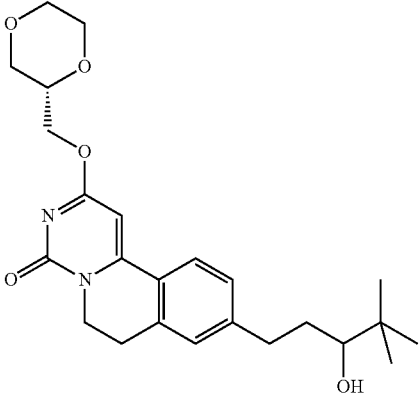 [SMILES: CC(C)(C)C(O)CCc1ccc2c(c1)CCn1c-2cc(OC[C@@H]2COCCO2)nc1=O] | 2-((S)-1-[1,4]Dioxan-2-ylmethoxy)-9-(3-hydroxy-4,4-dimethyl-pentyl)-6,7-dihydro-pyrimido[6,1-a]isoquinolin-4-one | 428 | 429 |
| 147 | 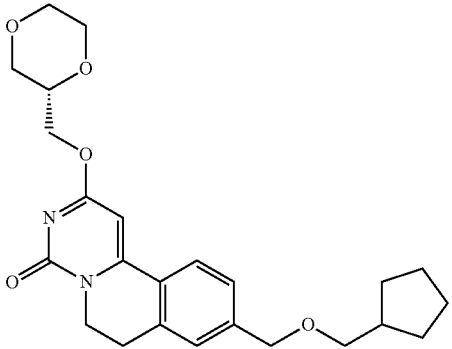 [SMILES: O=c1nc(OC[C@@H]2COCCO2)cc2n1CCc1cc(COCC3CCCC3)ccc1-2] | 9-Cyclopentylmethoxymethyl-2-((S)-1-[1,4]dioxan-2-ylmethoxy)-6,7-dihydro-pyrimido[6,1-a]isoquinolin-4-one | 426 | 427 |
| 148 | 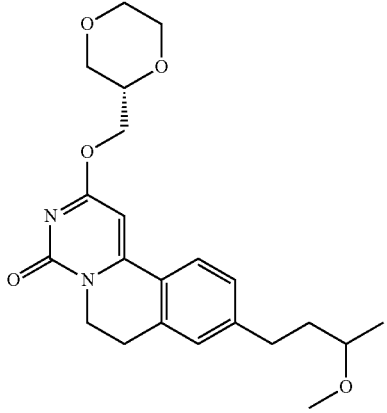 [SMILES: COC(C)CCc1ccc2c(c1)CCn1c-2cc(OC[C@@H]2COCCO2)nc1=O] | 2-((S)-1-[1,4]Dioxan-2-ylmethoxy)-9-(3-methoxy-butyl)-6,7-dihydro-pyrimido[6,1-a]isoquinolin-4-one | 400 | 401 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 149 | 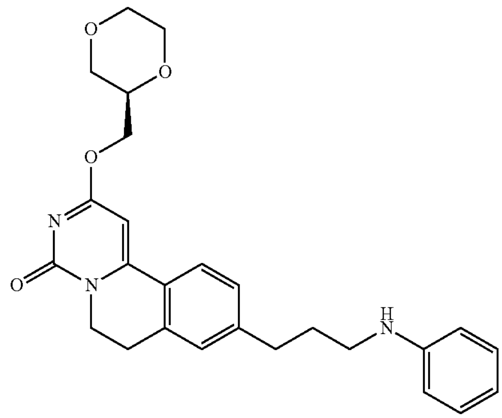 [SMILES: O=c1nc(OC[C@H]2COCCO2)cc2n1CCc1cc(CCCNc3ccccc3)ccc1-2] | 2-((S)-1-[1,4]Dioxan-2-ylmethoxy)-9-(3-phenylamino-propyl)-6,7-dihydro-pyrimido[6,1-a]isoquinolin-4-one | 447 | 448 |
| 150 | 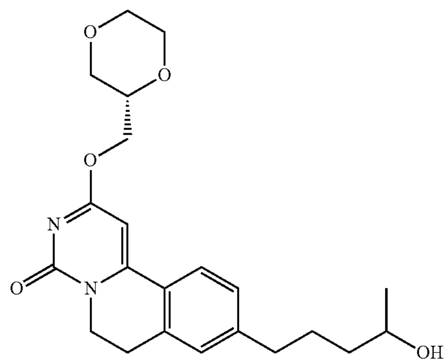 [SMILES: CC(O)CCCc1ccc2c(c1)CCn1c-2cc(OC[C@@H]2COCCO2)nc1=O] | 2-((S)-1-[1,4]Dioxan-2-ylmethoxy)-9-(4-hydroxy-pentyl)-6,7-dihydro-pyrimido[6,1-a]isoquinolin-4-one | 400 | 401 |
| 151 | 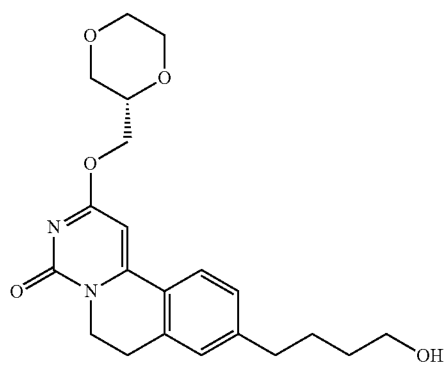 [SMILES: O=c1nc(OC[C@@H]2COCCO2)cc2n1CCc1cc(CCCCO)ccc1-2] | 2-((S)-1-[1,4]Dioxan-2-ylmethoxy)-9-(4-hydroxy-butyl)-6,7-dihydro-pyrimido[6,1-a]isoquinolin-4-one | 386 | 387 |
| 152 | 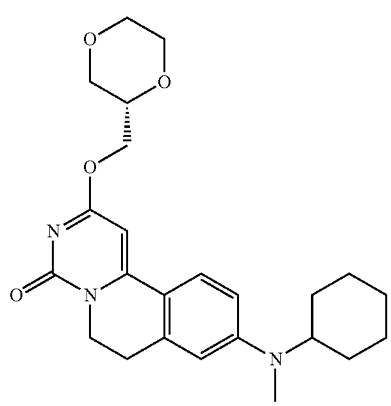 [SMILES: CN(c1ccc2c(c1)CCn1c-2cc(OC[C@@H]2COCCO2)nc1=O)C1CCCCC1] | 9-(Cyclohexyl-methyl-amino)-2-((S)-1-[1,4]dioxan-2-ylmethoxy)-6,7-dihydro-pyrimido[6,1-a]isoquinolin-4-one | 425 | 426 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 153 | 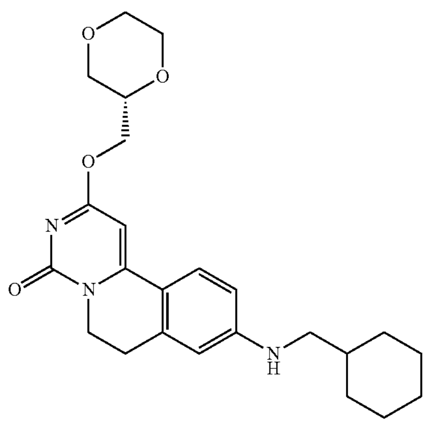 [SMILES: O=c1nc(OC[C@@H]2COCCO2)cc2n1CCc1cc(NCC3CCCCC3)ccc1-2] | 9-(Cyclohexylmethyl-amino)-2-((S)-1-[1,4]dioxan-2-ylmethoxy)-6,7-dihydro-pyrimido[6,1-a]isoquinolin-4-one | 425 | 426 |
| 154 | 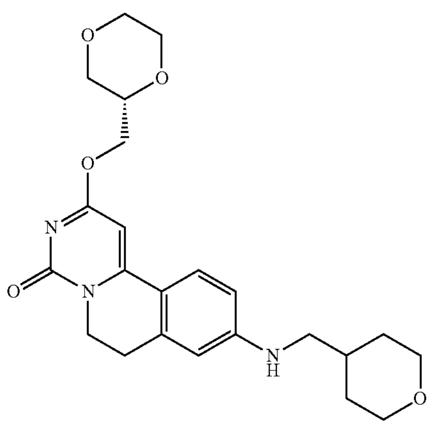 [SMILES: O=c1nc(OC[C@@H]2COCCO2)cc2n1CCc1cc(NCC3CCOCC3)ccc1-2] | 2-((S)-1-[1,4]Dioxan-2-ylmethoxy)-9-[(tetrahydro-pyran-4-ylmethyl)-amino]-6,7-dihydro-pyrimido[6,1-a]isoquinolin-4-one | 427 | 428 |
| 155 | 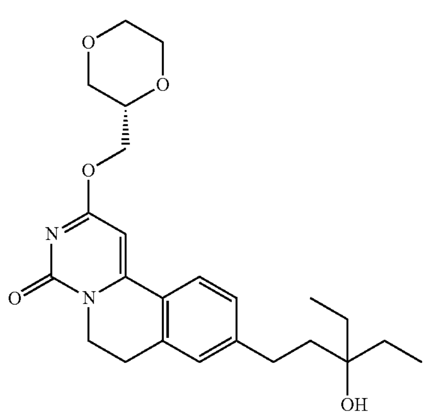 [SMILES: CCC(O)(CC)CCc1ccc2c(c1)CCn1c-2cc(OC[C@@H]2COCCO2)nc1=O] | 2-((S)-1-[1,4]Dioxan-2-ylmethoxy)-9-(3-ethyl-3-hydroxy-pentyl)-6,7-dihydro-pyrimido[6,1-a]isoquinolin-4-one | 428 | 429 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 156 | 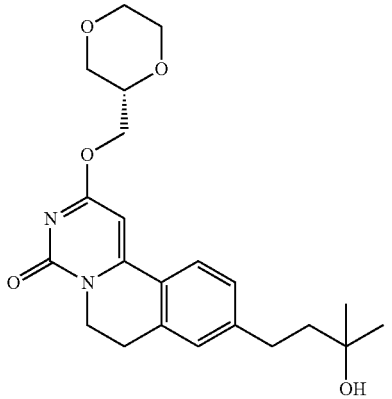 [SMILES: CC(C)(O)CCc1ccc2c(c1)CCn1c-2cc(OC[C@@H]2COCCO2)nc1=O] | 2-((S)-1-[1,4]Dioxan-2-ylmethoxy)-9-(3-hydroxy-3-methyl-butyl)-6,7-dihydro-pyrimido[6,1-a]isoquinolin-4-one | 400 | 401 |
| 157 | 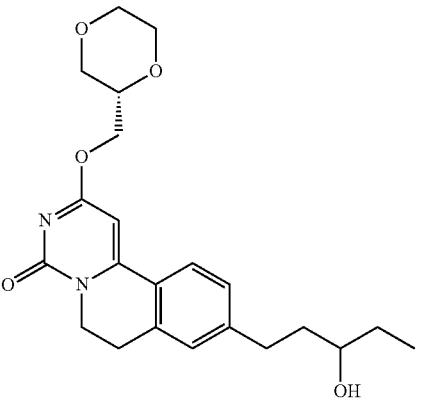 [SMILES: CCC(O)CCc1ccc2c(c1)CCn1c-2cc(OC[C@@H]2COCCO2)nc1=O] | 2-((S)-1-[1,4]Dioxan-2-ylmethoxy)-9-(3-hydroxy-pentyl)-6,7-dihydro-pyrimido[6,1-a]isoquinolin-4-one | 400 | 401 |
| 158 | 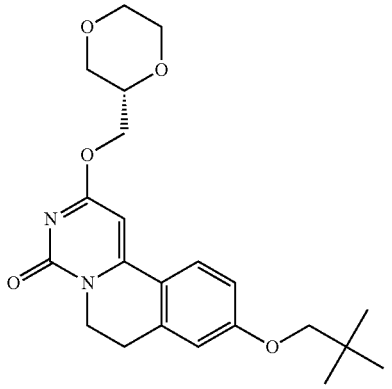 [SMILES: CC(C)(C)COc1ccc2c(c1)CCn1c-2cc(OC[C@@H]2COCCO2)nc1=O] | 9-(2,2-Dimethyl-propoxy)-2-((S)-1-[1,4]dioxan-2-ylmethoxy)-6,7-dihydro-pyrimido[6,1-a]isoquinolin-4-one | 400 | 401 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 159 | 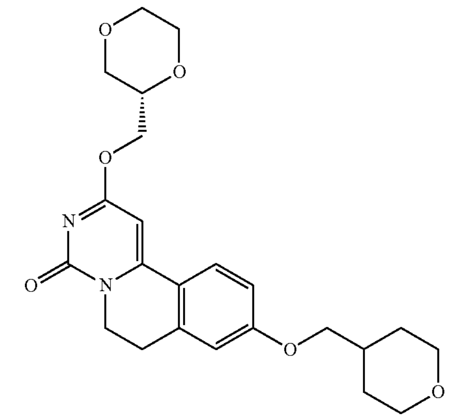 [SMILES: O=c1nc(OC[C@@H]2COCCO2)cc2n1CCc1cc(OCC3CCOCC3)ccc1-2] | 2-((S)-1-[1,4]Dioxan-2-ylmethoxy)-9-(tetrahydro-pyran-4-ylmethoxy)-6,7-dihydro-pyrimido[6,1-a]isoquinolin-4-one | 428 | 429 |
| 160 | 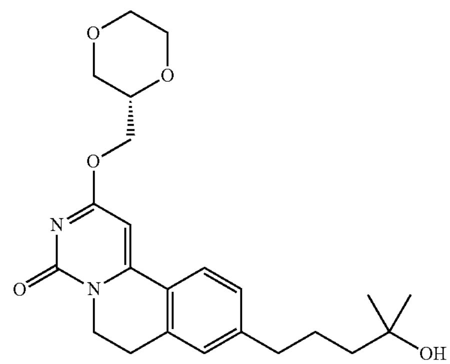 [SMILES: CC(C)(O)CCCc1ccc2c(c1)CCn1c-2cc(OC[C@@H]2COCCO2)nc1=O] | 2-((S)-1-[1,4]Dioxan-2-ylmethoxy)-9-(4-hydroxy-4-methyl-pentyl)-6,7-dihydro-pyrimido[6,1-a]isoquinolin-4-one | 414 | 415 |
| 161 | 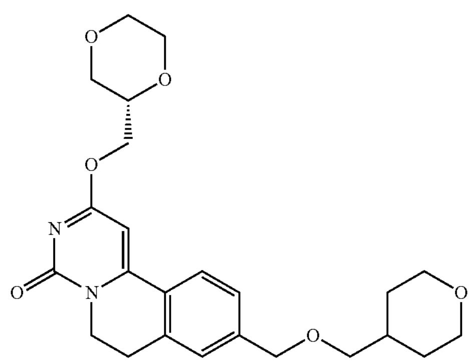 [SMILES: O=c1nc(OC[C@@H]2COCCO2)cc2n1CCc1cc(COCC3CCOCC3)ccc1-2] | 2-((S)-1-[1,4]Dioxan-2-ylmethoxy)-9-(tetrahydro-pyran-4-ylmethoxymethyl)-6,7-dihydro-pyrimido[6,1-a]isoquinolin-4-one | 442 | 443 |
| 162 | 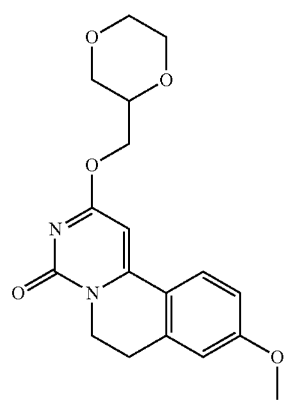 [SMILES: COc1ccc2c(c1)CCn1c-2cc(OCC2COCCO2)nc1=O] | 2-([1,4]Dioxan-2-ylmethoxy)-9-methoxy-6,7-dihydro-pyrimido[6,1-a]isoquinolin-4-one | 344 | 345 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 163 | 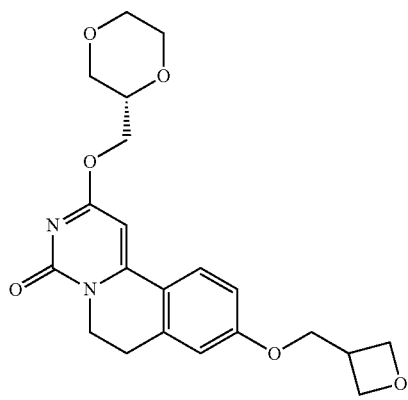 [SMILES: O=c1nc(OC[C@@H]2COCCO2)cc2n1CCc1cc(OCC3COC3)ccc1-2] | 2-((S)-1-[1,4]Dioxan-2-ylmethoxy)-9-(oxetan-3-ylmethoxy)-6,7-dihydro-pyrimido[6,1-a]isoquinolin-4-one | 400 | 401 |
| 164 | 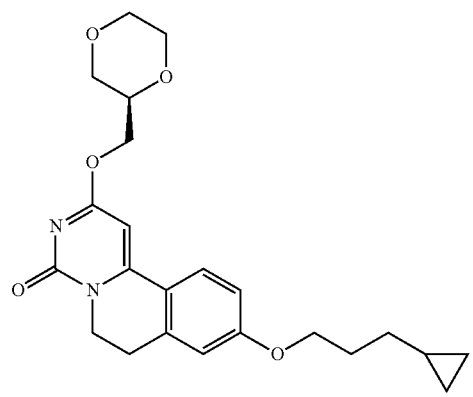 [SMILES: O=c1nc(OC[C@H]2COCCO2)cc2n1CCc1cc(OCCCC3CC3)ccc1-2] | 9-(3-Cyclopropyl-propoxy)-2-((R)-1-[1,4]dioxan-2-ylmethoxy)-6,7-dihydro-pyrimido[6,1-a]isoquinolin-4-one | 412 | 413 |
| 165 | 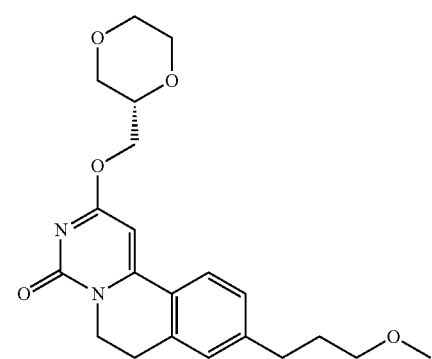 [SMILES: COCCCc1ccc2c(c1)CCn1c-2cc(OC[C@@H]2COCCO2)nc1=O] | 2-((S)-1-[1,4]Dioxan-2-ylmethoxy)-9-(3-methoxy-propyl)-6,7-dihydro-pyrimido[6,1-a]isoquinolin-4-one | 386 | 387 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 166 | 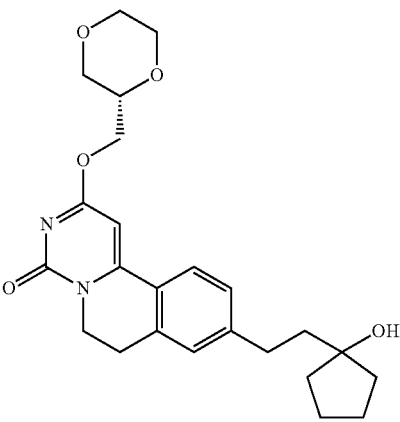 [SMILES: O=c1nc(OC[C@@H]2COCCO2)cc2n1CCc1cc(CCC3(O)CCCC3)ccc1-2] | 2-((S)-1-[1,4]Dioxan-2-ylmethoxy)-9-[2-(1-hydroxy-cyclopentyl)-ethyl]-6,7-dihydro-pyrimido[6,1-a]isoquinolin-4-one | 426 | 427 |
| 167 | 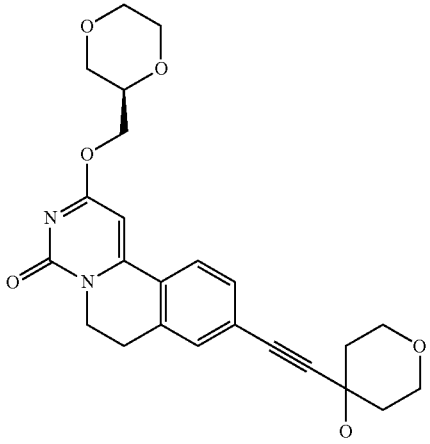 [SMILES: O=c1nc(OC[C@H]2COCCO2)cc2n1CCc1cc(C#CC3(O)CCOCC3)ccc1-2] | 2-((R)-1-[1,4]Dioxan-2-ylmethoxy)-9-(4-hydroxy-tetrahydro-pyran-4-ylethynyl)-6,7-dihydro-pyrimido[6,1-a]isoquinolin-4-one | 438 | |
| 168 | 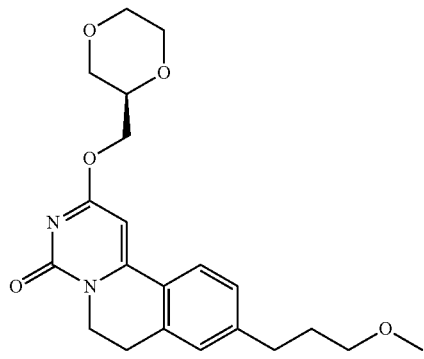 [SMILES: COCCCc1ccc2c(c1)CCn1c-2cc(OC[C@H]2COCCO2)nc1=O] | 2-((R)-1-[1,4]Dioxan-2-ylmethoxy)-9-(3-methoxy-propyl)-6,7-dihydro-pyrimido[6,1-a]isoquinolin-4-one | 386 | 387 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 169 | 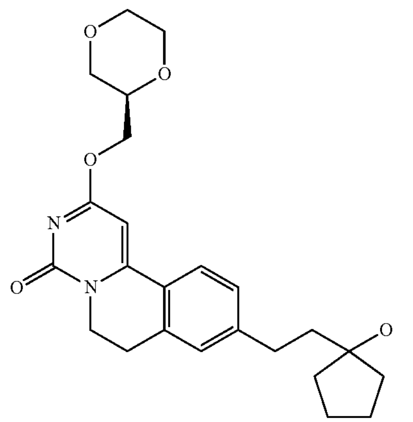 [SMILES: O=c1nc(OC[C@H]2COCCO2)cc2n1CCc1cc(CCC3(O)CCCC3)ccc1-2] | 2-((R)-1-[1,4]Dioxan-2-ylmethoxy)-9-[2-(1-hydroxy-cyclopentyl)-ethyl]-6,7-dihydro-pyrimido[6,1-a]isoquinolin-4-one | 426 | 427 |
| 170 | 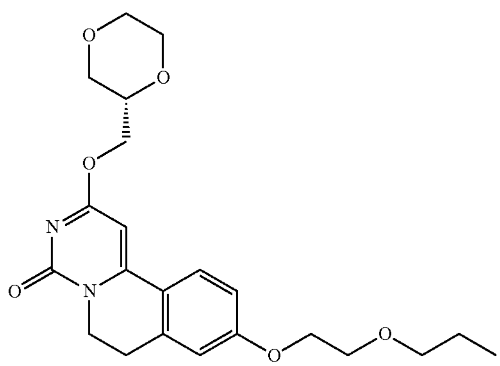 [SMILES: CCCOCCOc1ccc2c(c1)CCn1c-2cc(OC[C@@H]2COCCO2)nc1=O] | 2-((S)-1-[1,4]Dioxan-2-ylmethoxy)-9-(2-propoxy-ethoxy)-6,7-dihydro-pyrimido[6,1-a]isoquinolin-4-one | 416 | 417 |
| 171 | 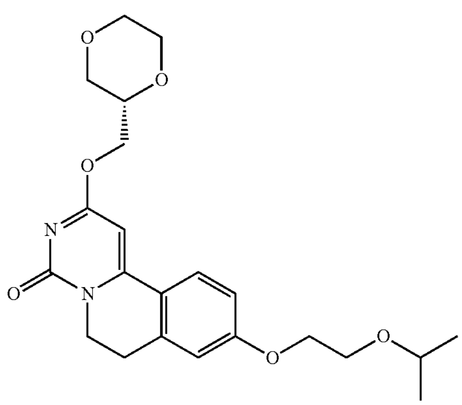 [SMILES: CC(C)OCCOc1ccc2c(c1)CCn1c-2cc(OC[C@@H]2COCCO2)nc1=O] | 2-((S)-1-[1,4]Dioxan-2-ylmethoxy)-9-(2-isopropoxy-ethoxy)-6,7-dihydro-pyrimido[6,1-a]isoquinolin-4-one | 416 | 417 |
| 172 | 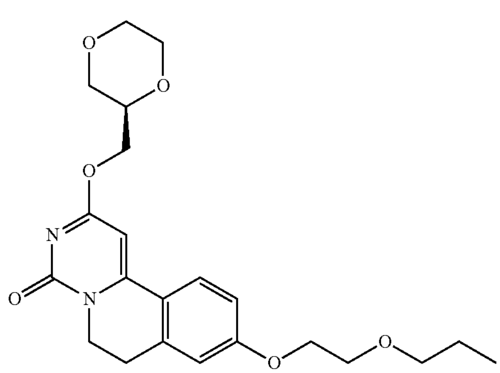 [SMILES: CCCOCCOc1ccc2c(c1)CCn1c-2cc(OC[C@H]2COCCO2)nc1=O] | 2-((R)-1-[1,4]Dioxan-2-ylmethoxy)-9-(2-propoxy-ethoxy)-6,7-dihydro-pyrimido[6,1-a]isoquinolin-4-one | 416 | 417 |

TABLE II-continued

Mass spectral data of the Compounds of the Invention
MW: Molecular weight calc: calculated obs: observed

| Cpd # | Structures | Name | MW (calc) | MW (obsd) |
|---|---|---|---|---|
| 173 | 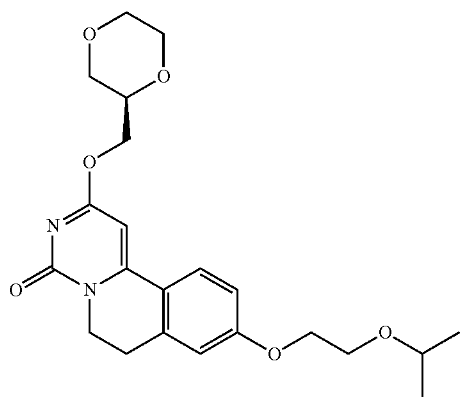 [SMILES: CC(C)OCCOc1ccc2c(c1)CCn1c-2cc(OC[C@H]2COCCO2)nc1=O] | 2-((R)-1-[1,4]Dioxan-2-ylmethoxy)-9-(2-isopropoxy-ethoxy)-6,7-dihydro-pyrimido[6,1-a]isoquinolin-4-one | 416 | 417 |
| 174 | 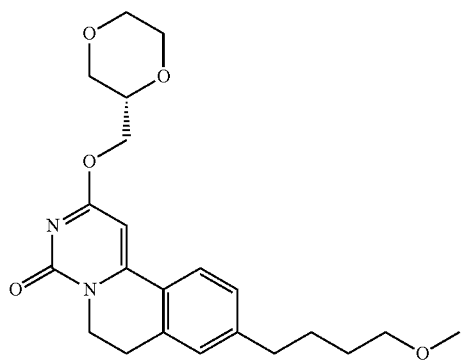 [SMILES: COCCCCc1ccc2c(c1)CCn1c-2cc(OC[C@@H]2COCCO2)nc1=O] | 2-((S)-1-[1,4]Dioxan-2-ylmethoxy)-9-(4-methoxy-butyl)-6,7-dihydro-pyrimido[6,1-a]isoquinolin-4-one | 400 | 401 |

TABLE III

NMR Data of the Compounds of the Invention

Cpd# NMR data (δ)

1. ($^1$H, CDCl$_3$) δ ppm 7.61 (1 H, d), 6.89 (1 H, dd), 6.78 (1 H, d), 6.26 (1 H, s), 6.13-5.94 (1 H, m), 5.48-5.24 (2 H, m), 4.59 (2 H, dt), 4.48-4.30 (2 H, m), 4.18 (2 H, t), 4.10-4.02 (1 H, m), 3.96 (1 H, m), 3.89-3.57 (4 H, m), 3.46 (1 H, dd), 2.95 (2 H, t)
2. ($^1$H, CDCl$_3$) δ ppm 8.89 (1 H, s), 8.67 (1 H, d), 7.93 (1 H, d), 7.82 (1 H, d), 7.61 (1 H, d), 7.53 (1 H, s), 7.43 (1 H, dd), 6.43 (1 H, s), 4.51-4.37 (2 H, m), 4.26 (2 H, t), 3.99 (1 H, m), 3.92-3.60 (5 H, m), 3.49 (1 H, m), 3.10 (2 H, t)
3. ($^1$H, CDCl$_3$) δ ppm 8.77 (2 H, br. s.), 7.86 (1 H, d), 7.76-7.46 (4 H, m), 6.48 (1 H, br. s.), 4.60-4.36 (2 H, m), 4.30 (2 H, br. s.), 4.04 (1 H, br. s.), 3.94-3.67 (5 H, m), 3.54 (1 H, t), 3.15 (2 H, br. s.)
4. ($^1$H, CDCl$_3$) δ ppm 7.83-7.94 (2 H, m), 7.78-7.71 (1 H, m), 7.67-7.53 (4 H, m), 6.48 (1 H, s), 4.53-4.43 (2 H, m), 4.34-4.27 (2 H, m), 4.07-4.01 (1 H, m), 3.93-3.67 (5 H, m), 3.54 (1 H, dd), 3.14 (2 H, t)
5. ($^1$H, CDCl$_3$) δ ppm 7.90 (1 H, d), 7.87-7.79 (2 H, m), 7.73-7.69 (1 H, m), 7.65-7.56 (2 H, m), 7.52 (1 H, s), 6.45 (1 H, s), 4.51-4.37 (2 H, m), 4.27 (2 H, t), 4.06-3.95 (1 H, m), 3.91-3.61 (5 H, m), 3.51 (1 H, dd), 3.11 (2 H, t)
6. ($^1$H, CDCl$_3$) δ ppm 7.85-7.68 (5 H, m), 7.61 (1 H, dd), 7.54 (1 H, d), 6.44 (1 H, s), 4.51-4.36 (2 H, m), 4.26 (2 H, t), 4.00 (1 H, m), 3.91-3.61 (5 H, m), 3.50 (1 H, dd), 3.11 (2 H, t)
7. ($^1$H, CDCl$_3$) δ ppm 7.71 (1 H, d), 7.00 (1 H, dd), 6.90 (1 H, d), 6.31 (1 H, s), 4.86 (2 H, s), 4.51-4.34 (2 H, m), 4.22 (2 H, t), 3.99 (1 H, m), 3.92-3.58 (5 H, m), 3.49 (1 H, dd), 3.03 (2 H, t)
8. ($^1$H, CDCl$_3$) δ ppm 7.72 (1 H, d), 7.68-7.60 (1 H, m), 7.18 (1 H, d), 7.02 (1 H, dd), 6.93 (1 H, d), 6.28 (1 H, s), 5.23 (2 H, s), 4.49-4.33 (2 H, m), 4.19 (2 H, t), 4.02-3.94 (1 H, m), 3.89-3.61 (5 H, m), 3.48 (1 H, dd), 2.98 (2 H, t)
9. ($^1$H, CDCl$_3$) δ ppm 8.63 (1 H, d), 7.75 (1 H, td), 7.64 (1 H, d), 7.50 (1 H, d), 7.29-7.24 (1 H, m), 6.99 (1 H, dd), 6.89 (1 H, d), 6.27 (1 H, s), 5.29 (2 H, d),

TABLE III-continued

NMR Data of the Compounds of the Invention

| Cpd# | NMR data (δ) |
|---|---|
| | 4.48-4.34 (2 H, m), 4.19 (2 H, t), 4.02-3.93 (1 H, m), 3.90-3.60 (5 H, m), 3.48 (1 H, dd), 2.97 (2 H, t) |
| 10 | ($^1$H, CDCl$_3$) δ ppm 7.79 (1 H, d), 7.56 (1 H, d), 7.49 (3 H, d), 7.40 (1 H, s), 6.42 (1 H, s), 4.51-4.36 (2 H, m), 4.25 (2 H, t), 4.00 (1 H, m), 3.91-3.60 (5 H, m), 3.50 (1 H, t), 3.09 (2 H, t) |
| 11 | ($^1$H, CDCl$_3$) δ ppm 7.87 (1 H, d), 7.83-7.76 (2 H, m), 7.64 (1 H, d), 7.56 (1 H, d), 7.41-7.32 (1 H, m), 7.31-7.23 (3 H, m), 7.18 (1 H, s), 6.43 (1 H, s), 4.46 (2 H, br. s.), 4.27 (2 H, t), 4.06-3.96 (1 H, m), 3.97-3.61 (5 H, m), 3.51 (1 H, t), 3.11 (2 H, t) |
| 12 | ($^1$H, CDCl$_3$) δ ppm 8.20 (1 H, d), 7.76 (1 H, d), 7.60 (1 H, d), 7.47 (1 H, dd), 7.42-7.35 (2 H, m), 7.336-7.26 (1 H, m), 6.68 (1 H, s), 6.44 (1 H, s), 4.54-4.40 (2 H, m), 4.27 (2 H, t), 4.08-3.96 (1 H, m), 3.91-3.65 (5 H, m), 3.52 (1 H, dd), 3.08 (2 H, t), 1.42 (9 H, s) |
| 13 | ($^1$H DMSO-d$_6$) δ ppm 8.11 (1 H, d), 7.95-7.86 (2 H, m), 7.57 (1 H, d), 7.43 (1 H, d), 7.15 (1 H, t), 7.10 (1 H, d), 6.71 (1 H, s), 4.31-4.25 (2 H, m), 4.09 (2 H, t), 3.92-3.84 (1 H, m), 3.79 (2 H, td), 3.71-3.57 (2 H, m), 3.55-3.46 (1 H, m), 3.40 (1 H, dd), 3.08 (2 H, t) |
| 14 | ($^1$H, CDCl$_3$) δ ppm 8.45 (1 H, d), 7.84 (1 H, dd), 7.79 (1 H, d), 7.56 (1 H, dd), 7.50-7.46 (1 H, m), 6.87 (1 H, d), 6.43 (1 H, s), 4.49-4.36 (2 H, m), 4.30-4.19 (2 H, m), 4.04-3.98 (4 H, m), 3.93-3.62 (5 H, m), 3.51 (1 H, dd), 3.10 (2 H, t) |
| 15 | ($^1$H, CDCl$_3$) δ ppm 8.97 (1 H, d), 8.09 (1 H, dd), 7.83 (2 H, dd), 7.63 (1 H, dd), 7.55 (1 H, s), 6.44 (1 H, s), 4.52-4.36 (2 H, m), 4.27 (2 H, t), 3.99 (1 H, tt), 3.91-3.59 (5 H, m), 3.49 (1 H, dd), 3.13 (2 H, t) |
| 16 | ($^1$H, CDCl$_3$) δ ppm 7.73 (1 H, d), 7.57-7.50 (2 H, m), 7.48-7.45 (1 H, m), 7.42 (1 H, d), 6.42 (1 H, s), 4.53-4.39 (2 H, m), 4.28-4.23 (2 H, m), 4.07-3.97 (1 H, m), 3.94-3.64 (8 H, m), 3.52 (1 H, dd), 3.06 (2 H, t) |
| 17 | ($^1$H, CDCl$_3$) δ ppm 7.66 (1 H, d), 7.03 (1 H, dd), 6.94 (1 H, d), 6.29 (1 H, s), 5.22 (2 H, s), 4.50-4.33 (2 H, m), 4.27-4.14 (2 H, m), 4.03-3.93 (1 H, m), 3.90-3.61 (5 H, m), 3.49 (1 H, dd), 2.99 (2 H, t), 1.47 (9 H, s) |
| 18 | ($^1$H, CDCl$_3$) δ ppm 8.80 (1 H, d), 8.32 (1 H, d), 8.16-7.96 (2 H, m), 7.85 (1 H, d), 7.65 (1 H, dd), 7.57 (1 H, s), 6.45 (1 H, s), 4.56-4.37 (2 H, m), 4.28 (2 H, t), 4.01 (1 H, qd), 3.93-3.60 (5 H, m), 3.58-3.44 (1 H, m), 3.20-3.02 (5 H, m) |
| 19 | ($^1$H, CDCl$_3$) δ ppm 7.65 (1 H, d), 7.41 (1 H, dd), 7.36 (1 H, s), 6.38 (1 H, s), 4.50-4.40 (2 H, m), 4.28-4.18 (2 H, m), 4.01 (1 H, m), 3.92-3.66 (5 H, m), 3.52 (1 H, dd), 3.01 (2 H, t), 2.45 (2 H, t), 1.68 (2 H, sxt), 1.09 (3 H, t) |
| 20 | ($^1$H, CDCl$_3$) δ ppm 8.58 (1 H, dd), 7.66-7.56 (2 H, m), 7.22 (1 H, dd), 7.19-7.09 (3 H, m), 6.36 (1 H, s), 4.50-4.36 (2 H, m), 4.25-4.17 (2 H, m), 4.04-3.95 (1 H, m), 3.91-3.62 (5 H, m), 3.50 (1 H, dd), 3.14 (4 H, s), 2.98 (2 H, t) |
| 21 | ($^1$H, CDCl$_3$) δ ppm 8.55 (1 H, dd), 8.44 (2 H, dd), 7.63 (1 H, d), 7.22 (1 H, dd), 7.15 (1 H, s), 6.36 (1 H, s), 4.53-4.36 (2 H, m), 4.26-4.17 (2 H, m), 4.07-3.95 (1 H, m), 3.93-3.61 (5 H, m), 3.51 (1 H, dd), 3.17 (4 H, s), 2.99 (2 H, t) |
| 22 | ($^1$H, CDCl$_3$) δ ppm 8.51 (1 H, br. s.), 7.94 (1 H, s), 7.79-7.67 (2 H, m), 7.61 (1 H, s), 7.58-7.47 (2 H, m), 7.33 (1 H, t), 6.67 (1 H, br. s.), 6.43 (1 H, s), 4.56-4.40 (2 H, m), 4.29 (2 H, t), 4.04 (1 H, td), 3.97-3.65 (5 H, m), 3.61-3.48 (1 H, m), 3.11 (2 H, t) |
| 23 | ($^1$H, CDCl$_3$) δ ppm 7.76 (1 H, d), 7.58 (1 H, d), 7.50 (1 H, s), 7.45-7.32 (2 H, m), 7.13-7.01 (2 H, m), 6.43 (1 H, s), 4.45 (2 H, m), 4.27 (2 H, t), 4.01 (1 H, m), 3.94-3.63 (8 H, m), 3.52 (1 H, t), 3.08 (2 H, t) |
| 24 | ($^1$H, CDCl$_3$) δ ppm 8.56-8.45 (1 H, m), 8.38 (1 H, d), 7.83 (1 H, d), 7.63 (1 H, dd), 7.54 (1 H, s), 7.42 (1 H, t), 6.45 (1 H, s), 4.54-4.36 (2 H, m), 4.31-4.23 (2 H, m), 4.05-3.96 (4 H, m), 3.93-3.62 (5 H, m), 3.52 (1 H, dd), 3.13 (2 H, t) |
| 25 | ($^1$H, CDCl$_3$) δ ppm 8.17 (1 H, d), 8.01 (1 H, s), 7.78 (1 H, d), 7.72-7.60 (3 H, m), 7.57 (1 H, d), 6.42 (1 H, s), 4.52-4.38 (2 H, m), 4.32-4.24 (2 H, m), 4.01 (1 H, qd), 3.93-3.62 (5 H, m), 3.51 (1 H, dd), 3.10 (2 H, t) |
| 26 | ($^1$H, CDCl$_3$) δ ppm 7.74 (1 H, d), 7.57 (3 H, d), 7.48 (1 H, s), 7.01 (2 H, d), 6.40 (1 H, s), 4.51-4.36 (2 H, m), 4.25 (2 H, t), 3.99 (1 H, dd), 3.92-3.60 (8 H, m), 3.50 (1 H, t), 3.06 (2 H, t) |
| 27 | ($^1$H, CDCl$_3$) δ ppm 8.18 (1 H, s), 7.84 (3 H, d), 7.68 (1 H, dd), 7.64-7.55 (2 H, m), 6.47 (1 H, s), 4.57-4.39 (2 H, m), 4.30 (2 H, t), 4.09-3.98 (1 H, m), 3.96-3.64 (5 H, m), 3.54 (1 H, dd), 3.13 (2 H, t) |
| 28 | ($^1$H, CDCl$_3$) δ ppm 8.45 (1 H, dd), 7.88-7.74 (2 H, m), 7.65 (1 H, d), 7.58 (1 H, s), 7.36-7.25 (1 H, m), 6.46 (1 H, s), 4.57-4.40 (2 H, m), 4.29 (2 H, t), 4.03 (1 H, td), 3.96-3.64 (5 H, m), 3.60-3.46 (1 H, m), 3.12 (2 H, t) |
| 29 | ($^1$H, CDCl$_3$) δ ppm 7.99 (1 H, s), 7.80 (1 H, d), 7.64 (1 H, d), 7.56 (1 H, s), 7.50-7.32 (3 H, m), 6.45 (1 H, s), 4.56-4.40 (2 H, m), 4.29 (2 H, t), 4.11-3.97 (1 H, m), 3.95-3.64 (5 H, m), 3.60-3.46 (1 H, m), 3.11 (2 H, t), 2.26 (5 H, s) |
| 30 | ($^1$H, CDCl$_3$) δ ppm 7.63 (1 H, d), 7.39 (1 H, dd), 7.33 (1 H, s), 6.41-6.34 (1 H, m), 4.53-4.39 (2 H, m), 4.29-4.18 (1 H, m), 4.06-3.97 (1 H, m), 3.93-3.64 (5 H, m), 3.52 (1 H, dd), 3.00 (2 H, t), 1.56-1.45 (1 H, m), 1.01-0.83 (4 H, m) |
| 31 | ($^1$H, CDCl$_3$) δ ppm 7.67 (1 H, d), 7.45 (1 H, d), 7.39 (1 H, s), 6.40 (1 H, s), 4.53-4.38 (2 H, m), 4.31-4.17 (2 H, m), 4.02 (1 H, dd), 3.94-3.64 (5 H, m), 3.52 (1 H, dd), 3.08-2.96 (2 H, m), 2.18-1.75 (7 H, m), 1.29 (1 H, s) |
| 32 | ($^1$H, CDCl$_3$) δ ppm 9.32 (1 H, s), 9.04 (2 H, s), 7.90 (1 H, d), 7.66 (1 H, dd), 7.58 (1 H, s), 6.48 (1 H, s), 4.56-4.40 (2 H, m), 4.37-4.27 (2 H, m), 4.11-3.99 (1 H, m), 3.96-3.64 (5 H, m), 3.60-3.46 (1 H, m), 3.17 (2 H, t) |

TABLE III-continued

NMR Data of the Compounds of the Invention

| Cpd# | NMR data (δ) |
|---|---|
| 33 | ($^1$H, CDCl$_3$) δ ppm 7.67 (1 H, d), 7.42 (1 H, d), 7.32 (1 H, s), 6.39 (1 H, s), 6.31 (1 H, t), 4.54-4.38 (2 H, m), 4.25 (2 H, t), 4.02 (1 H, dd), 3.94-3.64 (5 H, m), 3.53 (1 H, t), 3.03 (2 H, t), 2.45 (2 H, d), 2.29 (2 H, dd), 1.91-1.58 (4 H, m) |
| 34 | ($^1$H, DMSO-d$_6$) δ ppm 8.07 (1 H, d), 7.97 (1 H, s), 7.78-7.72 (2 H, m), 7.62-7.53 (2 H, m), 7.39 (1 H, d), 6.68 (1 H, s), 6.52 (1 H, d), 4.33-4.24 (2 H, m), 4.09 (2 H, t), 3.91-3.76 (5 H, m), 3.71-3.58 (2 H, m), 3.55-3.47 (1 H, m), 3.40 (1 H, m), 3.29 (1 H, s), 3.10 (2 H, t) |
| 35 | ($^1$H, CDCl$_3$) δ ppm 8.84 (1 H, d), 7.96 (1 H, d), 7.85 (1 H, d), 7.64 (1 H, dd), 7.56 (1 H, s), 7.40 (1 H, d), 6.47 (1 H, s), 4.55-4.40 (2 H, m), 4.37-4.23 (2 H, m), 4.04 (1 H, m), 3.95-3.65 (5 H, m), 3.54 (1 H, dd), 3.14 (2 H, t), 2.74 (3 H, s) |
| 36 | ($^1$H, CDCl$_3$) δ ppm 8.69 (1 H, d), 7.78-7.72 (2 H, m), 7.65-7.57 (3 H, m), 7.33 (1 H, m), 6.43 (1 H, s), 4.54-4.39 (2 H, m), 4.27 (2 H, t), 4.05 (1 H, s), 3.95-3.64 (5 H, m), 3.53 (1 H, dd), 3.07 (2 H, t) |
| 37 | ($^1$H, CDCl$_3$) δ ppm 7.68 (1 H, d), 7.47 (1 H, dd), 7.42 (1 H, s), 6.40 (1 H, s), 4.53-4.41 (2 H, m), 4.38 (2 H, s), 4.24 (2 H, t), 4.07-3.96 (1 H, m), 3.93-3.63 (5 H, m), 3.55-3.33 (4 H, m), 3.03 (2 H, t) |
| 38 | ($^1$H, CDCl$_3$) δ ppm 7.67 (1 H, d), 7.44 (1 H, dd), 7.39 (1 H, s), 6.39 (1 H, s), 4.50-4.40 (2 H, m), 4.26-4.20 (2 H, m), 4.04-3.98 (1 H, m), 3.91-3.65 (5 H, m), 3.52 (1 H, dd), 3.02 (2 H, t), 2.90-2.83 (2 H, m), 2.75-2.68 (2 H, m) |
| 39 | ($^1$H, CDCl$_3$) δ ppm 7.64 (1 H, d), 7.42 (1 H, dd), 7.37 (1 H, s), 6.38 (1 H, s), 4.51 (2 H, s), 4.48-4.378 (2 H, m), 4.19 (2 H, t), 4.03-3.96 (1 H, m), 3.89-3.64 (5 H, m), 3.51 (1 H, dd), 2.99 (2 H, t) |
| 40 | ($^1$H, CDCl$_3$) δ ppm 7.65 (1 H, d), 7.50-7.44 (3 H, m), 7.41 (1 H, s), 6.94-6.84 (2 H, m), 6.35 (1 H, s), 4.45-4.36 (2 H, m), 4.19 (2 H, t), 4.04-3.91 (1 H, m), 3.87-3.62 (8 H, m), 3.48 (1 H, dd), 7.81 (1 H, d), 7.59-7.48 (2 H, m), 7.43 (1 H, s), 7.41-7.33 (3 H, m), 6.47 (1 H, s), 4.54-4.42 (2 H, m), 4.30 (2 H, t), 4.03 (1 H, dt), 3.95-3.65 (5 H, m), 3.54 (1 H, dd), 3.11 (2 H, t) |
| 41 | ($^1$H, CDCl$_3$) δ ppm 8.78 (1 H, d), 8.59 (1 H, dd), 7.83 (1 H, dt), 7.71 (1 H, d), 7.54 (1 H, dd), 7.49 (1 H, s), 7.39-7.25 (1 H, m), 6.40 (1 H, s), 4.51-4.33 (2 H, m), 4.30-4.16 (2 H, m), 4.07-3.93 (1 H, m), 3.90-3.59 (5 H, m), 3.49 (1 H, dd), 3.04 (2 H, t) |
| 42 | ($^1$H, CDCl$_3$) δ ppm 7.93 (2 H, d), 7.78 (1 H, d), 7.72-7.59 (3 H, m), 7.54 (1 H, s), 6.42 (1 H, s), 4.49-4.35 (2 H, m), 4.23 (2 H, t), 4.05-3.95 (1 H, m), 3.91-3.61 (5 H, m), 3.49 (1 H, t), 3.16-2.97 (5 H, m) |
| 43 | ($^1$H, CDCl$_3$) δ ppm 7.81 (1 H, d), 7.64 (1 H, d), 7.55 (1 H, br. s.), 7.50-7.37 (1 H, m), 7.24 (1 H, d), 7.18 (1 H, br. s.), 7.00 (1 H, d), 6.46 (1 H, br. s.), 4.47 (2 H, d), 4.30 (2 H, br. s.), 4.04 (1 H, br. s.), 3.98-3.66 (7 H, m), 3.54 (1 H, t), 3.12 (2 H, br. s.), 1.83 (1 H, br. s.) |
| 44 | ($^1$H, CDCl$_3$) δ ppm 7.81 (1 H, d), 7.59-7.48 (2 H, m), 7.43 (1 H, s), 7.41-7.33 (3 H, m), 6.47 (1 H, s), 4.54-4.42 (2 H, m), 4.30 (2 H, t), 4.03 (1 H, dt), 3.95-3.65 (5 H, m), 3.54 (1 H, dd), 3.11 (2 H, t) |
| 45 | ($^1$H, CDCl$_3$) δ ppm 7.62 (1 H, d), 7.39 (1 H, d), 7.34 (1 H, s), 6.36 (1 H, s), 4.51-4.34 (2 H, m), 4.19 (2 H, t), 3.99 (1 H, td), 3.91-3.59 (7 H, m), 3.50 (1 H, dd), 2.98 (2 H, t), 2.74 (2 H, t) |
| 46 | ($^1$H, CDCl$_3$) δ ppm 7.64 (1 H, d), 7.02 (1 H, dd), 6.92 (1 H, d), 6.30 (1 H, s), 6.13 (1 H, s), 5.09 (2 H, s), 4.51-4.36 (2 H, m), 4.22 (2 H, t), 4.07-3.97 (1 H, m), 3.92-3.61 (8 H, m), 3.57-3.44 (1 H, m), 2.99 (2 H, t), 2.30 (3 H, s) |
| 47 | ($^1$H, CDCl$_3$) δ ppm 7.62 (1 H, d), 7.37 (1 H, d), 7.00 (1 H, dd), 6.90 (1 H, d), 6.33 (1 H, d), 6.27 (1 H, s), 5.12 (2 H, s), 4.47-4.34 (2 H, m), 4.23-4.143 (2 H, m), 4.02-3.89 (4 H, m), 3.88-3.59 (5 H, m), 3.48 (1 H, dd), 2.96 (2 H, t) |
| 48 | ($^1$H, CDCl$_3$) δ ppm 7.67 (1 H, d), 6.99 (1 H, dd), 6.90 (1 H, d), 6.29 (1 H, s), 5.33 (2 H, s), 4.47-4.35 (2 H, m), 4.20 (2 H, t), 4.03-3.93 (1 H, m), 3.89-3.60 (5 H, m), 3.48 (1 H, dd), 2.99 (2 H, t), 2.45 (3 H, s) |
| 49 | ($^1$H, CDCl$_3$) δ ppm 7.77 (1 H, d), 7.66-7.57 (3 H, m), 7.52 (1 H, d), 7.04 (2 H, d), 6.43 (1 H, s), 4.55-4.40 (2 H, m), 4.35-4.24 (2 H, m), 4.04 (1 H, dd), 3.97-3.66 (9 H, m), 3.54 (1 H, dd), 3.32-3.20 (4 H, m), 3.10 (2 H, s) |
| 50 | ($^1$H, CDCl$_3$) δ ppm 8.06 (1 H, dd), 7.92-7.78 (2 H, m), 7.63 (1 H, d), 7.56 (1 H, s), 7.36-7.24 (1 H, m), 6.47 (1 H, s), 4.55-4.38 (2 H, m), 4.28 (2 H, t), 4.13-3.99 (1 H, m), 3.95-3.65 (5 H, m), 3.54 (1 H, t), 3.11 (2 H, t) |
| 51 | ($^1$H, CDCl$_3$) δ ppm 7.95 (1 H, t), 7.80 (1 H, d), 7.67-7.54 (3 H, m), 7.54-7.45 (1 H, m), 6.44 (1 H, s), 4.52-4.35 (2 H, m), 4.31-4.19 (2 H, m), 4.09-3.96 (1 H, m), 3.95-3.64 (5 H, m), 3.58-3.46 (1 H, m), 3.10 (2 H, t) |
| 52 | ($^1$H, CDCl$_3$) δ ppm 7.64 (1 H, d), 7.40 (1 H, dd), 7.35 (1 H, d), 6.38 (1 H, s), 4.52-4.39 (2 H, m), 4.26-4.16 (2 H, m), 4.04-3.96 (1 H, m), 3.93-3.63 (5 H, m), 3.51 (1 H, dd), 3.00 (2 H, t), 1.36 (9 H, s) |
| 53 | ($^1$H, CDCl$_3$) δ ppm 8.72-8.64 (2 H, m), 7.75 (1 H, d), 7.59 (1 H, dd), 7.54 (1 H, s), 7.48-7.42 (2 H, m), 6.44 (1 H, s), 4.55-4.39 (2 H, m), 4.34-4.22 (2 H, m), 4.03 (1 H, dd), 3.95-3.64 (5 H, m), 3.53 (1 H, dd), 3.08 (2 H, t) |
| 54 | ($^1$H, CDCl$_3$) δ ppm 7.68 (1 H, d), 6.98 (1 H, dd), 6.89 (1 H, d), 6.31 (1 H, s), 6.23 (1 H, s), 5.22 (2 H, s), 4.52-4.36 (2 H, m), 4.29-4.18 (2 H, m), 4.07-3.96 (1 H, m), 3.93-3.63 (5 H, m), 3.51 (1 H, dd), 3.06-2.96 (2 H, m), 2.35 (3 H, s) |
| 55 | ($^1$H, CDCl$_3$) δ ppm 7.60 (1 H, d), 7.39-7.35 (1 H, m), 7.32 (1 H, d), 6.33 (1 H, s), 4.45-4.35 (2 H, m), 4.17 (2 H, t), 3.97 (1 H, m), 3.87-3.60 (5 H, m), 3.47 (1 H, dd), 2.95 (2 H, t), 1.62 (6 H, s) |

TABLE III-continued

NMR Data of the Compounds of the Invention

| Cpd# | NMR data (δ) |
|---|---|
| 56 | ($^1$H, CDCl$_3$) δ ppm 8.24 (1 H, dd), 7.78 (1 H, d), 7.67 (1 H, dd), 7.61 (1 H, dd), 7.54 (1 H, s), 7.04 (1 H, dd), 6.45 (1 H, s), 4.52-4.41 (2 H, m), 4.28 (2 H, t), 4.02 (4 H, s), 3.93-3.64 (5 H, m), 3.52 (1 H, dd), 3.10 (2 H, t) |
| 58 | ($^1$H, CDCl$_3$) δ ppm 7.70 (1 H, d), 7.43 (1 H, dd), 7.33 (1 H, d), 6.39 (1 H, s), 6.31 (1 H, dt), 4.53-4.34 (4 H, m), 4.31-4.19 (2 H, m), 4.06-3.94 (3 H, m), 3.92-3.61 (5 H, m), 3.51 (1 H, dd), 3.04 (2 H, t), 2.62-2.50 (2 H, m) |
| 59 | ($^1$H, CDCl$_3$) δ ppm 9.02 (1 H, d), 8.09 (1 H, dd), 7.97-7.80 (2 H, m), 7.67 (1 H, dd), 7.59 (1 H, d), 6.48 (1 H, s), 4.56-4.38 (2 H, m), 4.36-4.25 (2 H, m), 4.03 (1 H, m), 3.95-3.63 (5 H, m), 3.53 (1 H, dd), 3.16 (2 H, t) |
| 60 | ($^1$H, CDCl$_3$) δ ppm 8.43 (1 H, d), 7.86-7.74 (2 H, m), 7.56 (1 H, dd), 7.47 (1 H, d), 6.80 (1 H, d), 6.43 (1 H, s), 5.44-5.31 (1 H, m), 4.53-4.37 (2 H, m), 4.26 (2 H, t), 4.01 (1 H, m), 3.92-3.62 (5 H, m), 3.51 (1 H, dd), 3.09 (2 H, t), 1.40 (6 H, d) |
| 61 | ($^1$H, CDCl$_3$) δ ppm 8.44 (1 H, d), 7.84 (1 H, dd), 7.79 (1 H, d), 7.57 (1 H, dd), 7.48 (1 H, d), 6.85 (1 H, d), 6.43 (1 H, s), 4.54-4.37 (4 H, m), 4.27 (2 H, t), 4.02 (1 H, m), 3.93-3.62 (5 H, m), 3.52 (1 H, dd), 3.10 (2 H, t), 1.45 (3 H, t) |
| 62 | ($^1$H, CDCl$_3$) δ ppm 8.52 (1 H, d), 7.85-7.72 (2 H, m), 7.56 (1 H, dd), 7.47 (1 H, d), 6.75 (1 H, d), 6.42 (1 H, s), 4.52-4.38 (2 H, m), 4.32-4.22 (2 H, m), 4.06-3.97 (1 H, m), 3.93-3.58 (13 H, m), 3.52 (1 H, dd), 3.09 (2 H, s) |
| 63 | ($^1$H, CDCl$_3$) δ ppm 7.77 (1 H, d), 7.60 (1 H, dd), 7.52 (1 H, d), 7.21-7.12 (1 H, m), 6.99 (2 H, ddd), 6.45 (1 H, s), 4.53-4.40 (2 H, m), 4.28 (2 H, t), 4.06-3.98 (1 H, m), 3.95 (3 H, s), 3.92-3.63 (8 H, m), 3.52 (1 H, dd), 3.08 (2 H, t) |
| 64 | ($^1$H, CDCl$_3$) δ ppm 8.15 (1 H, d), 7.82 (1 H, d), 7.50 (1 H, dd), 7.45-7.40 (1 H, m), 6.91 (1 H, d), 6.46 (1 H, s), 4.54-4.40 (2 H, m), 4.29 (2 H, t), 4.11 (2 H, s), 4.07-3.98 (1 H, m), 3.94-3.64 (4 H, m), 3.53 (1 H, dd), 3.11 (2 H, t) |
| 65 | ($^1$H, CDCl$_3$) δ ppm 8.62 (1 H, d), 7.84 (1 H, d), 7.67 (1 H, dd), 7.59 (1 H, d), 7.42 (1 H, s), 7.36 (1 H, dd), 6.46 (1 H, s), 4.54-4.38 (2 H, m), 4.33-4.24 (2 H, m), 4.07-3.97 (1 H, m), 3.94-3.63 (5 H, m), 3.52 (1 H, dd), 3.13 (2 H, t), 2.68 (3 H, s) |
| 66 | ($^1$H, CDCl$_3$) δ ppm 8.88 (1 H, s), 8.82 (1 H, d), 7.88 (1 H, d), 7.68 (1 H, dd), 7.61 (1 H, dd), 7.53 (1 H, s), 6.45 (1 H, s), 4.49-4.38 (2 H, m), 4.27 (2 H, t), 4.00 (1 H, ddt), 3.90-3.61 (5 H, m), 3.49 (1 H, dd), 3.13 (2 H, t) |
| 67 | ($^1$H, CDCl$_3$) δ ppm 7.76 (1 H, d), 7.58 (1 H, dd), 7.50 (1 H, s), 6.88-7.03 (3 H, m), 6.44 (1 H, s), 4.54-4.39 (2 H, m), 4.28 (2 H, t), 4.03 (1 H, m), 3.95-3.63 (11 H, m), 3.53 (1 H, dd), 3.08 (2 H, t) |
| 68 | ($^1$H, CDCl$_3$) δ ppm 8.50 (1 H, d), 7.74 (2 H, td), 7.55 (1 H, dd), 7.45 (1 H, s), 6.75 (1 H, d), 6.40 (1 H, s), 4.56-4.38 (2 H, m), 4.26 (2 H, t), 4.01 (1 H, m), 3.94-3.58 (9 H, m), 3.52 (1 H, dd), 3.08 (2 H, t), 1.70 (6 H, br. s.) |
| 69 | ($^1$H, CDCl$_3$) δ ppm 8.21 (1 H, dd), 7.78 (1 H, d), 7.66 (2 H, ddd), 7.56 (1 H, s), 7.01 (1 H, dd), 6.45 (1 H, s), 4.54-4.39 (4 H, m), 4.28 (2 H, t), 4.03 (1 H, m), 3.94-3.64 (5 H, m), 3.53 (1 H, dd), 3.09 (2 H, t), 1.42 (3 H, t) |
| 70 | ($^1$H, CDCl$_3$) δ ppm 7.75 (1 H, d), 7.64 (1 H, d), 7.60 (1 H, dd), 7.52 (1 H, d), 6.47 (1 H, d), 6.43 (1 H, s), 4.53-4.39 (2 H, m), 4.33-4.23 (2 H, m), 4.03 (6 H, d), 3.94-3.64 (5 H, m), 3.59-3.48 (2 H, m), 3.08 (2 H, t) |
| 71 | ($^1$H, CDCl$_3$) δ ppm 9.00 (1 H, s), 8.87 (1 H, d), 7.87 (1 H, d), 7.63 (1 H, dd), 7.56 (1 H, s), 7.52-7.48 (1 H, m), 6.45 (1 H, s), 4.51-4.36 (2 H, m), 4.26 (2 H, t), 3.99 (1 H, ddt), 3.90-3.60 (5 H, m), 3.54-3.44 (1 H, m), 3.12 (2 H, t) |
| 72 | ($^1$H, CDCl$_3$) δ ppm 7.65 (1 H, d), 7.34 (1 H, d), 7.30 (1 H, s), 6.36 (1 H, s), 4.48 (2 H, s), 4.46-4.34 (2 H, m), 4.18 (2 H, t), 4.02-3.92 (1 H, m), 3.89-3.60 (5 H, m), 3.54-3.42 (1 H, m), 3.00 (2 H, t), 1.30 (9 H, s) |
| 73 | ($^1$H, CDCl$_3$) δ ppm 8.19 (1 H, dd), 7.69 (1 H, d), 7.38 (2 H, ddd), 7.29 (1 H, d), 6.72 (1 H, dd), 6.40 (1 H, s), 4.47-4.37 (2 H, m), 4.24 (2 H, t), 4.03-3.93 (1 H, m), 3.89-3.59 (5 H, m), 3.49 (1 H, t), 3.18-3.08 (4 H, m), 3.04 (2 H, t), 1.82-1.72 (4 H, m) |
| 74 | ($^1$H, CDCl$_3$) δ ppm 8.51 (1 H, d), 7.75 (2 H, td), 7.56 (1 H, dd), 7.46 (1 H, s), 6.48 (1 H, d), 6.41 (1 H, s), 4.56-4.37 (2 H, m), 4.27 (2 H, t), 4.02 (1 H, dd), 3.95-3.63 (5 H, m), 3.61-3.45 (5 H, m), 3.09 (2 H, t), 2.14-1.99 (4 H, m) |
| 75 | ($^1$H, CDCl$_3$) δ ppm 7.70-7.57 (2 H, m), 7.47-7.20 (5 H, m), 7.05 (1 H, dd), 6.96 (1 H, d), 6.27 (1 H, s), 5.26 (2 H, s), 4.47-4.32 (2 H, m), 4.23-4.15 (2 H, m), 4.03-3.91 (1 H, m), 3.89-3.56 (5 H, m), 3.47 (1 H, dd), 2.97 (2 H, t) |
| 76 | ($^1$H, CDCl$_3$) δ ppm 7.67 (1 H, d), 7.05 (1 H, dd), 6.96 (1 H, d), 6.75 (1 H, s), 6.31 (1 H, s), 5.18 (2 H, s), 4.53-4.34 (2 H, m), 4.22 (2 H, t), 4.00 (1 H, m), 3.92-3.62 (5 H, m), 3.50 (1 H, dd), 3.00 (2 H, t), 1.32 (9 H, s) |
| 77 | ($^1$H, CDCl$_3$) δ ppm 7.64 (1 H, d), 7.00 (1 H, dd), 6.91 (1 H, d), 6.27 (1 H, s), 5.17 (2 H, s), 4.47-4.32 (2 H, m), 4.23-4.14 (2 H, m), 3.96 (1 H, qd), 3.89-3.58 (5 H, m), 3.47 (1 H, dd), 2.97 (2 H, t), 2.29-2.17 (1 H, m), 1.30-1.24 (4 H, m) |
| 78 | ($^1$H, CDCl$_3$) δ ppm 7.65 (1 H, d), 7.01 (1 H, dd), 6.92 (1 H, d), 6.27 (1 H, s), 5.22 (2 H, s), 4.47-4.30 (2 H, m), 4.24-4.13 (2 H, m), 3.96 (1 H, m), 3.90-3.580 (5 H, m), 3.47 (1 H, dd), 3.02-2.85 (4 H, m), 1.41 (3 H, t) |
| 79 | ($^1$H, CDCl$_3$) δ ppm 7.68 (1 H, d), 7.05 (1 H, dd), 6.95 (1 H, d), 6.32 (1 H, s), 5.26 (2 H, s), 4.52-4.37 (2 H, m), 4.28-4.20 (2 H, m), 4.06-3.96 (1 H, m), 3.94-3.62 (5 H, m), 3.51 (1 H, dd), 3.02 (2 H, t), 2.67 (3 H, s) |
| 80 | ($^1$H, CDCl$_3$) δ ppm 7.65 (1 H, d), 7.02 (1 H, dd), 6.93 (1 H, d), 6.28 (1 H, s), 5.22 (2 H, s), 4.47-4.33 (2 H, m), 4.19 (2 H, t), 4.03-3.91 (1 H, m), 3.89-3.59 (5 H, m), 3.48 (1 H, dd), 3.26 (1 H, dt), 2.99 (2 H, t), 1.43 (6 H, d) |

TABLE III-continued

NMR Data of the Compounds of the Invention

| Cpd# | NMR data (δ) |
|---|---|
| 81 | ($^1$H, CDCl$_3$) δ ppm 7.63 (1 H, d), 7.40 (1 H, dd), 7.34 (1 H, s), 6.38 (1 H, s), 4.53-4.37 (2 H, m), 4.27-4.17 (2 H, m), 4.05-3.96 (1 H, m), 3.93-3.63 (5 H, m), 3.58-3.46 (1 H, m), 3.00 (2 H, t), 2.88 (1 H, m), 2.13-1.97 (2 H, m), 1.90-1.56 (6 H, m) |
| 82 | ($^1$H, CDCl$_3$) δ ppm 7.64 (1 H, d), 7.41 (1 H, d), 7.35 (1 H, s), 6.38 (1 H, s), 4.52-4.36 (2 H, m), 4.22 (2 H, t), 4.01 (1 H, m), 3.93-3.63 (5 H, m), 3.51 (1 H, t), 3.00 (2 H, t), 2.71-2.58 (1 H, m), 1.99-1.31 (10 H, m) |
| 83 | ($^1$H, CDCl$_3$) δ ppm 7.64 (1 H, d), 7.40 (1 H, dd), 7.35 (1 H, s), 6.38 (1 H, s), 4.49-4.40 (2 H, m), 4.22 (2 H, t), 4.05-3.97 (1 H, m), 3.91-3.65 (5 H, m), 3.51 (1 H, dd), 3.00 (2 H, t), 2.88-2.78 (1 H, m), 1.31 (6 H, d) |
| 84 | ($^1$H, CDCl$_3$) δ ppm 7.64 (1 H, d), 7.40 (1 H, dd), 7.35 (1 H, s), 6.38 (1 H, s), 4.51-4.38 (2 H, m), 4.26-4.18 (2 H, m), 4.07-3.97 (1 H, m), 3.93-3.64 (5 H, m), 3.52 (1 H, dd), 3.00 (2 H, t), 2.47 (2 H, t), 1.70-1.45 (4 H, m), 0.99 (3 H, t) |
| 85 | ($^1$H, CDCl$_3$) δ ppm 7.65 (1 H, d), 7.45 (1 H, dd), 7.41-7.31 (5 H, m), 7.27 (1 H, s), 6.37 (1 H, s), 4.49-4.34 (2 H, m), 4.24-4.17 (2 H, m), 4.02-3.94 (1 H, m), 3.90-3.60 (7 H, m), 3.54 (2 H, s), 3.52-3.45 (1 H, m), 3.00 (2 H, t), 2.42 (3 H, s) |
| 86 | ($^1$H, CDCl$_3$) δ ppm 7.63 (1 H, d), 7.42 (1 H, dd), 7.36 (1 H, s), 6.37 (1 H, s), 4.70-4.65 (1 H, m), 4.47-4.37 (2 H, m), 4.20 (2 H, t), 4.00-3.97 (1 H, m), 3.88-3.63 (5 H, m), 3.49 (1 H, t), 2.99 (2 H, t), 1.93-1.65 (4 H, m), 1.00-0.97 (6 H, m) |
| 87 | ($^1$H, CDCl$_3$) δ ppm 7.63 (1 H, d), 7.42 (1 H, d), 7.36 (1 H, s), 6.37 (1 H, s), 4.80-4.77 (1 H, m), 4.46-4.37 (2 H, m), 4.20 (2 H, t), 4.01-3.97 (1 H, m), 3.89-3.65 (5 H, m), 3.49 (1 H, t), 2.99 (2 H, t), 1.99 (1 H, d), 1.57 (3 H, d) |
| 88 | ($^1$H, CDCl$_3$) δ ppm 7.60 (1 H, d), 7.07 (1 H, d), 6.99 (1 H, s), 6.35 (1 H, s), 4.49-4.38 (2 H, m), 4.21 (2 H, t), 4.01 (1 H, m), 3.94-3.62 (5 H, m), 3.51 (1 H, t), 2.99 (2 H, t), 2.07-1.86 (1 H, m), 1.15-1.06 (2 H, m), 0.85-0.78 (2 H, m) |
| 89 | ($^1$H, DMSO-d6) δ ppm 8.00 (1 H, d), 7.46 (1 H, s), 7.40 (1 H, d), 6.68 (1 H, s), 5.53 (1 H, d), 4.43-4.41 (1 H, m), 4.26-4.25 (2 H, m), 4.01 (2 H, t), 3.87-3.40 (7 H, m), 3.00 (2 H, t), 1.67-1.65 (2 H, m), 0.98 (3 H, t) |
| 90 | ($^1$H, DMSO-d6) δ ppm 8.00 (1 H, d), 7.46 (1 H, s), 7.40 (1 H, d), 6.68 (1 H, s), 5.53 (1 H, d), 4.28-4.25 (3 H, m), 4.01 (2 H, t), 3.85-3.38 (7 H, m), 3.00 (2 H, t), 1.85-1.80 (1 H, m), 0.98 (6 H, t) |
| 91 | ($^1$H, DMSO-d6) δ ppm 8.00 (1 H, d), 7.44 (1 H, s), 7.38 (1 H, d), 6.68 (1 H, s), 5.27 (1 H, S), 4.26-4.25 (2 H, m), 4.01 (2 H, t), 3.86-3.74 (3 H, m), 3.67-3.60 (2 H, m) 3.52-3.46 (1 H, m), 3.37-3.35 (1 H, m), 3.00 (2 H, t), 1.66-1.62 (4 H, m), 0.99 (6 H, t) |
| 92 | ($^1$H, CDCl$_3$) δ ppm 7.71 (2 H, d), 7.66 (1 H, d), 7.47 (1 H, d), 7.43-7.32 (4 H, m), 6.38 (1 H, s), 4.47-4.37 (2 H, m), 4.20 (2 H, t), 4.00-3.98 (1 H, m), 3.97-3.68 (5 H, m), 3.49 (1 H, t), 3.00 (2 H, t), 2.53 (1 H, s), 1.88 (3 H, s) |
| 93 | ($^1$H, CDCl$_3$) δ ppm 7.64 (1 H, d), 7.43-7.29 (7 H, m), 6.37 (1 H, s), 4.46-4.37 (2 H, m), 4.21 (2 H, t), 3.99-3.95 (3 H, m), 3.88-3.63 (7 H, m), 3.49 (1 H, t), 2.99 (2 H, t) |
| 94 | ($^1$H, CDCl$_3$) δ ppm 7.57-7.48 (1 H, d), 7.38 (1 H, s), 6.68-6.55 (1 H, d), 6.49 (1 H, s), 6.35 (1 H, s), 6.28 (1 H, s), 6.20 (1 H, s), 4.60-4.50 (1 H, m), 4.38-4.30 (4 H, m), 4.22-4.15 (2 H, m), 4.03-3.93 (1 H, m), 3.95-3.60 (5 H, m), 3.55-3.40 (1 H, t), 2.98-2.85 (2 H, m) |
| 95 | ($^1$H, CDCl$_3$) δ ppm 7.86 (1 H, s), 7.77 (1 H, s), 7.70 (1 H, d), 7.51 (1 H, d), 7.42 (1 H, s), 6.39 (1 H, s), 4.51-4.37 (2 H, m), 4.330-4.20 (4 H, m), 4.05-3.96 (1 H, m), 3.87 (5 H, s), 3.51 (1 H, dd), 3.05 (2 H, t), 1.57 (4 H, t) |
| 96 | ($^1$H, CDCl$_3$) δ ppm 7.85 (1 H, s), 7.75 (1 H, s), 7.70 (1 H, d), 7.50 (1 H, dd), 7.42 (1 H, s), 6.39 (1 H, s), 4.50-4.39 (2 H, m), 4.27-4.18 (4 H, m), 4.05-3.97 (1 H, m), 3.86 (5 H, m), 3.51 (1 H, dd), 3.05 (2 H, t), 1.88-1.79 (2 H, m), 1.69-1.59 (1 H, m), 1.00 (6 H, d) |
| 97 | ($^1$H, CDCl$_3$) δ ppm 8.03 (1 H, d), 7.67-7.63 (2 H, m), 7.05 (1 H, d), 6.65 (1 H, s), 6.28 (1 H, dd), 4.30-4.23 (2 H, m), 4.04 (2 H, t), 3.89-3.75 (3 H, m), 3.63 (2 H, dd), 3.50 (1 H, d), 3.39 (1 H, dd), 3.04 (2 H, t), 2.37 (3 H, s) |
| 98 | ($^1$H, CDCl$_3$) δ ppm 7.64 (1 H, d), 7.42 (1 H, d), 7.36 (1 H, s), 6.37 (1 H, s), 4.66-4.61 (1 H, m), 4.47-4.37 (2 H, t), 4.20 (2 H, t), 4.00-3.88 (1 H, m), 3.88-3.46 (5 H, m), 3.49 (1 H, t), 2.99 (2 H, t), 1.90-1.89 (1 H, m), 1.81-1.77 (2 H, m), 1.57-1.54 (2 H, m), 1.00 (3 H, t) |
| 99 | ($^1$H, CDCl$_3$) δ ppm 7.75 (1 H, d), 7.33-7.28 (1 H, m), 7.22 (1 H, s), 6.41 (1 H, s), 4.50-4.39 (2 H, m), 4.29-4.23 (2 H, m), 4.05-3.97 (1 H, m), 3.85 (5 H, m), 3.54-3.47 (1 H, m), 3.07 (2 H, d), 2.36 (6 H, s) |
| 100 | ($^1$H, CDCl$_3$) δ ppm 8.36 (1 H, br. s.), 8.07 (1 H, br. s.), 7.99 (1 H, d), 7.64-7.70 (2 H, m), 6.65 (1 H, s), 4.31-4.22 (2 H, m), 4.05 (2 H, t), 3.90-3.84 (1 H, m), 3.79 (2 H, td), 3.70-3.57 (2 H, m), 3.51-3.50 (1 H, m), 3.55-3.45 (1 H, m), 3.39 (1 H, dd), 3.01 (2 H, t) |
| 101 | ($^1$H, CDCl$_3$) δ ppm 7.85 (1 H, d), 7.74 (1 H, d), 7.70 (1 H, d), 7.50 (1 H, dd), 7.44-7.38 (1 H, m), 6.38 (1 H, s), 4.48-4.348 (2 H, m), 4.27-4.17 (2 H, m), 4.15 (2 H, t), 4.04-3.96 (1 H, m), 3.90-3.64 (5 H, m), 3.50 (1 H, dd), 3.04 (2 H, t), 2.02-1.90 (2 H, m), 0.97 (3 H, t) |
| 102 | ($^1$H, CDCl$_3$) δ ppm 7.91-7.80 (2 H, m), 7.71 (1 H, dd), 7.62-7.45 (4 H, m), 6.45 (1 H, s), 4.49-4.39 (2 H, m), 4.27 (2 H, t), 4.06-3.94 (1 H, m), 3.92-3.61 (5 H, m), 3.51 (1 H, dd), 3.11 (2 H, t) |
| 103 | ($^1$H, CDCl$_3$) δ ppm 7.80-7.90 (2 H, m), 7.79-7.69 (1 H, m), 7.66-7.51 (4 H, m), 6.47 (1 H, s), 4.57-4.41 (2 H, m), 4.30 (2 H, t), 4.03 (1 H, dt), 3.95-3.64 (5 H, m), 3.53 (1 H, t), 3.14 (2 H, t) |

TABLE III-continued

NMR Data of the Compounds of the Invention

| Cpd# | NMR data (δ) |
|---|---|
| 104 | ($^1$H, CDCl$_3$) δ ppm 7.65 (1 H, d), 7.01 (1 H, dd), 6.91 (1 H, d), 6.28 (1 H, s), 5.18 (2 H, s), 4.47-4.35 (2 H, m), 4.24-4.15 (2 H, m), 4.02-3.93 (1 H, m), 3.89-3.61 (5 H, m), 3.48 (1 H, dd), 2.98 (2 H, t), 2.29-2.18 (1 H, m), 1.33-1.20 (4 H, m) |
| 105 | ($^1$H, CDCl$_3$) δ ppm 7.65 (1 H, s), 7.51-7.46 (1 H, m), 7.45-7.41 (1 H, m), 6.37 (1 H, s), 4.49-4.36 (2 H, m), 4.21 (2 H, s), 4.04-3.94 (1 H, m), 3.90-3.610 (5 H, m), 3.53-3.44 (1 H, m), 3.25 (1 H, s), 3.00 (2 H, s) |
| 106 | ($^1$H, CDCl$_3$) δ ppm 9.18 (1 H, s), 8.88 (2 H, s), 7.72 (1 H, d), 7.60-7.53 (1 H, m), 7.51 (1 H, d), 6.40 (1 H, s), 4.49-4.36 (2 H, m), 4.23 (2 H, t), 4.02-3.95 (1 H, m), 3.89-3.58 (5 H, m), 3.49 (1 H, dd), 3.04 (2 H, t) |
| 107 | ($^1$H, CDCl$_3$) δ ppm: 7.54 (1 H, d), 7.37 (1 H, dd), 7.32 (1 H, s), 7.26-7.22 (2 H, m), 6.81 (1 H, t), 6.75 (2 H, dd), 6.35 (1 H, s), 4.46-4.36 (2 H, m), 4.20-4.17 (4 H, m), 4.00-3.91 (1 H, m), 3.88-3.63 (5 H, m), 3.49 (1 H, t), 2.97 (2 H, t) |
| 108 | ($^1$H, CDCl$_3$) δ ppm 8.36 (1 H, d), 7.89-7.65 (3 H, m), 7.62-7.55 (3 H, m), 6.44 (1 H, s), 4.51-4.38 (2 H, m), 4.26 (2 H, t), 4.00 (1 H, m), 3.91-3.62 (5 H, m), 3.50 (1 H, dd), 3.22-3.14 (1 H, m), 3.09 (2 H, t), 1.40 (1 H, t) |
| 110 | ($^1$H, CDCl$_3$) δ ppm 7.70-7.60 (1 H, d), 7.50-7.42 (1 H, m), 7.39 (1 H, s), 6.37 (1 H, s), 4.50-4.35 (2 H, m), 4.25-4.15 (2 H, m), 4.05-3.95 (2 H, m), 3.92-3.60 (5 H, m), 3.56-3.45 (4 H, m), 3.05-3.95 (2 H, m), 2.15-1.95 (1 H, m), 1.15-1 (6 H, t) |
| 111 | ($^1$H, CDCl$_3$) δ ppm 7.58 (1 H, d), 7.33 (1 H, d), 7.27 (1 H, s), 6.32 (1 H, s), 4.45-4.34 (2 H, m), 4.17 (2 H, t), 3.96 (1 H, qd), 3.86-3.60 (5 H, m), 3.46 (1 H, dd), 2.94 (2 H, t), 1.46 (1 H, tt), 0.94-0.86 (2 H, m), 0.86-0.79 (2 H, m) |
| 112 | ($^1$H, CDCl$_3$) δ ppm 7.61 (1 H, d), 7.22 (1 H, d), 7.14 (1 H, s), 6.34 (1 H, s), 4.48-4.34 (2 H, m), 4.19 (2 H, t), 4.02-3.93 (1 H, m), 3.89-3.60 (5 H, m), 3.48 (1 H, t), 3.43-3.35 (1 H, m), 2.98 (2 H, t), 2.95-2.85 (1 H, m), 2.76-2.64 (1 H, m), 1.84-1.62 (3 H, m), 0.92 (6 H, dd) |
| 113 | ($^1$H, CDCl$_3$) δ ppm 7.67 (1 H, d), 7.44 (1 H, d), 7.39 (1 H, s), 6.38 (1 H, s), 5.00 (2 H, s), 4.50-4.36 (2 H, m), 4.21 (2 H, t), 4.03-3.95 (1 H, m), 3.91-3.61 (5 H, m), 3.49 (1 H, dd), 3.01 (2 H, t) |
| 114 | ($^1$H, CDCl$_3$) δ ppm 7.64-7.58 (1 H, m), 7.24-7.19 (1 H, m), 7.13 (1 H, s), 6.35 (1 H, s), 4.49-4.36 (2 H, m), 4.25-4.17 (2 H, m), 4.03-3.95 (1 H, m), 3.90-3.61 (5 H, m), 3.54-3.45 (1 H, m), 3.02-2.95 (2 H, m), 2.81-2.72 (2 H, m), 1.59-1.49 (2 H, m), 0.77-0.64 (1 H, m), 0.49-0.42 (2 H, m), 0.10-0.02 (2 H, m) |
| 115 | ($^1$H, CDCl$_3$) δ ppm 7.66 (1 H, d), 7.33 (1 H, d), 7.29 (1 H, s), 6.36 (1 H, s), 4.50 (2 H, s), 4.47-4.35 (2 H, m), 4.19 (2 H, t), 4.07-3.93 (2 H, m), 3.90-3.60 (5 H, m), 3.48 (1 H, t), 3.00 (2 H, t), 1.82-1.70 (6 H, m), 1.62-1.50 (2 H, m) |
| 117 | ($^1$H, CDCl$_3$) δ ppm 7.64 (1 H, d), 6.91 (1 H, dd), 6.80 (1 H, s), 6.28 (1 H, s), 6.11-6.01 (1 H, m), 5.45 (1 H, dd), 5.34 (1 H, dd), 4.61 (2 H, dd), 4.47-4.37 (2 H, m), 4.21 (2 H, t), 4.03-3.95 (1 H, m), 3.89-3.64 (5 H, m), 3.49 (1 H, t), 2.98 (2 H, t) |
| 118 | ($^1$H, CDCl$_3$) δ ppm 7.63 (1 H, d), 6.91 (1 H, dd), 6.80 (1 H, d), 6.28 (1 H, s), 6.11-6.01 (1 H, m), 5.44 (1 H, m), 5.34 (1 H, dd), 4.61 (2 H, dt), 4.47-4.37 (2 H, m), 4.21 (2 H, t), 4.03-3.95 (1 H, m), 3.89-3.63 (5 H, m), 3.49 (1 H, dd), 2.98 (2 H, t) |
| 119 | ($^1$H, CDCl$_3$) δ ppm 7.68 (1 H, d), 7.36 (1 H, d), 7.31 (1 H, s), 6.41-6.38 (1 H, m), 4.61 (2 H, s), 4.47-4.37 (2 H, m), 4.25-4.17 (2 H, m), 3.99 (3 H, dt), 3.89-3.60 (6 H, m), 3.53-3.43 (3 H, m), 3.02 (2 H, t), 2.01-1.94 (2 H, m), 1.74-1.64 (2 H, m) |
| 120 | ($^1$H, CDCl$_3$) δ ppm 8.62 (1 H, br. s.), 8.53 (1 H, br. s.), 7.73 (1 H, d), 7.64 (1 H, d), 7.41 (1 H, dd), 7.35 (1 H, s), 7.29 (1 H, s), 6.36 (1 H, s), 4.48-4.34 (2 H, m), 4.20 (2 H, t), 4.03-3.93 (3 H, m), 3.89-3.61 (7 H, m), 3.48 (1 H, dd), 2.99 (2 H, t) |
| 121 | ($^1$H, CDCl$_3$) δ ppm 7.60 (1 H, d), 7.19 (1 H, dd), 7.10 (1 H, s), 6.34 (1 H, s), 4.49-4.34 (2 H, m), 4.20 (2 H, t), 4.02-3.93 (1 H, m), 3.90-3.60 (5 H, m), 3.48 (1 H, dd), 2.98 (2 H, t), 2.64 (2 H, t), 1.63 (2 H, m), 1.37-1.29 (4 H, m), 0.94-0.86 (3 H, m) |
| 122 | ($^1$H, CDCl$_3$) δ ppm 7.63 (1 H, d), 7.39 (1 H, dd), 7.31 (1 H, s), 6.36 (1 H, s), 4.50-4.39 (2 H, m), 4.20 (2 H, t), 4.02-3.98 (1 H, m), 3.89-3.66 (5 H, m), 3.49 (1 H, t), 2.96 (2 H, t), 1.59-1.48 (1 H, m), 0.98-0.81 (4 H, m) |
| 123 | ($^1$H, CDCl$_3$) δ ppm 7.64-7.58 (1 H, m), 7.24-7.19 (1 H, m), 7.13 (1 H, s), 6.35 (1 H, s), 4.49-4.36 (2 H, m), 4.24-4.17 (2 H, m), 4.03-3.95 (1 H, m), 3.91-3.62 (5 H, m), 3.49 (1 H, dd), 3.03-2.95 (2 H, m), 2.81-2.73 (2 H, m), 1.59-1.50 (2 H, m), 0.71 (1 H, s), 0.49-0.42 (2 H, m), 0.09-0.03 (2 H, m) |
| 124 | ($^1$H, CDCl$_3$) δ ppm 7.69 (1 H, d), 7.35 (1 H, d), 7.30 (1 H, s), 6.38 (1 H, s), 4.82-4.75 (2 H, m), 4.72-4.64 (3 H, m), 4.49 (2 H, s), 4.48-4.37 (2 H, m), 4.21 (2 H, dd), 4.03-3.95 (1 H, m), 3.90-3.62 (5 H, m), 3.49 (1 H, dd), 3.02 (2 H, t) |
| 125 | ($^1$H, CDCl$_3$) δ ppm 7.69 (1 H, d), 7.35 (1 H, d), 7.29 (1 H, s), 6.38 (1 H, s), 4.62 (2 H, s), 4.54 (2 H, d), 4.48-4.36 (4 H, m), 4.21 (2 H, t), 3.99 (1 H, ddt), 3.90-3.61 (5 H, m), 3.58 (2 H, s), 3.49 (1 H, dd), 3.02 (2 H, t), 1.36 (3 H, s) |
| 126 | ($^1$H, CDCl$_3$) δ ppm 7.50 (1 H, d), 6.63 (1 H, dd), 6.48 (1 H, s), 6.21 (1 H, s), 4.47-4.34 (2 H, m), 4.21-4.14 (2 H, m), 4.01-3.91 (1 H, m), 3.89-3.60 (5 H, m), 3.48 (1 H, dd), 2.98 (2 H, s), 2.90 (2 H, t), 1.36 (2 H, dd), 0.96 (6 H, dd), 0.87 (3 H, t) |
| 127 | ($^1$H, CDCl$_3$) δ ppm 7.61 (1 H, d), 7.22 (1 H, d), 7.14 (1 H, s), 6.34 (1 H, d), 4.46-4.34 (2 H, m), 4.19 (2 H, t), 3.97 (1 H, td), 3.89-3.60 (5 H, m), 3.48 (1 H, t), 3.42-3.35 (1 H, m), 2.97 (2 H, t), 2.93-2.85 (2 H, m), 2.70 (1 H, m), 1.84-1.63 (3 H, m), 0.92 (6 H, dd) |

TABLE III-continued

NMR Data of the Compounds of the Invention

| Cpd# | NMR data (δ) |
|---|---|
| 128 | (¹H, CDCl₃) δ ppm 7.51 (1 H, d), 6.63 (1 H, d), 6.49 (1 H, br. s.), 6.21 (1 H, s), 4.46-4.356 (2 H, m), 4.21-4.11 (2 H, m), 3.97 (1 H, ddt), 3.88-3.62 (5 H, m), 3.48 (1 H, dd), 3.10 (2 H, d), 2.91 (2 H, t), 1.61 (1 H, m), 1.47-1.26 (8 H, m), 0.97-0.88 (6 H, m) |
| 129 | (¹H, CDCl₃) δ ppm 7.63 (1 H, d), 6.93 (1 H, dd), 6.82 (1 H, d), 6.29 (1 H, s), 5.30 (1 H, s), 4.47-4.36 (2 H, m), 4.22-4.14 (4 H, m), 4.03-3.94 (1 H, m), 3.88-3.628 (7 H, m), 3.53-3.453 (4 H, m), 2.97 (2 H, t) |
| 130 | (¹H, CDCl₃) δ ppm 7.64-7.58 (1 H, m), 6.90 (1 H, dd), 6.80 (1 H, d), 6.29-6.24 (1 H, m), 4.46-4.32 (2 H, m), 4.22-4.12 (4 H, m), 4.01-3.90 (1 H, m), 3.88-3.54 (9 H, m), 3.46 (1 H, dd), 2.95 (2 H, s), 1.23 (3 H, t) |
| 131 | (¹H, CDCl₃) δ ppm 7.60-7.67 (1 H, m), 6.93-6.86 (1 H, m), 6.78 (1 H, d), 6.29 (1 H, s), 4.50-4.36 (2 H, m), 4.25-4.17 (2 H, m), 4.04-3.94 (1 H, m), 3.91-3.61 (7 H, m), 3.53-3.44 (1 H, m), 3.01-2.93 (2 H, m), 1.37-1.227 (1 H, m), 0.73-0.65 (2 H, m), 0.42-0.34 (2 H, m) |
| 132 | (¹H, CDCl₃) δ ppm 7.64 (1 H, d), 6.93 (1 H, s), 6.82 (1 H, d), 6.27 (1 H, s), 4.90-4.82 (1 H, m), 4.74-4.67 (1 H, m), 4.48-4.28 (3 H, m), 4.26-4.14 (3 H, m), 4.03-3.91 (1 H, m), 3.90-3.58 (5 H, m), 3.53-3.41 (1 H, m), 3.03-2.91 (2 H, m) |
| 133 | (¹H, CDCl₃) δ ppm 7.64 (1 H, s), 7.48-7.40 (1 H, m), 7.40-7.35 (1 H, m), 6.40-6.34 (1 H, m), 4.47 (4 H, s), 4.28-4.15 (1 H, m), 3.93-3.56 (10 H, m), 3.43 (5 H, s), 3.06-2.95 (2 H, m) |
| 134 | (¹H, CDCl₃) δ ppm 7.65 (1 H, d), 7.47-7.41 (1 H, m), 7.38 (1 H, s), 6.37 (1 H, s), 4.37-4.49 (4 H, m), 4.26-4.17 (2 H, m), 3.99 (1 H, m), 3.93-3.44 (12 H, m), 3.05-2.94 (2 H, m), 1.25 (3 H, t) |
| 135 | (¹H, CDCl₃) δ ppm 7.66 (1 H, d), 7.47-7.42 (1 H, m), 7.40 (1 H, s), 6.37 (1 H, s), 4.73-4.67 (1 H, m), 4.62-4.54 (1 H, m), 4.49 (4 H, s), 4.26-4.16 (2 H, m), 4.04-3.95 (1 H, m), 3.94-3.60 (7 H, m), 3.56-3.43 (1 H, m), 3.05-2.96 (2 H, m) |
| 136 | (¹H, CDCl₃) δ ppm 7.68 (1 H, d), 7.35 (1 H, d), 7.30 (1 H, s), 6.38 (1 H, s), 4.57 (2 H, s), 4.50-4.36 (2 H, m), 4.27-4.17 (2 H, m), 4.06-3.92 (1 H, m), 3.92-3.60 (5 H, m), 3.57-3.44 (1 H, m), 3.17 (2 H, s), 3.09-2.96 (2 H, m), 0.97 (9 H, s) |
| 137 | (¹H, CDCl₃) δ ppm 7.70-7.64 (1 H, m), 7.40-7.33 (1 H, m), 7.31 (1 H, s), 6.37 (1 H, s), 4.59 (2 H, s), 4.50-4.35 (2 H, m), 4.27-4.16 (2 H, m), 4.07-3.94 (1 H, m), 3.93-3.59 (5 H, m), 3.57-3.44 (1 H, m), 3.45-3.34 (1 H, m), 3.08-2.96 (2 H, m), 2.05-1.90 (2 H, m), 1.82-1.71 (2 H, m), 1.48-1.18 (6 H, m) |
| 138 | (¹H, CDCl₃) δ ppm 7.68 (1 H, d), 7.37 (1 H, d), 7.32 (1 H, s), 6.38 (1 H, s), 4.58 (2 H, s), 4.51-4.36 (2 H, m), 4.26-4.176 (2 H, m), 4.05-3.94 (1 H, m), 3.92-3.61 (5 H, m), 3.54-3.44 (1 H, m), 3.38 (2 H, d), 3.07-2.98 (2 H, m), 1.20-1.05 (1 H, m), 0.63-0.54 (2 H, m), 0.29-0.20 (2 H, m) |
| 139 | (¹H, CDCl₃) δ ppm 7.62 (1 H, s), 6.91 (1 H, m), 6.81 (1 H, m), 6.27 (1 H, s), 4.41 (2 H, s), 4.25-4.21 (2 H, m), 4.10-3.41 (12 H, m), 2.96 (2 H, t), 2.01-1.84 (1 H, m), 1.76-1.36 (5 H, m) |
| 140 | (¹H, DMSO-d₆) δ ppm 7.91 (1 H, d), 7.28-7.18 (2 H, m), 6.60 (1 H, s), 4.32-4.17 (2 H, m), 4.07-3.96 (2 H, m), 3.92-3.71 (3 H, m), 3.70-3.43 (4 H, m), 3.38 (2 H, m), 3.03-2.91 (2 H, m), 2.78-2.58 (2 H, m), 1.68-1.58 (2 H, m), 1.08 (3 H, d) |
| 141 | (¹H, CDCl₃) δ ppm 7.70-7.58 (1 H, d), 6.95-6.82 (1 H, d), 6.77 (1 H, s), 6.27 (1 H, s), 4.50-4.32 (2 H, m), 4.38-4.15 (2 H, m), 4.05-3.92 (3 H, m), 3.92-3.60 (5 H, m), 3.55-3.42 (1 H, t), 3.05-2.92 (2 H, m), 1.85-1.70 (2 H, m), 1.40-1.30 (2 H, m), 0.92 (9 H, s) |
| 142 | (¹H, CDCl₃) δ ppm 7.61 (1 H, d), 7.21 (1 H, d), 7.13 (1 H, s) 6.35 (1 H, s), 4.46-4.40 (2 H, m), 4.20 (2 H, t), 3.99-3.97 (1 H, m), 3.87-3.65 (5 H, m), 3.49 (1 H, t), 3.39 (3 H, s), 3.00-2.93 (3 H, m), 2.83-2.82 (1 H, m), 2.66-2.64 (1 H, m), 1.95-1.91 (1 H, m), 1.75-1.73 (2 H, m), 0.90 (6 H, t) |
| 143 | (¹H, CDCl₃) δ ppm 7.66-7.60 (1 H, m), 6.91-6.86 (1 H, m), 6.80-6.76 (1 H, m), 6.28 (1 H, s), 4.48-4.35 (2 H, m), 4.24-4.17 (2 H, m), 4.11-4.04 (2 H, m), 4.02-3.95 (1 H, m), 3.91-3.61 (5 H, m), 3.54-3.45 (1 H, m), 3.03-2.94 (2 H, m), 1.98-1.88 (2 H, m), 1.45-1.36 (2 H, m), 0.78-0.66 (1 H, m), 0.50-0.43 (2 H, m), 0.09-0.03 (2 H, m) |
| 145 | (¹H, CDCl₃) δ ppm 7.47 (1 H, d), 6.55-6.48 (1 H, m), 6.40-6.34 (1 H, m), 6.18 (1 H, s), 4.47-4.33 (2 H, m), 4.22-4.12 (2 H, m), 4.02-3.92 (1 H, m), 3.83 (5 H, dd), 3.53-3.43 (1 H, m), 3.40-3.28 (1 H, m), 2.89 (2 H, t), 2.13-1.98 (2 H, m), 1.86-1.73 (2 H, m), 1.73-1.63 (1 H, m), 1.50-1.11 (5 H, m) |
| 146 | (¹H, DMSO-d₆) δ ppm 7.95-7.87 (1 H, m), 7.29-7.19 (2 H, m), 6.60 (1 H, s), 4.54-4.44 (1 H, m), 4.29-4.17 (2 H, m), 4.07-3.97 (2 H, m), 3.91-3.72 (3 H, m), 3.70-3.54 (2 H, m), 3.54-3.43 (1 H, m), 3.43-3.34 (1 H, m), 3.06-2.81 (4 H, m), 2.63-2.52 (1 H, m), 1.81-1.64 (1 H, m), 1.52-1.36 (1 H, m), 0.81 (9 H, s) |
| 147 | (¹H, CDCl₃) δ ppm 7.68 (1 H, d), 7.38-7.32 (1 H, m), 7.30 (1 H, s), 6.38 (1 H, s), 4.56 (2 H, s), 4.50-4.36 (2 H, m), 4.26-4.18 (2 H, m), 4.04-3.94 (1 H, m), 3.94-3.5994 (4 H, m), 3.55-3.44 (1 H, m), 3.40 (2 H, d), 3.07-2.98 (2 H, m), 2.30-2.16 (1 H, m), 1.86-1.72 (2 H, m), 1.66-1.51 (5 H, m), 1.35-1.20 (2 H, m) |
| 148 | (¹H, CDCl₃) δ ppm 7.61 (1 H, d), 7.18 (1 H, dd), 7.12 (1 H, s), 6.35 (1 H, s), 4.46-4.36 (2 H, m), 4.21 (2 H, t), 4.00-3.97 (1 H, m), 3.88-3.64 (5 H, m), 3.49 (1 H, t), 3.34-3.30 (4 H, m), 2.98 (2 H, t), 2.81-2.60 (2 H, m), 1.89-1.676 (2 H, m), 1.18 (3 H, d) |
| 149 | (¹H, CDCl₃) δ ppm: 7.62 (1 H, d), 7.23-7.13 (4 H, m), 6.71 (1 H, t), 6.58 (2 H, d), 6.12 (1 H, s), 4.47-4.37 (2 H, m), 4.21 (2 H, t), 4.08-3.98 (1 H, m), |

TABLE III-continued

NMR Data of the Compounds of the Invention

| Cpd# | NMR data (δ) |
|---|---|
| | 3.88-3.63 (6 H, m), 3.49 (1 H, t), 3.17 (2 H, t), 2.98 (2 H, t), 2.79 (2 H, t), 2.01-1.94 (2 H, m) |
| 150 | ($^1$H, CDCl$_3$) δ ppm 7.61 (1 H, d), 7.20 (1 H, d), 7.12 (1 H, s), 6.35 (1 H, s), 4.47-4.37 (2 H, m), 4.21 (2 H, t), 4.01-3.97 (1 H, m), 3.88-3.63 (6 H, m), 3.49 (1 H, t), 2.98 (2 H, t), 2.69 (2 H, t), 1.89-1.62 (2 H, m), 1.52-1.45 (2 H, m), 1.31-1.30 (1 H, m), 1.20 (3 H, d) |
| 151 | ($^1$H, CDCl$_3$) δ ppm 7.61 (1 H, d), 7.20 (1 H, d), 7.12 (1 H, s), 6.35 (1 H, s), 4.47-4.37 (2 H, m), 4.21 (2 H, t), 4.01-3.97 (1 H, m), 3.88-3.63 (7 H, m), 3.49 (1 H, t), 2.98 (2 H, t), 2.70 (2 H, t), 1.76-1.60 (4 H, m), 1.31-1.26 (1 H, m) |
| 152 | ($^1$H, CDCl$_3$) δ ppm 7.57-7.50 (1 H, m), 6.71 (1 H, d), 6.53 (1 H, br. s.), 6.21 (1 H, s), 4.513-4.33 (2 H, m), 4.26-4.14 (2 H, m), 4.06-3.93 (1 H, m), 3.92-3.56 (6 H, m), 3.56-3.41 (1 H, m), 3.00-2.90 (2 H, m), 2.88 (3 H, s), 2.04-1.63 (2 H, m), 1.60-1.31 (5 H, m), 1.28-1.08 (1 H, m) |
| 153 | ($^1$H, CDCl$_3$) δ ppm 7.52-7.46 (1 H, m), 6.55-6.50 (1 H, m), 6.40-6.36 (1 H, m), 6.19 (1 H, s), 4.48-4.33 (2 H, m), 4.23-4.13 (2 H, m), 4.04-3.92 (1 H, m), 3.85 (5 H, d), 3.56-3.42 (1 H, m), 3.06-2.99 (2 H, m), 2.93-2.84 (2 H, m), 1.92-1.50 (6 H, m), 1.36-1.12 (3 H, m), 1.08-0.91 (2 H, m) |
| 154 | ($^1$H, CDCl$_3$) δ ppm 7.50 (1 H, d), 6.59-6.49 (1 H, m), 6.44-6.35 (1 H, m), 6.20 (1 H, s), 4.49-4.33 (2 H, m), 4.24-4.13 (2 H, m), 4.05-3.93 (3 H, m), 3.92-3.59 (5 H, m), 3.56-3.32 (3 H, m), 3.16-3.07 (2 H, m), 2.96-2.84 (2 H, m), 1.98-1.80 (1 H, m), 1.79-1.64 (2 H, m), 1.428-1.28 (2 H, m) |
| 155 | ($^1$H, CDCl$_3$) δ ppm 7.54-7.46 (1 H, m), 7.14-7.08 (1 H, m), 7.04 (1 H, s), 6.23 (1 H, s), 4.35-4.21 (2 H, m), 4.13-3.99 (2 H, m), 3.91-3.80 (1 H, m), 3.79-3.45 (5 H, m), 3.41-3.30 (1 H, m), 2.86 (2 H, t), 2.64-2.54 (2 H, m), 1.67-1.58 (2 H, m), 1.45 (4 H, d), 0.80 (6 H, m) |
| 156 | ($^1$H, CDCl$_3$) δ ppm 7.60 (1 H, d), 7.23-7.19 (1 H, m), 7.13 (1 H, s), 6.34 (1 H, s), 4.45-4.35 (2 H, m), 4.18 (2 H, t), 4.02-3.92 (1 H, m), 3.82 (5 H, m), 3.48 (1 H, dd), 2.97 (2 H, br. t), 2.79-2.70 (2 H, m), 1.82-1.74 (2 H, m), 1.30 (6 H, s) |
| 157 | ($^1$H, CDCl$_3$) δ ppm 7.64-7.59 (1 H, m), 7.25-7.20 (1 H, m), 7.14 (1 H, s), 6.35 (1 H, s), 4.48-4.35 (2 H, m), 4.24-4.16 (2 H, m), 4.02-3.94 (1 H, m), 3.90-3.44 (7 H, m), 3.02-2.95 (2 H, m), 2.92-2.81 (1 H, m), 2.78-2.67 (1 H, m), 1.87-1.68 (2 H, m), 1.62-1.42 (2 H, m), 0.96 (3 H, s) |
| 158 | ($^1$H, CDCl$_3$) δ ppm 7.70-7.56 (1 H, d), 6.95-6.85 (1 H, d), 6.80 (1 H, s), 6.28 (1 H, s), 4.50-4.35 (2 H, m), 4.25-4.10 (2 H, m), 4.05-3.92 (1 H, m), 3.10-3.57 (8 H, m), 3.55-3.40 (1 H, m), 3.05-2.90 (2 H, m), 1.05 (9H, s) |
| 159 | ($^1$H, CDCl$_3$) δ ppm 7.63 (1 H, d), 6.88 (1 H, dd), 6.77 (1H, d), 6.28 (1 H, s), 4.46-4.36 (2 H, m), 4.20 (2 H, t), 4.05-3.96 (3 H, m), 3.88-3.65 (7 H, m), 3.51-3.43 (3 H, m), 2.97 (2 H, t), 2.12-2.01 (1 H, m), 1.78-1.75 (2 H, m), 1.59-1.42 (2 H, m) |
| 160 | ($^1$H, CDCl$_3$) δ ppm 7.63 (1 H, d), 7.35-7.18 (1 H, m), 7.12 (1H, s), 6.36 (1 H, s), 4.50-4.35 (2 H, m), 4.28-4.15 (2 H, m), 4.05-3.95 (1 H, m), 3.95-3.60 (5 H, m), 3.55-3.42 (1 H, m), 3.05-2.90 (2 H, m), 2.75-2.60 (2 H, m), 1.80-1.65 (2 H, m), 1.55-1.48 (2 H, m), 1.22 (6 H, s) |
| 161 | ($^1$H, CDCl$_3$) δ ppm 7.68 (1 H, d), 7.34 (1 H, d), 7.29 (1 H, s), 6.38 (1 H, s), 4.55 (2 H, s), 4.48-4.38 (2 H, m), 4.22 (2 H, t), 4.02-3.96 (3 H, m), 3.91-3.61 (5 H, m), 3.55-3.35 (5 H, m), 3.02 (2 H, t), 2.00-1.86 (1 H, m), 1.69 (2 H, dd), 1.38 (2 H, dd) |
| 162 | ($^1$H, CDCl$_3$) δ ppm 7.68-7.62 (1 H, m), 6.95-6.87 (1 H, m), 6.82-6.77 (1 H, m), 6.29 (1 H, s), 4.51-4.35 (2 H, m), 4.26-4.17 (2 H, m), 4.05-3.92 (1 H, m), 3.91-3.60 (8 H, m), 3.55-3.44 (1 H, m), 3.04-2.94 (2 H, m) |
| 163 | ($^1$H, CDCl$_3$) δ ppm 7.64 (1 H, d), 6.91 (1 H, dd), 6.81 (1 H, d), 6.29 (1H, s), 4.91 (2 H, t), 4.56 (2 H, t), 4.47-4.36 (2 H, m), 4.26 (2H, d), 4.21 (2 H, t), 4.00-3.96 (1 H, m), 3.88-3.63 (5 H, m), 3.51-3.45 (2 H, m), 2.98 (2H, t) |
| 164 | ($^1$H, DMSO-d$_6$) δ ppm 7.93 (1 H, d), 6.97-6.92 (1 H, m), 6.53 (1 H, s), 4.24-4.23 (2H, m), 4.08 (2 H, t), 4.00 (2 H, t), 3.98-3.74 (3 H, m), 3.68-3.57 (2 H, m), 3.51-3.48 (1 H, m), 3.37 (1 H, t), 2.96 (2 H, t), 1.84-1.80 (2 H, m), 1.36-1.30 (2 H, m), 0.81-0.63 (1 H, m), 0.42-0.39 (2 H, m), 0.04-0.02 (2 H, m) |
| 165 | ($^1$H, CDCl$_3$) δ ppm 7.65 (1 H, d), 7.24 (1H, dd), 7.16 (1H, s), 6.38 (1 H, s), 4.49-4.40 (2 H, m), 4.24 (2 H, t), 4.02-4.00 (1 H, m), 3.89-3.66 (5 H, m), 3.52 (3 H, m), 3.43 (2 H, t), 3.38 (3 H, s), 3.02 (2H, t), 2.78 (2 H, t), 1.96-1.92 (2 H, m) |
| 166 | ($^1$H, CDCl$_3$) δ ppm 7.61 (1 H, d), 7.23 (1H, dd), 7.15 (1H, s), 6.35 (1 H, s), 4.46-4.36 (2 H, m), 4.20 (2 H, t), 4.01-3.95 (1 H, m), 3.88-3.62 (5 H, m), 3.49 (1 H, t), 2.98 (2 H, t), 2.85-2.81 (2 H, m), 2.13 (1H, br s), 1.93-1.79 (4 H, m), 1.72-1.55 (6 H, m) |
| 167 | ($^1$H, CDCl$_3$) δ ppm 7.59 (1 H, d), 7.37 (1H, dd), 7.15 (1H, s), 6.34 (1 H, s), 4.44-4.35 (2 H, m), 4.17 (2 H, t), 4.01-3.92 (3 H, m), 3.88-3.60 (7 H, m), 3.47 (1 H, t), 2.94 (2 H, t), 2.07-2.02 (2 H, m), 1.95-1.88 (2H, m) |
| 168 | ($^1$H, CDCl$_3$) δ ppm 7.66 (1 H, d), 7.23 (1H, dd), 7.17 (1H, s), 6.39 (1 H, s), 4.51-4.40 (2 H, m), 4.24 (2 H, t), 4.09-3.96 (1 H, m), 3.93-3.65 (5 H, m), 3.57-3.49 (1H, m), 3.44 (2 H, t), 3.40 (3H, s), 3.02 (2 H, t), 2.79 (2 H, t), 2.00-1.89 (2H, m) |
| 169 | ($^1$H, CDCl$_3$) δ ppm 7.55 (1 H, d), 7.16 (1H, dd), 7.08 (1H, s), 6.29 (1 H, s), 4.41-4.29 (2 H, m), 4.13 (2 H, t), 3.95-3.86 (1 H, m), 3.81-3.54 (5 H, m), 3.46-3.38 (1H, m), 2.91 (2 H, t), 2.78-2.72 (2H, m), 1.87-1.75 (4 H, m), 1.72-1.53 (6 H, m) |
| 170 | ($^1$H, CDCl$_3$) δ ppm 7.66 (1 H, d), 6.95 (1H, dd), 6.84 (1H, s), 6.31 (1 H, s), 4.50-4.39 (2 H, m), 4.25-4.21 (4 H, m), 4.05-3.98 (1 H, m), 3.91-3.65 (7 H, m), 3.55-3.49 (3H, m), 3.00 (2 H, t), 1.71-1.62 (2 H, m), 0.96 (3 H, t) |

TABLE III-continued

NMR Data of the Compounds of the Invention

| Cpd# | NMR data (δ) |
|---|---|
| 171 | ($^1$H, CDCl$_3$) δ ppm 7.65 (1 H, d), 6.94 (1H, dd), 6.83 (1H, s), 6.31 (1 H, s), 4.50-4.39 (2 H, m), 4.25-4.18 (4 H, m), 4.04-3.97 (1 H, m), 3.91-3.65 (8 H, m), 3.51 (1H, t), 3.00 (2 H, t), 1.23 (6 H, d) |
| 172 | ($^1$H, CDCl$_3$) δ ppm 7.67 (1 H, d), 6.95 (1H, dd), 6.85 (1H, s), 6.31 (1 H, s), 4.50-4.40 (2 H, m), 4.25-4.21 (4 H, m), 4.05-3.98 (1 H, m), 3.91-3.65 (7 H, m), 3.55-3.49 (3H, m), 3.00 (2 H, t), 1.72-1.62 (2 H, m), 0.97 (3 H, t) |
| 173 | ($^1$H, CDCl$_3$) δ ppm 7.65 (1 H, d), 6.94 (1H, dd), 6.84 (1H, s), 6.31 (1 H, s), 4.50-4.40 (2 H, m), 4.26-4.19 (4 H, m), 4.04-3.97 (1 H, m), 3.92-3.65 (8 H, m), 3.52 (1H, t), 3.00 (2 H, t), 1.23 (6 H, d) |
| 174 | ($^1$H, CDCl$_3$) δ ppm 7.64 (1 H, d), 7.22 (1H, dd), 7.15 (1H, s), 6.38 (1 H, s), 4.51-4.41 (2 H, m), 4.23 (2 H, t), 4.06-4.00 (1 H, m), 3.92-3.66 (5 H, m), 3.57-3.50 (1H, m), 3.43 (2 H, t), 3.37 (3H, s), 3.01 (2 H, t), 2.71 (2 H, t), 1.80-1.61 (2H, m), 1.69-1.62 (2H, m) |

Biological Examples

1. In Vitro Assays

1.1. Cell Based Assay: GTp-γS Binding Assay.

The following assay can be used for determination of GPR84 activation. The [$^{35}$S]GTPγS binding assay measures the level of G protein activation following agonist occupation of a GPCR, by determining the binding of the non-hydrolysable analog [$^{35}$S]GTPγS to Gα subunits.

The assay is performed in a 96 well plate where the following reagents are added. First 50 μL compound is added into the assay plate, followed by addition of 20 μL 3,3' di indolylmethane at EC$_{80}$ concentration (concentration which gives 80% of the activity of GPR84). In a last step, 30 μL of a mixture consisting of membranes-GTPγS-SpA beads is added [mixture consists of 20 μg/well membranes derived from stable cell line over expressing GPR84 (membranes are pre-incubated with 0.1 μM GDP for 15 min at 4° C.), 0.1 nM [$^{35}$S]GTPγS (Perkin Elmer, NEG030) and 0.5 mg/well PVT-WGA SpA beads (Perkin Elmer, RPNQ0001)]. All components are diluted in assay buffer containing 20 mM HEPES pH 7.4; 5 mM MgCl$_2$; 250 mM NaCl; 0.05% BSA; 75 ug/mL saponin. Reactions are incubated for 90 min at room temperature followed by centrifugation at 2000 rpm during 15 min. Plates are read on a Topcount reader (Perkin Elmer) immediately after centrifugation (readout time, 1 min/well).

TABLE IV

GPR84 assay GTPγS IC$_{50}$ (nM) of selected Compounds of the invention.

| Cpd# | GPR84 |
|---|---|
| 1 | *** |
| 3 | ** |
| 4 | *** |
| 5 | ** |
| 6 | *** |
| 7 | *** |
| 8 | *** |
| 9 | **** |
| 16 | *** |
| 20 | **** |
| 28 | ** |
| 30 | **** |
| 36 | **** |
| 41 | *** |
| 42 | *** |
| 43 | *** |
| 45 | ** |
| 50 | *** |
| 51 | *** |
| 52 | **** |
| 53 | *** |
| 54 | *** |
| 55 | * |
| 56 | *** |
| 57 | *** |
| 58 | *** |
| 59 | ** |
| 60 | **** |
| 61 | **** |
| 62 | **** |
| 63 | *** |
| 64 | *** |
| 65 | ** |
| 66 | *** |
| 67 | **** |
| 68 | **** |
| 69 | **** |
| 70 | **** |
| 72 | **** |
| 74 | **** |
| 75 | **** |
| 76 | **** |
| 77 | **** |
| 78 | **** |
| 79 | *** |
| 80 | **** |
| 81 | **** |
| 82 | **** |
| 83 | **** |
| 84 | **** |
| 85 | **** |
| 86 | **** |
| 87 | *** |
| 89 | *** |
| 90 | **** |
| 91 | *** |
| 93 | **** |
| 94 | **** |
| 95 | ** |
| 96 | *** |
| 97 | *** |
| 98 | **** |
| 101 | *** |
| 102 | *** |
| 103 | *** |
| 104 | **** |
| 105 | *** |
| 106 | ** |
| 107 | **** |
| 108 | **** |
| 109 | **** |
| 110 | *** |
| 111 | *** |

TABLE IV-continued

GPR84 assay GTPγS IC$_{50}$ (nM) of selected Compounds of the invention.

| Cpd# | GPR84 |
|---|---|
| 112 | **** |
| 113 | *** |
| 114 | **** |
| 115 | **** |
| 116 | *** |
| 117 | *** |
| 118 | *** |
| 119 | *** |
| 120 | *** |
| 121 | **** |
| 122 | **** |
| 123 | **** |
| 124 | *** |
| 125 | ** |
| 126 | **** |
| 127 | **** |
| 128 | *** |
| 129 | *** |
| 130 | *** |
| 131 | **** |
| 132 | ** |
| 133 | *** |
| 134 | *** |
| 135 | *** |
| 136 | **** |
| 137 | **** |
| 138 | **** |
| 139 | **** |
| 140 | *** |
| 141 | *** |
| 142 | **** |
| 145 | *** |
| 146 | **** |
| 147 | **** |
| 148 | **** |
| 149 | **** |
| 150 | *** |
| 151 | *** |
| 152 | ** |
| 153 | *** |
| 154 | ** |
| 155 | **** |
| 156 | *** |
| 157 | *** |
| 158 | *** |
| 159 | **** |
| 160 | *** |
| 161 | *** |
| 162 | *** |
| 163 | **** |
| 164 | **** |
| 165 | **** |
| 166 | **** |
| 167 | ** |
| 168 | *** |
| 169 | *** |
| 170 | **** |
| 171 | **** |
| 172 | *** |
| 173 | ** |
| 174 | **** | na: not active
* >1001 nM
** 501-1000 nM
*** 101-500 nM
**** 0.01-100 nM

2. Cellular Assays 2.1. Human Neutrophil Migration Assay

We have established that GPR84 agonists (MCFA such as sodiumdecanoate, 3,3' di indolylmethane and Embelin induce neutrophil chemo taxis and that GPR84 antagonists could block GPR84 agonist-induced chemo taxis but not IL8-induced chemotaxis, indicating that G Protein-Coupled Receptor 84 (GPR84) is an essential player in the process of neutrophil recruitment.

The effect of agonists or antagonists for GPR84 can therefore be assayed in a neutrophil migration test. In the neutrophil migration assay, neutrophils, freshly isolated from buffy coats from human volunteers, are treated with a compound for 30 minutes. Subsequently, the neutrophils are transferred to the upper wells of a Corning HTS transwell 96 permeable support system, of which the lower wells are filled with a embelin solution at EC$_{80}$ (concentration which gives 80% of the activity of GPR84). After 1 h of incubation, migration of the neutrophils towards embelin in the lower compartment can be quantified by measuring the ATP-content of the lower wells using the ATPlite luminescence ATP detection assay system (Perkin Elmer, Cat. No.: 436110).

2.1.1 Isolation of Neutrophils from Human Buffy Coat

A human buffy coat is diluted with an equal volume of ice cold DPBS. 20 mL of the diluted buffy coat is gently mixed with 4 mL of ACD buffer (140 mM citric acid, 200 mM sodium citrate and 220 mM dextrose). Then, 12 mL of the 6% dextran/0.9% NaCl solution (15 g dextran T2000 and 2.25 g NaCl dissolved in 250 mL H$_2$O) is added to the mixture and the samples are inverted gently up to 20 times. The total volume was transferred to a new recipient and incubated at room temperature for 1 h for complete separation of the two phases to occur. The yellowish supernatant is then transferred to a clean centrifugation tube and centrifuged for 12 minutes at 1300 rpm and 4° C. After centrifugation, the supernatant is discarded and the remaining cell pellet is rapidly resuspended in 12 mL of ice-cold H$_2$O for red blood cell lysis to occur. After 20 seconds, 4 mL of ice-cold 0.6 M KCl is added. Samples are mixed carefully and centrifuged for 6 minutes at 1300 rpm, 4° C. The supernatant is discarded and the red blood cell lysis procedure is repeated one more time. Subsequently, the cell pellet is resuspended in 4 mL of DPBS and layered over 5 mL of Lymphoprep (Nycomed Pharma, Cat. No.: 1114545) in a 15 mL centrifuge tube. After centrifugation for 12 min at 1300 rpm, 4° C., the supernatant is removed and the cell pellet, containing the neutrophils, is resuspended in 25 mL chemotaxis buffer (RPMI 1640 medium, supplemented with 10 mM HEPES; freshly made for each experiment)

2.1.2 Migration Assay

A cell suspension of 8.9×10$^6$ cells per milliliter is prepared. 20 µL of compound solution in chemotaxis buffer is added to 180 µL cell suspension. The mixture is incubated at 37° C. for 30 minutes with intermediate resuspension of the cells after 15 minutes. Following this, 70 µL cell suspension is transferred to the upper compartment of a Corning HTS transwell 96 permeable support system with 5.0 µm pore size polycarbonate membrane (Corning, Cat. No.: 3387). The receiver well of the transwell system is then filled with 200 µL chemotaxis buffer containing compound and chemotactic agent (embelin). After incubation at 37° C. in 5% CO$_2$ for 1 h, the upper plate of the transwell system is removed and the cell suspension in the receiver plate is transferred to a 96-well V-bottom plate. 50 µL of DPBS is added to the receiver plate to prevent remaining cells from drying out. The V-bottom plate is centrifuged for 6 minutes at 1500 rpm. The supernatant is removed and the cells are resuspended in 50 µL DPBS. The cells are then transferred back to the receiver plate of the transwell system. After this, 100 µL ATPlite solution (Perkin Elmer, Cat. No: 436110) was added to the cells. The plate is incubated for 10 minutes in the dark, while shaking. 170 µL of cell lysate is then transferred to a white 96-well plate and luminescence is measured. The detected luminescent signal is considered as linearely related to the number of cells having migrated from the upper well to the receiver well.

TABLE VII human neutrophil migration inhibition

| Cpd# | Neutrophils |
|---|---|
| 4 | *** |
| 7 | *** |
| 8 | *** |
| 9 | **** |
| 16 | *** |
| 17 | **** |
| 19 | **** |
| 20 | **** |
| 22 | **** |
| 23 | *** |
| 30 | **** |
| 34 | **** |
| 35 | *** |
| 36 | *** |
| 41 | **** |
| 42 | *** |
| 52 | **** |
| 56 | *** |
| 60 | **** |
| 62 | **** |
| 63 | **** |
| 68 | **** |
| 69 | **** |
| 72 | **** |
| 77 | **** |
| 80 | **** |
| 83 | **** |
| 85 | **** |
| 89 | **** |
| 90 | **** |
| 92 | **** |
| 98 | **** |
| 107 | **** |
| 109 | **** |
| 111 | **** |
| 112 | **** |
| 114 | **** |
| 115 | **** |
| 116 | **** |
| 121 | *** |
| 122 | **** |
| 123 | **** |
| 126 | **** |
| 133 | **** |
| 139 | **** |
| 140 | **** |
| 147 | **** |
| 149 | **** |
| 150 | **** |
| 158 | **** |
| 159 | **** |
| 160 | *** |
| 161 | **** |
| 168 | **** |
| 169 | **** |
| 170 | **** |
| 171 | **** |
| 174 | **** |

\* >1001 nM
\*\* 501-1000 nM
\*\*\* 101-500 nM
\*\*\*\* 0.01-100 nM 2.2. Rat Neutrophil Migration Assay We have established that GPR84 agonists (MCFA such as sodiumdecanoate, 3,3' di indolylmethane and Embelin induce neutrophil chemotaxis and that GPR84 antagonists could block GPR84 agonist-induced chemotaxis but not IL8-induced chemotaxis, indicating that G Protein-Coupled Receptor 84 (GPR84) is an essential player in the process of neutrophil recruitment.

The effect of agonists or antagonists for GPR84 can therefore be assayed in a neutrophil migration test. In the rat neutrophil migration assay, neutrophils, freshly isolated from rat after intraperitoneal injection of glycogen (0.1%, w/v), are treated with a compound for 30 minutes. Subsequently, the neutrophils are transferred to the upper wells of a Corning HTS transwell 96 permeable support system, of which the lower wells are filled with a embelin solution at EC80 (concentration which give 80% of the activity of the GPR84). After 1 h of incubation, migration of the neutrophils towards embelin in the lower compartment can be quantified by measuring the ATP-content of the lower wells using the Cell Titer Glow Substrate assay system (Promega, Cat. No.: G755B).

2.2.1. Isolation of Neutrophils from Rats 24 h after intraperitoneal injection of glycogen (0.1%, w/v), cells are harvested by peritoneal lavage with 25 mL HBSS then centrifuged for 12 minutes at 1300 rpm and 4° C. After centrifugation, the supernatant is discarded and the remaining cell pellet is rapidly resuspended in 12 mL of ice-cold $H_2O$ for red blood cell lysis to occur. After 20 seconds, 4 mL of ice-cold 0.6 M KCl is added. Samples are mixed carefully and centrifuged for 6 minutes at 1300 rpm, 4° C. The supernatant is discarded and the cell pellet is resuspended in 4 mL of DPBS and layered over 5 mL of Lymphoprep (Axis Shield, Cat. No.: 1114544) in a 15 mL centrifuge tube. After centrifugation for 30 min at 1500 rpm, 4° C., the supernatant is removed and the cell pellet, containing the neutrophils, is resuspended in 5 mL chemotaxis buffer (RPMI 1640 medium, supplemented with 10 mM HEPES; freshly made for each experiment).

2.2.2. Migration Assay

A cell suspension of 8.9×106 cells per milliliter is prepared. 10 μL of compound solution in chemotaxis buffer is added to 90 μL cell suspension. The mixture is incubated at 37° C. for 30 minutes with intermediate resuspension of the cells after 15 minutes. Following this, 75 μL cell suspension is transferred to the upper compartment of a Corning HTS transwell 96 permeable support system with 5.0 μm pore size polycarbonate membrane (Corning, Cat. No.: 3387). The receiver well of the transwell system is then filled with 200 μL chemotaxis buffer containing compound and chemotactic agent (embelin). After incubation at 37° C. in 5% CO2 for 1 h, the upper plate of the transwell system is removed and 70 μL Cell Titer Glow Substrate (Promega, Cat. No.: G755B) are added in the receiver plate. The receiver plate is incubated for 10 minutes in the dark, while shaking. 180 μL of cell lysate is then transferred to a white 96-well plate and luminescence is measured. The detected luminescent signal is considered as linearely related to the number of cells having migrated from the upper well to the receiver well.

3. ADME, PK and Safety Models 3.1 Aqueous Solubility

Starting from a 10 mM stock in DMSO, a serial dilution of the compound is prepared in DMSO. The dilution series is transferred to a 96 NUNC Maxisorb plate F-bottom and 0.1M phosphate buffer pH 7.4 or 0.1M citrate buffer pH3.0 at room temperature is added.

The final concentrations range from 18.75 to 300 μM in 5 equal dilution steps. The final DMSO concentration does not exceed 3%.

200 µM Pyrene is added to the corner points of each 96 well plate and serves as a reference point for calibration of Z-axis on the microscope.

The assay plates are sealed and incubated for 1 h at 37° C. while shaking at 230 rpm. The plates are then scanned under a white light microscope, yielding individual pictures of the precipitate per concentration. The precipitate is analyzed and converted into a number by a custom-developed software tool. The first concentration at which the compound appears completely dissolved is the concentration reported, however the true concentration lies somewhere between this concentration and one dilution step higher.

Solubility values are reported in µM and in g/mL.

3.2. Thermodynamic Solubility

Two individual solutions of 2 mg/mL of compound are prepared in a 0.1 M phosphate buffer pH 7.4 or a 0.1 M citrate buffer pH 3.0 at room temperature in a 2 mL glass vial.

After addition of a magnetic stir, the samples are stirred at room temperature for 24 h.

After 24 h, the vials are centrifuged 10 min at 1400 rpm. The supernatant of the sample is then transferred to a Multiscreen® Solubility Plate (Millipore, MSSLBPC50) and filtered (10-12" Hg) with the aid of a vacuum manifold into a clean Greiner polypropylene V-bottom 96 well plate. Per sample, two dilutions (factor 10 and 100) are made in DMSO. Other dilutions can be made if the acquired peak area is not within the standard curve.

A 10 mM DMSO stock, made from dry matter, is used to make a 200 µg/mL working stock. The standard curve for the compound is prepared in DMSO starting from the 200 µg/mL working stock. Eight concentrations and two quality control samples (QC) are made in 2 mL tubes. The first 3 concentrations (50, 35 and 15 µg/mL) and the first QC sample (20 µg/mL) are made starting with the 200 µg/mL working stock. The $4^{th}$ concentration (5 µg/mL) is made with the 50 µg/mL solution and the $5^{th}$ concentration (1 µg/mL) with the 15 µg/mL. The last three concentrations (0.2, 0.1 and 0.05 µg/mL) are made with the 1 µg/mL solution. The second QC sample (0.5 µg/mL) is made with the first QC sample.

Of every step of the dilution series, quality control and sample dilutions, a volume is transferred to a 96-well Deepwell plate. The samples are injected on a LC-MS/MS system (API2000 from Applied Biosystems).

The samples are analyzed on LC-MS/MS with a flow rate of 0.5 mL/min. Solvent A is 0.1% Formic Acid in water and solvent B is 0.1% Formic Acid in methanol. The sample is run under positive ion spray on a Pursuit 5 C18 2.0 mm column (Varian). The solvent gradient has a total run time of 1.4 minutes and ranges from 10% B to 100% B.

The thermodynamic solubility samples are analyzed with the aid of QuanLynx software. For the standard curve a linear or quadratic curve can be used in the analysis. Samples of the standard curve that have more than 15% deviation are excluded; the lowest concentrations of the curve may vary up to 20%. Peak areas of the samples are plotted against the standard curve to obtain the solubility of the compound.

Solubility values are reported in µM or µg/mL.

3.3 Microsomal Stability

A 10 mM stock solution of compound in DMSO is 1,668 fold diluted in a 105 mM phosphate buffer pH 7.4. Of this compound dilution, 50 µL is transferred in two 96 assay plates: one for time point 0 min (T0 plate) and one for time point 30 min (T30 plate) and pre-warmed at 37° C.

In the time zero reference sample (T0 plate), 100 µL MeOH (1:1) is added to the wells. In each assay plate (T0 and T30 min), 50 µL of microsomal mix is then added.

Final reaction concentrations are: 3 µM compound, 0.5 mg/mL microsomes, 0.4 U/mL GDPDH, 3.3 mM $MgCl_2$, 3.3 mM glucose-6-phosphate and 1.3 mM $NADP^+$.

The T30 plate is incubated at 37° C., 300 rpm and after 30 minutes of incubation the reaction is stopped with MeOH (1:1). The samples are mixed, centrifuged and the supernatant is harvested for analysis on LC-MS/MS (API2000 from Applied Biosystems).

The samples are analyzed on LC-MS/MS with a flow rate of 0.5 mL/min. Solvent A is 0.1% Formic Acid in water and solvent B is 0.1% Formic Acid in methanol. The sample is run under positive ion spray on a Pursuit 5 C18 2.0 mm column (Varian). The solvent gradient has a total run time of 1.4 minutes and ranges from 10% B to 100% B. Peak area from the parent compound at time 0 is considered to be 100% remaining. The percentage remaining after 30 minutes incubation is calculated from time 0 The solubility of the compound in the final test concentration in buffer is inspected by microscope and results are also reported.

3.4 Hepatocyte Stability.

Test compounds (1 µM initial concentration, n=2) are incubated in Williams' Medium E, containing 4 mM L-gutamine and 2 mM magnesium sulphate, with pooled cryopreserved hepatocytes (Celsis International) in suspension at cell densities of 0.25-0.5 million viable cells/mL. The incubations are performed at 37° C. in a shaking water bath with 100 µL samples taken from the incubation at 0, 10, 20, 45 and 90 minutes, and reactions terminated by addition of 100 µL of acetonitrile containing carbamazepine as analytical internal standard. Samples are centrifuged and the supernatant fractions analysed by LC-MS/MS. The instrument responses (i.e. peak heights) are referenced to the zero time-point samples (as 100%) in order to determine the percentage of compound remaining. Ln plots of the % remaining for each compound are used to determine the half-life for the hepatocyte incubations. Half-life values are calculated from the relationship: $T_{1/2}$ (min)=$-0.693/\lambda$, where $\lambda$ is the slope of the Ln concentration vs time curve. Standard compounds testosterone, midazolam, and 4-methylumbelliferone are included in the assay design.

3.5 Plasma Protein Binding (Equilibrium Dialysis)

A 10 mM stock solution of the compound in DMSO is diluted with a factor 10 in DMSO. This solution is further diluted in freshly thawed human, rat, mouse or dog plasma (BioReclamation INC) with a final concentration of 5 µM and final DMSO concentration of 0.5%.

A Pierce Red Device plate with inserts (ThermoScientific) is prepared and filled with 450 µL PBS in the buffer chamber and 300 µL of the spiked plasma in the plasma chamber. The plate is incubated for 4 h at 37° C. while shaking at 100 rpm. After incubation, 120 µL of both chambers is transferred to 480 µL methanol in a 96-well round bottom, PP deep-well plates (Nunc) and sealed with an aluminum foil lid. The samples are mixed and immediately centrifuged 30 min at 1400 rcf at 4° C. and the supernatant is transferred to a 96 v-bottom PP plate (Greiner, 651201) for analysis on LC-MS/MS (API2000 from Applied Biosystems).

The samples are analyzed on LC-MS/MS with a flow rate of 0.5 mL/min. Solvent A is 0.1% Formic Acid in water and solvent B is 0.1% Formic Acid in methanol. The sample is run under positive ion spray on a Pursuit 5 C18 2.0 mm column (Varian). The solvent gradient has a total run time of 1.4 minutes and ranges from 10% B to 100% B.

Peak area from the compound in the buffer chamber and the plasma chamber are considered to be 100% compound. The percentage bound to plasma is derived from these results and is reported as percentage bound to plasma.

The solubility of the compound in the final test concentration in PBS is inspected by microscope to indicate whether precipitation is observed or not.

3.6 Caco2 Permeability

Bi-directional Caco-2 assays are performed as described below. Caco-2 cells are obtained from European Collection of Cell Cultures (ECACC, cat 86010202) and used after a 21 day cell culture in 24-well Transwell plates (Corning, cell growth area: 0.33 cm$^2$, Membrane pore size: 0.4 μM, membrane diameter: 6.5 mm).

$2 \times 10^5$ cells/well are seeded in plating medium consisting of DMEM+GlutaMAX™-I+1% NEAA+10% FBS (Fetal-Clone II)+1% Pen/Strep. The medium is changed every 2-3 days.

Test and reference compounds (propranolol and rhodamine 123 or vinblastine, all purchased from Sigma) are prepared in Hanks' Balanced Salt Solution containing 25 mM HEPES (pH7.4) and added to either the apical (125 μL) or basolateral (600 μL) chambers of the Transwell plate assembly at a concentration of 10 μM with a final DMSO concentration of 0.25%.

50 μM Lucifer Yellow (Sigma) is added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 h incubation at 37° C. while shaking at an orbital shaker at 150 rpm, 70 μL aliquots are taken from both apical (A) and basal (B) chambers and added to 100 μL 50:50 acetonitrile:water solution containing analytical internal standard (0.5 μM carbamazepine) in a 96 well plate.

Lucifer yellow is measured with a Spectramax Gemini XS (Ex 426 nm and Em 538 nm) in a clean 96 well plate containing 150 μL of liquid from basolateral and apical side.

Concentrations of compound in the samples are measured by high performance liquid-chromatography/mass spectroscopy (LC-MS/MS).

Apparent permeability ($P_{app}$) values are calculated from the relationship:

$$P_{app} = [\text{compound}]_{acceptor\ final} \times V_{acceptor} / ([\text{compound}]_{donor\ initial} \times V_{donor}) / T_{inc} \times V_{donor} / \text{surface area} \times 60 \times 10^{-6}\ \text{cm/s}$$

V=chamber volume
$T_{inc}$=incubation time.
Surface area=0.33 cm$^2$

The Efflux ratios, as an indication of active efflux from the apical cell surface, are calculated using the ratio of $P_{app}$ B>A/$P_{app}$ A>B.

The following assay acceptance criteria are used:
Propranolol:$P_{app}$(A>B)value≥20($\times 10^{-6}$ cm/s)
Rhodamine 123 or Vinblastine: $P_{app}$ (A>B) value ⊐<5 ($\times 10^{-6}$ cm/s) with Efflux ratio ≥5.
Lucifer yellow permeability: ≤100 nm/s 3.7 Liability for QT Prolongation Potential for QT prolongation is assessed in the hERG manual patch clamp assay.

3.7.1 Conventional Whole-Cell Patch-Clamp

Whole-cell patch-clamp recordings are performed using an EPC10 amplifier controlled by Pulse v 8.77 software (HEKA). Series resistance is typically less than 10 MΩ and compensated by greater than 60%, recordings are not leak subtracted. Electrodes are manufactured from GC150TF pipette glass (Harvard).

The external bathing solution contains: 135 mM NaCl, 5 mM KCl, 1.8 mM CaCl$_2$, 5 mM Glucose, 10 mM HEPES, pH 7.4.

The internal patch pipette solution contains: 100 mM Kgluconate, 20 mM KC, 1 mM CaCl$_2$, 1 mM MgCl$_2$, 5 mM Na$_2$ ATP, 2 mM Glutathione, 11 mM EGTA, 10 mM HEPES, pH 7.2.

Drugs are perfused using a Biologic MEV-9/EVH-9 rapid perfusion system.

All recordings are performed on HEK293 cells stably expressing hERG channels. Cells are cultured on 12 mm round coverslips (German glass, Bellco) anchored in the recording chamber using two platinum rods (Goodfellow). hERG currents are evoked using an activating pulse to +40 mV for 1000 ms followed by a tail current pulse to −50 mV for 2000 ms, holding potential is −80 mV. Pulses are applied every 20 s and all experiments are performed at room temperature.

3.7.2 Data Analysis

IC$_{50}$ values are calculated for each compound tested. The fold difference between the IC$_{50}$ in the manual hERG patch clamp and the unbound IC$_{50}$ in the whole blood assay is calculated.

For the concentration response curves, peak tail current amplitude is measured during the voltage step to −50 mV. Curve-fitting of concentration-response data is performed using the equation:

$$y = a + [(b-a)/(1+10^{\wedge}((\log c - x)d)]$$

where a is minimum response, b is maximum response and d is Hill slope, this equation can be used to calculate both IC$_{50}$ (where y=50 and c is the IC$_{50}$ value) and IC$_{20}$ (where y=20 and c is the IC$_{20}$ value). GraphPad® Prism® (Graphpad® Software Inc.) software is used for all curve fitting. A difference of 100 fold or greater indicates a low potential for QT prolongation.

3.8 Pharmacokinetic Study 3.8.1 Single Dose Pharmacokinetic Study in Rats

Compounds are formulated in PEG200/physiological saline mixtures for the intravenous route and in PEG400/0.5% methylcellulose (10/90 v/v) for the oral route. Test compounds are orally dosed as a single esophageal gavage at 5-10 mg/kg and intravenously dosed as a bolus via the caudal vein at 1 mg/kg to male Sprague-Dawley rats. Each group consists of 3 rats. Blood samples are collected either via the jugular vein using cannulated rats or at the retro-orbital sinus with lithium heparin as anti-coagulant at the time points in the following range: 0.05 to 8 h (intravenous route), and 0.25 to 6 or 24 h (oral route). Whole blood samples are centrifuged at 5000 rpm for 10 min and the resulting plasma samples are stored at −20° C. pending analysis.

3.8.2 Multiple Dose Pharmacokinetic Study in Rats

Compounds are formulated in PEG400/0.5% methylcellulose (10/90 v/v) for the oral route. Test compounds are orally dosed as an esophageal daily gavage at 30 or 300 mg/kg to male Sprague-Dawley rats for 14 days. Each group consists of 3 rats. Blood samples are collected via the tail vein with lithium heparin as anti-coagulant at the following time points on day 1, 7 and 14: 0.25, 1, 4, 8 and 24 h. In addition, on day 2 blood samples are taken at 0.25, 1 and 4 h and at day 4 and 11 at 0.25 h. Whole blood samples are centrifuged at 5000 rpm for 10 min and the resulting plasma samples are stored at −20° C. pending analysis.

3.8.3 Quantification of Compound Levels in Plasma

Plasma concentrations of each test compound are determined by an LC-MS/MS method in which the mass spectrometer is operated in positive or negative electrospray mode.

3.8.4 Determination of Pharmacokinetic Parameters

Pharmacokinetic parameters are calculated using Winnonlin® (Pharsight®, US).

3.9 7-Day Rat Toxicity Study

A 7-day oral toxicity study with test compounds is performed in Sprague-Dawley male rats to assess their toxic potential and toxicokinetics, at daily doses of 100, 300 and 1000 mg/kg/day, by gavage, at the constant dosage-volume of 10 mL/kg/day.

The test compounds are formulated in PEG400/0.5% methylcellulose (10/90, v/v). Each group includes 6 principal male rats as well as 3 satellite animals for toxicokinetics. A fourth group is given PEG400/0.5% methylcellulose (10/90, v/v) only, at the same frequency, dosage volume and by the same route of administration, and acts as the vehicle control group.

The goal of the study is to determine the lowest dose that results in no adverse events being identified (no observable adverse effect level—NOAEL).

3.10 Cytochrome P450 Inhibition

Reversible CYP inhibition and time-dependent CYP3A4 inhibition is determined in human liver microsomes and specific probe substrates.

3.10.1 P450 Inhibition in Human Liver Microsomes, Reversible Inhibition

The inhibitory potential of a test compound is assessed for human cytochrome P450 isoenzymes CYP1A2, 2C8, 2C9, 2C19, 2D6 and 3A4.

A 10 mM stock solution of the test compound is prepared in DMSO, serially diluted in Tris buffer (100 mM pH 7.4) and added to hepatic microsomes (Xenotech LLC) and NADPH at 37° C. in a shaking water bath. Seven different test compounds concentrations (0.05 to 100 µM), 1% DMSO and 1 mM NADPH are obtained to react.

After 15 or 30 minutes reactions are terminated by addition of 100 µL of acetonitrile containing carbamazepine as analytical internal standard. Samples are centrifuged and the supernatant fractions analysed by LC-MS/MS. For each isoform, the instrument responses (peak heights) are referenced to those for DMSO controls (considered as 100%) in order to determine the percentage reduction in probe metabolism, using midazolam and testosterone as probe substrate. Percentage inhibition of probe metabolism and Log [test compound concentration] are plotted using Graphpad Prism software. The sigmoidal dose response model is fitted to the data in order to determine the $IC_{50}$.

Inhibition of CYP3A4 using nifedipine and atorvastatin as probe substrate is carried out as follows.

A 1.67 mM stock solution of test compound is prepared in methanol, serially diluted 1:3 in 50 mM potassium phosphate buffer pH7.4 and added to human hepatic microsomes (BD Gentest) and probe substrate. Seven different test compounds concentrations (0.045-33.3 µM), 2% methanol, 0.1 mg/mL microsomes, 10 µM atorvastatin or 5 µM nifedipine. After pre-warming 5 minutes at 37° C., the reaction was started by adding cofactor mix (7.65 mg/mL glucose-6-phosphate, 1.7 mg/mL NADP, 6 U/mL of glucose-6-phosphate dehydrogenase).

After 5 min (nifedipine) or 10 min (atorvastatin) at 37° C., the reaction (50 µL) is terminated with 150 µL acetonitrile: methanol (2:1) solution with internal standard (Warfarin). Samples are centrifuged and the supernatant fractions analyzed by LC-MS/MS. The instrument responses (ratio of test compound/internal standard peak areas) are referenced to those for solvent controls (assumed as 100%) in order to determine the percentage reduction in probe metabolism. Percent of control activity vs concentration plots are generated and fitted using GraphPad Prism software to generate $IC_{50}$.

3.10.2 CYP3A4 Inhibition in Human Liver Microsomes, Time-Dependent

The time-dependent inhibitory potential of a test compound is assessed for human cytochrome P450 isoenzyme 3A4. The compound is pre-incubated with the human liver microsomes before addition of the probe substrates. The result is compared to the condition where the compound is not pre-incubated with the human liver microsomes to see if there was a shift in $IC_{50}$, indicating time-dependent inhibition.

A 10 mM stock solution of test compound is prepared in DMSO and diluted 1:20 with Tris buffer (100 mM pH 7.4) and further serially diluted in Tris buffer/5% DMSO.

The cofactor, NADPH, and each test compound dilution is mixed in two separate plates for 0 and 30 min pre-incubation. Human hepatic microsomes (Xenotech LLC) are added only to the "30 minute pre-incubation" plate and both plates are then incubated for 30 minutes at 37° C. in a shaking water bath. Following the pre-incubation, microsomes are added to the "0 minute" plate and appropriate probe substrates (in 0.5% DMSO) are added to both plates. Plates are then returned to the water bath for a further incubation.

In total, six different test compound concentrations (1.6 to 50 µM) are assessed. Reactions are terminated with 100 µL of acetonitrile containing carbamazepine as analytical internal standard. Samples are centrifuged and the supernatant fractions analysed by LC-MS/MS. For each isoform, the instrument responses (peak height ratio with internal standard) are referenced to those for DMSO controls (considered as 100%) in order to determine the percentage reduction in probe metabolism. Percentage inhibition of probe metabolism and Log [Test Compound concentration] are plotted using Graphpad Prism software. The sigmoidal dose response model is fitted to the data in order to determine the $IC_{50}$.

4. In-Vivo Studies

The in-vivo activity of the compounds of the invention may be demonstrated in the following in vivo efficacy inflammation models.

4.1 Inflammatory Bowel Disease (Mice).

The mouse chronic DSS-induced inflammatory bowel disease model (IBD) is a well validated disease model for inflammatory bowel disease (Wirtz S. et al., 2007 Nature Protocols 2, 541-546; Sina C. et al., 2009 J. Immunol. 183 7514-7522).

To induce a chronic colitis, female BALB/c mice are fed with 4% dextran sodium sulfate (DSS) dissolved in drinking water for 4 days, followed by 3 days of regular drinking water. This cycle is repeated three times. This protocol allows inducing a strong colitis while avoiding high mortality rates. Animals are divided into several groups:

a. intact water; vehicle alone, n=10), b. diseased (DSS; vehicle alone, n=10), c. sulfazalazine used as reference (DSS; 20 mg/kg/day, p.o., n=10) and d. the tested compound (DSS; 1, 3, 10, 30 mg/kg/day, p.o., n=10).

Clinical parameters are measured every other day. The disease activity index (DAI) is a composite measure combining of the individual scores for weight loss, stool consistency and rectal bleeding. Mice are sacrificed at day 20 of the experiment according to the protocol introduced by Sina et al. (2009). At sacrifice time, the complete colon is removed and rinsed with sterile PBS. Segments of the distal colon are dissected for histological analysis, gene expression and protein level measurement.

4.2 Collagen-Induced Arthritis (Mice).

The mouse collagen-induced arthritis (CIA) is the gold standard rheumatoid arthritis model (Brand, et al., 2007 Nature Protocols 2, 1269-1275, Lin et al., 2007 Br J Pharmacol 1, 829-831). DBA1//J male mice are injected with a collagen II solution (Completed Freund's adjuvant). Immune reaction is boosted by a second injection (incomplete Freund's adjuvant) 21 days later. At day 31, arthritis is scored according to the method of Khachigian et al. (Khachigian et al., 2006 Nature Protocols 1, 2512-2516) and animals are randomized to reach an average clinical score of 2 per group. Animals are divided into several groups: intact (no treatment, n=5), diseased (vehicle alone, n=10), Enbrel® as reference (10 mg/kg, 3× week., i.p., n=10), and the tested compound (3, 10 or 30 mg/kg/day, p.o., n=10). Therapeutic dosing lasted from day 31 to day 46 and the arthritis is scored every day. Mice are sacrificed at day 46, X-ray photos are taken of the hind paws of each individual animal and the severity of bone erosion is ranked with the radiological Larsen's score (Salvemini et al., 2001 Arthritis Rheum 44, 2909-2921).

4.3 Tabacco Smoke Model (Mice)

Daily exposures of female inbred C57BL/6J mice to tobacco smoke (TS) for 11 consecutive days result in pulmonary inflammation, as indicated by an increase in the total number of cells recovered in the bronchoalveolar lavage (BAL), when compared with a similarly treated air-exposed group, 24 h after the final exposure. The exposure period to TS is increased initially from 25 minutes at the start of the study (day 1) to a maximum of 45 minutes on day 3 until day 11. Animals are divided into several groups: intact (no treatment, n=5), diseased (vehicle alone, n=10), Roflumilast as reference (5 mg/kg/day p.o., n=10), and the tested compounds (10 or 30 mg/kg/bid, p.o., n=10). At the end of 11 days, the numbers of macrophages, epithelial cells, neutrophils and lymphocytes are counted in the BAL. BAL is further analysed for gene expression and protein level. Lung tissue is dissected for histological analysis, gene expression and protein level measurement.

It will be appreciated by those skilled in the art that the foregoing descriptions are exemplary and explanatory in nature, and intended to illustrate the invention and its preferred embodiments. Through routine experimentation, an artisan will recognise apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication were specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

REFERENCES

Wittenberger et al., 2001 J Mol Biol, 307, 799-813

Yousefi S et al., 2001 J Leukoc Biol, 69, 1045-52

Wang et al., 2006 The Journal of Biological Chemistry, 281, 45, 34457-34464

Venkataraman et al., 2005, Immunology Letters, 101, 144-153

WO2007/027661 A2

Berry et al., 2010, Nature, 466, 973-979

Bouchard et al., 2007, Glia, 55:790-800

Bundgard, H., 1985 Design of Prodrugs, pp. 7-9, 21-24, Elsevier, Amsterdam 1985

Part 8 of Remington's Pharmaceutical Sciences, 17th edition, 1985, Mack Publishing Company, Easton, Pa.

T. W. Greene and P. G. M. Wuts, 2006 *Protecting Groups in Organic Synthesis*, Wiley-Blackwell; 4th Revised edition Young Kim et al., 2007 Bioorganic & Medicinal Chemistry 15, 2667-2679

Le Pouls et al., 2003, The Journal of Biological Chemistry, 278, 28, 25481-25489

Brown et al., 2003, The Journal of Biological Chemistry, 278, 13, 11312-11319

Stoddart et al., 2008, Pharmacological Reviews, 60, 405-417

Wirtz S. et al., 2007 Nature Protocols 2, 541-546

Sina C. et al., 2009 J. Immunol. 183 7514-7522

Brand, et al., 2007 Nature Protocols 2, 1269-1275

Lin et al., 2007 Br J Pharmacol 1, 862-872

Khachigian et al., 2006 Nature Protocols 1, 2512-2516

Salvemini et al., 2001 Arthritis Rheum 44, 2909-2921

Du Bois, 2010, Nat Rev, Drug Discovery, 9, 129

Nagasaki et. al., 2012, FEBS Letters, 586, 368-372

What is claimed:

1. A method of treating a mammal having, or at risk of having multiple sclerosis, said method comprising administering to the mammal a compound according to Formula Ia:

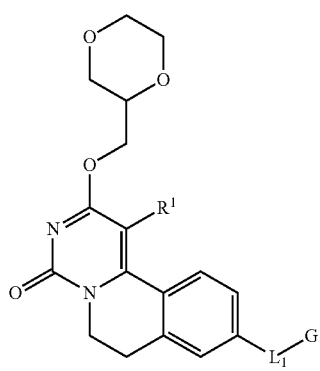

wherein
R¹ is H, Me, or halo;
L₁ is absent or is —O—, —S—, or —NR$^{4a}$—;
G is
R²,
—W-L₂-R², or
—W-L₃-R³;
W is C$_{1-4}$ alkylene, C$_{2-4}$ alkenylene having one double bond, or C$_{2-4}$ alkynylene having one triple bond;
L₂ is absent or is —O—;
R² is
H,
C$_{1-8}$ alkyl, optionally substituted with one to three groups independently selected from
OH,
halo,
CN,
C$_{1-6}$ alkoxy,
C$_{3-7}$ cycloalkyl,
4-6 membered heterocycloalkyl comprising one to three heteroatoms independently selected from S, and O,
5-6 membered heteroaryl comprising one to three heteroatoms independently selected from N, S, and O, and
phenyl,
C$_{4-7}$ cycloalkenyl comprising one double bond,
5-7 membered heterocycloalkenyl comprising one double bond, and one to three heteroatoms independently selected from N, O, and S,
C$_{3-7}$ cycloalkyl optionally substituted with one or more independently selected R⁵ groups,
4-10 membered heterocycloalkyl comprising one to two heteroatoms independently selected from S, and O, optionally substituted with one to three independently selected R⁵ groups,
5-10 membered heteroaryl comprising one to three heteroatoms independently selected from N, S, and O optionally substituted with one to three independently selected R⁶ groups, or
C$_{6-10}$ aryl optionally substituted with one or more independently selected R⁶ groups;
L₃ is —NR$^{4b}$—;
R³ is
C$_{1-4}$ alkyl substituted with
C$_{6-10}$ aryl optionally substituted with one or more independently selected R⁷ groups, or
5-10 membered heteroaryl comprising one to three heteroatoms independently selected from N, S, and O, optionally substituted with one or more independently selected R⁷ groups,
5-10 membered heteroaryl comprising one to three heteroatoms independently selected from N, S, and O, optionally substituted with one or more independently selected R⁷ group, or
C$_{6-10}$ aryl optionally substituted with one or more independently selected R⁷ groups;
Each R$^{4a}$ and R$^{4b}$ is independently selected from H, C$_{1-4}$ alkyl, and C$_{3-7}$ cycloalkyl;
R⁵ is oxo or R⁶;
R⁶ is
OH,
halo,
—NO₂,
C$_{1-6}$ alkyl optionally substituted with one to three groups independently selected from halo, and OH,
C$_{1-6}$ alkoxy optionally substituted with one to three groups independently selected from halo, and OH,
C$_{3-7}$ cycloalkyl,
—C(=O)OR⁸,
—C(=O)NR⁹R¹⁰,
—NHC(=O)—C$_{1-4}$ alkyl,
—CN,
phenyl,
—O-phenyl,
4-7 membered heterocycloalkyl comprising one to three heteroatoms independently selected from N, O, and S, or
5-6 membered heteroaryl comprising one to three heteroatoms independently selected from N, O, and S, optionally substituted with one or more independently selected C$_{1-4}$ alkyl, C$_{1-4}$ alkoxy, CN, halo, and —C(=O)OR¹¹;
R⁷ is C$_{1-4}$ alkyl, or halo; and
each of R⁸, R⁹, R¹⁰ and R¹¹ is independently selected from H and C$_{1-4}$ alkyl,
or a pharmaceutically acceptable salt, or a solvate, or a solvate of the pharmaceutically acceptable salt thereof.

2. A method according to claim 1, comprising administering a compound according to Formula Ia or pharmaceutically acceptable salt thereof, wherein R¹ is H.

3. A method according to claim 1, comprising administering a compound according to Formula Ia or pharmaceutically acceptable salt thereof, wherein the compound is according to Formula IIa or IIIa:

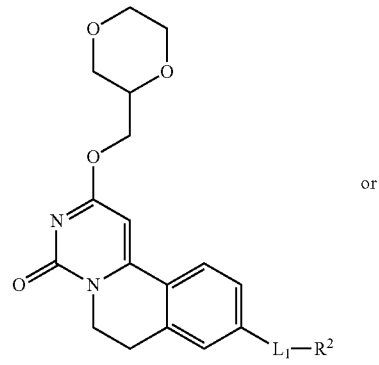

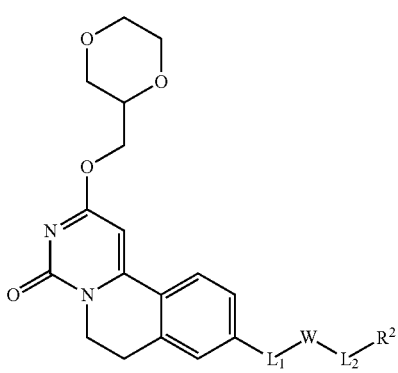

IIIa or a pharmaceutically acceptable salt thereof, wherein $L_1$, W, $L_2$, and $R^2$ are as described in claim 1.

4. A method according to claim 3, comprising administering a compound according to Formula IIa or pharmaceutically acceptable salt thereof, wherein $L_1$ is absent.

5. A method according to claim 3, comprising administering a compound according to Formula IIIa, or pharmaceutically acceptable salt thereof, wherein $L_1$ is absent or is —O—; and W is $C_{1-4}$ alkylene, or $C_{2-4}$ alkenylene having one double bond.

6. A method according to claim 3, comprising administering a compound according to Formula IIIa, or pharmaceutically acceptable salt thereof, wherein $L_1$ is absent; and W is $C_{2-4}$ alkynylene having one triple bond.

7. A method according to claim 5, comprising administering a compound or pharmaceutically acceptable salt thereof, wherein $L_2$ is absent.

8. A method according to claim 3, comprising administering a compound according to Formula IIIa or a pharmaceutically acceptable salt thereof, wherein $L_1$ and $L_2$ are absent, and W is —CH$_2$—CH$_2$—, —CH═CH—, or —C≡C—.

9. A method according to claim 3, comprising administering a compound or pharmaceutically acceptable salt thereof, wherein $R^2$ is 5-10 membered heteroaryl comprising one to three heteroatoms independently selected from N, S, and O, optionally substituted with one to three independently selected $R^6$ groups.

10. A method according to claim 9, comprising administering a compound or pharmaceutically acceptable salt thereof, wherein $R^6$ is selected from OH, halo, $C_{1-6}$ alkyl, $C_{1-6}$ alkyl substituted with one or more halo, $C_{1-6}$ alkoxy, —CN, $C_{3-7}$ cycloalkyl, 4-7 membered heterocycloalkyl comprising one to three heteroatoms independently selected from N, O, and S, and phenyl.

11. A method according to claim 3, comprising administering a compound or pharmaceutically acceptable salt thereof, wherein $R^2$ is $C_{1-8}$ alkyl optionally substituted with one to three groups independently selected from OH, halo, CN, $C_{1-6}$ alkoxy, $C_{3-7}$ cycloalkyl, 4-6 membered heterocycloalkyl comprising one to three heteroatoms independently selected from S, and O, 5-6 membered heteroaryl comprising one to three heteroatoms independently selected from N, S, and O, and phenyl.

12. A method according to claim 3, comprising administering a compound or pharmaceutically acceptable salt thereof, wherein $R^2$ is $C_{3-7}$ cycloalkyl.

13. A method according to claim 1, comprising administering a compound or pharmaceutically acceptable salt thereof, wherein the compound is selected from:

9-Allyloxy-2-([1,4]dioxan-2-ylmethoxy)-6,7-dihydro-pyrimido[6,1-a]isoquinolin-4-one,
2-([1,4]Dioxan-2-ylmethoxy)-9-pyridin-3-yl-6,7-dihydro-pyrimido[6,1-a]isoquinolin-4-one,
2-([1,4]Dioxan-2-ylmethoxy)-9-pyridin-4-yl-6,7-dihydro-pyrimido[6,1-a]isoquinolin-4-one,
2-[2-([1,4]Dioxan-2-ylmethoxy)-4-oxo-6,7-dihydro-4H-pyrimido[6,1-a]isoquinolin-9-yl]-benzonitrile,
3-[2-([1,4]Dioxan-2-ylmethoxy)-4-oxo-6,7-dihydro-4H-pyrimido[6,1-a]isoquinolin-9-yl]-benzonitrile,
4-[2-([1,4]Dioxan-2-ylmethoxy)-4-oxo-6,7-dihydro-4H-pyrimido[6,1-a]isoquinolin-9-yl]-benzonitrile,
[2-([1,4]Dioxan-2-ylmethoxy)-4-oxo-6,7-dihydro-4H-pyrimido[6,1-a]isoquinolin-9-yloxy]-acetonitrile,
2-([1,4]Dioxan-2-ylmethoxy)-9-(oxazol-2-ylmethoxy)-6,7-dihydro-pyrimido[6,1-a]-isoquinolin-4-one,
2-([1,4]Dioxan-2-ylmethoxy)-9-(pyridin-2-ylmethoxy)-6,7-dihydro-pyrimido[6,1-a]isoquinolin-4-one,
9-(3,5-Dichloro-phenyl)-2-([1,4]dioxan-2-ylmethoxy)-6,7-dihydro-pyrimido[6,1-a]isoquinolin-4-one,
9-Benzofuran-2-yl-2-([1,4]dioxan-2-ylmethoxy)-6,7-dihydro-pyrimido[6,1-a]isoquinolin-4-one,
2-[2-([1,4]Dioxan-2-ylmethoxy)-4-oxo-6,7-dihydro-4H-pyrimido[6,1-a]isoquinolin-9-yl]-indole-1-carboxylic acid tert-butyl ester,
2-([1,4]Dioxan-2-ylmethoxy)-9-(1H-indo-2-yl)-6,7-dihydro-pyrimido[6,1-a]isoquinolin-4-one,
2-([1,4]Dioxan-2-ylmethoxy)-9-(6-methoxy-pyridin-3-yl)-6,7-dihydro-pyrimido[6,1-a]isoquinolin-4-one,
2-([1,4]Dioxan-2-ylmethoxy)-9-(6-trifluoromethyl-pyridin-3-yl)-6,7-dihydro-pyrimido[6,1-a]isoquinolin-4-one,
2-([1,4]Dioxan-2-ylmethoxy)-9-(3-methyl-3H-imidazol-4-ylethynyl)-6,7-dihydro-pyrimido[6,1-a]isoquinolin-4-one,
9-(5-tert-Butyl-[1,2,4]oxadiazol-3-ylmethoxy)-2-([1,4]dioxan-2-ylmethoxy)-6,7-dihydro-pyrimido[6,1-a]isoquinolin-4-one,
5-[2-([1,4]Dioxan-2-ylmethoxy)-4-oxo-6,7-dihydro-4H-pyrimido[6,1-a]isoquinolin-9-yl]-pyridine-2-carboxylic acid methylamide,
2-([1,4]Dioxan-2-ylmethoxy)-9-pent-1-ynyl-6,7-dihydro-pyrimido[6,1-a]isoquinolin-4-one,
2-([1,4]Dioxan-2-ylmethoxy)-9-(2-pyridin-2-yl-ethyl)-6,7-dihydro-pyrimido[6,1-a]isoquinolin-4-one,
2-([1,4]Dioxan-2-ylmethoxy)-9-(2-pyrazin-2-yl-ethyl)-6,7-dihydro-pyrimido[6,1-a]isoquinolin-4-one,
2-([1,4]Dioxan-2-ylmethoxy)-9-(1H-indo-5-yl)-6,7-dihydro-pyrimido[6,1-a]isoquinolin-4-one,
2-([1,4]Dioxan-2-ylmethoxy)-9-(2-methoxy-phenyl)-6,7-dihydro-pyrimido[6,1-a]isoquinolin-4-one,
2-([1,4]Dioxan-2-ylmethoxy)-9-(5-methoxy-pyridin-3-yl)-6,7-dihydro-pyrimido[6,1-a]isoquinolin-4-one,
2-([1,4]Dioxan-2-ylmethoxy)-9-(1H-indazol-5-yl)-6,7-dihydro-pyrimido[6,1-a]isoquinolin-4-one,
2-([1,4]Dioxan-2-ylmethoxy)-9-(4-methoxy-phenyl)-6,7-dihydro-pyrimido[6,1-a]isoquinolin-4-one,
3-[2-([1,4]Dioxan-2-ylmethoxy)-4-oxo-6,7-dihydro-4H-pyrimido[6,1-a]isoquinolin-9-yl]-benzamide,
5-[2-([1,4]Dioxan-2-ylmethoxy)-4-oxo-6,7-dihydro-4H-pyrimido[6,1-a]isoquinolin-9-yl]-2-fluoro-benzamide,
N-{3-[2-([1,4]Dioxan-2-ylmethoxy)-4-oxo-6,7-dihydro-4H-pyrimido[6,1-a]isoquinolin-9-yl]-phenyl}-acetamide,
9-Cyclopropylethynyl-2-([1,4]dioxan-2-ylmethoxy)-6,7-dihydro-pyrimido[6,1-a]isoquinolin-4-one, 2-([1,4]Dioxan-2-ylmethoxy)-9-(1-hydroxy-cyclopentyl-ethynyl)-6,7-dihydro-pyrimido[6,1-a]isoquinolin-4-one,
2-([1,4]Dioxan-2-ylmethoxy)-9-pyrimidin-5-yl-6,7-dihydro-pyrimido[6,1-a]isoquinolin-4-one,
9-Cyclohex-1-enyl-2-([1,4]dioxan-2-ylmethoxy)-6,7-dihydro-pyrimido[6,1-a]isoquinolin-4-one,
2-([1,4]Dioxan-2-ylmethoxy)-9-(1-methyl-1H-indol-5-yl)-6,7-dihydro-pyrimido[6,1-a]isoquinolin-4-one,
2-([1,4]Dioxan-2-ylmethoxy)-9-(6-methyl-pyridin-3-yl)-6,7-dihydro-pyrimido[6,1-a]isoquinolin-4-one,
2-([1,4]Dioxan-2-ylmethoxy)-9-pyridin-2-ylethynyl-6,7-dihydro-pyrimido[6,1-a]isoquinolin-4-one,
2-([1,4]Dioxan-2-ylmethoxy)-9-(3-methoxy-prop-1-ynyl)-6,7-dihydro-pyrimido[6,1-a]isoquinolin-4-one,
5-[2-([1,4]Dioxan-2-ylmethoxy)-4-oxo-6,7-dihydro-4H-pyrimido[6,1-a]isoquinolin-9-yl]-pent-4-ynenitrile,
2-([1,4]Dioxan-2-ylmethoxy)-9-(3-hydroxy-prop-1-ynyl)-6,7-dihydro-pyrimido[6,1-a]isoquinolin-4-one,
2-([1,4]Dioxan-2-ylmethoxy)-9-(4-methoxy-phenylethynyl)-6,7-dihydro-pyrimido[6,1-a]isoquinolin-4-one,
2-([1,4]Dioxan-2-ylmethoxy)-9-pyridin-3-ylethynyl-6,7-dihydro-pyrimido[6,1-a]isoquinolin-4-one,
4-[2-([1,4]Dioxan-2-ylmethoxy)-4-oxo-6,7-dihydro-4H-pyrimido[6,1-a]isoquinolin-9-yl]-N-methyl-benzamide,
2-([1,4]Dioxan-2-ylmethoxy)-9-(3-methoxy-phenyl)-6,7-dihydro-pyrimido[6,1-a]isoquinolin-4-one,
9-(2-Chloro-phenyl)-2-([1,4]dioxan-2-ylmethoxy)-6,7-dihydro-pyrimido[6,1-a]isoquinolin-4-one,
2-([1,4]Dioxan-2-ylmethoxy)-9-(4-hydroxy-but-1-ynyl)-6,7-dihydro-pyrimido[6,1-a]isoquinolin-4-one,
9-(1,5-Dimethyl-1H-pyrazol-3-ylmethoxy)-2-([1,4]dioxan-2-ylmethoxy)-6,7-dihydro-pyrimido[6,1-a]isoquinolin-4-one,
2-([1,4]Dioxan-2-ylmethoxy)-9-(1-methyl-1H-pyrazol-3-ylmethoxy)-6,7-dihydro-pyrimido[6,1-a]isoquinolin-4-one,
2-([1,4]Dioxan-2-ylmethoxy)-9-(3-methyl-[1,2,4]oxadiazol-5-ylmethoxy)-6,7-dihydro-pyrimido[6,1-a]isoquinolin-4-one,
2-([1,4]Dioxan-2-ylmethoxy)-9-(4-morpholin-4-yl-phenyl)-6,7-dihydro-pyrimido[6,1-a]isoquinolin-4-one,
3-[2-([1,4]Dioxan-2-ylmethoxy)-4-oxo-6,7-dihydro-4H-pyrimido[6,1-a]isoquinolin-9-yl]-4-fluoro-benzamide,
3-[2-([1,4]Dioxan-2-ylmethoxy)-4-oxo-6,7-dihydro-4H-pyrimido[6,1-a]isoquinolin-9-yl]-5-fluoro-benzamide,
9-(3,3-Dimethyl-but-1-ynyl)-2-([1,4]dioxan-2-ylmethoxy)-6,7-dihydro-pyrimido[6,1-a]isoquinolin-4-one,
2-([1,4]Dioxan-2-ylmethoxy)-9-pyridin-4-ylethynyl-6,7-dihydro-pyrimido[6,1-a]isoquinolin-4-one,
2-([1,4]Dioxan-2-ylmethoxy)-9-(3-methyl-isoxazol-5-ylmethoxy)-6,7-dihydro-pyrimido[6,1-a]isoquinolin-4-one,
2-([1,4]Dioxan-2-ylmethoxy)-9-(3-hydroxy-3-methyl-but-1-ynyl)-6,7-dihydro-pyrimido[6,1-a]isoquinolin-4-one,
2-([1,4]Dioxan-2-ylmethoxy)-9-(2-methoxy-pyridin-3-yl)-6,7-dihydro-pyrimido[6,1-a]isoquinolin-4-one,
2-([1,4]Dioxan-2-ylmethoxy)-6,7-dihydro-pyrimido[6,1-a]isoquinolin-4-one,
9-(3,6-Dihydro-2H-pyran-4-yl)-2-([1,4]dioxan-2-ylmethoxy)-6,7-dihydro-pyrimido[6,1-a]isoquinolin-4-one,
5-[2-([1,4]Dioxan-2-ylmethoxy)-4-oxo-6,7-dihydro-4H-pyrimido[6,1-a]isoquinolin-9-yl]-pyridine-2-carbonitrile,
2-([1,4]Dioxan-2-ylmethoxy)-9-(6-isopropoxy-pyridin-3-yl)-6,7-dihydro-pyrimido[6,1-a]isoquinolin-4-one,
2-([1,4]Dioxan-2-ylmethoxy)-9-(6-ethoxy-pyridin-3-yl)-6,7-dihydro-pyrimido[6,1-a]isoquinolin-4-one,
2-([1,4]Dioxan-2-ylmethoxy)-9-(6-morpholin-4-yl-pyridin-3-yl)-6,7-dihydro-pyrimido[6,1-a]isoquinolin-4-one,
9-(2,3-Dimethoxy-phenyl)-2-([1,4]dioxan-2-ylmethoxy)-6,7-dihydro-pyrimido[6,1-a]isoquinolin-4-one,
9-(3-Chloro-2-methoxy-pyridin-4-yl)-2-([1,4]dioxan-2-ylmethoxy)-6,7-dihydro-pyrimido[6,1-a]isoquinolin-4-one,
2-([1,4]Dioxan-2-ylmethoxy)-9-(2-methyl-pyridin-4-yl)-6,7-dihydro-pyrimido[6,1-a]isoquinolin-4-one,
3-[2-([1,4]Dioxan-2-ylmethoxy)-4-oxo-6,7-dihydro-4H-pyrimido[6,1-a]isoquinolin-9-yl]-isonicotinonitrile,
9-(2,5-Dimethoxy-phenyl)-2-([1,4]dioxan-2-ylmethoxy)-6,7-dihydro-pyrimido[6,1-a]isoquinolin-4-one,
2-([1,4]Dioxan-2-ylmethoxy)-9-(3,4,5,6-tetrahydro-2H-[1,2']bipyridinyl-5'-yl)-6,7-dihydro-pyrimido[6,1-a]isoquinolin-4-one,
2-([1,4]Dioxan-2-ylmethoxy)-9-(2-ethoxy-pyridin-3-yl)-6,7-dihydro-pyrimido[6,1-a]isoquinolin-4-one,
9-(2,6-Dimethoxy-pyridin-3-yl)-2-([1,4]dioxan-2-ylmethoxy)-6,7-dihydro-pyrimido[6,1-a]isoquinolin-4-one,
4-[2-([1,4]Dioxan-2-ylmethoxy)-4-oxo-6,7-dihydro-4H-pyrimido[6,1-a]isoquinolin-9-yl]-nicotinonitrile,
9-tert-Butoxymethyl-2-([1,4]dioxan-2-ylmethoxy)-6,7-dihydro-pyrimido[6,1-a]isoquinolin-4-one,
2-([1,4]Dioxan-2-ylmethoxy)-9-(2-pyrrolidin-1-yl-pyridin-3-yl)-6,7-dihydro-pyrimido[6,1-a]isoquinolin-4-one,
2-([1,4]Dioxan-2-ylmethoxy)-9-(6-pyrrolidin-1-yl-pyridin-3-yl)-6,7-dihydro-pyrimido[6,1-a]isoquinolin-4-one,
2-([1,4]Dioxan-2-ylmethoxy)-9-(5-phenyl-oxazol-2-ylmethoxy)-6,7-dihydro-pyrimido[6,1-a]isoquinolin-4-one,
9-(5-tert-Butyl-oxazol-2-ylmethoxy)-2-([1,4]dioxan-2-ylmethoxy)-6,7-dihydro-pyrimido[6,1-a]isoquinolin-4-one,
9-(5-Cyclopropyl-[1,2,4]oxadiazol-3-ylmethoxy)-2-([1,4]dioxan-2-ylmethoxy)-6,7-dihydro-pyrimido[6,1-a]isoquinolin-4-one,
2-([1,4]Dioxan-2-ylmethoxy)-9-(5-ethyl-[1,2,4]oxadiazol-3-ylmethoxy)-6,7-dihydro-pyrimido[6,1-a]isoquinolin-4-one,
2-([1,4]Dioxan-2-ylmethoxy)-9-(5-methyl-[1,2,4]oxadiazol-3-ylmethoxy)-6,7-dihydro-pyrimido[6,1-a]isoquinolin-4-one,
2-([1,4]Dioxan-2-ylmethoxy)-9-(5-isopropyl-[1,2,4]oxadiazol-3-ylmethoxy)-6,7-dihydro-pyrimido[6,1-a]isoquinolin-4-one,
9-Cyclopentylethynyl-2-([1,4]dioxan-2-ylmethoxy)-6,7-dihydro-pyrimido[6,1-a]isoquinolin-4-one,
9-Cyclohexylethynyl-2-([1,4]dioxan-2-ylmethoxy)-6,7-dihydro-pyrimido[6,1-a]isoquinolin-4-one,
2-([1,4]Dioxan-2-ylmethoxy)-9-(3-methyl-but-1-ynyl)-6,7-dihydro-pyrimido[6,1-a]isoquinolin-4-one,
2-([1,4]Dioxan-2-ylmethoxy)-9-hex-1-ynyl-6,7-dihydro-pyrimido[6,1-a]isoquinolin-4-one, 9-[3-(Benzyl-methyl-amino)-prop-1-ynyl]-2-([1,4]dioxan-2-ylmethoxy)-6,7-dihydro-pyrimido[6,1-a]isoquinolin-4-one,
2-([1,4]Dioxan-2-ylmethoxy)-9-(3-hydroxy-5-methyl-hex-1-ynyl)-6,7-dihydro-pyrimido[6,1-a]isoquinolin-4-one,
2-([1,4]Dioxan-2-ylmethoxy)-9-(3-hydroxy-but-1-ynyl)-6,7-dihydro-pyrimido[6,1-a]isoquinolin-4-one,
9-Cyclopropyl-2-([1,4]dioxan-2-ylmethoxy)-6,7-dihydro-pyrimido[6,1-a]isoquinolin-4-one,
2-([1,4]Dioxan-2-ylmethoxy)-9-(3-hydroxy-pent-1-ynyl)-6,7-dihydro-pyrimido[6,1-a]isoquinolin-4-one,
2-([1,4]Dioxan-2-ylmethoxy)-9-(3-hydroxy-4-methyl-pent-1-ynyl)-6,7-dihydro-pyrimido[6,1-a]isoquinolin-4-one,
2-([1,4]Dioxan-2-ylmethoxy)-9-(3-ethyl-3-hydroxy-pent-1-ynyl)-6,7-dihydro-pyrimido[6,1-a]isoquinolin-4-one,
2-([1,4]Dioxan-2-ylmethoxy)-9-(3-hydroxy-3-phenyl-but-1-ynyl)-6,7-dihydro-pyrimido[6,1-a]isoquinolin-4-one,
9-(3-Benzylamino-prop-1-ynyl)-2-([1,4]dioxan-2-ylmethoxy)-6,7-dihydro-pyrimido[6,1-a]isoquinolin-4-one,
2-([1,4]Dioxan-2-ylmethoxy)-9-[(furan-2-ylmethyl)-amino]-6,7-dihydro-pyrimido[6,1-a]isoquinolin-4-one,
2-([1,4]Dioxan-2-ylmethoxy)-9-(1-ethyl-1H-pyrazol-4-yl)-6,7-dihydro-pyrimido[6,1-a]isoquinolin-4-one,
2-([1,4]Dioxan-2-ylmethoxy)-9-[1-(3-methyl-butyl)-1H-pyrazol-4-yl]-6,7-dihydro-pyrimido[6,1-a]isoquinolin-4-one,
2-([1,4]Dioxan-2-ylmethoxy)-9-(5-methyl-furan-2-yl)-6,7-dihydro-pyrimido[6,1-a]isoquinolin-4-one,
2-([1,4]Dioxan-2-ylmethoxy)-9-(3-hydroxy-hex-1-ynyl)-6,7-dihydro-pyrimido[6,1-a]isoquinolin-4-one,
9-(3,5-Dimethyl-1H-pyrazol-4-yl)-2-([1,4]dioxan-2-ylmethoxy)-6,7-dihydro-pyrimido[6,1-a]isoquinolin-4-one,
2-([1,4]Dioxan-2-ylmethoxy)-9-(1H-pyrazol-4-yl)-6,7-dihydro-pyrimido[6,1-a]isoquinolin-4-one,
2-([1,4]Dioxan-2-ylmethoxy)-9-(1-propyl-1H-pyrazol-4-yl)-6,7-dihydro-pyrimido[6,1-a]isoquinolin-4-one,
2-[2-((R)-1-[1,4]Dioxan-2-ylmethoxy)-4-oxo-6,7-dihydro-4H-pyrimido[6,1-a]isoquinolin-9-yl]-benzonitrile,
2-[2-((S)-1-[1,4]Dioxan-2-ylmethoxy)-4-oxo-6,7-dihydro-4H-pyrimido[6,1-a]isoquinolin-9-yl]-benzonitrile,
9-(5-Cyclopropyl-[1,2,4]oxadiazol-3-ylmethoxy)-2-((R)-1-[1,4]dioxan-2-ylmethoxy)-6,7-dihydro-pyrimido[6,1-a]isoquinolin-4-one,
2-([1,4]Dioxan-2-ylmethoxy)-9-ethynyl-6,7-dihydro-pyrimido[6,1-a]isoquinolin-4-one,
2-([1,4]Dioxan-2-ylmethoxy)-9-pyrimidin-2-ylethynyl-6,7-dihydro-pyrimido[6,1-a]isoquinolin-4-one,
2-([1,4]Dioxan-2-ylmethoxy)-9-(3-phenylamino-prop-1-ynyl)-6,7-dihydro-pyrimido[6,1-a]isoquinolin-4-one,
2-([1,4]Dioxan-2-ylmethoxy)-9-(3-hydroxy-3-pyridin-3-yl-prop-1-ynyl)-6,7-dihydro-pyrimido[6,1-a]isoquinolin-4-one,
9-Cyclopentyloxymethyl-2-([1,4]dioxan-2-ylmethoxy)-6,7-dihydro-pyrimido[6,1-a]isoquinolin-4-one,
2-([1,4]Dioxan-2-ylmethoxy)-9-(3-methoxy-4-methyl-pent-1-ynyl)-6,7-dihydro-pyrimido[6,1-a]isoquinolin-4-one,
9-Cyclopropylethynyl-2-((R)-1-[1,4]dioxan-2-ylmethoxy)-6,7-dihydro-pyrimido[6,1-a]isoquinolin-4-one,
2-((S)-1-[1,4]Dioxan-2-ylmethoxy)-9-(3-methyl-but-1-ynyl)-6,7-dihydro-pyrimido[6,1-a]isoquinolin-4-one,
2-([1,4]Dioxan-2-ylmethoxy)-9-(3-imidazol-1-yl-prop-1-ynyl)-6,7-dihydro-pyrimido[6,1-a]isoquinolin-4-one,
9-(2-Cyclopropyl-ethyl)-2-((R)-1-[1,4]dioxan-2-ylmethoxy)-6,7-dihydro-pyrimido[6,1-a]isoquinolin-4-one,
9-Cyclopentyloxymethyl-2-((R)-1-[1,4]dioxan-2-ylmethoxy)-6,7-dihydro-pyrimido[6,1-a]isoquinolin-4-one,
2-([1,4]Dioxan-2-ylmethoxy)-9-(3-hydroxy-3-pyridin-3-yl-propyl)-6,7-dihydro-pyrimido[6,1-a]isoquinolin-4-one,
9-Allyloxy-2-((R)-1-[1,4]dioxan-2-ylmethoxy)-6,7-dihydro-pyrimido[6,1-a]isoquinolin-4-one,
9-Allyloxy-2-((S)-1-[1,4]dioxan-2-ylmethoxy)-6,7-dihydro-pyrimido[6,1-a]isoquinolin-4-one,
2-((R)-1-[1,4]Dioxan-2-ylmethoxy)-9-(tetrahydro-pyran-4-yloxymethyl)-6,7-dihydro-pyrimido[6,1-a]isoquinolin-4-one,
2-([1,4]Dioxan-2-ylmethoxy)-9-{3-[(pyridin-3-ylmethyl)-amino]-prop-1-ynyl}-6,7-dihydro-pyrimido[6,1-a]isoquinolin-4-one,
2-((R)-1-[1,4]Dioxan-2-ylmethoxy)-9-pentyl-6,7-dihydro-pyrimido[6,1-a]isoquinolin-4-one,
9-Cyclopropylethynyl-2-((S)-1-[1,4]dioxan-2-ylmethoxy)-6,7-dihydro-pyrimido[6,1-a]isoquinolin-4-one,
9-(2-Cyclopropyl-ethyl)-2-((S)-1-[1,4]dioxan-2-ylmethoxy)-6,7-dihydro-pyrimido[6,1-a]isoquinolin-4-one,
2-((S)-1-[1,4]Dioxan-2-ylmethoxy)-9-(oxetan-3-yloxymethyl)-6,7-dihydro-pyrimido[6,1-a]isoquinolin-4-one,
2-((S)-1-[1,4]Dioxan-2-ylmethoxy)-9-(3-methyl-oxetan-3-ylmethoxymethyl)-6,7-dihydro-pyrimido[6,1-a]isoquinolin-4-one,
9-(2,2-Dimethyl-butylamino)-2-((S)-1-[1,4]dioxan-2-ylmethoxy)-6,7-dihydro-pyrimido[6,1-a]isoquinolin-4-one,
2-((S)-1-[1,4]Dioxan-2-ylmethoxy)-9-(3-hydroxy-4-methyl-pentyl)-6,7-dihydro-pyrimido[6,1-a]isoquinolin-4-one,
2-((S)-1-[1,4]Dioxan-2-ylmethoxy)-9-(2-ethyl-hexylamino)-6,7-dihydro-pyrimido[6,1-a]isoquinolin-4-one,
2-((S)-1-[1,4]Dioxan-2-ylmethoxy)-9-(2-methoxy-ethoxy)-6,7-dihydro-pyrimido[6,1-a]isoquinolin-4-one,
2-((S)-1-[1,4]Dioxan-2-ylmethoxy)-9-(2-ethoxy-ethoxy)-6,7-dihydro-pyrimido[6,1-a]isoquinolin-4-one,
9-Cyclopropylmethoxy-2-((S)-1-[1,4]dioxan-2-ylmethoxy)-6,7-dihydro-pyrimido[6,1-a]isoquinolin-4-one,
2-((S)-1-[1,4]Dioxan-2-ylmethoxy)-9-(2-fluoro-ethoxy)-6,7-dihydro-pyrimido[6,1-a]isoquinolin-4-one,
2-((S)-1-[1,4]Dioxan-2-ylmethoxy)-9-[3-(2-methoxy-ethoxy)-prop-1-ynyl]-6,7-dihydro-pyrimido[6,1-a]isoquinolin-4-one,
2-((S)-1-[1,4]Dioxan-2-ylmethoxy)-9-[3-(2-ethoxy-ethoxy)-prop-1-ynyl]-6,7-dihydro-pyrimido[6,1-a]isoquinolin-4-one,
2-((S)-1-[1,4]Dioxan-2-ylmethoxy)-9-[3-(2-fluoro-ethoxy)-prop-1-ynyl]-6,7-dihydro-pyrimido[6,1-a]isoquinolin-4-one, 9-(2,2-Dimethyl-propoxymethyl)-2-((S)-1-[1,4]dioxan-2-ylmethoxy)-6,7-dihydro-pyrimido[6,1-a]isoquinolin-4-one, 9-Cyclohexyloxymethyl-2-((S)-1-[1,4]dioxan-2-ylmethoxy)-6,7-dihydro-pyrimido[6,1-a]isoquinolin-4-one, 9-Cyclopropylmethoxymethyl-2((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(tetrahydro-pyran-2-ylmethoxy)-6,7-dihydro-pyrimido[6,1-a]isoquinolin-4-one, 2-((S)-1-[1,4]Dioxan-2-ylmethoxy)-9-(3-hydroxy-butyl)-6,7-dihydro-pyrimido[6,1-a]isoquinolin-4-one, 9-(4,4-Dimethyl-pentyloxy)-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(3-methoxy-4-methyl-pentyl)-6,7-dihydro-pyrimido[6,1-a]isoquinolin-4-one, 9-(3-Cyclopropyl-propoxy)-2-((S)-1-[1,4]dioxan-2-ylmethoxy)-6,7-dihydro-pyrimido[6,1-a]isoquinolin-4-one, 9-Cyclohexylamino-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(3-hydroxy-4,4-dimethyl-pentyl)-6,7-dihydro-pyrimido[6,1-a]isoquinolin-4-one, 9-Cyclopentylmethoxymethyl-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(3-methoxy-butyl)-6,7-dihydro-pyrimido[6,1-a]isoquinolin-4-one, 2-((S)-1-[1,4]Dioxan-2-ylmethoxy)-9-(3-phenylamino-propyl)-6,7-dihydro-pyrimido[6,1-a]isoquinolin-4-one, 2-((S)-1-[1,4]Dioxan-2-ylmethoxy)-9-(4-hydroxy-pentyl)-6,7-dihydro-pyrimido[6,1-a]isoquinolin-4-one, 2-((S)-1-[1,4]Dioxan-2-ylmethoxy)-9-(4-hydroxy-butyl)-6,7-dihydro-pyrimido[6,1-a]isoquinolin-4-one, 9-(Cyclohexyl-methyl-amino)-2-((S)-1-[1,4]dioxan-2-ylmethoxy)-6,7-dihydro-pyrimido[6,1-a]isoquinolin-4-one, 9-(Cyclohexylmethyl-amino)-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-[(tetrahydro-pyran-4-ylmethyl)-amino]-6,7-dihydro-pyrimido[6,1-a]isoquinolin-4-one, 2-((S)-1-[1,4]Dioxan-2-ylmethoxy)-9-(3-ethyl-3-hydroxy-pentyl)-6,7-dihydro-pyrimido[6,1-a]isoquinolin-4-one, 2-((S)-1-[1,4]Dioxan-2-ylmethoxy)-9-(3-hydroxy-3-methyl-butyl)-6,7-dihydro-pyrimido[6,1-a]isoquinolin-4-one, 2-((S)-1-[1,4]Dioxan-2-ylmethoxy)-9-(3-hydroxy-pentyl)-6,7-dihydro-pyrimido[6,1-a]isoquinolin-4-one, 9-(2,2-Dimethyl-propoxy)-2-((S)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(tetrahydro-pyran-4-ylmethoxy)-6,7-dihydro-pyrimido[6,1-a]isoquinolin-4-one, 2-((S)-1-[1,4]Dioxan-2-ylmethoxy)-9-(4-hydroxy-4-methyl-pentyl)-6,7-dihydro-pyrimido[6,1-a]isoquino lin-4-one, 2-((S)-1-[1,4]Dioxan-2-ylmethoxy)-9-(tetrahydro-pyran-4-ylmethoxymethyl)-6,7-dihydro-pyrimido[6,1-a]isoquinolin-4-one, 2-([1,4]Dioxan-2-ylmethoxy)-9-methoxy-6,7-dihydro-pyrimido[6,1-a]isoquinolin-4-one, 2-((S)-1-[1,4]Dioxan-2-ylmethoxy)-9-(oxetan-3-ylmethoxy)-6,7-dihydro-pyrimido[6,1-a]isoquinolin-4-one, 9-(3-Cyclopropyl-propoxy)-2-((R)-1-[1,4]dioxan-2-ylmethoxy)-6,7-dihydro-pyrimido[6,1-a]isoquinolin-4-one, 2-((S)-1-[1,4]Dioxan-2-ylmethoxy)-9-(3-methoxy-propyl)-6,7-dihydro-pyrimido[6,1-a]isoquinolin-4-one, 2-((S)-1-[1,4]Dioxan-2-ylmethoxy)-9-[2-(1-hydroxy-cyclopentyl)-ethyl]-6,7-dihydro-pyrimido[6,1-a]isoquinolin-4-one, 2-((R)-1-[1,4]Dioxan-2-ylmethoxy)-9-(4-hydroxy-tetrahydro-pyran-4-ylethynyl)-6,7-dihydro-pyrimido[6,1-a]isoquinolin-4-one, 2-((R)-1-[1,4]Dioxan-2-ylmethoxy)-9-(3-methoxy-propyl)-6,7-dihydro-pyrimido[6,1-a]isoquinolin-4-one, 2-((R)-1-[1,4]Dioxan-2-ylmethoxy)-9-[2-(1-hydroxy-cyclopentyl)-ethyl]-6,7-dihydro-pyrimido[6,1-a]isoquinolin-4-one, 2-((S)-1-[1,4]Dioxan-2-ylmethoxy)-9-(2-propoxy-ethoxy)-6,7-dihydro-pyrimido[6,1-a]isoquinolin-4-one, 2-((S)-1-[1,4]Dioxan-2-ylmethoxy)-9-(2-isopropoxy-ethoxy)-6,7-dihydro-pyrimido[6,1-a]isoquinolin-4-one, 2-((R)-1-[1,4]Dioxan-2-ylmethoxy)-9-(2-propoxy-ethoxy)-6,7-dihydro-pyrimido[6,1-a]isoquinolin-4-one, 2-((R)-1-[1,4]Dioxan-2-ylmethoxy)-9-(2-isopropoxy-ethoxy)-6,7-dihydro-pyrimido[6,1-a]isoquinolin-4-one, and 2-((S)-1-[1,4]Dioxan-2-ylmethoxy)-9-(4-methoxy-butyl)-6,7-dihydro-pyrimido[6,1-a]isoquinolin-4-one.

14. A method according to claim 1, comprising administering a pharmaceutical composition comprising a compound or pharmaceutically acceptable salt thereof, according to claim 1, and a pharmaceutically acceptable carrier.

15. The method according to claim 14, wherein the pharmaceutical composition comprises a further therapeutic agent.

16. The method according to claim 1, wherein the compound, or pharmaceutically acceptable salt thereof, according to claim 1 is administered in combination with a further therapeutic agent.

* * * * *